(12) United States Patent
Egawa et al.

(10) Patent No.: US 8,546,792 B2
(45) Date of Patent: Oct. 1, 2013

(54) ANTHRACENE DERIVATIVE, AND LIGHT EMITTING ELEMENT, LIGHT EMITTING DEVICE, AND ELECTRONIC DEVICE USING THE ANTHRACENE DERIVATIVE

(75) Inventors: Masakazu Egawa, Tochigi (JP); Harue Osaka, Kanagawa (JP); Sachiko Kawakami, Kanagawa (JP); Satoko Shitagaki, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 206 days.

(21) Appl. No.: 13/014,887

(22) Filed: Jan. 27, 2011

(65) Prior Publication Data
US 2011/0121275 A1 May 26, 2011

Related U.S. Application Data

(63) Continuation of application No. 11/860,146, filed on Sep. 24, 2007, now Pat. No. 7,880,019.

(30) Foreign Application Priority Data

Sep. 28, 2006 (JP) .................................. 2006-266002

(51) Int. Cl.
*H01L 51/54* (2006.01)
*C07D 403/12* (2006.01)

(52) U.S. Cl.
USPC ............................................ 257/40; 548/442

(58) Field of Classification Search
None
See application file for complete search history.

(56) References Cited

U.S. PATENT DOCUMENTS

| | | | |
|---|---|---|---|
| 7,649,211 B2 | 1/2010 | Ohsawa | |
| 2003/0064246 A1 | 4/2003 | Kim et al. | |
| 2003/0118866 A1 | 6/2003 | Oh et al. | |
| 2003/0215667 A1 | 11/2003 | Xie | |
| 2004/0146746 A1 | 7/2004 | Lee et al. | |
| 2004/0161632 A1 | 8/2004 | Seo et al. | |
| 2004/0161633 A1 | 8/2004 | Seo et al. | |
| 2005/0225235 A1 | 10/2005 | Kim et al. | |
| 2007/0037011 A1 | 2/2007 | Nakashima et al. | |
| 2007/0075632 A1* | 4/2007 | Kawakami et al. | 313/504 |
| 2007/0247063 A1 | 10/2007 | Murase et al. | |
| 2007/0267969 A1 | 11/2007 | Nakashima et al. | |
| 2008/0006822 A1 | 1/2008 | Ohsawa | |
| 2008/0231177 A1 | 9/2008 | Nomura et al. | |
| 2008/0261075 A1 | 10/2008 | Seo et al. | |
| 2008/0284328 A1 | 11/2008 | Nakashima et al. | |
| 2009/0015140 A1 | 1/2009 | Kawakami et al. | |
| 2009/0072725 A1 | 3/2009 | Suzuki et al. | |
| 2009/0236590 A1 | 9/2009 | Ohsawa | |
| 2009/0236980 A1 | 9/2009 | Ohsawa | |
| 2010/0133573 A1 | 6/2010 | Nowatari et al. | |

FOREIGN PATENT DOCUMENTS

| | | |
|---|---|---|
| EP | 1 317 005 A2 | 6/2003 |
| EP | 1 748 045 A1 | 1/2007 |
| EP | 1 829 855 A1 | 9/2007 |
| JP | 2003-142269 | 5/2003 |
| JP | 2004-87395 | 3/2004 |
| WO | WO 2005/090512 A1 | 9/2005 |
| WO | WO 2006/049316 A1 | 5/2006 |
| WO | WO 2006/070907 A1 | 7/2006 |
| WO | WO 2006/104221 A1 | 10/2006 |
| WO | WO 2007/029530 A1 | 3/2007 |

OTHER PUBLICATIONS

Ishii et al., caplus an 2004:219376.*
Ishii et al. 2, caplus an 2004:219375.*
International Search Report re application No. PCT/JP2007/068480, dated Nov. 6, 2007.
Written Opinion re application No. PCT/JP2007/068480, dated Nov. 6, 2007.
Suda et al, Caplus AN 2007:172617.
Kawakami et al, Caplus AN 2007:283606.
European Search Report re application No. EP 07828313.2, dated Nov. 23, 2010.

* cited by examiner

*Primary Examiner* — Sun Jae Loewe
(74) *Attorney, Agent, or Firm* — Husch Blackwell LLP

(57) ABSTRACT

It is an object to provide a noble anthracene derivative, a light emitting element with a high luminous efficiency, and further a light emitting element with a long lifetime. It is another object to provide a light emitting device and electronic device with a long lifetime by using the light emitting element. An anthracene derivative represented by General Formula (1) is provided. Since the anthracene derivative represented by General Formula (1) has a high luminous efficiency, when the anthracene derivative is used for a light emitting element, the light emitting element can have a high luminous efficiency. Further, when the anthracene derivative represented by General Formula (1) is used for a light emitting element, the light emitting element can have a long lifetime.

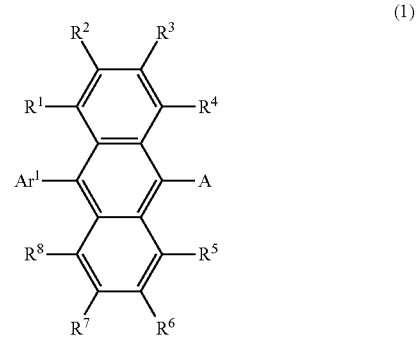

(1)

21 Claims, 47 Drawing Sheets

ANTHRACENE DERIVATIVE, AND LIGHT EMITTING ELEMENT, LIGHT EMITTING DEVICE, AND ELECTRONIC DEVICE USING THE ANTHRACENE DERIVATIVE

This application is a continuation of application Ser. No. 11/860,146 filed on Sep. 24, 2007 now U.S. Pat. No. 7,880,019.

TECHNICAL FIELD

The present invention relates to anthracene derivatives, and a light emitting element, a light emitting device, and an electronic device which use the anthracene derivatives.

BACKGROUND ART

An organic compound can take various structures compared with an inorganic compound, and it is possible to synthesize a material having various functions by appropriate molecular-design of an organic compound. Owing to these advantages, photo electronics and electronics which employ a functional organic material have been attracting attention in recent years.

For example, a solar cell, a light emitting element, an organic transistor, and the like are exemplified as an electronic device using an organic compound as a functional organic material. These devices take advantage of electrical properties and optical properties of the organic compound. Among them, in particular, a light emitting element has been making remarkable progress.

It is considered that the light emission mechanism of a light emitting element is as follows: when a voltage is applied to a pair of electrodes between which a light emitting layer is interposed, electrons injected from a cathode and holes injected from an anode are recombined at a luminescent center in the light emitting layer to form a molecular exciton, and energy is released to emit light when the molecular exciton returns to the ground state. As excited states, a singlet excited state and a triplet excited state are known, and light emission is considered to be possible through either of these excited states.

In an attempt to improve the performances of such a light emitting element, there are many problems which depend on the material, and in order to solve these problems, improvement of the element structure and development of a material have been carried out.

As a material used for a light emitting element, anthracene derivatives can be given.

For example, Patent Document 1 (Japanese Published Patent Application No. 2003-142269) mentions an organic EL display which uses an anthracene derivative or the like as a host material of a red light emitting layer.

In addition, Patent Document 2 (PCT International Publication No. 2006-049316) mentions an organic electroluminescent element which uses aromatic tertiary amine having an anthracene skeleton for a hole injecting material.

As mentioned in Patent Document 1 and Patent Document 2, the anthracene derivatives are often used in light emitting elements. However, in order to put a light emitting element to practical use, development of a material with more superior characteristics has been demanded.

DISCLOSURE OF INVENTION

In view of the foregoing problems, it is an object of the present invention to provide a novel anthracene derivative.

In addition, it is an object to provide a light emitting element with a high luminous efficiency and a light emitting element with a reduced driving voltage. Another object is to provide a light emitting device and an electronic device each having reduced power consumption by using the light emitting element.

One feature of the present invention is an anthracene derivative represented by General Formula (1).

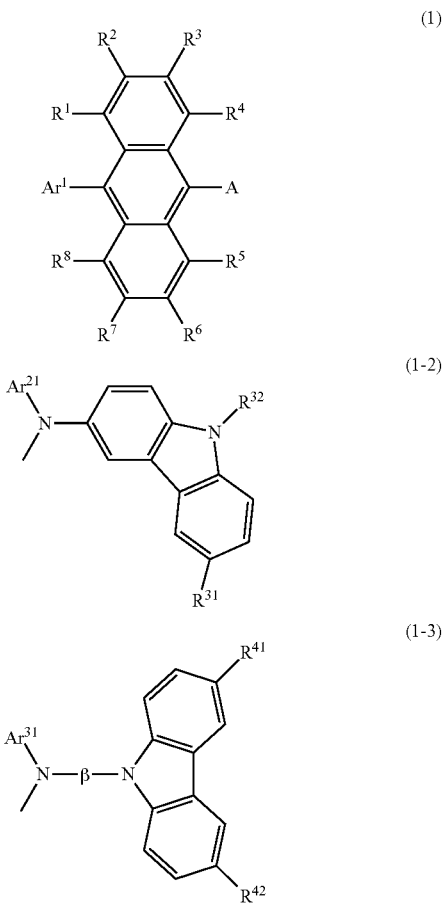

(In the formula, $Ar^1$ represents an aryl group having 6 to 25 carbon atoms; each of $R^1$ to $R^8$ represents a hydrogen atom or an alkyl group having 1 to 4 carbon atoms; and A represents either of substituents shown by General Formulae (1-2) and (1-3). In General Formulae (1-2) and (1-3), $Ar^{21}$ represents an aryl group having 6 to 25 carbon atoms; $R^{31}$ represents any of a hydrogen atom, an alkyl group having 1 to 4 carbon atoms, and an aryl group having 6 to 25 carbon atoms; and $R^{32}$ represents any of an alkyl group having 1 to 4 carbon atoms and an aryl group having 6 to 25 carbon atoms. $Ar^{31}$ represents an aryl group having 6 to 25 carbon atoms; β represents an arylene group having 6 to 25 carbon atoms; and each of $R^{41}$ and $R^{42}$ represents any of a hydrogen atom, an alkyl group having 1 to 4 carbon atoms, and an aryl group having 6 to 25 carbon atoms.)

Another feature of the present invention is an anthracene derivative represented by General Formula (2).

Yet another feature of the present invention is an anthracene derivative represented by General Formula (3).

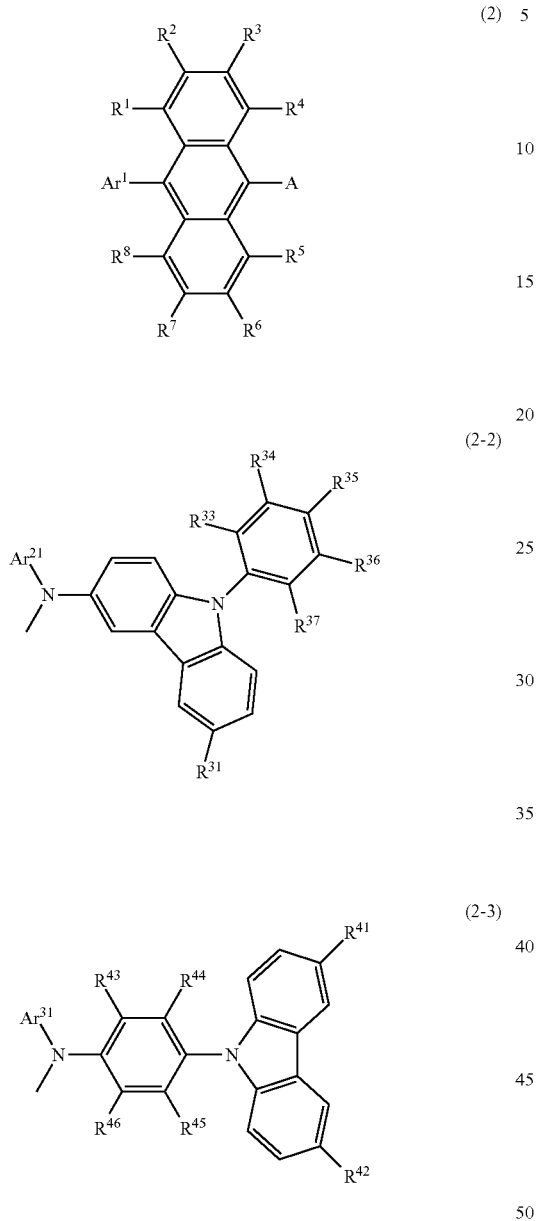

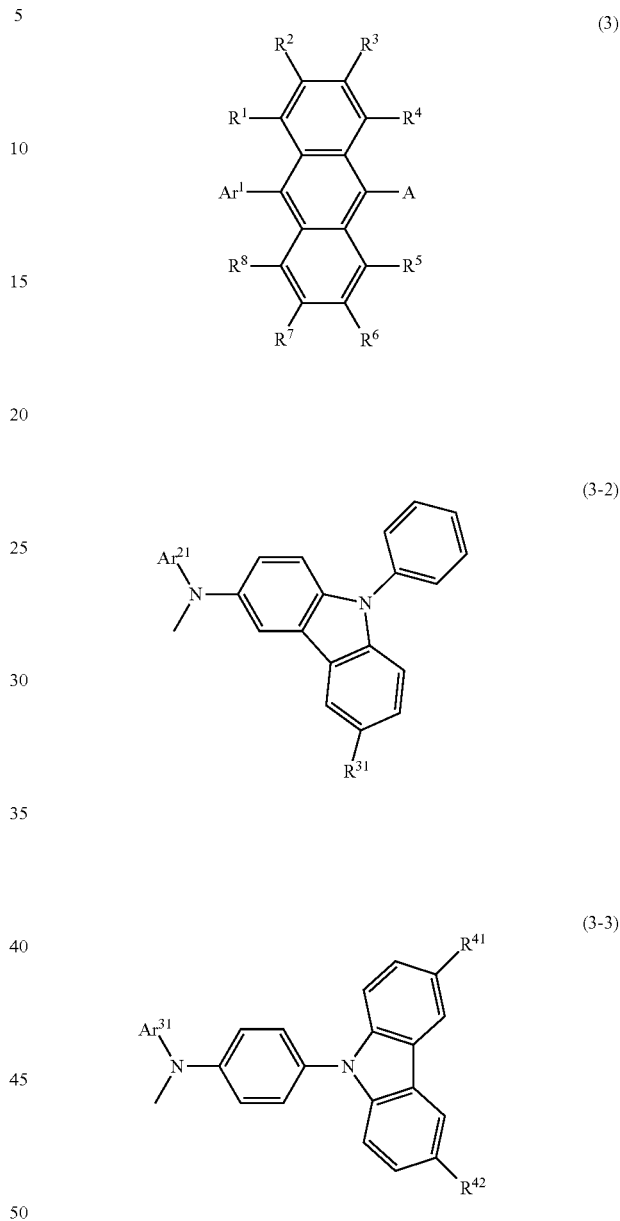

(In the formula, $Ar^1$ represents an aryl group having 6 to 25 carbon atoms; each of $R^1$ to $R^8$ represents a hydrogen atom or an alkyl group having 1 to 4 carbon atoms; and A represents either of substituents shown by General Formulae (2-2) and (2-3). In General Formulae (2-2) and (2-3), $Ar^{21}$ represents an aryl group having 6 to 25 carbon atoms; $R^{31}$ represents any of a hydrogen atom, an alkyl group having 1 to 4 carbon atoms, and an aryl group having 6 to 25 carbon atoms; and each of $R^{33}$ to $R^{37}$ represents any of a hydrogen atom, an alkyl group having 1 to 4 carbon atoms, and an aryl group having 6 to 25 carbon atoms. $Ar^{31}$ represents an aryl group having 6 to 25 carbon atoms; each of $R^{41}$ and $R^{42}$ represents any of a hydrogen atom, an alkyl group having 1 to 4 carbon atoms, and an aryl group having 6 to 25 carbon atoms; and each of $R^{43}$ to $R^{46}$ represents a hydrogen atom, an alkyl group having 1 to 4 carbon atoms, or an aryl group having 6 to 15 carbon atoms.)

(In the formula, $Ar^1$ represents an aryl group having 6 to 25 carbon atoms; each of $R^1$ to $R^8$ represents a hydrogen atom or an alkyl group having 1 to 4 carbon atoms; and A represents either of substituents shown by General Formulae (3-2) and (3-3). In General Formulae (3-2) and (3-3), $Ar^{21}$ represents an aryl group having 6 to 25 carbon atoms; $R^{31}$ represents any of a hydrogen atom, an alkyl group having 1 to 4 carbon atoms, and an aryl group having 6 to 25 carbon atoms; and $Ar^{31}$ represents an aryl group having 6 to 25 carbon atoms. Each of $R^{41}$ and $R^{42}$ represents any of a hydrogen atom, an alkyl group having 1 to 4 carbon atoms, and an aryl group having 6 to 25 carbon atoms.)

Still another feature of the present invention is an anthracene derivative represented by General Formula (4).

(4)

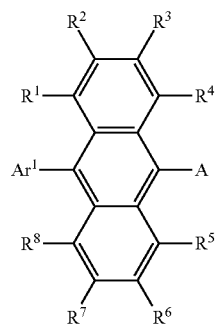

(4-2)

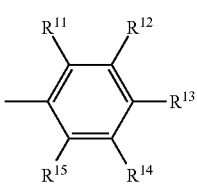

(4-3)

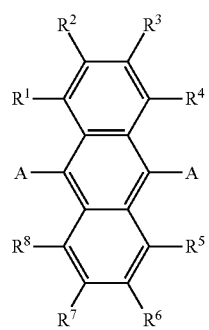

(In the formula, Ar$^1$ represents an aryl group having 6 to 25 carbon atoms; each of R$^1$ to R$^8$ represents a hydrogen atom or an alkyl group having 1 to 4 carbon atoms; and A represents either of substituents shown by General Formulae (4-2) and (4-3). In General Formulae (4-2) and (4-3), Ar$^{21}$ represents any of a phenyl group, a 1-naphthyl group, and a 2-naphthyl group; R$^{31}$ represents any of a hydrogen atom, an alkyl group having 1 to 4 carbon atoms, and an aryl group having 6 to 25 carbon atoms; and Ar$^{31}$ represents any of a phenyl group, a 1-naphthyl group, and a 2-naphthyl group. Each of R$^{41}$ and R$^{42}$ represents any of a hydrogen atom, an alkyl group having 1 to 4 carbon atoms, and an aryl group having 6 to 25 carbon atoms.)

In the above structure, Ar$^1$ is preferably a substituent represented by General Formula (11-1).

(11-1)

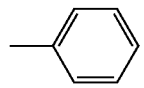

(Each of R$^{11}$ to R$^{15}$ represents a hydrogen atom, an alkyl group having 1 to 4 carbon atoms, or an aryl group having 6 to 15 carbon atoms.)

In the above structure, Ar$^1$ is preferably a substituent represented by Structural Formula (11-2) or (11-3).

(11-2)

(11-3)

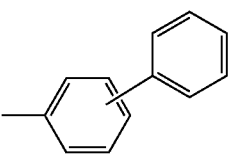

In the above structure, Ar$^1$ is preferably a substituent represented by Structural Formula (11-4).

(11-4)

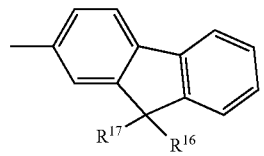

(In the formula, each of R$^{16}$ and R$^{17}$ represents an alkyl group having 1 to 4 carbon atoms or a phenyl group.)

In the above structure, Ar$^1$ is preferably a substituent represented by Structural Formula (11-5) or (11-6).

(11-5)

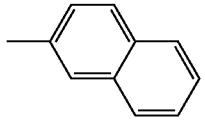

(11-6)

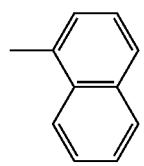

One feature of the present invention is an anthracene derivative represented by General Formula (5).

(5)

(5-2)

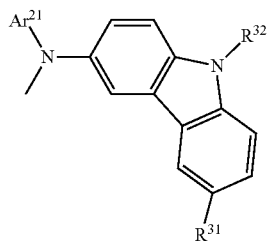

(5-3)

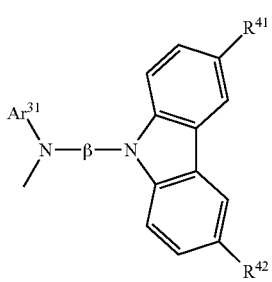

(In the formula, each of $R^1$ to $R^8$ represents a hydrogen atom or an alkyl group having 1 to 4 carbon atoms; and A represents either of substituents shown by General Formulae (5-2) and (5-3). In General Formulae (5-2) and (5-3), $Ar^{21}$ represents an aryl group having 6 to 25 carbon atoms; $R^{31}$ represents any of a hydrogen atom, an alkyl group having 1 to 4 carbon atoms, and an aryl group having 6 to 25 carbon atoms; and $R^{32}$ represents any of an alkyl group having 1 to 4 carbon atoms and an aryl group having 6 to 25 carbon atoms. $Ar^{31}$ represents an aryl group having 6 to 25 carbon atoms; β represents an arylene group having 6 to 25 carbon atoms; and each of $R^{41}$ and $R^{42}$ represents any of a hydrogen atom, an alkyl group having 1 to 4 carbon atoms, and an aryl group having 6 to 25 carbon atoms.)

Another feature of the present invention is an anthracene derivative represented by General Formula (6).

(6)

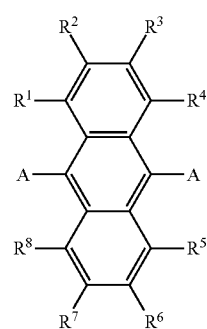

(6-2)

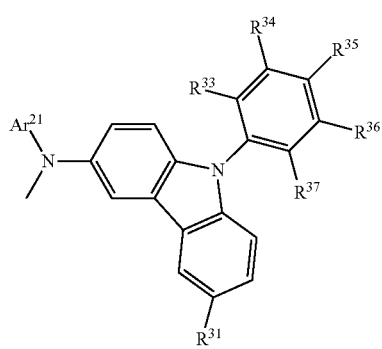

(6-3)

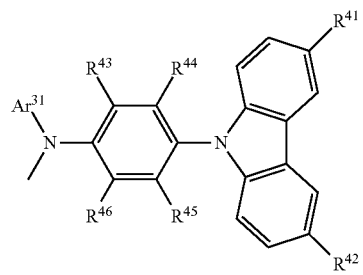

(In the formula, each of $R^1$ to $R^8$ represents a hydrogen atom or an alkyl group having 1 to 4 carbon atoms; and A represents either of substituents shown by General Formulae (6-2) and (6-3). In General Formulae (6-2) and (6-3), $Ar^{21}$ represents an aryl group having 6 to 25 carbon atoms; $R^{31}$ represents any of a hydrogen atom, an alkyl group having 1 to 4 carbon atoms, and an aryl group having 6 to 25 carbon atoms; and each of $R^{33}$ to $R^{37}$ represents any of a hydrogen atom, an alkyl group having 1 to 4 carbon atoms, and an aryl group having 6 to 15 carbon atoms. $Ar^{31}$ represents an aryl group having 6 to 25 carbon atoms; each of $R^{41}$ and $R^{42}$ represents any of a hydrogen atom, an alkyl group having 1 to 4 carbon atoms, and an aryl group having 6 to 25 carbon atoms; and each of $R^{43}$ to $R^{46}$ represents a hydrogen atom, an alkyl group having 1 to 4 carbon atoms, or an aryl group having 6 to 15 carbon atoms.)

One feature of the present invention is an anthracene derivative represented by General Formula (7).

(7)

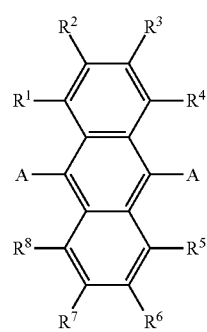

(7-2)

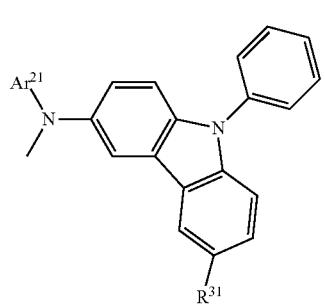

-continued

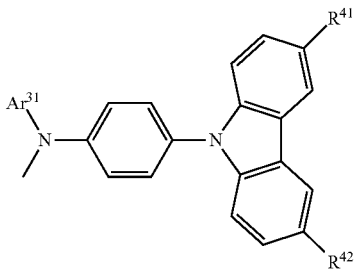

(7-3)

(In the formula, each of $R^1$ to $R^8$ represents a hydrogen atom or an alkyl group having 1 to 4 carbon atoms; and A represents either of substituents shown by General Formulae (7-2) and (7-3). In General Formulae (7-2) and (7-3), $Ar^{21}$ represents an aryl group having 6 to 25 carbon atoms; $R^{31}$ represents any of a hydrogen atom, an alkyl group having 1 to 4 carbon atoms, and an aryl group having 6 to 25 carbon atoms; and $Ar^{31}$ represents an aryl group having 6 to 25 carbon atoms. Each of $R^{41}$ and $R^{42}$ represents any of a hydrogen atom, an alkyl group having 1 to 4 carbon atoms, and an aryl group having 6 to 25 carbon atoms.)

One feature of the present invention is an anthracene derivative represented by General Formula (8).

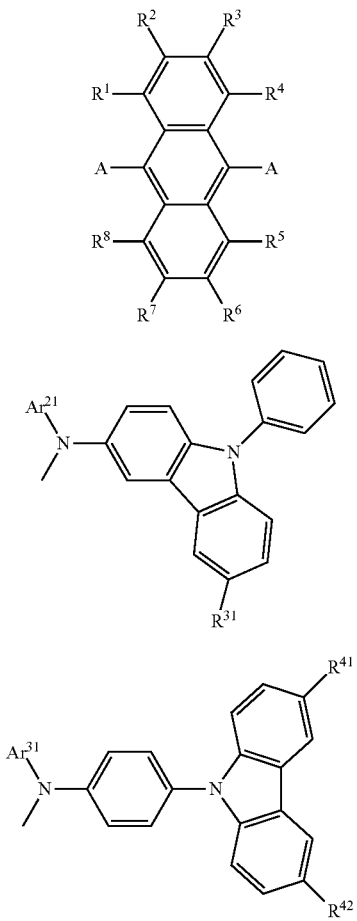

(8)

(8-2)

(8-3)

(In the formula, each of $R^1$ to $R^8$ represents a hydrogen atom or an alkyl group having 1 to 4 carbon atoms; and A represents either of substituents shown by General Formulae (8-2) and (8-3). In General Formulae (8-2) and (8-3), $Ar^{21}$ represents any of a phenyl group, a 1-naphthyl group, and a 2-naphthyl group; $R^{31}$ represents any of a hydrogen atom, an alkyl group having 1 to 4 carbon atoms, and an aryl group having 6 to 25 carbon atoms; and $Ar^{31}$ represents any of a phenyl group, a 1-naphthyl group, and a 2-naphthyl group. Each of $R^{41}$ and $R^{42}$ represents any of a hydrogen atom, an alkyl group having 1 to 4 carbon atoms, and an aryl group having 6 to 25 carbon atoms.)

Further, one feature of the present invention is a light emitting element using any of the foregoing anthracene derivatives. Specifically, the feature of the present invention is a light emitting element having the anthracene derivative between a pair of electrodes.

Another feature of the present invention is a light emitting element having a light emitting layer between a pair of electrodes, in which the light emitting layer includes any of the above-described anthracene derivatives. It is particularly preferable to use any of the above-mentioned anthracene derivatives as a light emitting substance. That is, it is preferable to have a structure in which the anthracene derivative emits light.

The light emitting device of the present invention possesses a light emitting element which includes a layer including a light emitting substance between a pair of electrodes and in which the layer including a light emitting substance includes any of the foregoing anthracene derivatives. The light emitting device of the present invention also possesses a controller for controlling light emission of the light emitting element. The light emitting device in this specification includes an image display device, a light emitting device, and a light source (including a lighting device). Further, the light emitting device also includes all types of modules, e.g., a module in which a connector such as an FPC (Flexible Printed Circuit), a TAB (Tape Automated Bonding) tape, or a TCP (Tape Carrier Package) is attached to a panel, a module in which a printed wiring board is provided at an end of a TAB tape or a TCP, and a module in which an IC (Integrated Circuit) is directly mounted on the light emitting element by a COG (Chip On Glass) method.

Further, an electronic device using the light emitting element of the present invention in its display portion is also included in the category of the present invention. Therefore, the electronic device of the present invention has a display portion, and the display portion is equipped with the above-described light emitting element and the controller for controlling light emission of the light emitting element.

An anthracene derivative of the present invention emits light efficiently. Therefore, by using the anthracene derivative of the present invention in a light emitting element, a light emitting element with a high luminous efficiency can be provided. Also, the anthracene derivative of the present invention is superior in a hole transporting property. Therefore, by using the anthracene derivative of the present invention in a light emitting element, a light emitting element with a reduced driving voltage can be provided.

Further, by using an anthracene derivative of the present invention, a light emitting device and an electronic device with reduced power consumption can be provided.

BEST MODE FOR CARRYING OUT THE INVENTION

Figure 1A:
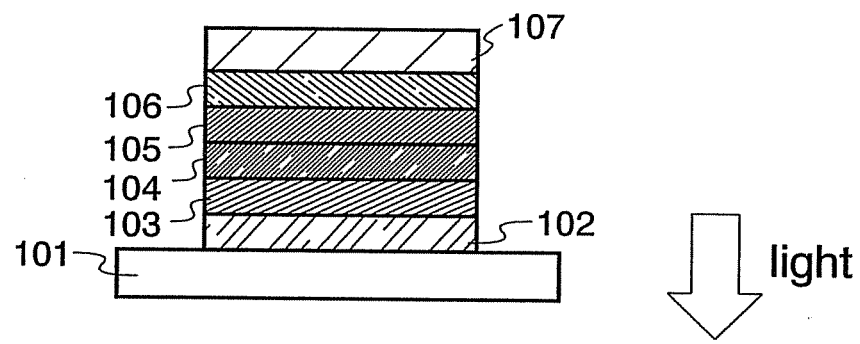
FIGS. 1A to 1C show light emitting elements according to the present invention.

Embodiment modes and examples of the present invention will be described in detail with reference to the drawings. It is easily understood by those skilled in the art that various changes may be made in forms and details without departing from the spirit and the scope of the invention. Therefore, the present invention should not be limited to the descriptions of the embodiment modes and the examples below.

Embodiment Mode 1

Embodiment Mode 1 will describe an anthracene derivative of the present invention.

An anthracene derivative of the present invention has an amino group having a 9-arylcarbazole skeleton in position 9 of the anthracene skeleton and also has an aryl group in position 10 of the anthracene skeleton. That is, the anthracene derivative of the present invention is an anthracene derivative represented by General Formula (1).

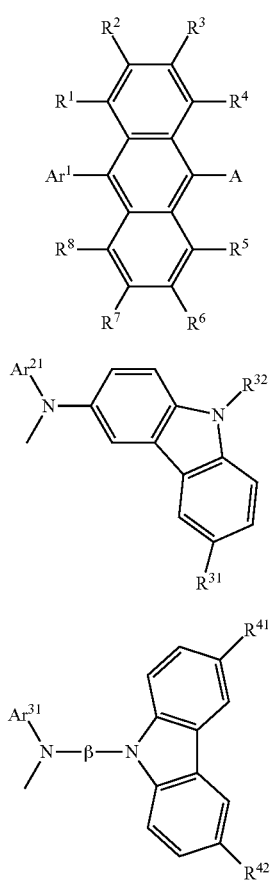

(In the formula, $Ar^1$ represents an aryl group having 6 to 25 carbon atoms; each of $R^1$ to $R^8$ represents a hydrogen atom or an alkyl group having 1 to 4 carbon atoms; and A represents either of substituents shown by General Formulae (1-2) and (1-3). In General Formulae (1-2) and (1-3), $Ar^{21}$ represents an aryl group having 6 to 25 carbon atoms; $R^{31}$ represents any of a hydrogen atom, an alkyl group having 1 to 4 carbon atoms, and an aryl group having 6 to 25 carbon atoms; and $R^{32}$ represents any of an alkyl group having 1 to 4 carbon atoms and an aryl group having 6 to 25 carbon atoms. $Ar^{31}$ represents an aryl group having 6 to 25 carbon atoms; β represents an arylene group having 6 to 25 carbon atoms; and each of $R^{41}$ and $R^{42}$ represents any of a hydrogen atom, an alkyl group having 1 to 4 carbon atoms, and an aryl group having 6 to 25 carbon atoms.)

In General Formula (1), a substituent represented by $Ar^1$ is, for example, any of substituents represented by Structural Formulae (20-1) to (20-9).

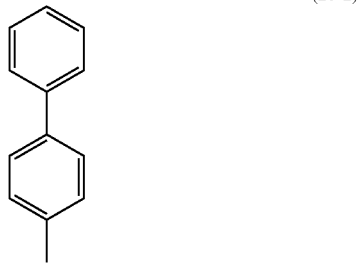

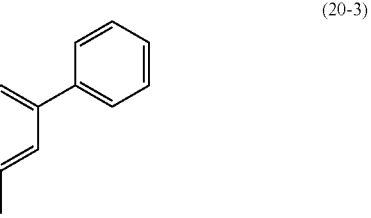

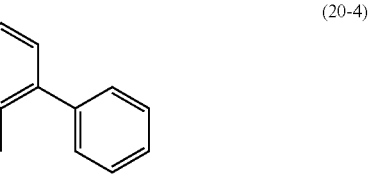

(20-6)
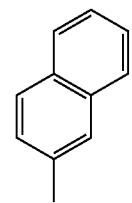
(20-7)
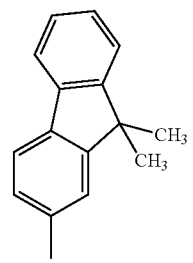
(20-8)
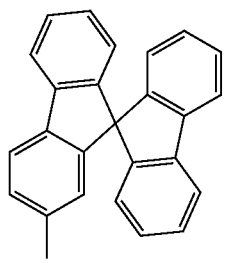
(20-9)
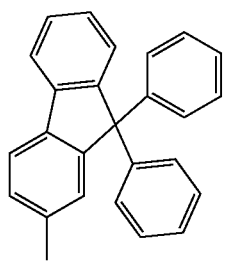
In General Formula (1-2), a substituent represented by Ar$^{21}$ is, for example, any of substituents represented by Structural Formulae (21-1) to (21-9).
(21-1)
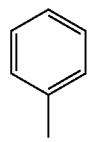
(21-2)
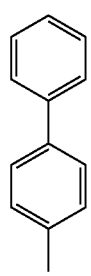
(21-3)
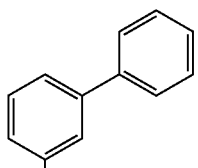
(21-4)
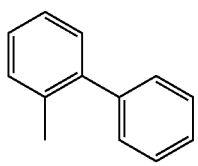
(21-5)
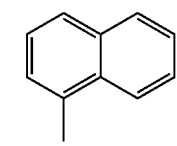
(21-6)
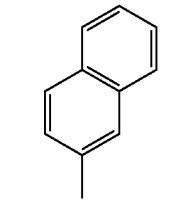
(21-7)
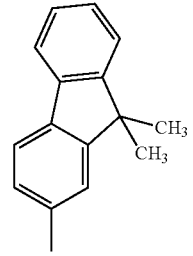
(21-8)
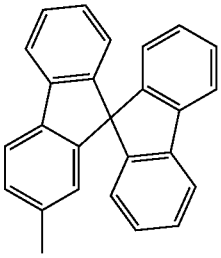
(21-9)
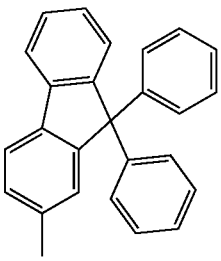
In General Formula (1-2), a substituent represented by R$^{31}$ is, for example, any of substituents represented by Structural Formulae (22-1) to (22-18).

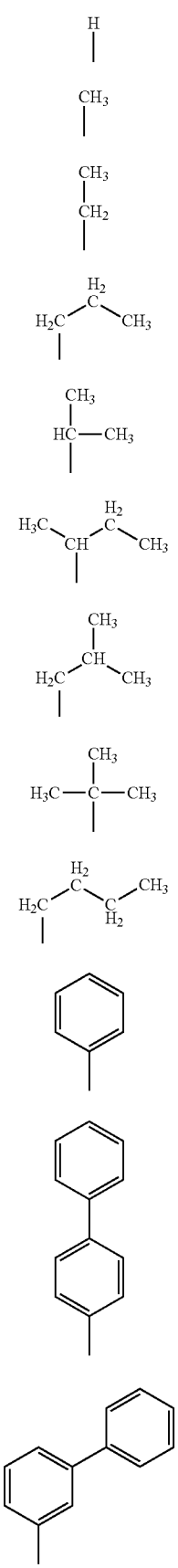
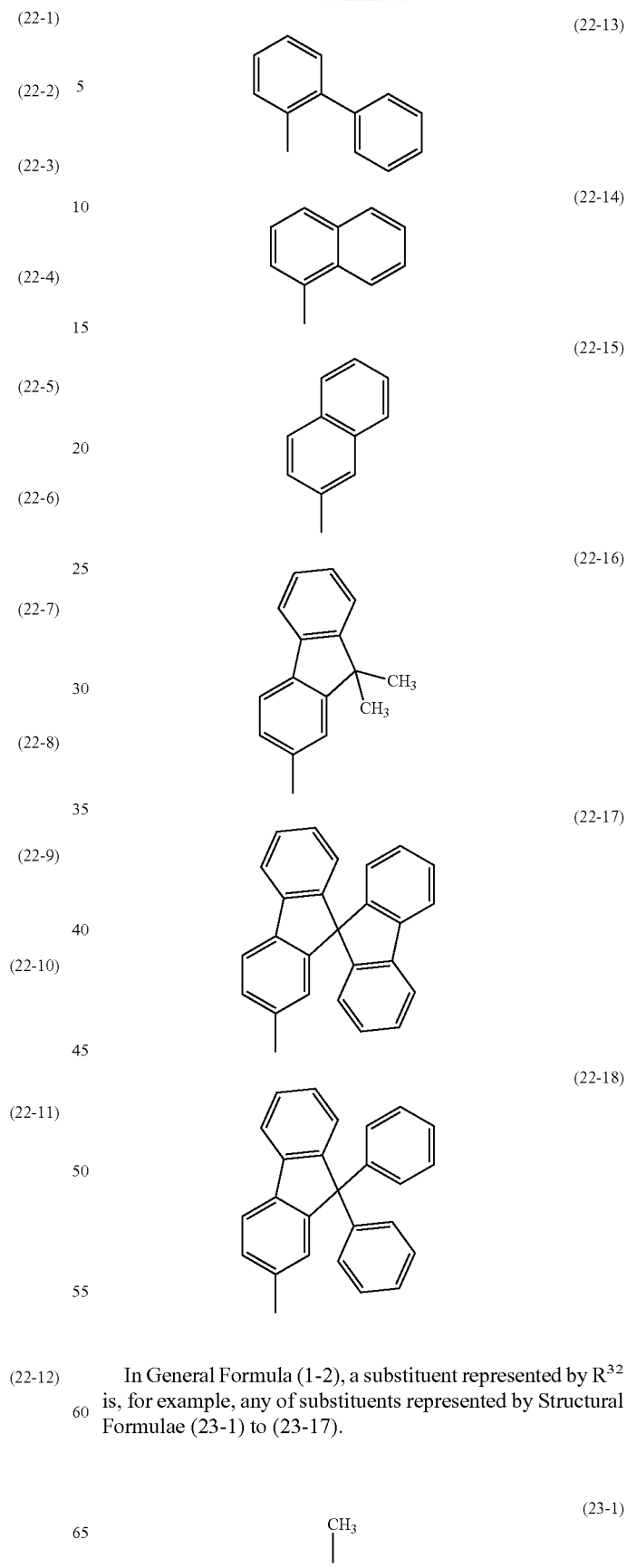
In General Formula (1-2), a substituent represented by R³² is, for example, any of substituents represented by Structural Formulae (23-1) to (23-17).

(23-2) 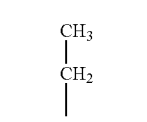
(23-3) 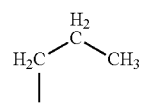
(23-4) 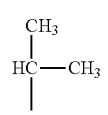
(23-5) 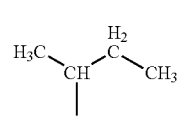
(23-6) 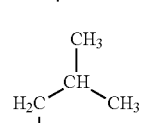
(23-7) 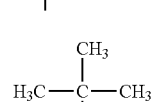
(23-8) 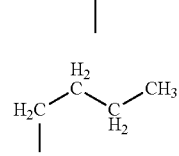
(23-9) 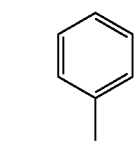
(23-10) 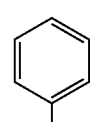
(23-11) 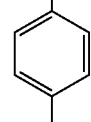
(23-12) 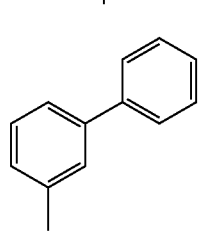
(23-13) 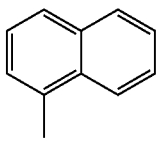
(23-14) 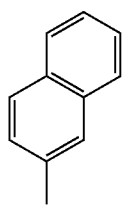
(23-15) 
(23-16) 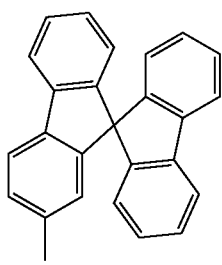
(23-17) 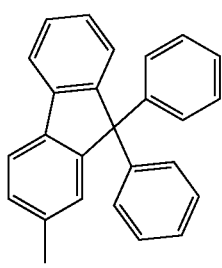
Accordingly, the substituent represented by General Formula (1-2) is, for example, any of substituents represented by Structural Formulae (24-1) to (24-52).

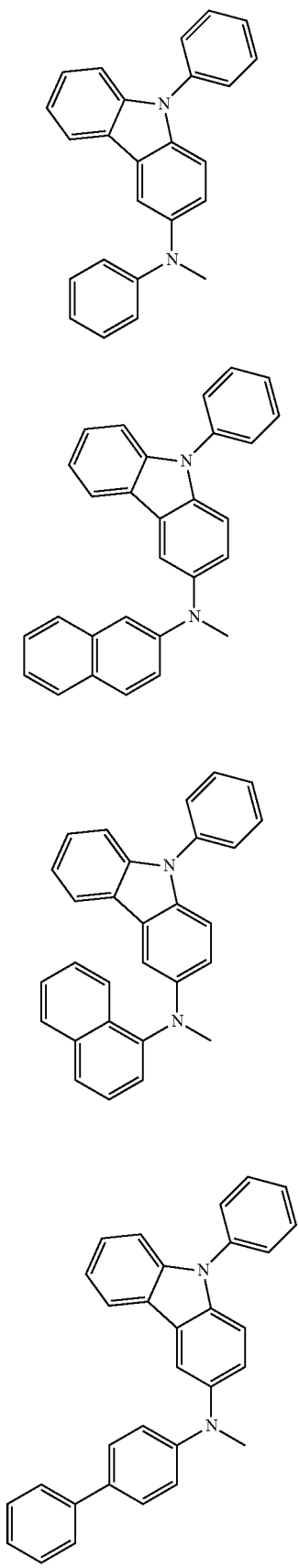
(24-1)
(24-2)
(24-3)
(24-4)
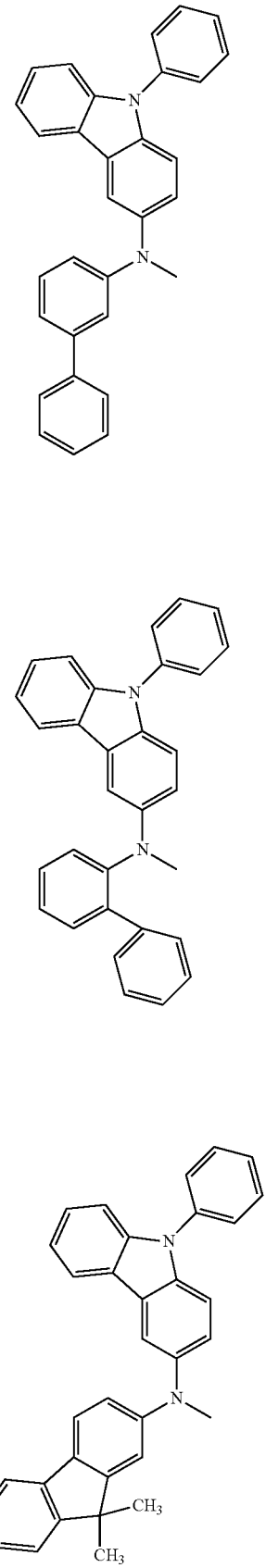
(24-5)
(24-6)
(24-7)

-continued
(24-8)
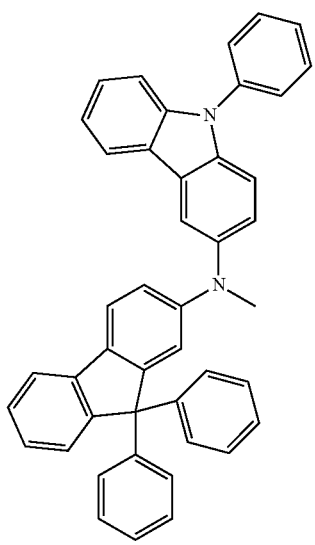
(24-9)
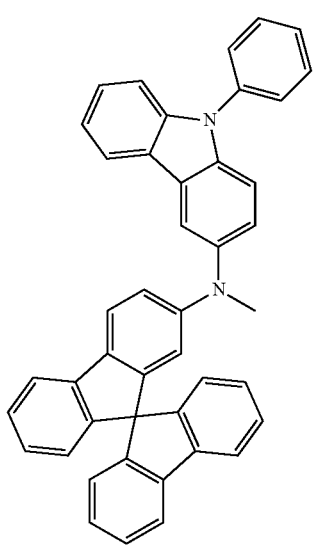
(24-10)
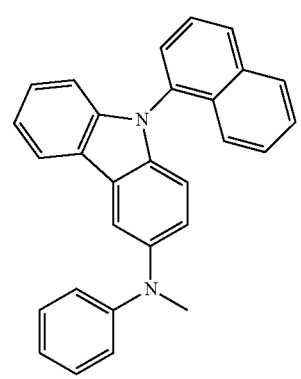
-continued
(24-11)
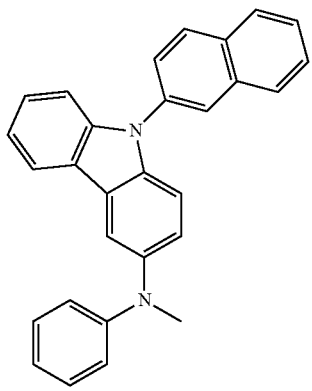
(24-12)
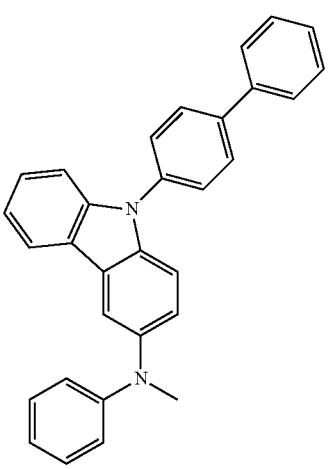
(24-13)
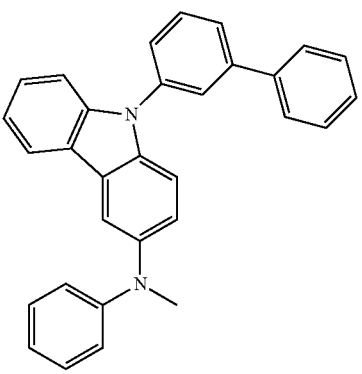
(24-14)
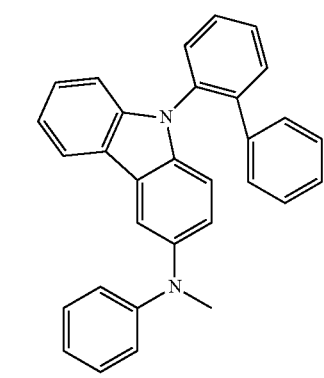

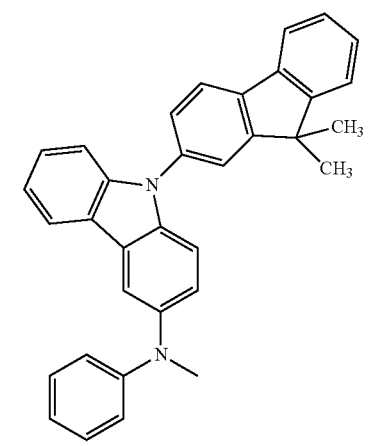
(24-15)
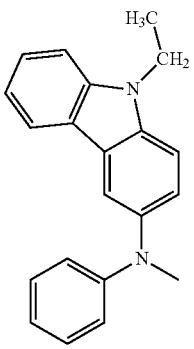
(24-19)
(24-16)
(24-20)
(24-17)
(24-21)
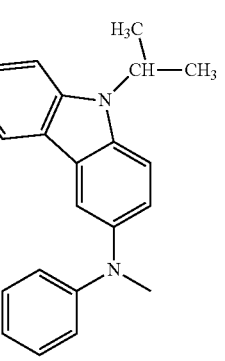
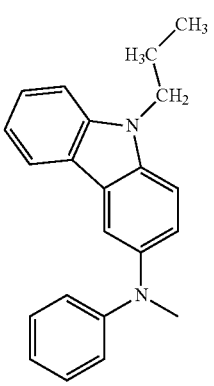
(24-18)
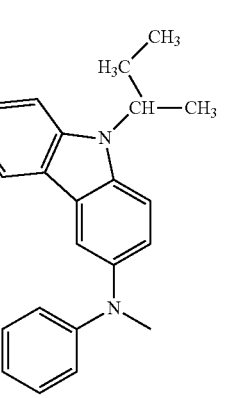
(24-22)

-continued
(24-23)
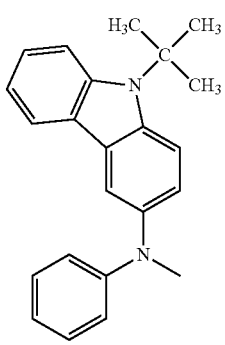
(24-24)
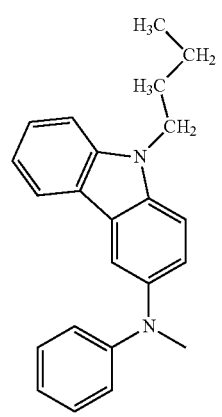
(24-25)
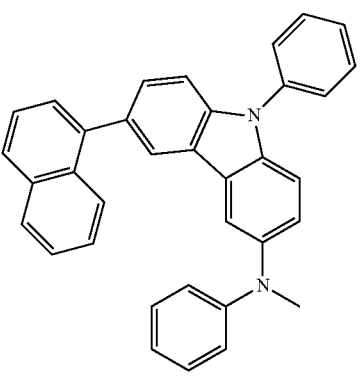
(24-26)
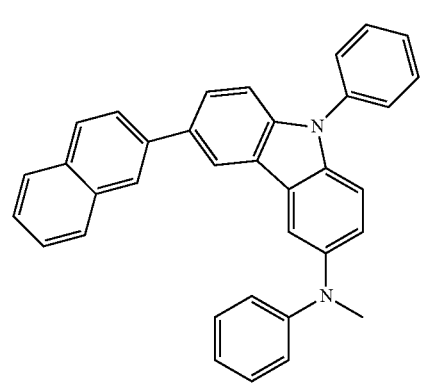
-continued
(24-27)
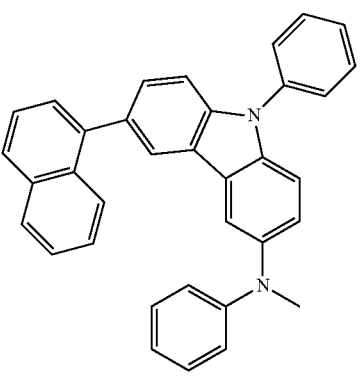
(24-28)
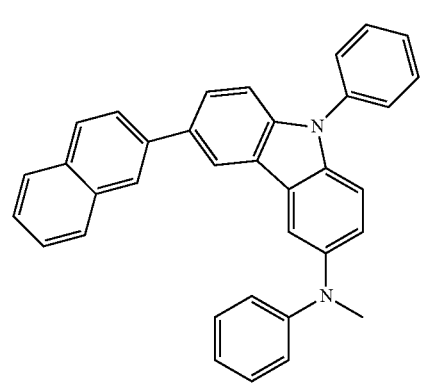
(24-29)
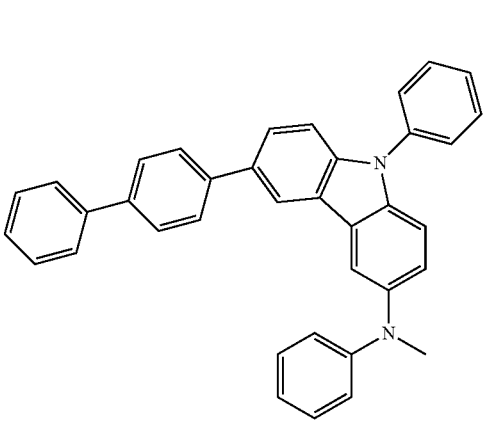
(24-30)
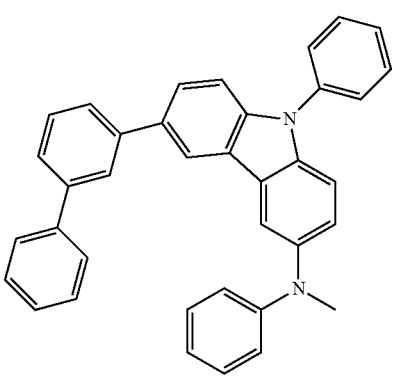

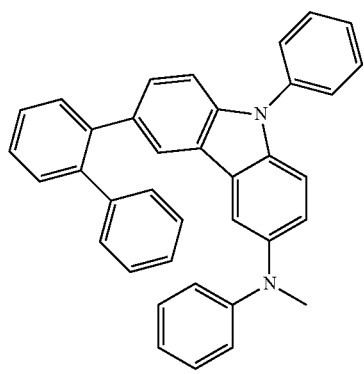
(24-31)
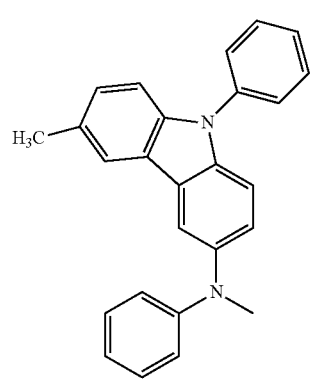
(24-32)
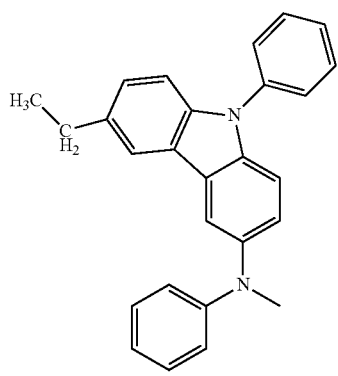
(24-33)
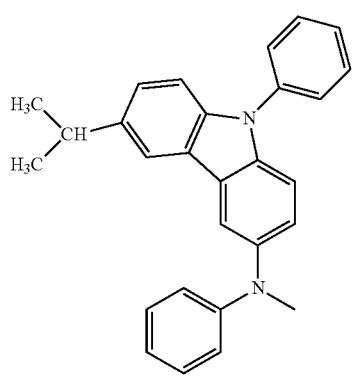
(24-34)
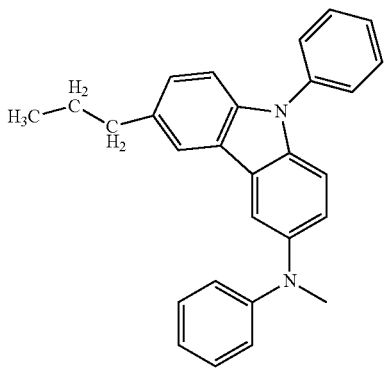
(24-35)
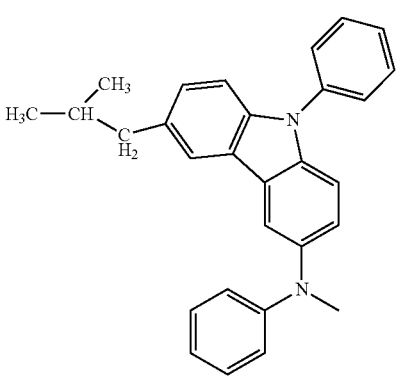
(24-36)
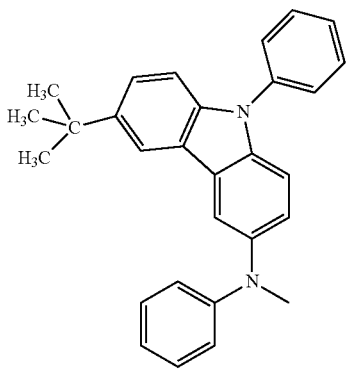
(24-37)
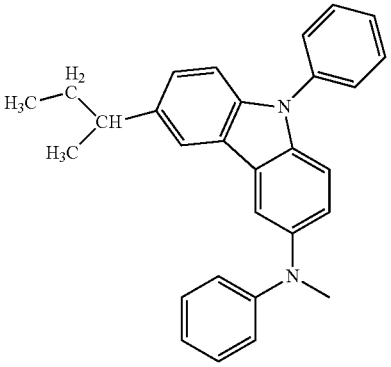
(24-38)

(24-39)
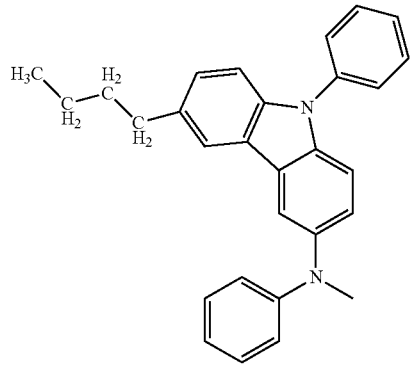
(24-40)
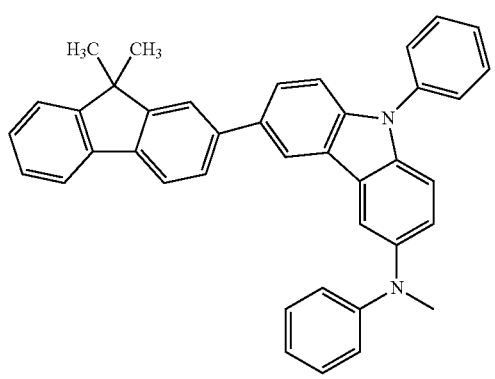
(24-41)
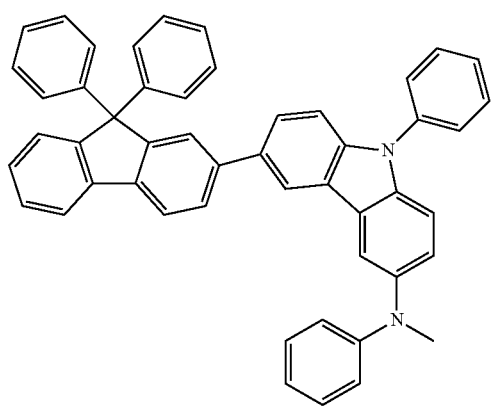
(24-42)
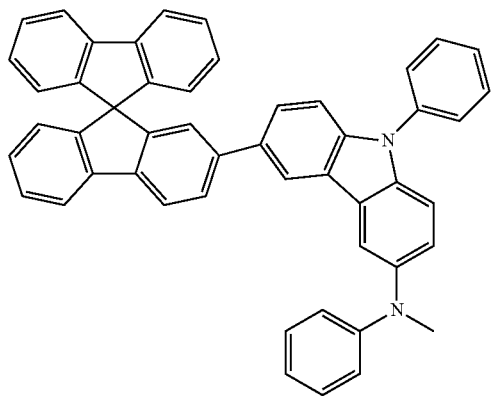
(24-43)
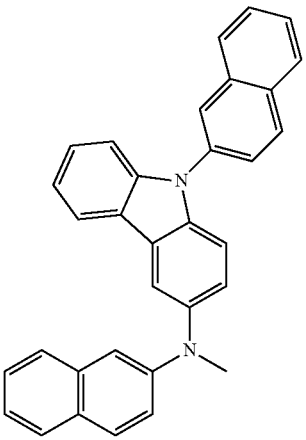
(24-44)
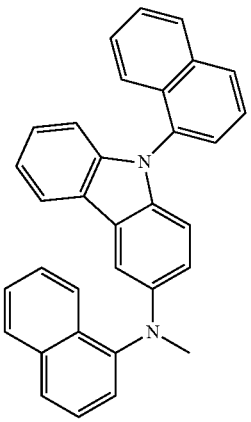
(24-45)
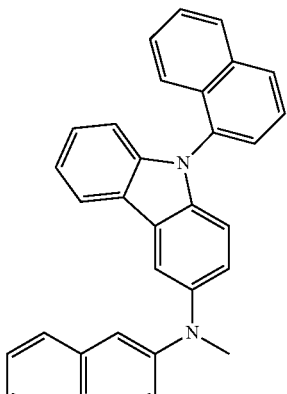

(24-46)
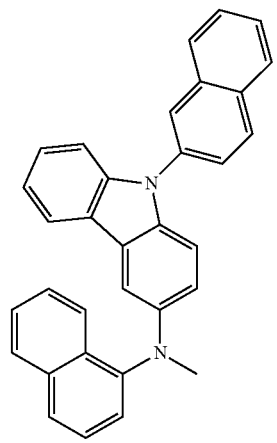
(24-47)
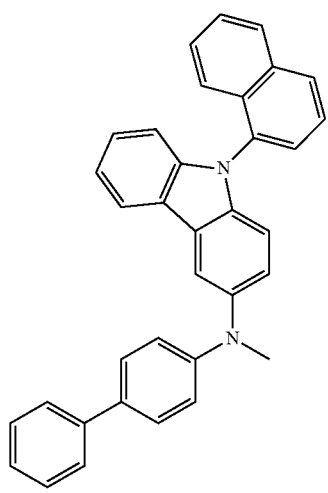
(24-48)
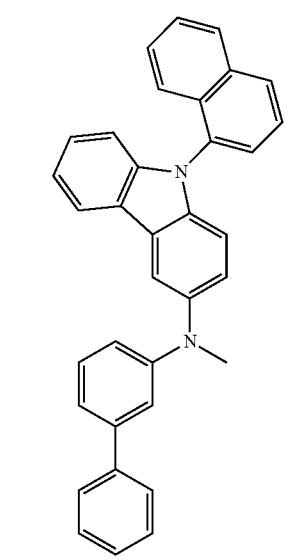
(24-49)
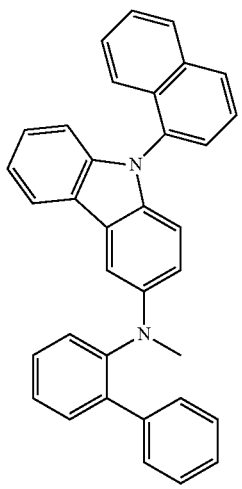
(24-50)
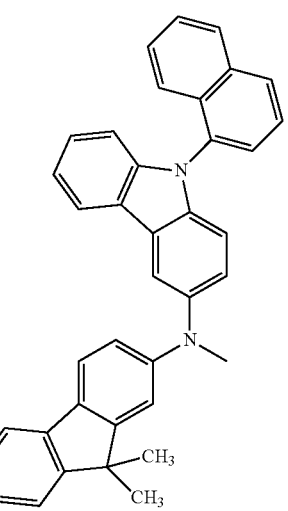
(24-51)
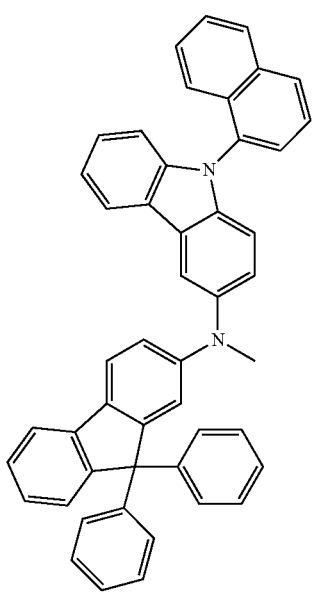

-continued
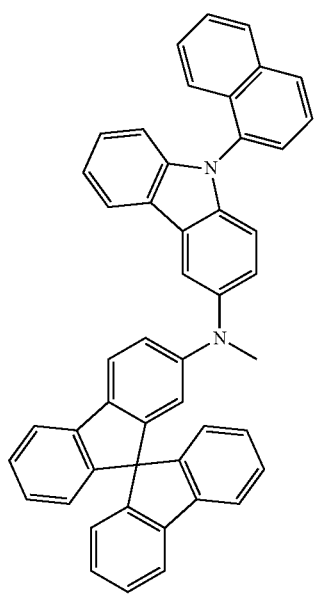
(24-52)
Further, in General Formula (1-3), a substituent represented by Ar³¹ is, for example, any of substituents represented by Structural Formulae (31-1) to (31-9).
(31-1)
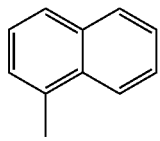
(31-2)
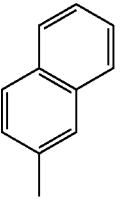
(31-3)
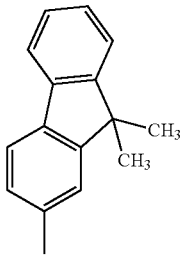
(31-4)
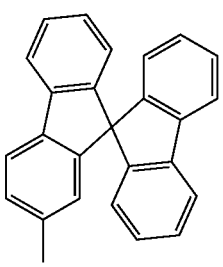
-continued
(31-5)
(31-6)
(31-7)
(31-8)
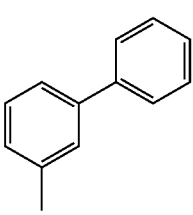
(31-9)
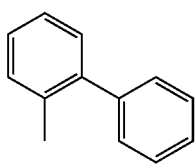
Further, in General Formula (1-3), a substituent represented by β is, for example, any of substituents represented by Structural Formulae (32-1) to (32-10).
(32-1)
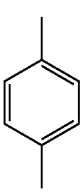

(32-2) 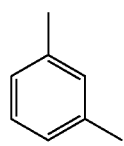
(32-3) 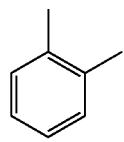
(32-4) 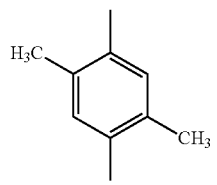
(32-5) 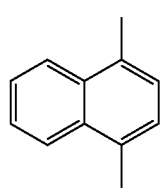
(32-6) 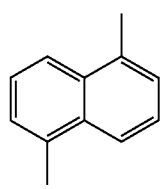
(32-7) 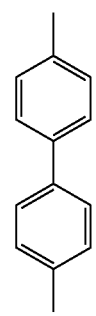
(32-8) 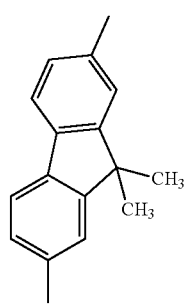
(32-9) 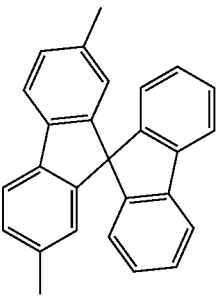
(32-10) 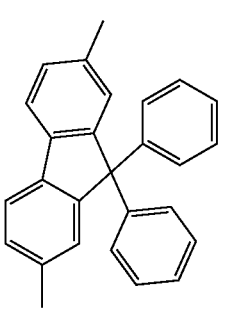
In addition, in General Formula (1-3), each of substituents represented by $R^{41}$ and $R^{42}$ is, for example, any of substituents represented by Structural Formulae (33-1) to (33-18).
(33-1) 
(33-2) 
(33-3) 
(33-4) 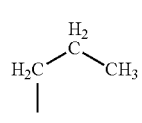
(33-5) 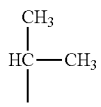
(33-6) 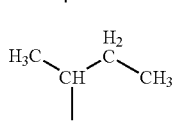
(33-7) 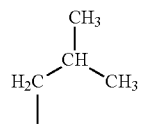
(33-8) 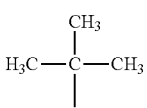

(33-9) 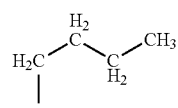
(33-10) 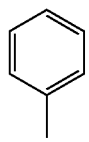
(33-11) 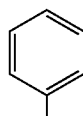
(33-12) 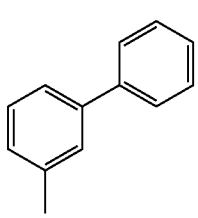
(33-13) 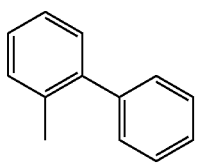
(33-14) 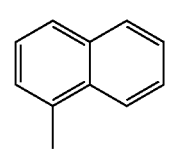
(33-15) 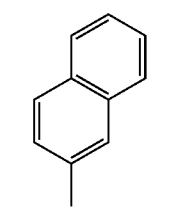
(33-16) 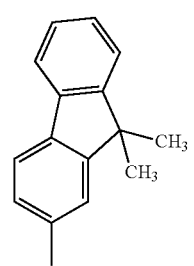
(33-17) 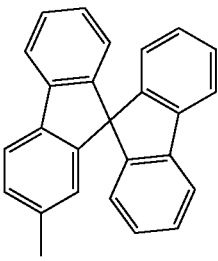
(33-18) 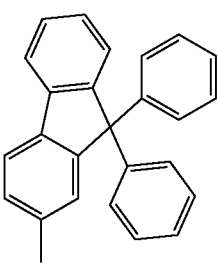
Accordingly, the substituent represented by General Formula (1-3) is, for example, any of substituents represented by Structural Formulae (34-1) to (34-35).
(34-1) 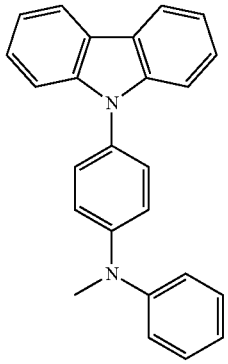
(34-2) 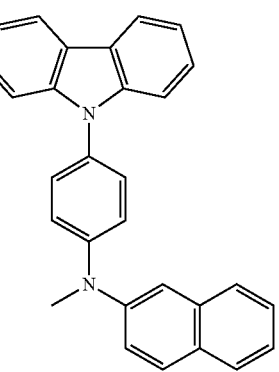

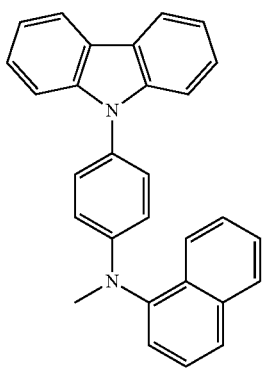
(34-3)
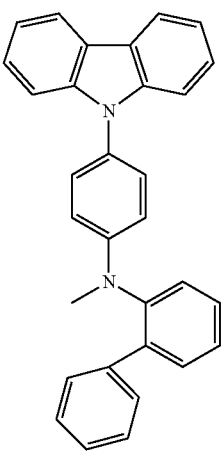
(34-6)
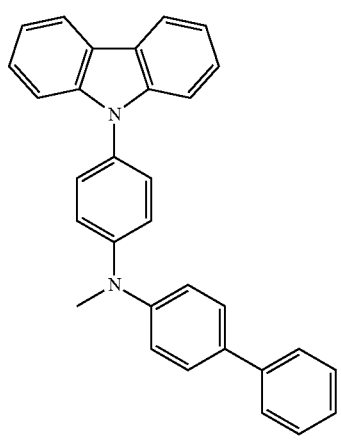
(34-4)
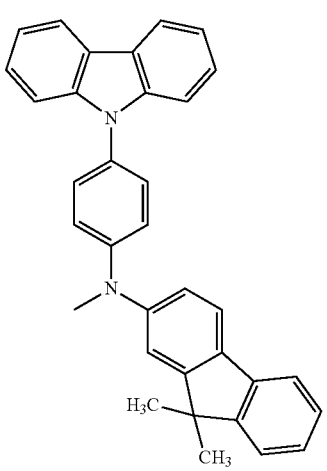
(34-7)
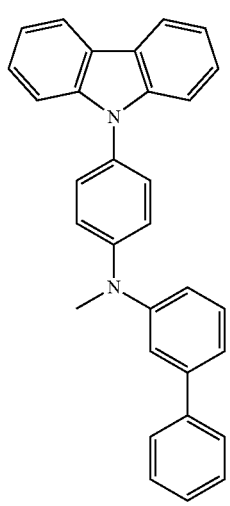
(34-5)
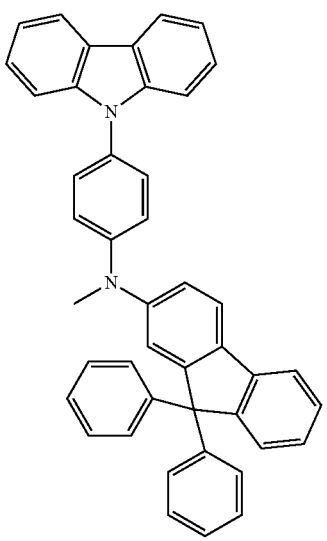
(34-8)

(34-9)
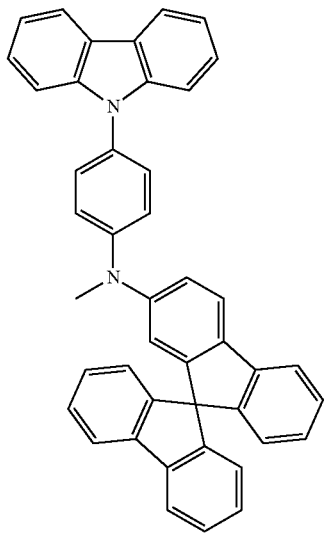
(34-10)
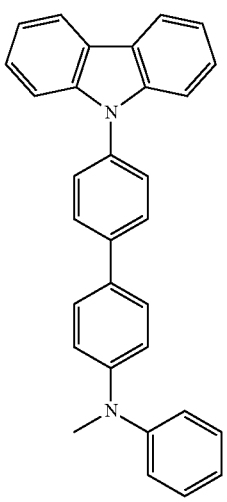
(34-11)
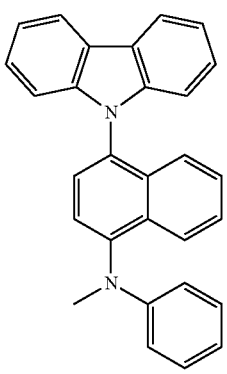
(34-12)
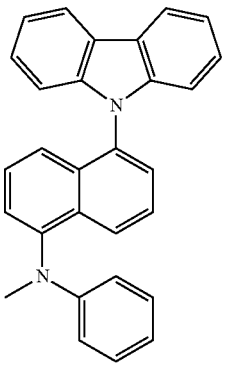
(34-13)
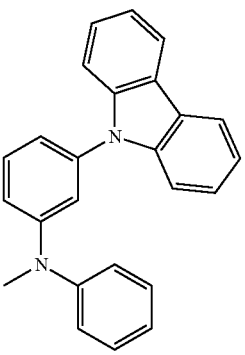
(34-14)
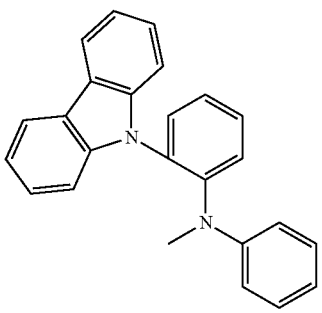
(34-15)
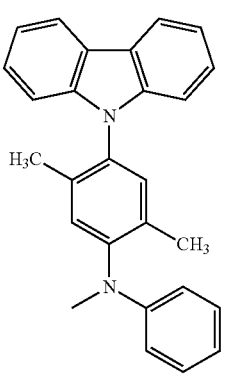

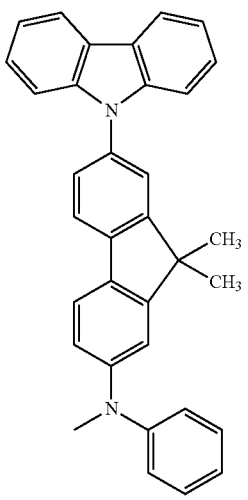
(34-16)
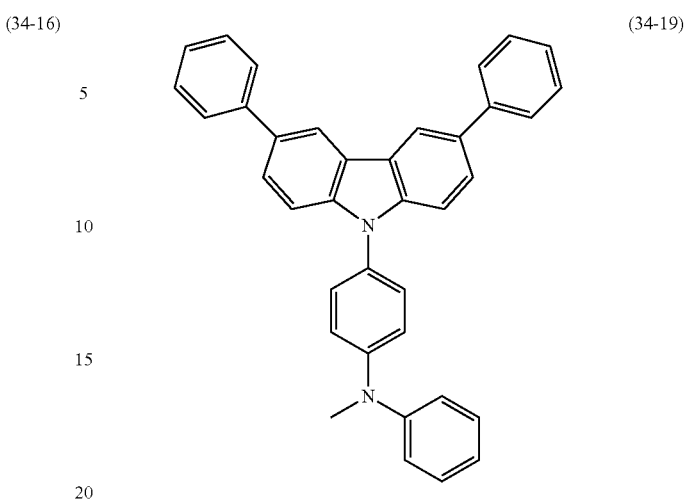
(34-19)
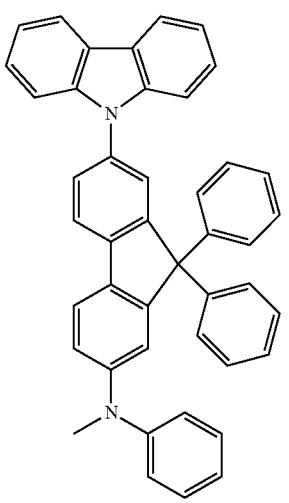
(34-17)
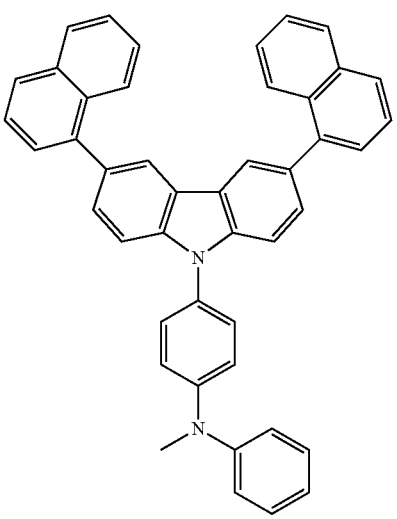
(34-20)
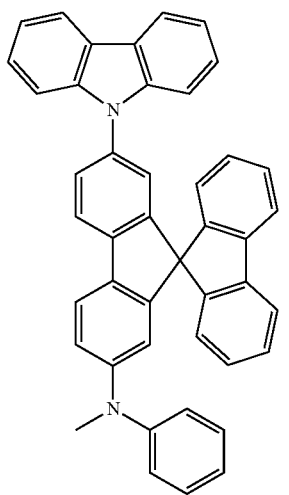
(34-18)
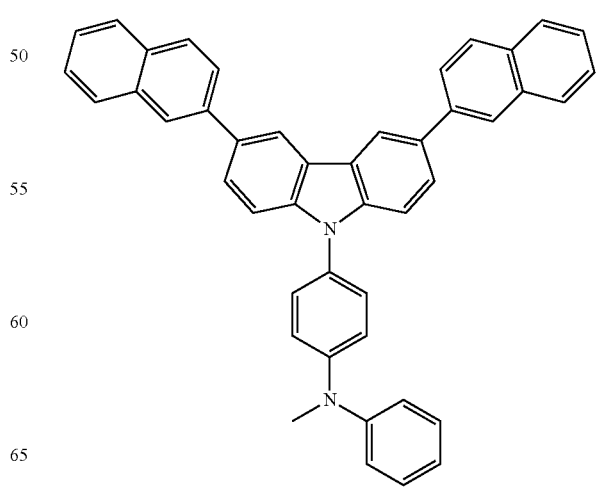
(34-21)

(34-22)
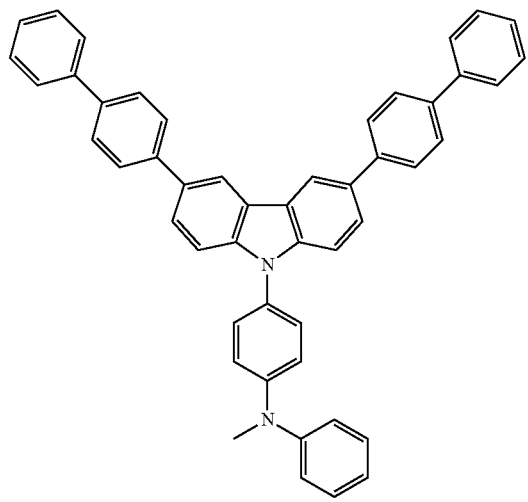
(34-23)
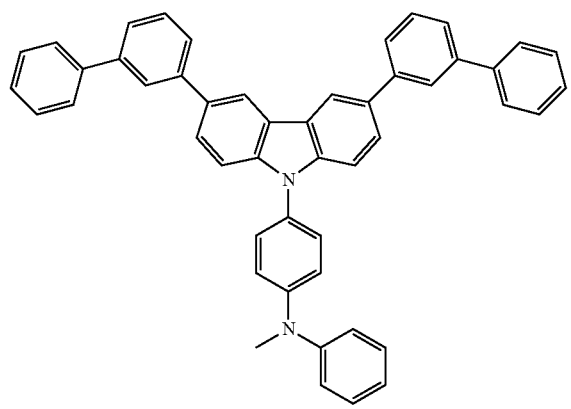
(34-24)
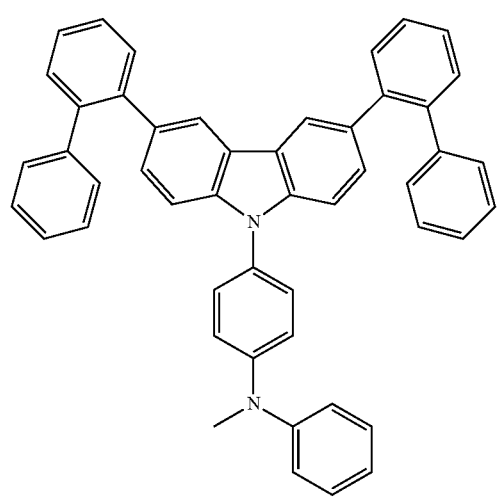
(34-25)
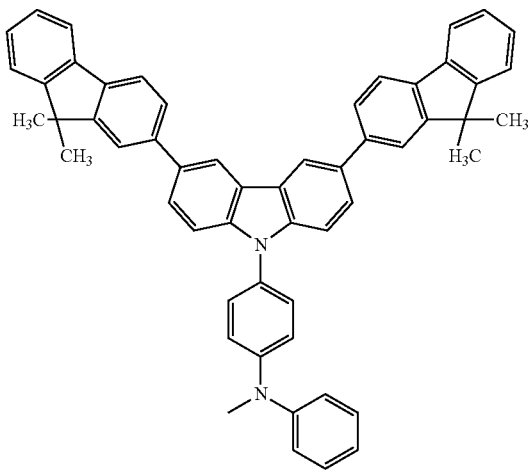
(34-26)
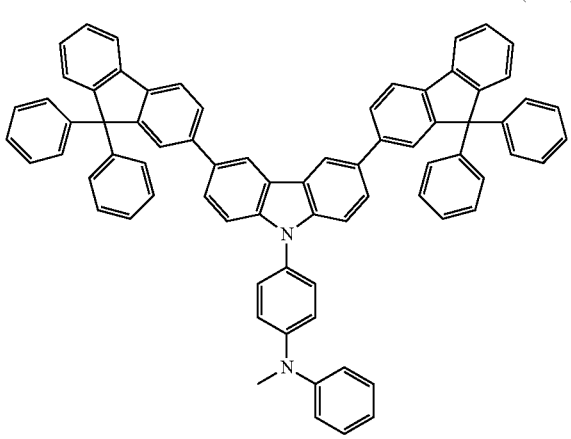
(34-27)
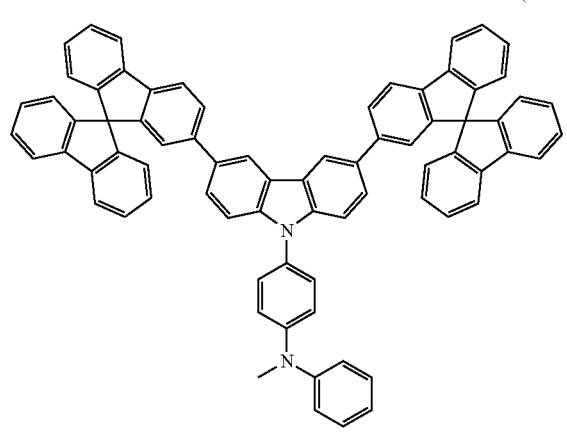

(34-28)
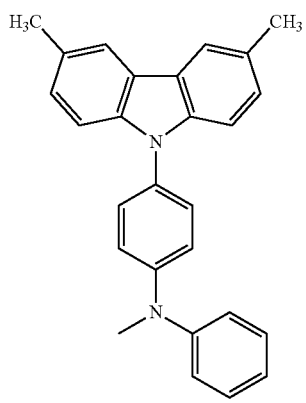
(34-29)
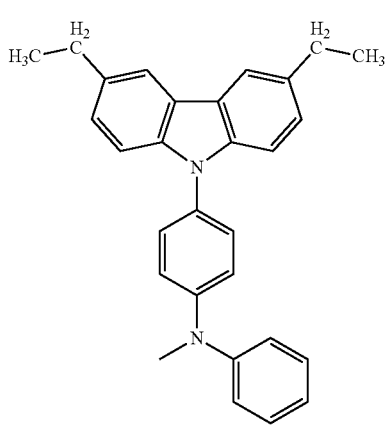
(34-30)
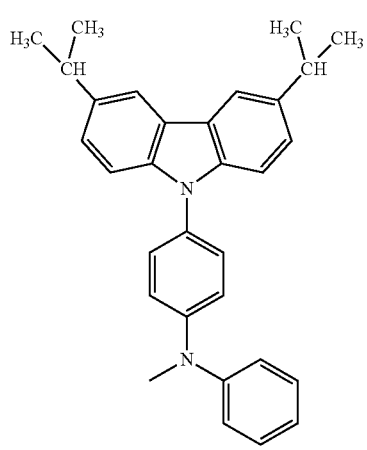
(34-31)
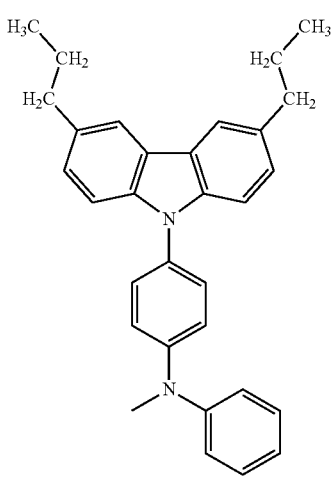
(34-32)
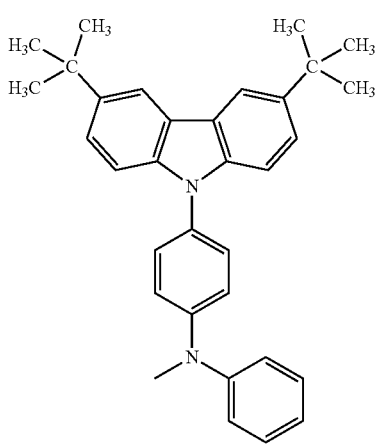
(34-33)

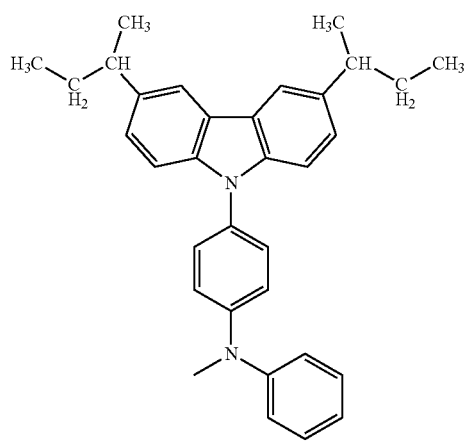

(34-34)

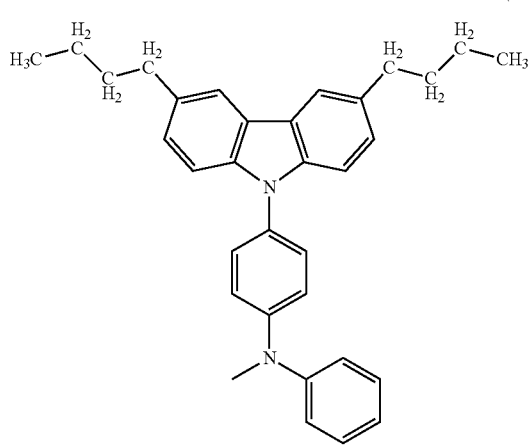

(34-35)

The anthracene derivative represented by General Formula (1) is preferably an anthracene derivative represented by General Formula (2).

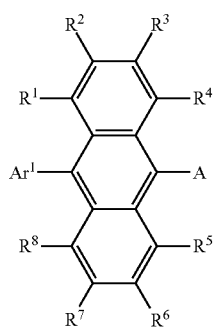
(2)

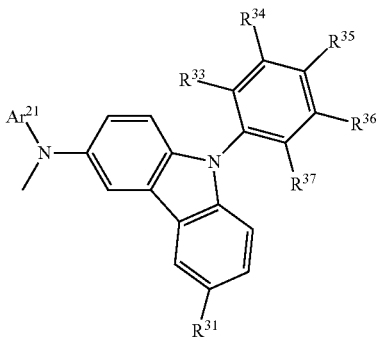

(2-2)

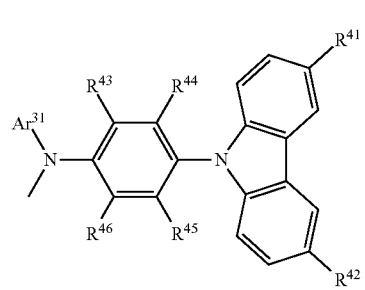

(2-3)

(In the formula, $Ar^1$ represents an aryl group having 6 to 25 carbon atoms; each of $R^1$ to $R^8$ represents a hydrogen atom or an alkyl group having 1 to 4 carbon atoms; and A represents either of substituents shown by General Formulae (2-2) and (2-3). In General Formulae (2-2) and (2-3), $Ar^{21}$ represents an aryl group having 6 to 25 carbon atoms; $R^{31}$ represents any of a hydrogen atom, an alkyl group having 1 to 4 carbon atoms, and an aryl group having 6 to 25 carbon atoms; and each of $R^{33}$ to $R^{37}$ represents any of a hydrogen atom, an alkyl group having 1 to 4 carbon atoms, and an aryl group having 6 to 15 carbon atoms. $Ar^{31}$ represents an aryl group having 6 to 25 carbon atoms; each of $R^{41}$ and $R^{42}$ represents any of a hydrogen atom, an alkyl group having 1 to 4 carbon atoms, and an aryl group having 6 to 25 carbon atoms; and each of $R^{43}$ to $R^{46}$ represents a hydrogen atom, an alkyl group having 1 to 4 carbon atoms, or an aryl group having 6 to 15 carbon atoms.)

The anthracene derivative represented by General Formula (1) is preferably an anthracene derivative represented by General Formula (3).

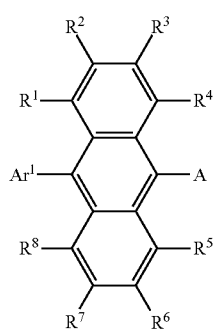
(3)

(3-2)

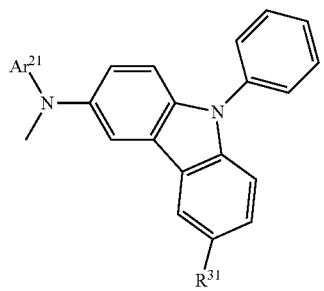

(3-3)

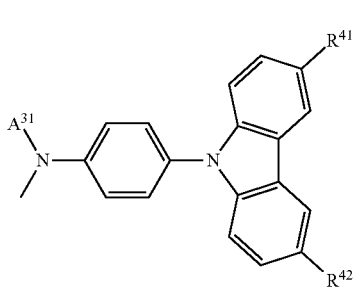

(In the formula, $Ar^1$ represents an aryl group having 6 to 25 carbon atoms; each of $R^1$ to $R^8$ represents a hydrogen atom or an alkyl group having 1 to 4 carbon atoms; and A represents either of substituents shown by General Formulae (3-2) and (3-3). In General Formulae (3-2) and (3-3), $Ar^{21}$ represents an aryl group having 6 to 25 carbon atoms; $R^{31}$ represents any of a hydrogen atom, an alkyl group having 1 to 4 carbon atoms, and an aryl group having 6 to 25 carbon atoms; and $Ar^{31}$ represents an aryl group having 6 to 25 carbon atoms. Each of $R^{41}$ and $R^{42}$ represents any of a hydrogen atom, an alkyl group having 1 to 4 carbon atoms, and an aryl group having 6 to 25 carbon atoms.)

The anthracene derivative represented by General Formula (1) is preferably an anthracene derivative represented by General Formula (4).

(4)

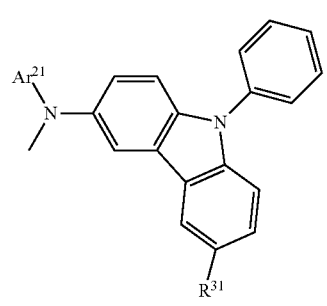

(4-2)

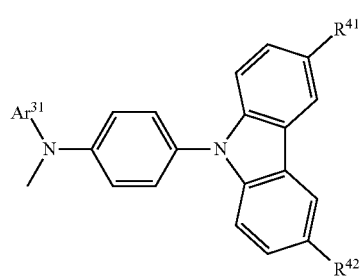

(4-3)

(In the formula, $Ar^1$ represents an aryl group having 6 to 25 carbon atoms; each of $R^1$ to $R^8$ represents a hydrogen atom or an alkyl group having 1 to 4 carbon atoms; and A represents either of substituents shown by General Formulae (4-2) and (4-3). In General Formulae (4-2) and (4-3), $Ar^{21}$ represents any of a phenyl group, a 1-naphthyl group, and a 2-naphthyl group; $R^{31}$ represents any of a hydrogen atom, an alkyl group having 1 to 4 carbon atoms, and an aryl group having 6 to 25 carbon atoms; and $Ar^{31}$ represents any of a phenyl group, a 1-naphthyl group, and a 2-naphthyl group. Each of $R^{41}$ and $R^{42}$ represents any of a hydrogen atom, an alkyl group having 1 to 4 carbon atoms, and an aryl group having 6 to 25 carbon atoms.)

In the General Formulae (1) to (4), $Ar^1$ is preferably a substituent represented by General Formula (11-1).

(11-1)

(In the formula, each of $R^{11}$ to $R^{15}$ represents any of a hydrogen atom, an alkyl group having 1 to 4 carbon atoms, and an aryl group having 6 to 15 carbon atoms.)

In the above General Formulae (1) to (4), $Ar^1$ is preferably either of substituents represented by Structural Formulae (11-2) and (11-3).

(11-2)

(11-3)

Further, in the above General Formulae (1) to (4), $Ar^1$ is preferably a substituent represented by Structural Formula (11-4).

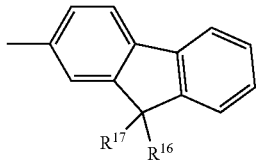

(11-4)

(In the formula, each of $R^{16}$ and $R^{17}$ represents an alkyl group having 1 to 4 carbon atoms or a phenyl group.)

Further, in the above General Formulae (1) to (4), $Ar^1$ is preferably either of substituents represented by Structural Formulae (11-5) and (11-6).

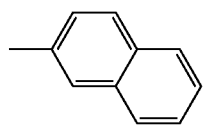

(11-5)

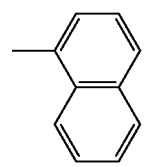

(11-6)

In addition, an anthracene derivative of the present invention has an amino group having a 9-arylcarbazole skeleton in position 9 and position 10 of the anthracene skeleton. That is, the anthracene derivative of the present invention is an anthracene derivative represented by General Formula (5).

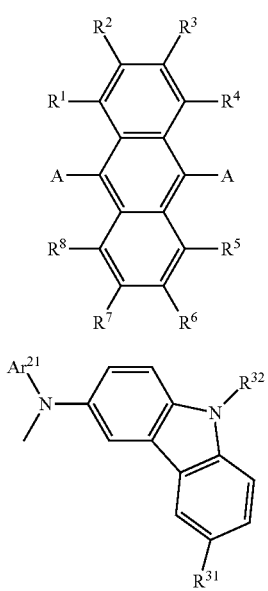

(5)

(5-2)

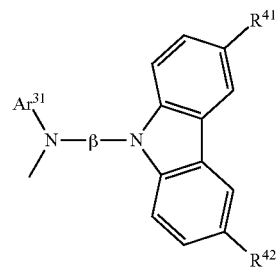

(5-3)

(In the formula, each of $R^1$ to $R^8$ represents a hydrogen atom or an alkyl group having 1 to 4 carbon atoms; and A represents either of substituents shown by General Formulae (5-2) and (5-3). In General Formulae (5-2) and (5-3), $Ar^{21}$ represents an aryl group having 6 to 25 carbon atoms; $R^{31}$ represents any of a hydrogen atom, an alkyl group having 1 to 4 carbon atoms, and an aryl group having 6 to 25 carbon atoms; and $R^{32}$ represents any of an alkyl group having 1 to 4 carbon atoms and an aryl group having 6 to 25 carbon atoms. $Ar^{31}$ represents an aryl group having 6 to 25 carbon atoms; β represents an arylene group having 6 to 25 carbon atoms; and each of $R^{41}$ and $R^{42}$ represents any of a hydrogen atom, an alkyl group having 1 to 4 carbon atoms, and an aryl group having 6 to 25 carbon atoms.)

In General Formula (5-2), a substituent represented by $Ar^{21}$ is, for example, any of the above-described substituents represented by Structural Formulae (21-1) to (21-9).

Further, in General Formula (5-2), a substituent represented by $R^{31}$ is, for example, any of the above-described substituents represented by Structural Formulae (22-1) to (22-18).

In addition, in General Formula (5-2), a substituent represented by $R^{32}$ is, for example, any of the above-described substituents represented by Structural Formulae (23-1) to (23-17).

Accordingly, the substituent represented by General Formula (5-2) is, for example, any of the above-described substituents represented by Structural Formulae (24-1) to (24-52).

In General Formula (5-3), a substituent represented by $Ar^{31}$ is, for example, any of the above-described substituents represented by Structural Formulae (31-1) to (31-9).

Further, in General Formula (5-3), a substituent represented by β is, for example, any of the above-described substituents represented by Structural Formulae (32-1) to (32-10).

In addition, in General Formula (5-3), each of substituents represented by $R^{41}$ and $R^{42}$ is, for example, any of the above-described substituents represented by Structural Formulae (33-1) to (33-18).

Accordingly, the substituent represented by General Formula (5-3) is, for example, any of the above-described substituents represented by Structural Formulae (34-1) to (34-35).

The anthracene derivative represented by General Formula (5) is preferably an anthracene derivative represented by General Formula (6).

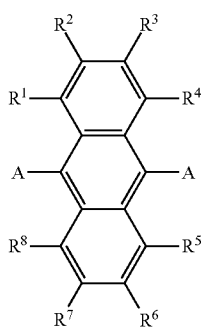

(6)

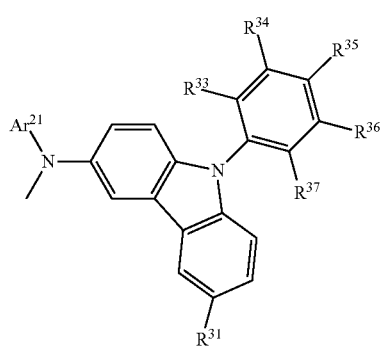

(6-2)

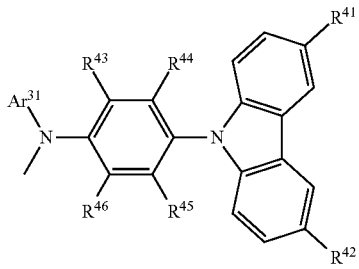

(6-3)

(In the formula, each of $R^1$ to $R^8$ represents a hydrogen atom or an alkyl group having 1 to 4 carbon atoms; and A represents either of substituents shown by General Formulae (6-2) and (6-3). In General Formulae (6-2) and (6-3), $Ar^{21}$ represents an aryl group having 6 to 25 carbon atoms; $R^{31}$ represents any of a hydrogen atom, an alkyl group having 1 to 4 carbon atoms, and an aryl group having 6 to 25 carbon atoms; and each of $R^{33}$ to $R^{37}$ represents any of a hydrogen atom, an alkyl group having 1 to 4 carbon atoms, and an aryl group having 6 to 15 carbon atoms. $Ar^{31}$ represents an aryl group having 6 to 25 carbon atoms; each of $R^{41}$ and $R^{42}$ represents any of a hydrogen atom, an alkyl group having 1 to 4 carbon atoms, and an aryl group having 6 to 25 carbon atoms; and each of $R^{43}$ to $R^{46}$ represents a hydrogen atom, an alkyl group having 1 to 4 carbon atoms, or an aryl group having 6 to 15 carbon atoms.)

Further, an anthracene derivative represented by General Formula (7) is preferable.

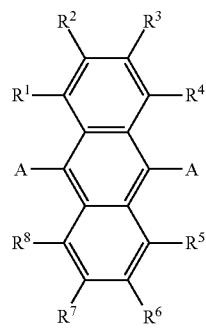

(7)

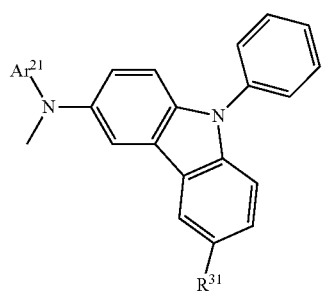

(7-2)

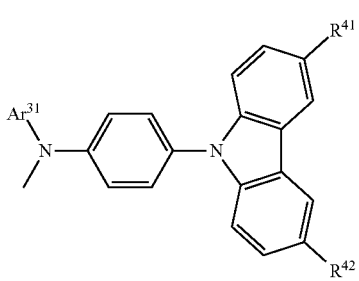

(7-3)

(In the formula, each of $R^1$ to $R^8$ represents a hydrogen atom or an alkyl group having 1 to 4 carbon atoms; and A represents either of substituents shown by General Formulae (7-2) and (7-3). In General Formulae (7-2) and (7-3), $Ar^{21}$ represents an aryl group having 6 to 25 carbon atoms; $R^{31}$ represents any of a hydrogen atom, an alkyl group having 1 to 4 carbon atoms, and an aryl group having 6 to 25 carbon atoms; and $Ar^{31}$ represents an aryl group having 6 to 25 carbon atoms. Each of $R^{41}$ and $R^{42}$ represents any of a hydrogen atom, an alkyl group having 1 to 4 carbon atoms, and an aryl group having 6 to 25 carbon atoms.)

Further, an anthracene derivative represented by General Formula (8) is preferable.

(8)

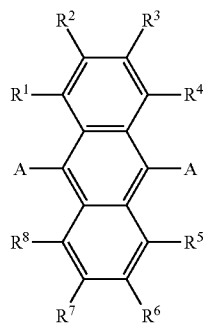

(8-2)

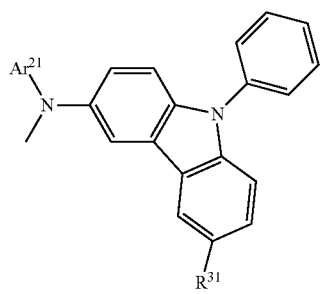

(8-3)

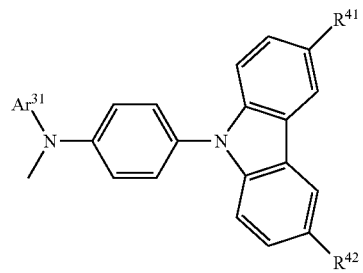

(In the formula, each of $R^1$ to $R^8$ represents a hydrogen atom or an alkyl group having 1 to 4 carbon atoms; and A represents either of substituents shown by General Formulae (8-2) and (8-3). In General Formulae (8-2) and (8-3), $Ar^{21}$ represents any of a phenyl group, a 1-naphthyl group, and a 2-naphthyl group; $R^{31}$ represents any of a hydrogen atom, an alkyl group having 1 to 4 carbon atoms, and an aryl group having 6 to 25 carbon atoms; and $Ar^{31}$ represents any of a phenyl group, a 1-naphthyl group, and a 2-naphthyl group. Each of $R^{41}$ and $R^{42}$ represents any of a hydrogen atom, an alkyl group having 1 to 4 carbon atoms, and an aryl group having 6 to 25 carbon atoms.)

As specific examples of the anthracene derivatives represented by General Formula (1) or (5), anthracene derivatives represented by Structural Formulae (201) to (256) and Structural Formulae (301) to (348) can be given. However, the present invention is not limited to these examples.

(201)

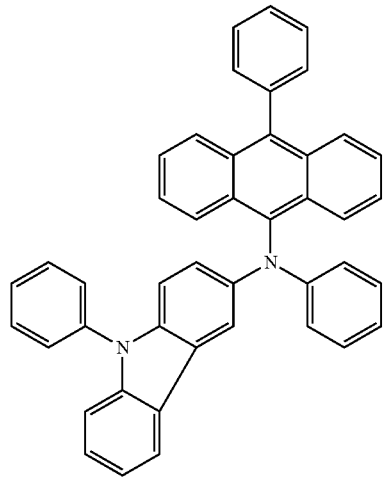

(202)

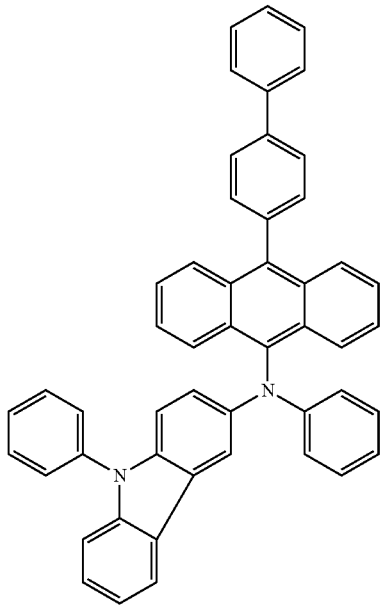

-continued
(203)
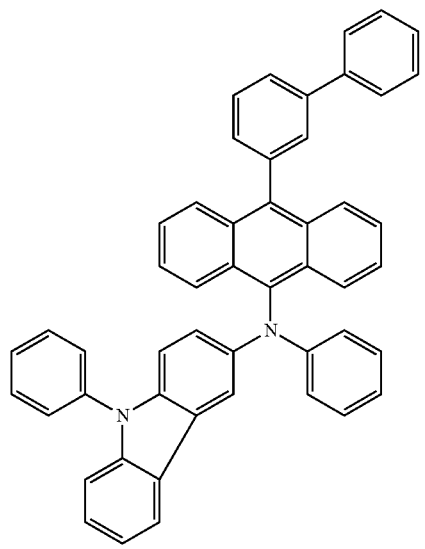
(204)
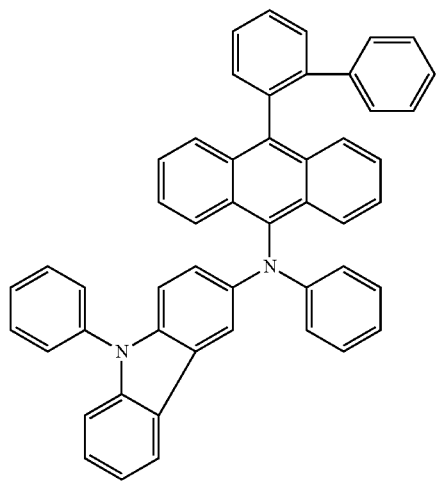
(205)
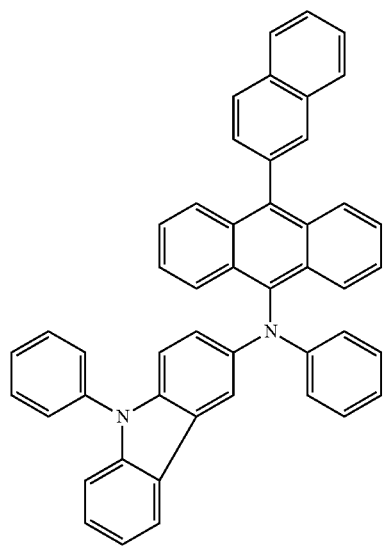
(206)
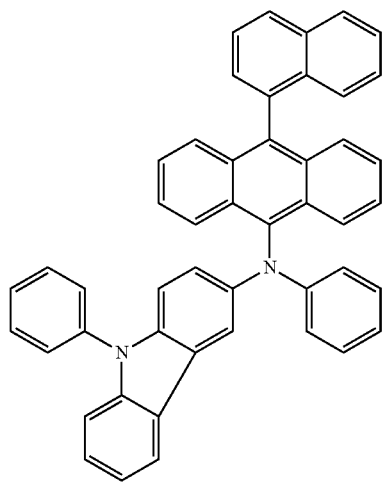

-continued
(207)
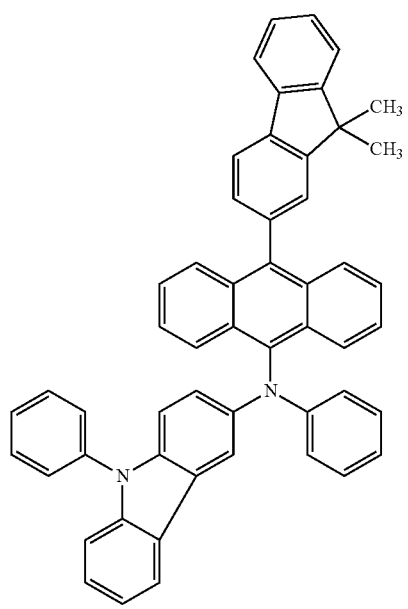
(208)
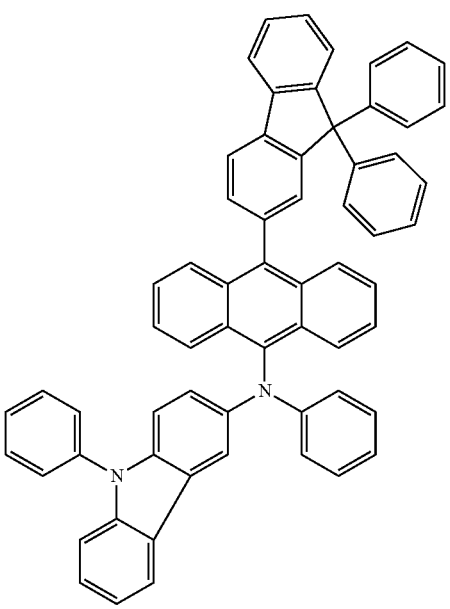
(209)
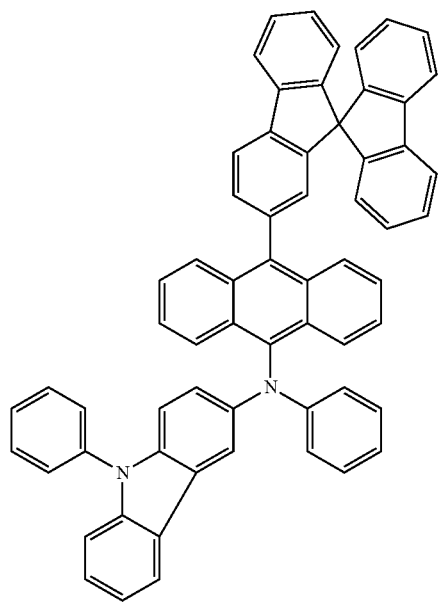
(210)
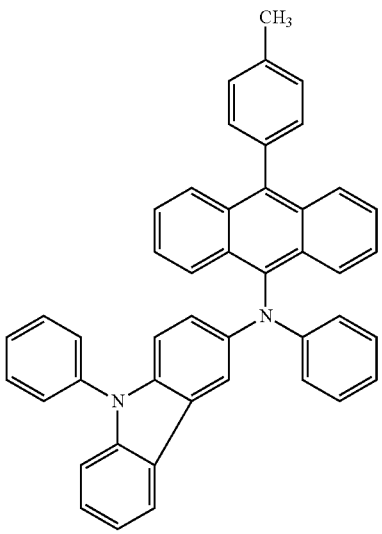

-continued
(211)
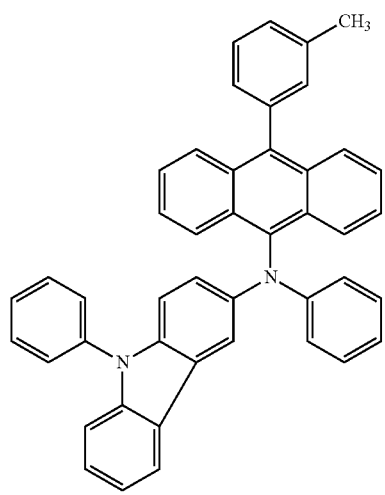
(212)
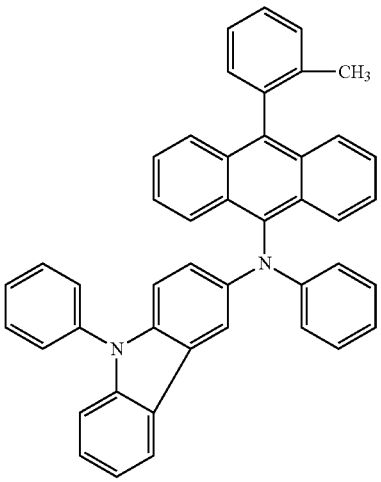
(213)
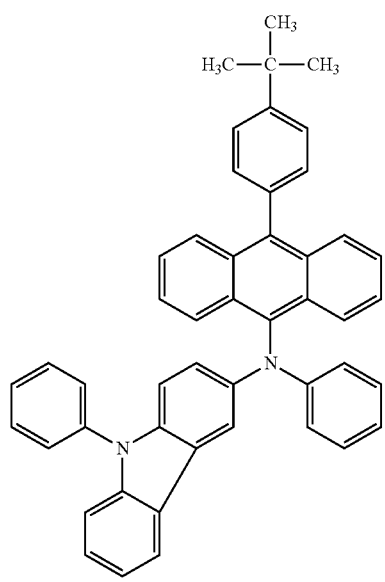
(214)
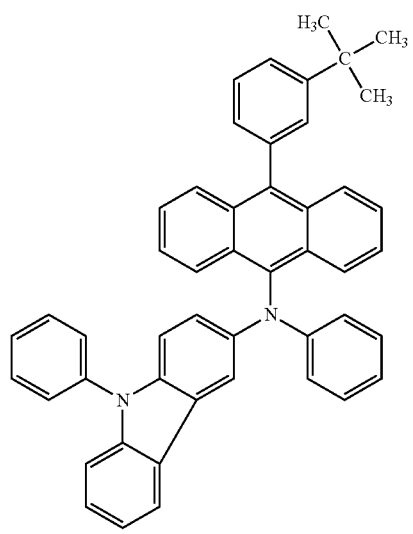
(215)
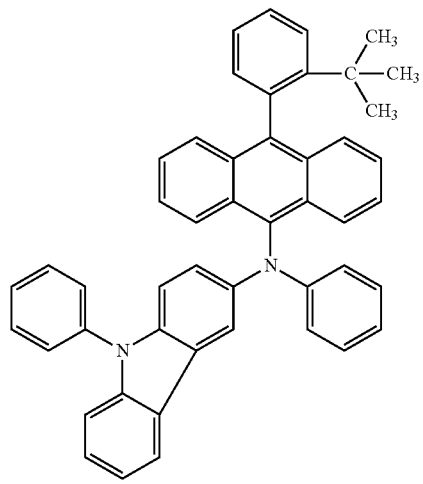
(216)
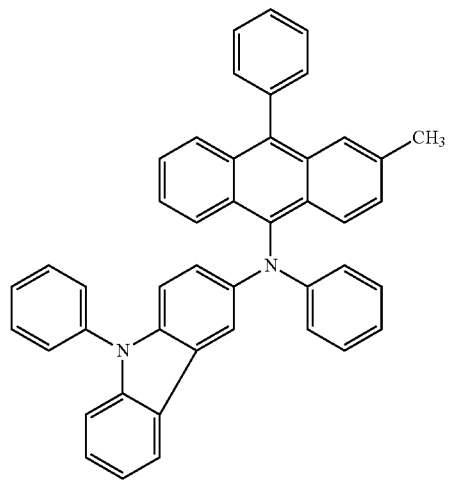

-continued
(217)
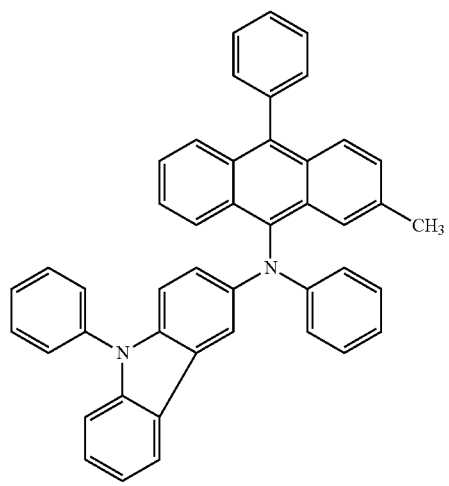
(218)
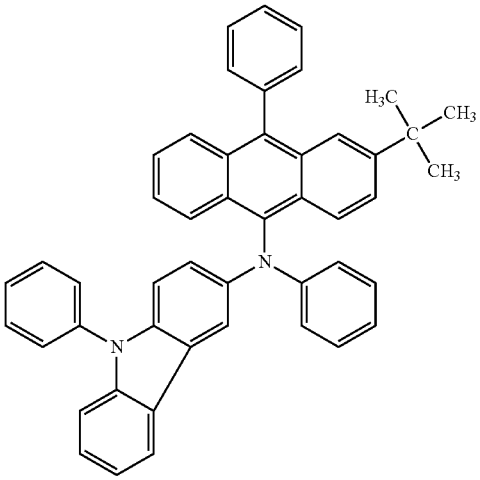
(219)
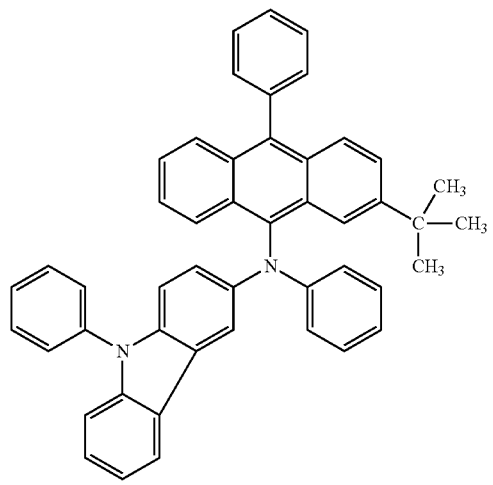
(220)
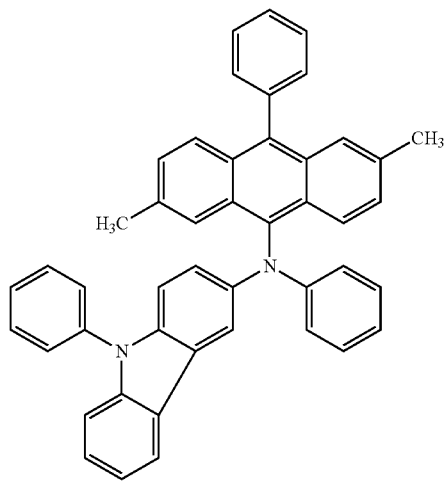
(221)
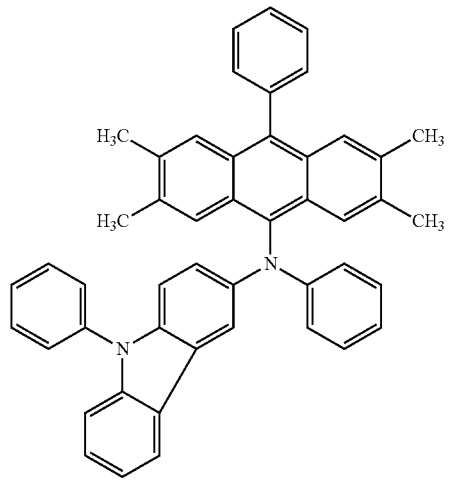
(222)
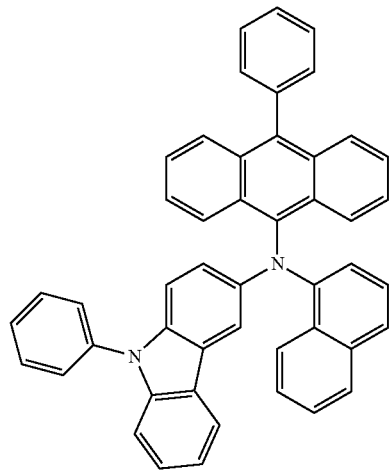

-continued
(223)
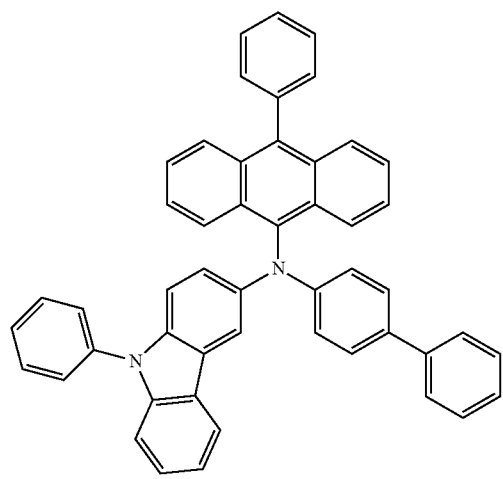
(224)
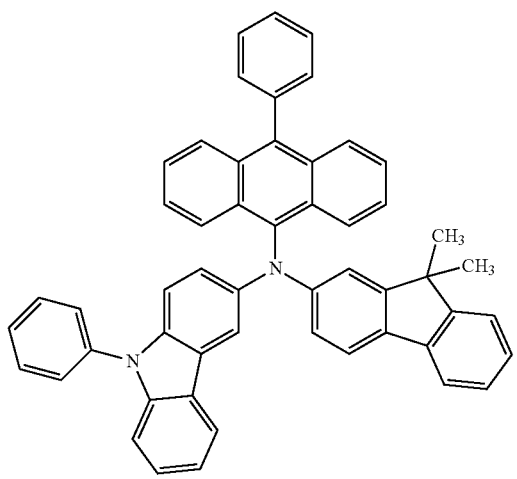
(225)
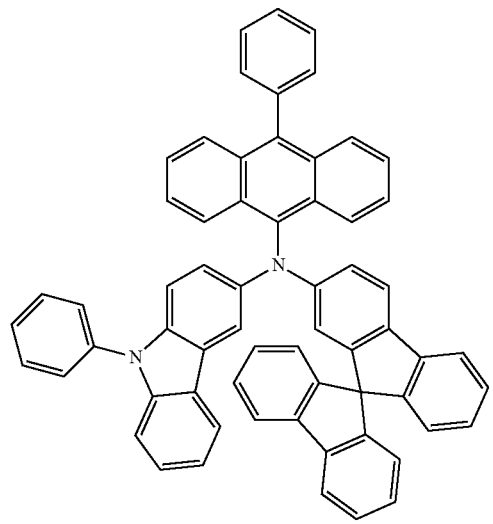
(226)
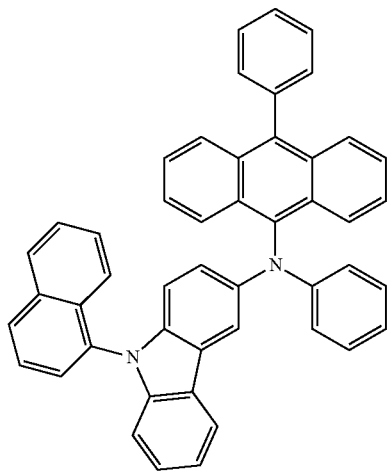
(227)
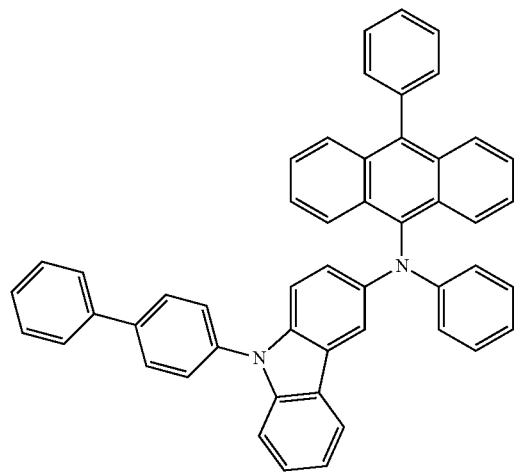
(228)
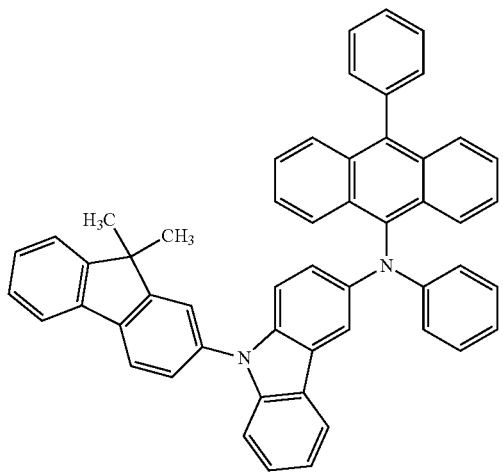

-continued
(229)
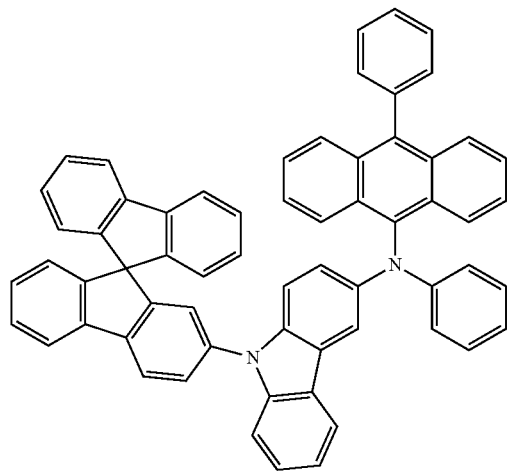
(230)
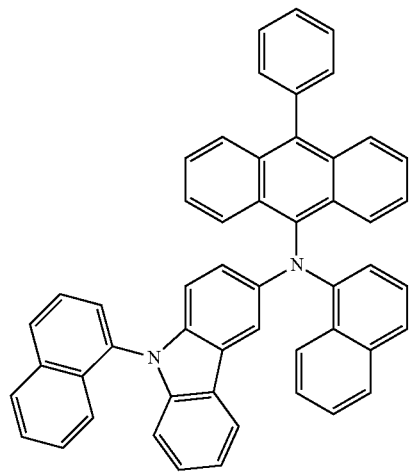
(231)
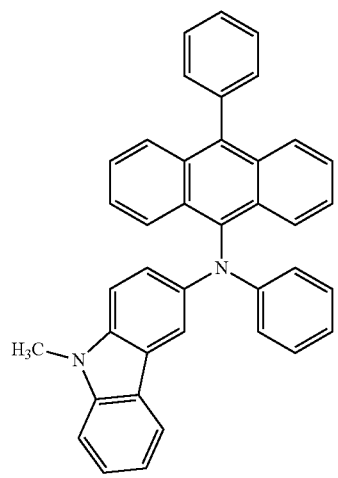
(232)
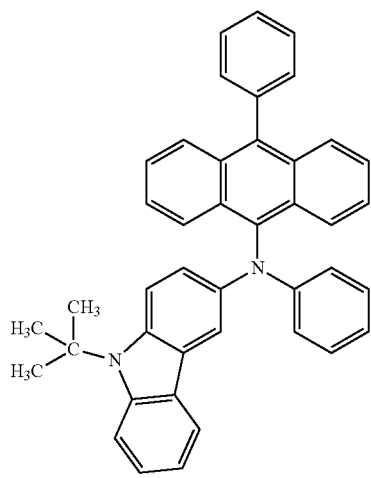
(233)
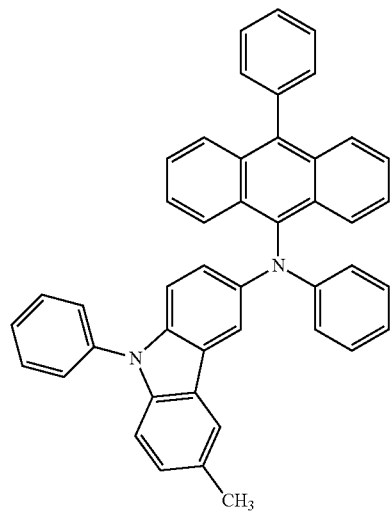
(234)
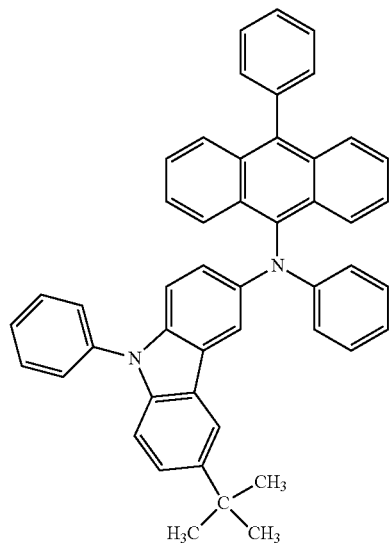

-continued
(235)
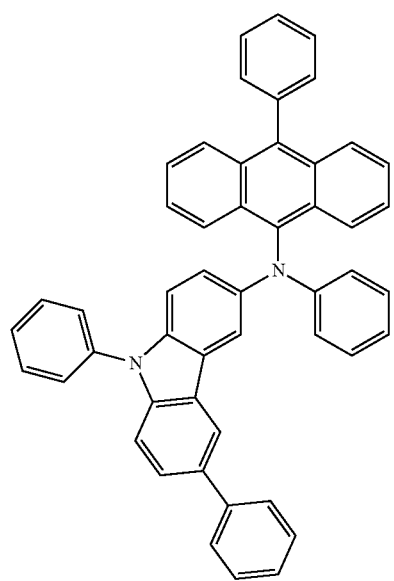
(236)
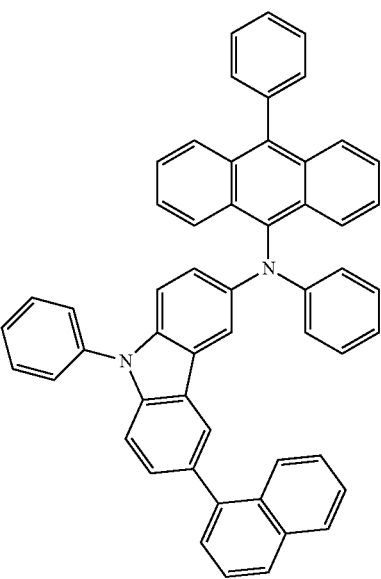
(237)
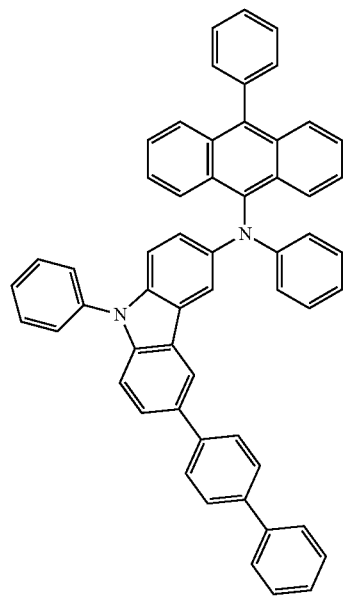
(238)
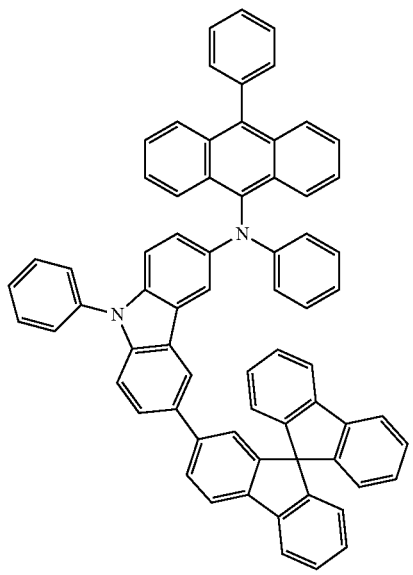

-continued
(239) 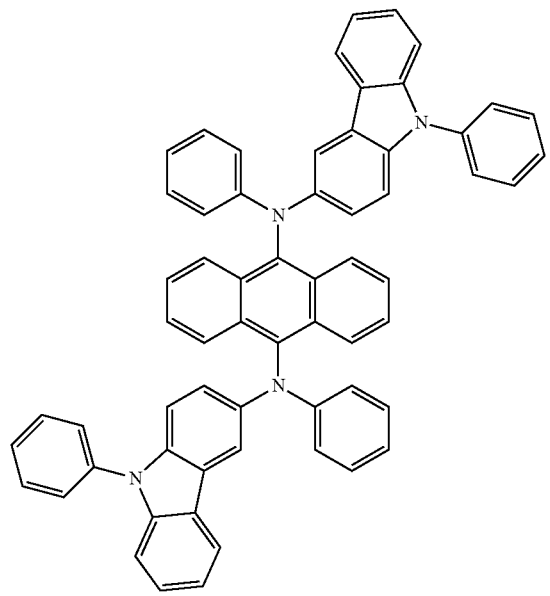
(240) 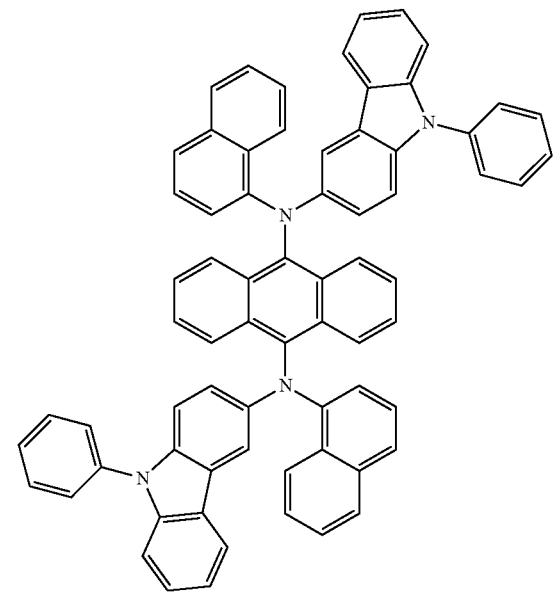
(241) 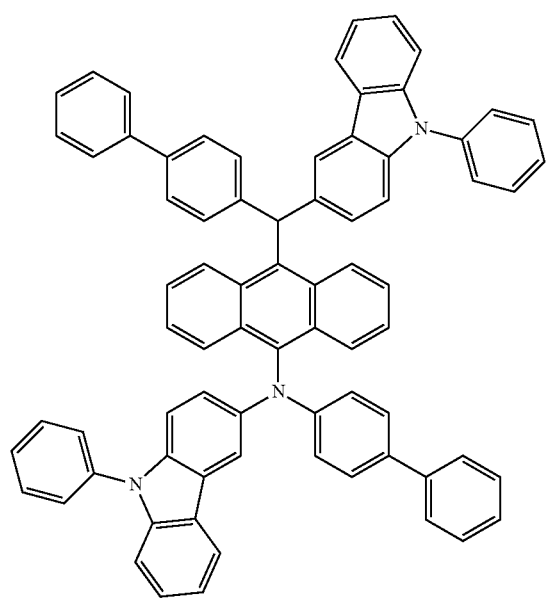
(242) 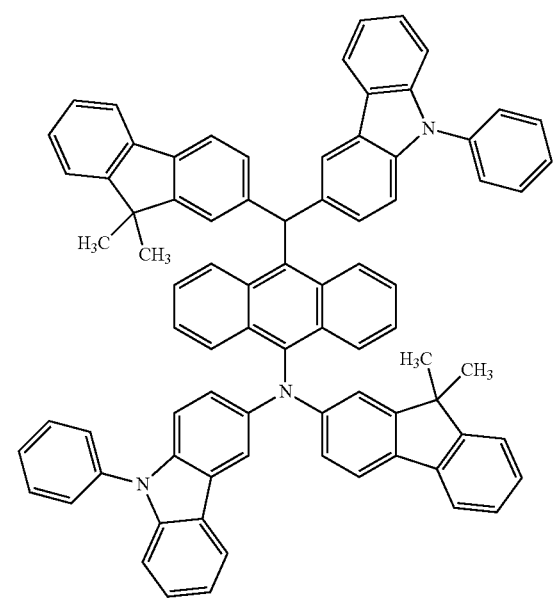
(243) 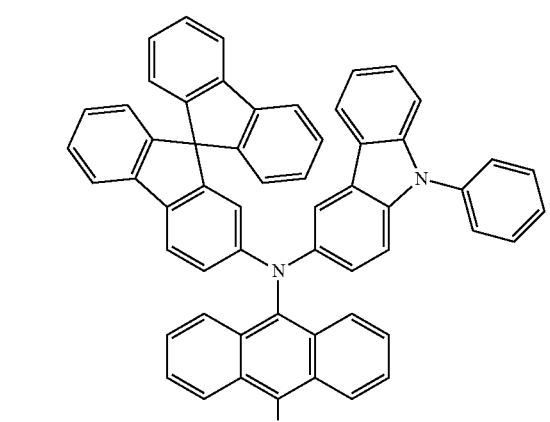

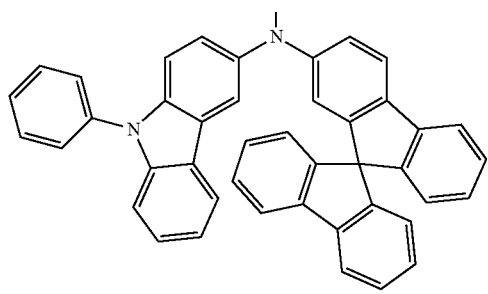
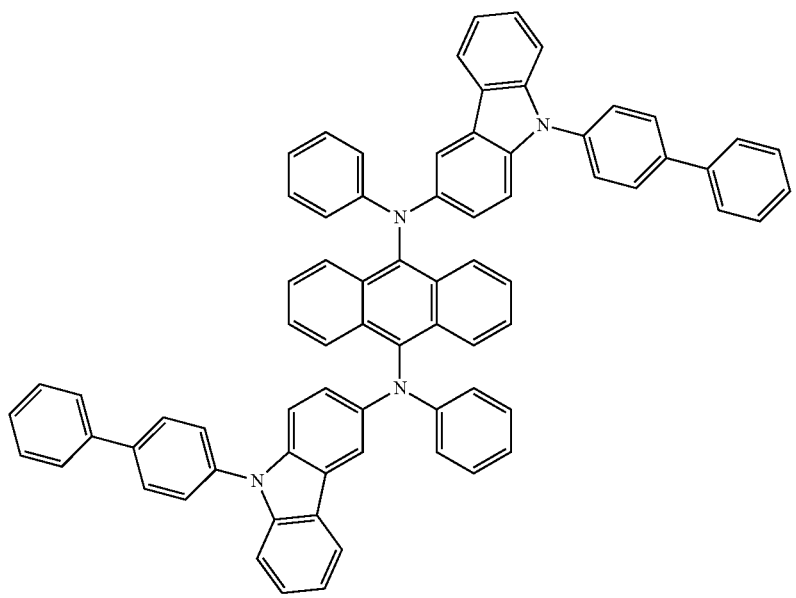
(244)
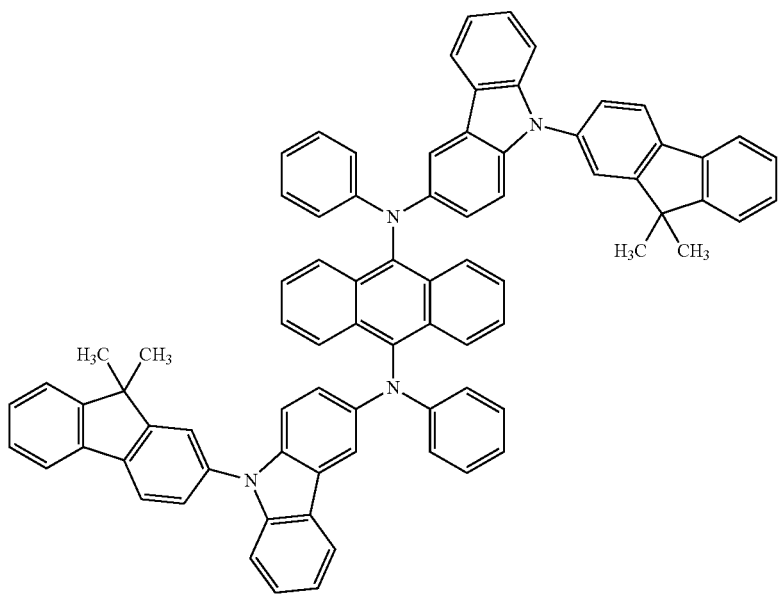
(245)

(246)
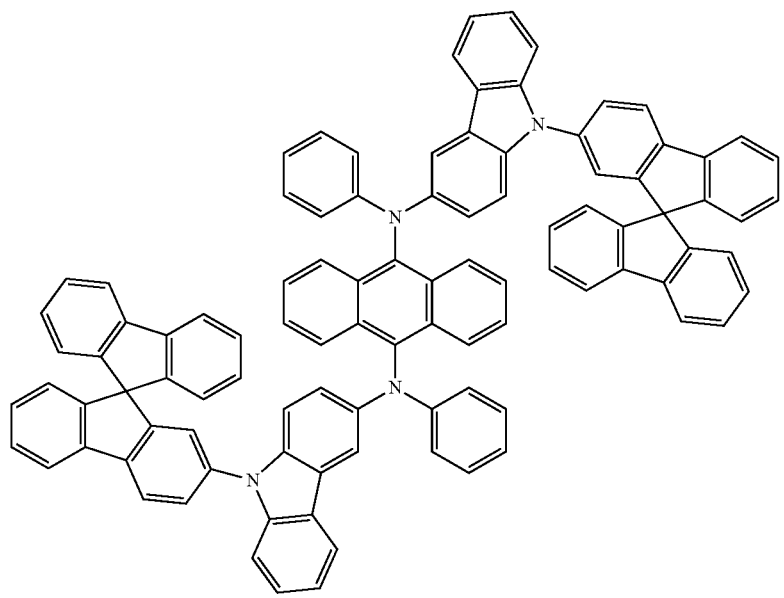
(247)
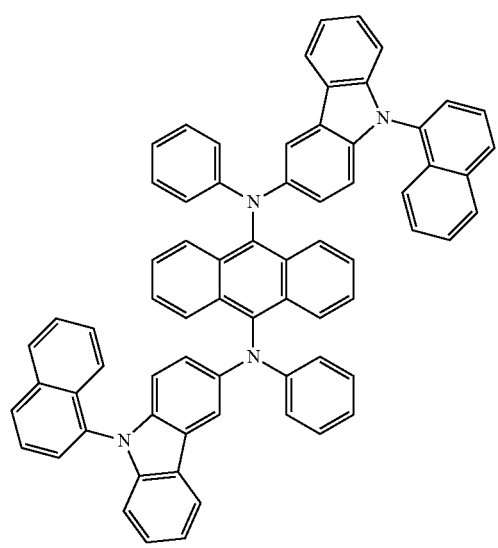
(248)
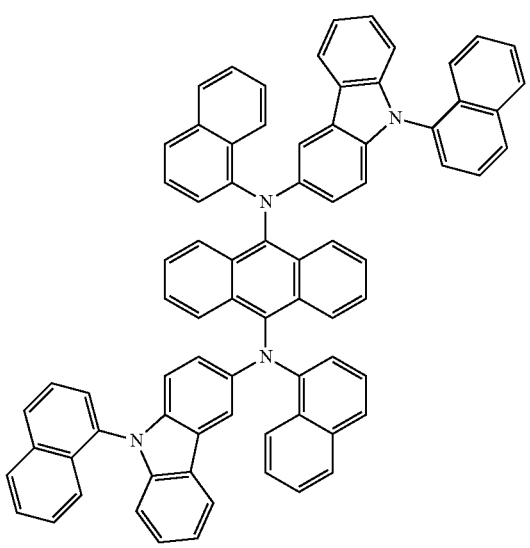

-continued
(249)
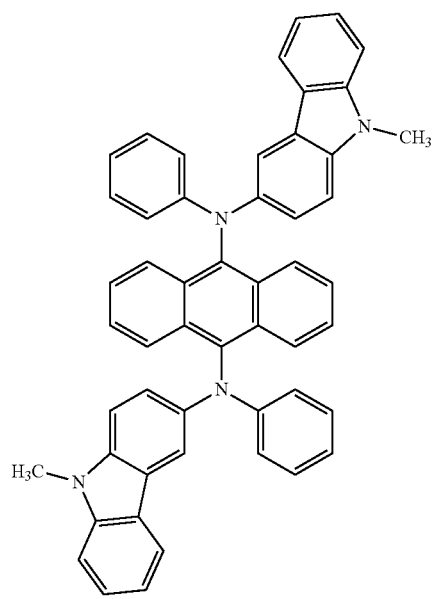
(250)
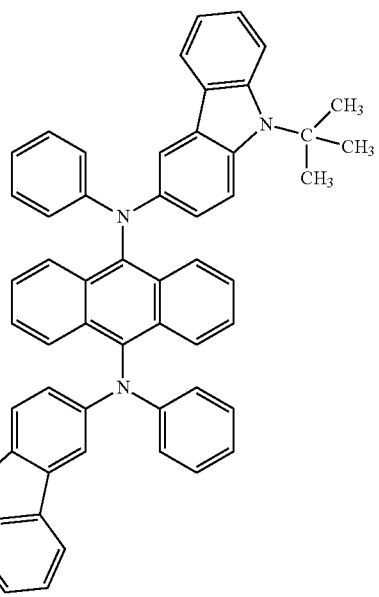
(251)
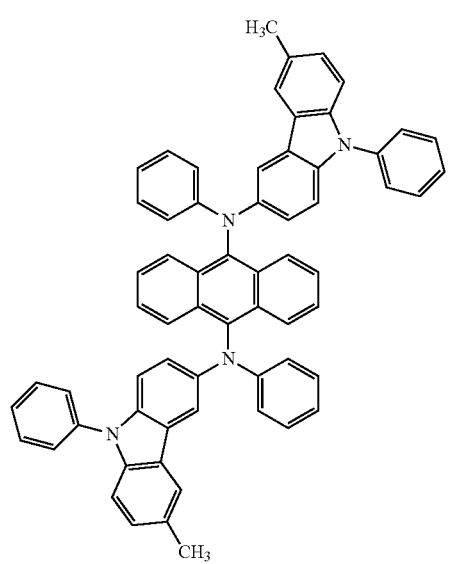
(252)
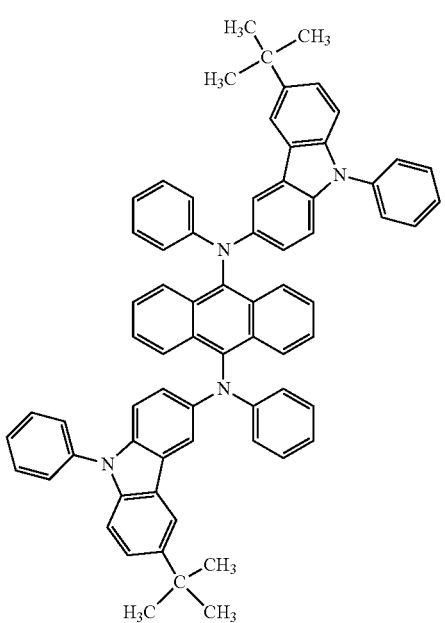

-continued
(253)
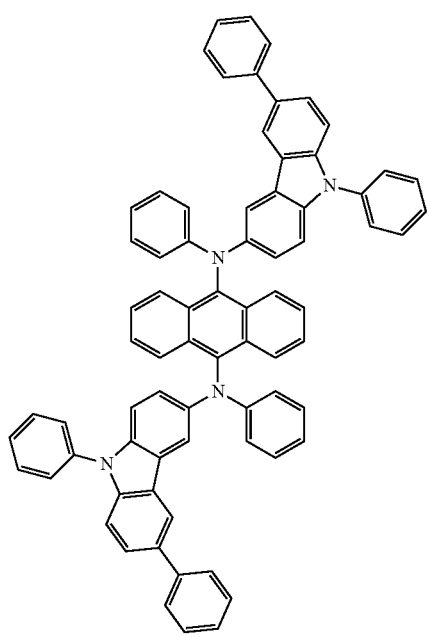
(254)
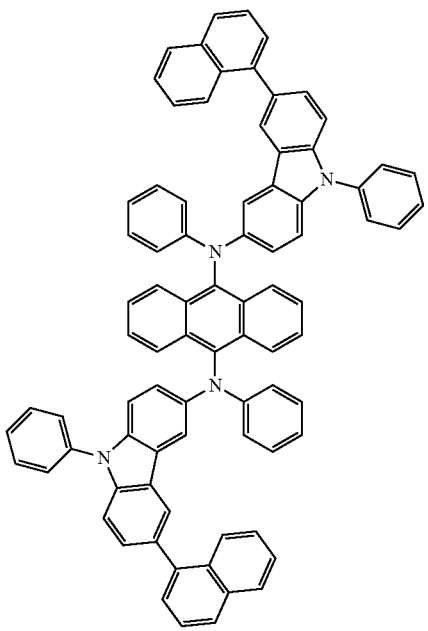
(255)
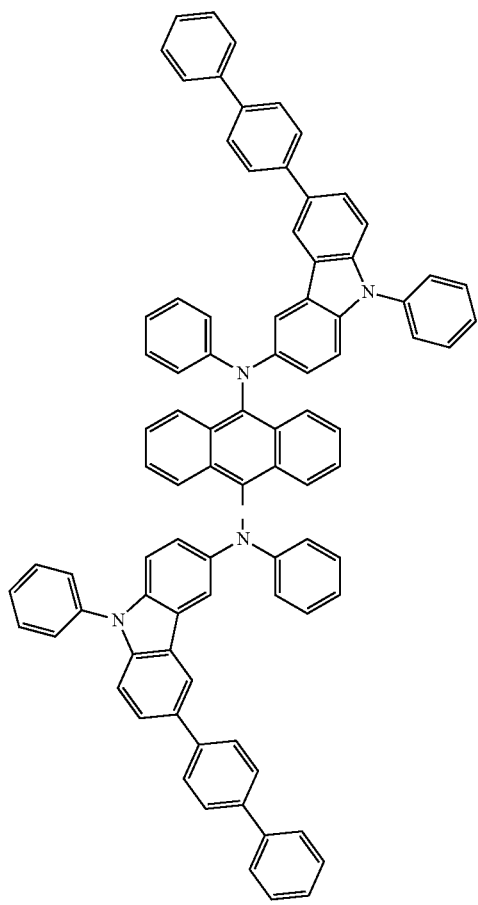
(256)
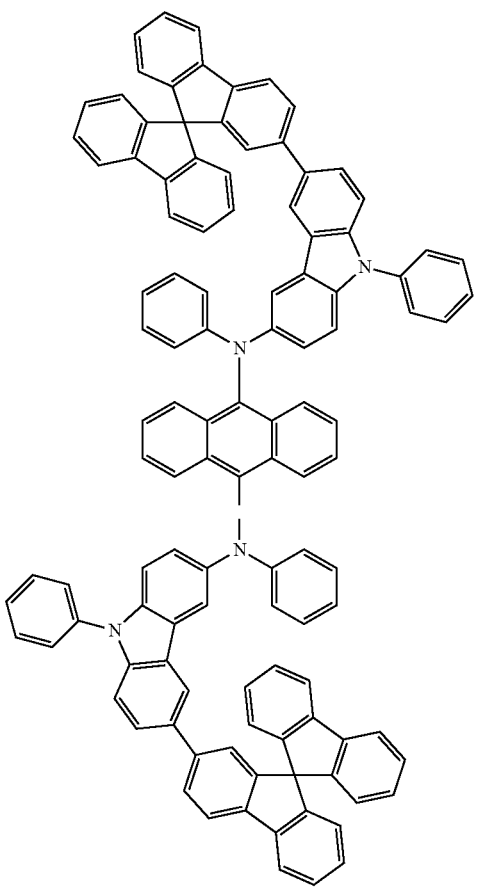

-continued
(301)
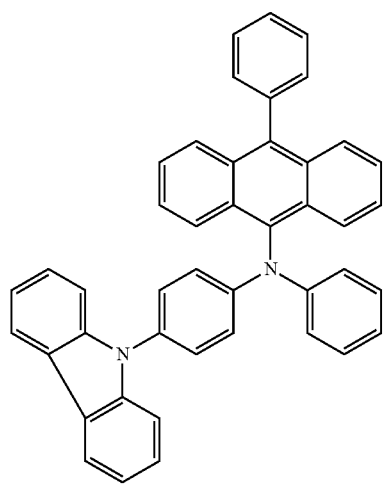
(302)
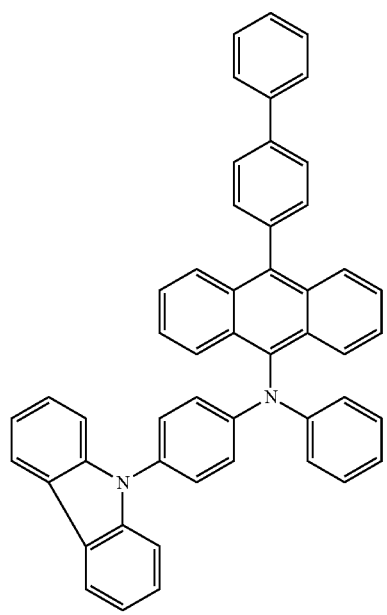
(303)
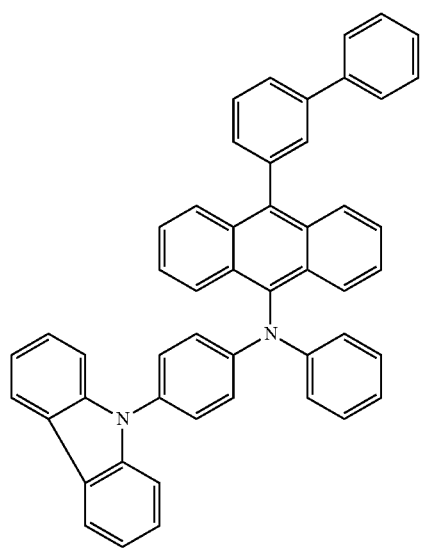
(304)
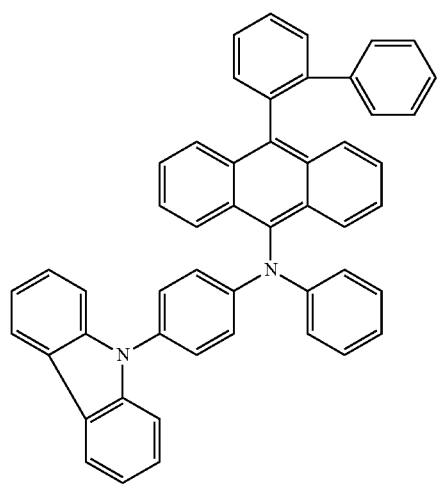

-continued
(305)
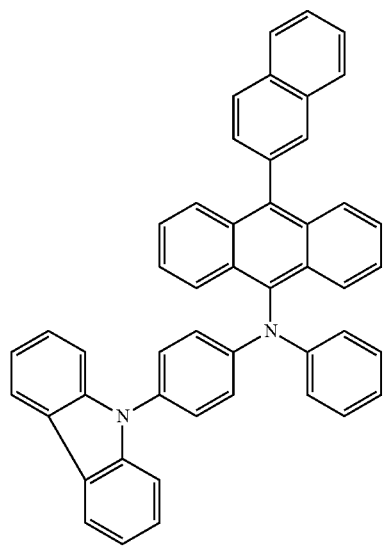
(306)
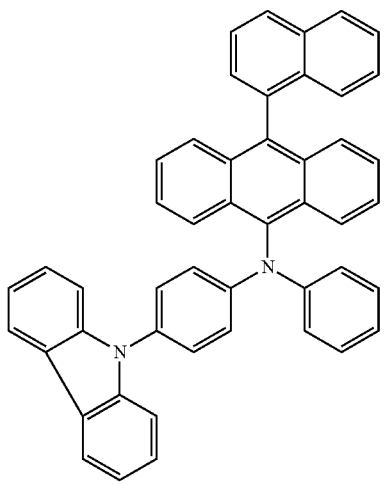
(307)
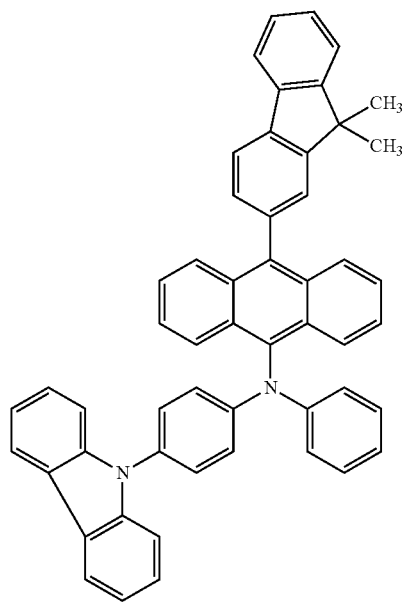
(308)
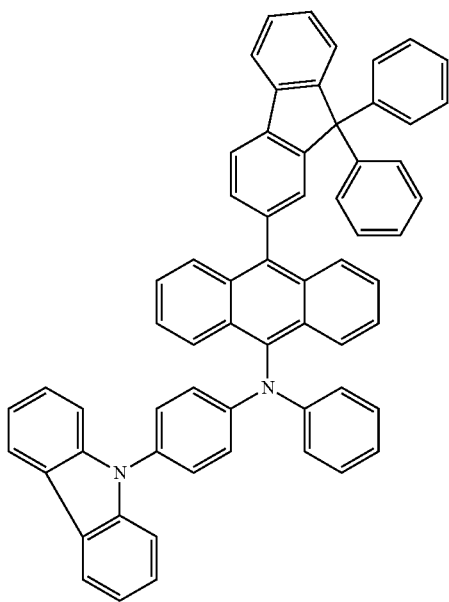

-continued
(309)
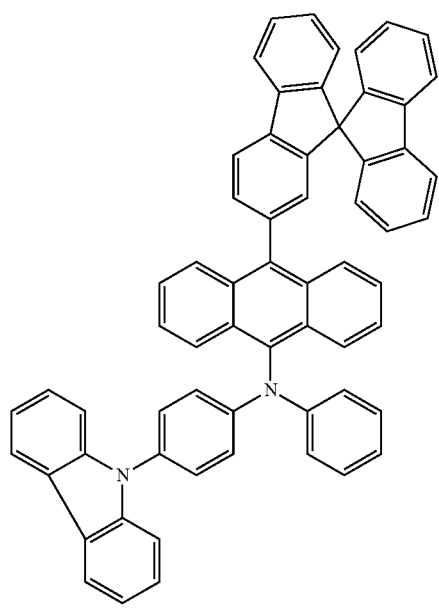
(310)
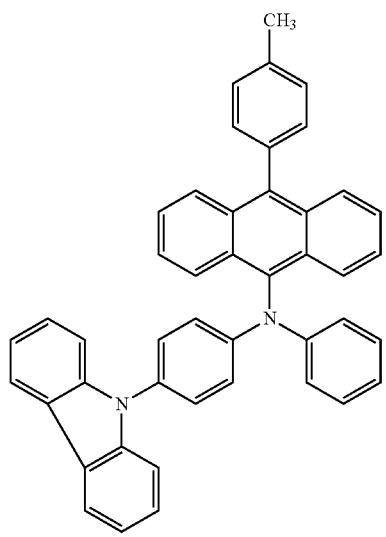
(311)
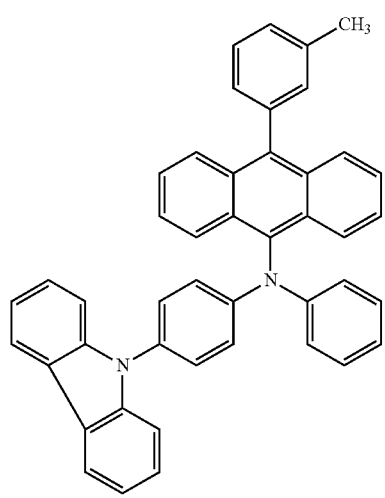
(312)
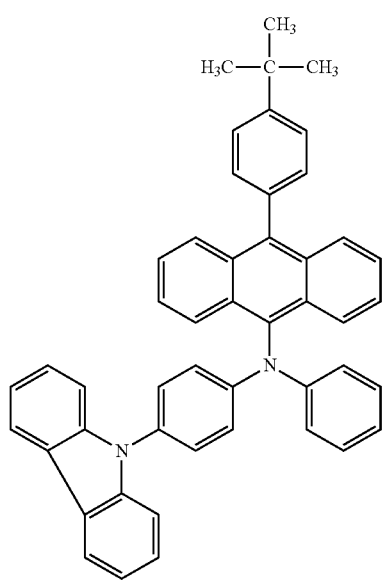

-continued
(313)
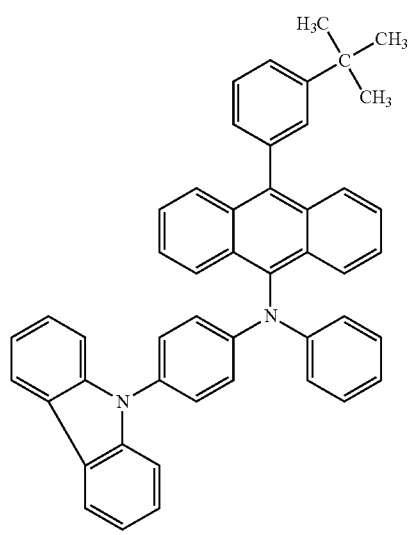
(314)
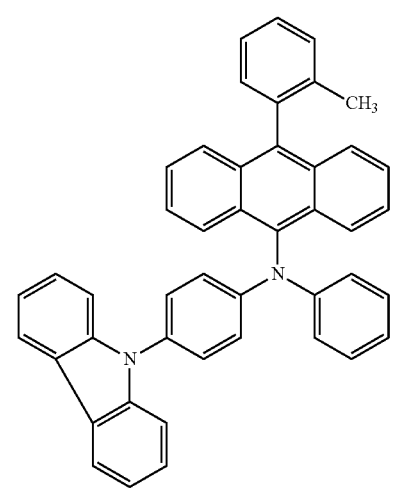
(315)
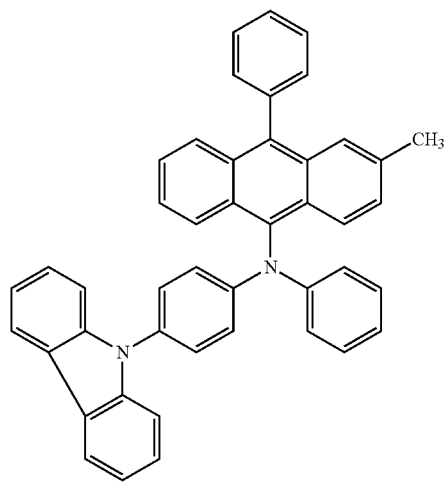
(316)
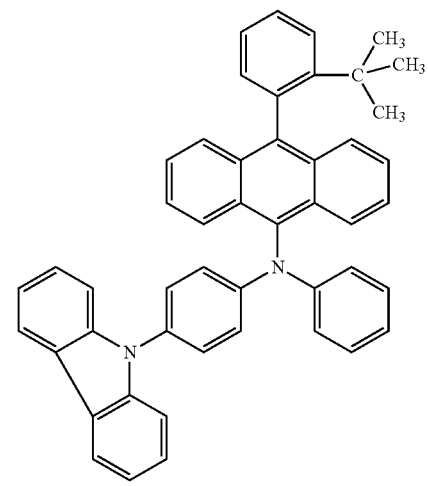
(317)
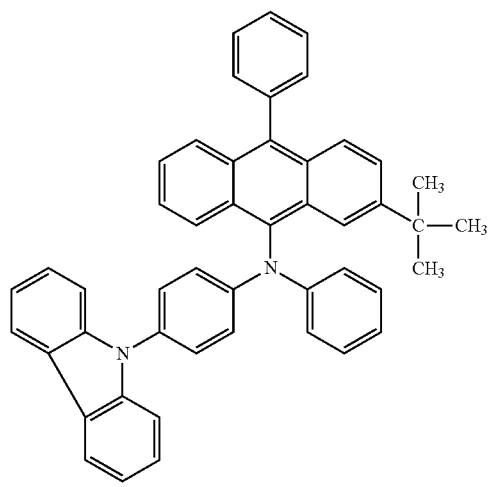
(318)
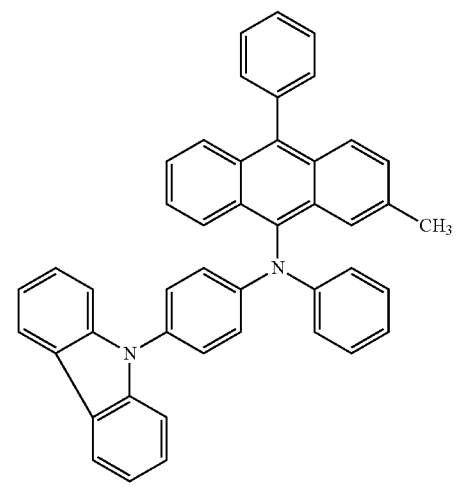

-continued
(319)
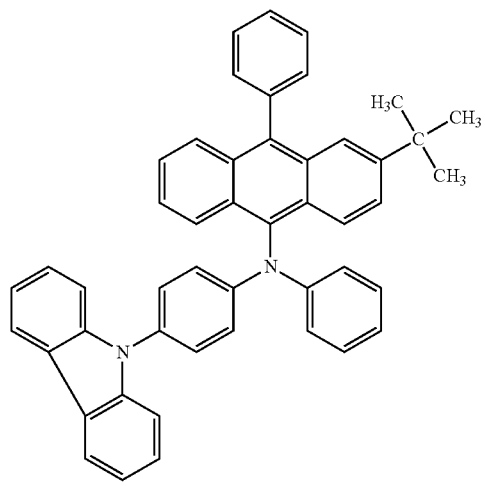
(320)
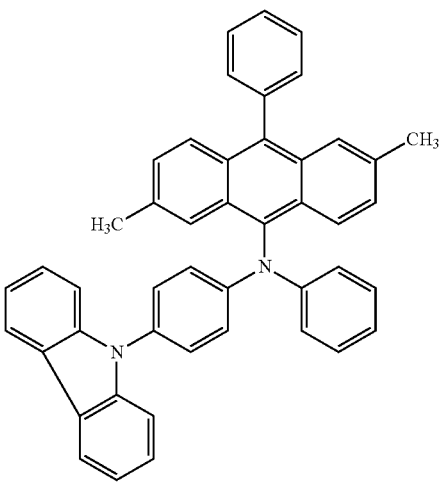
(321)
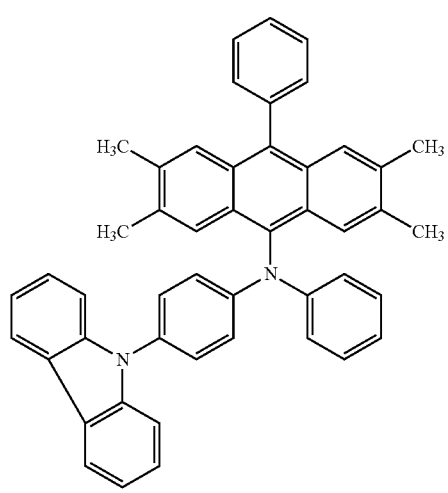
(322)
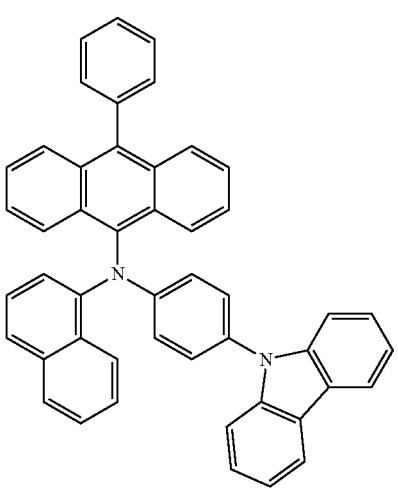
(323)
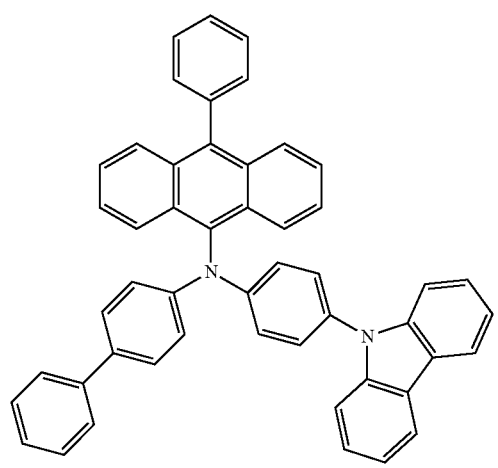
(324)
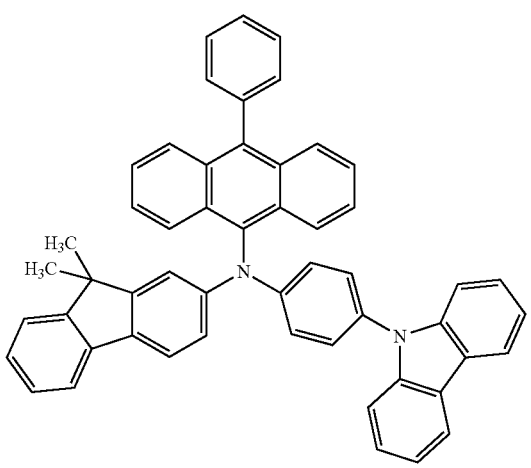

-continued
(325)
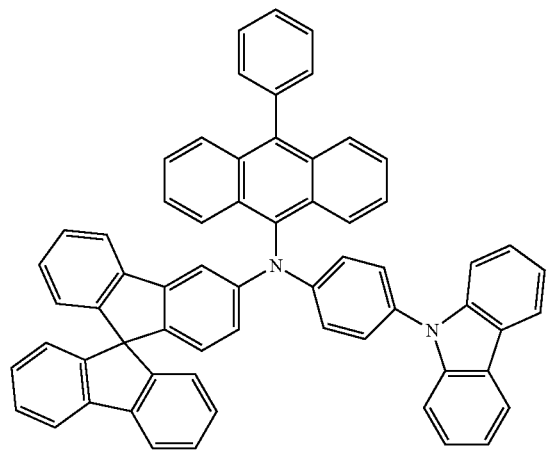
(326)
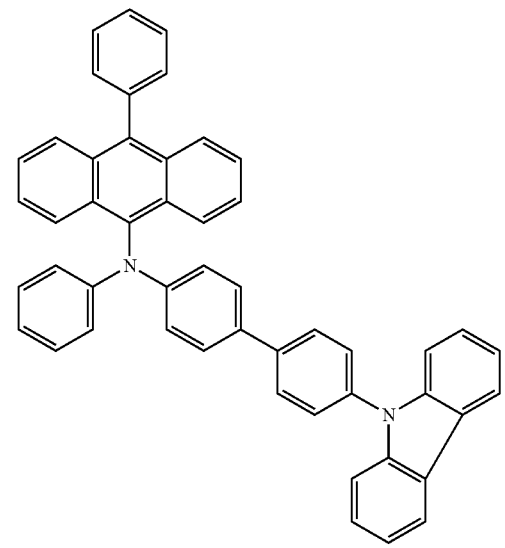
(327)
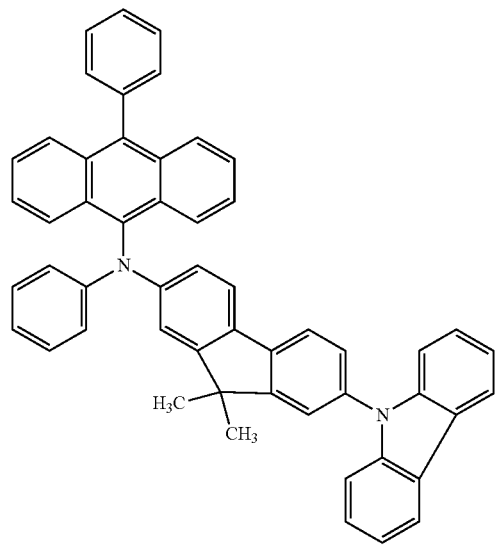
(328)
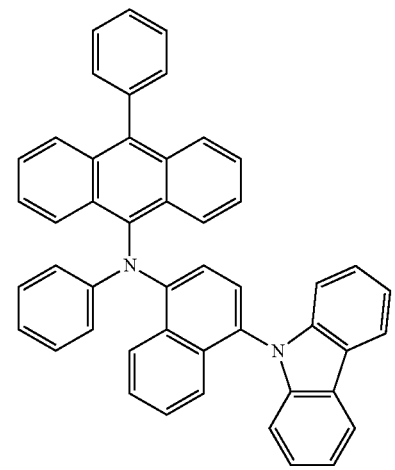

-continued
(329)
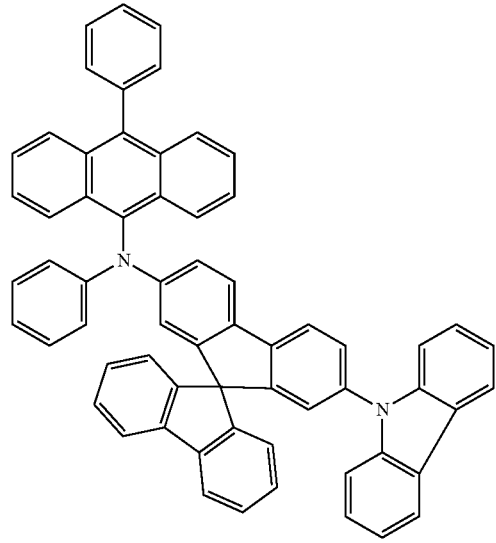
(330)
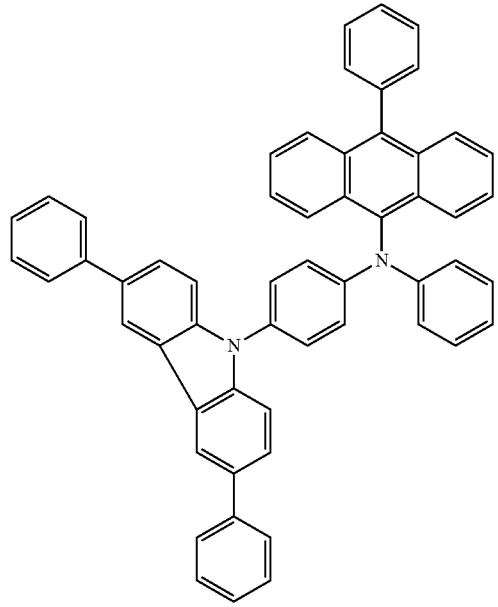
(331)
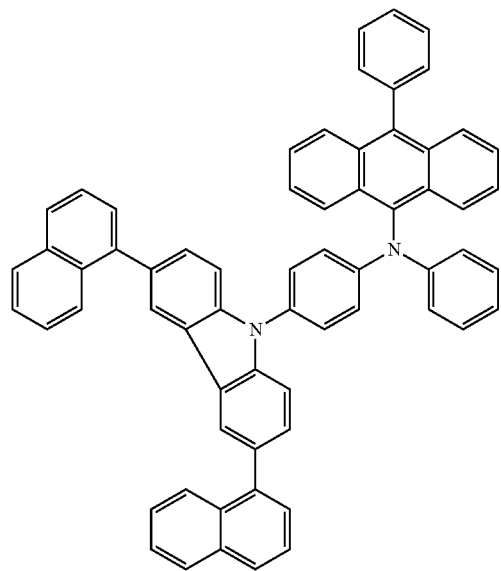
(332)
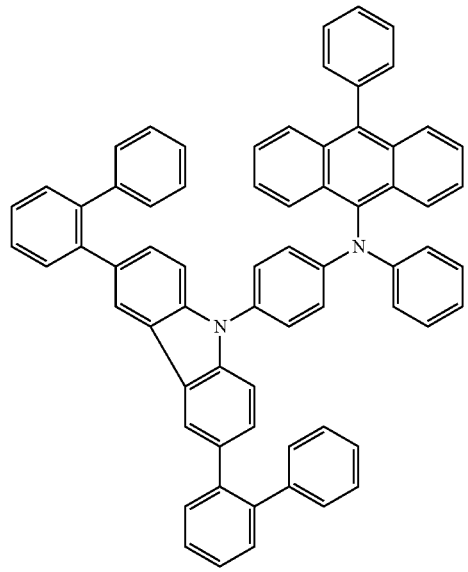

-continued
(333)
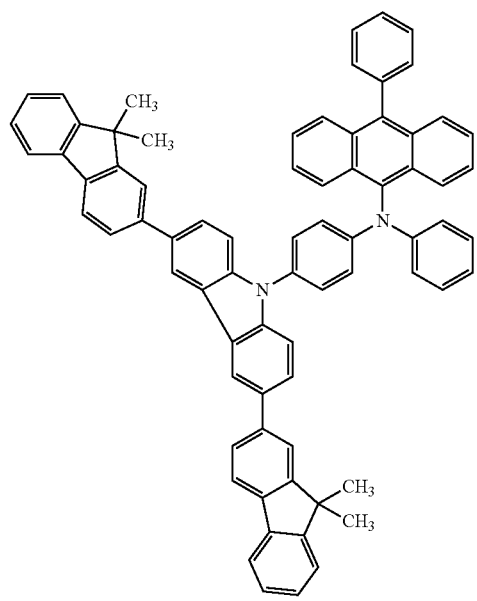
(334)
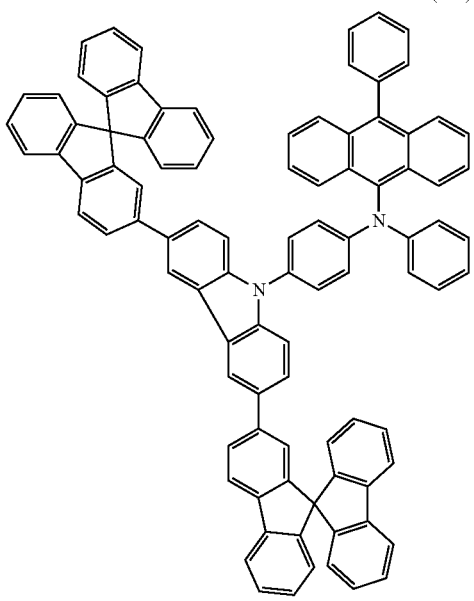
(335)
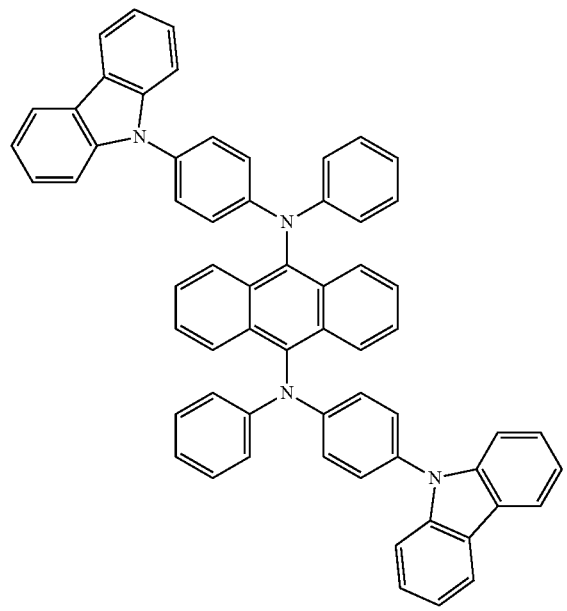
(336)
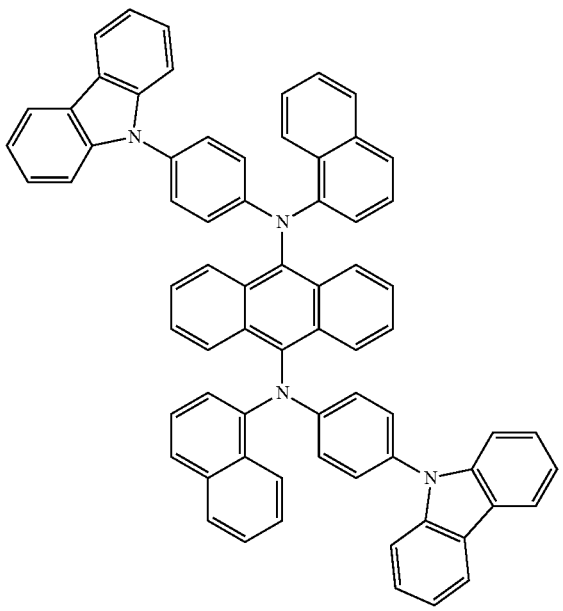

-continued
(337)
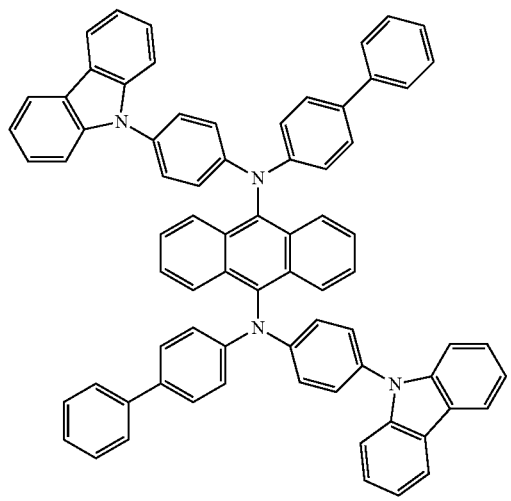
(338)
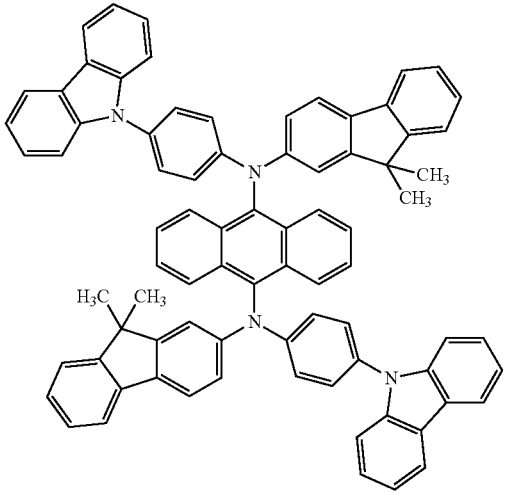
(339)
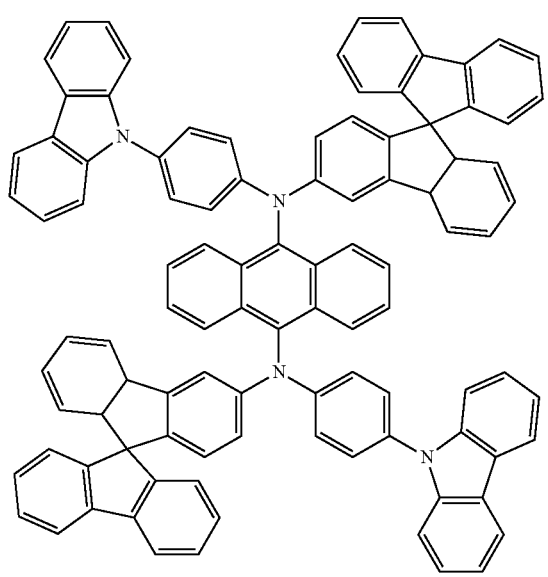
(340)
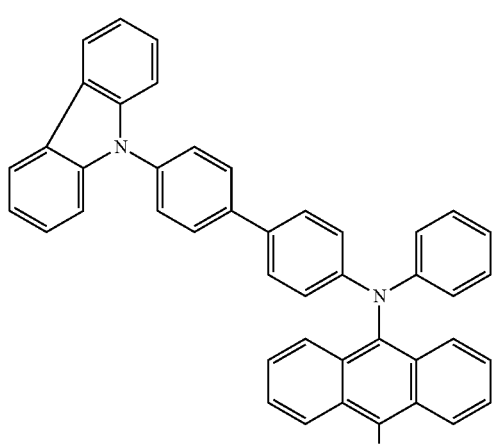

-continued
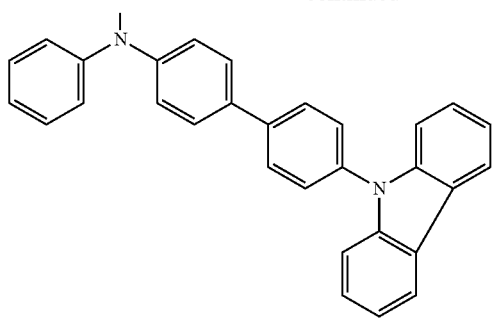
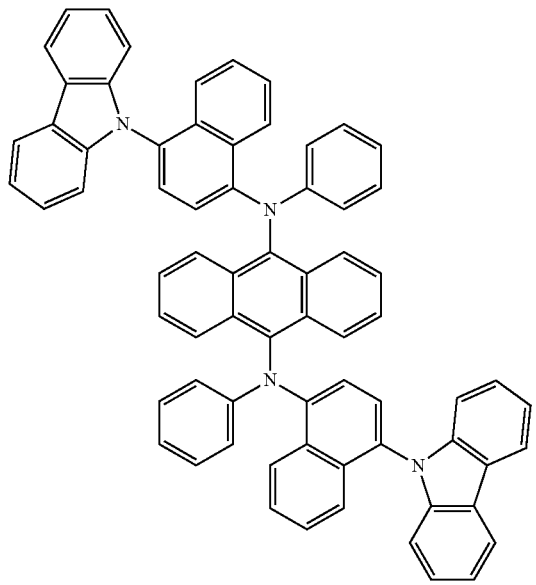
(341)
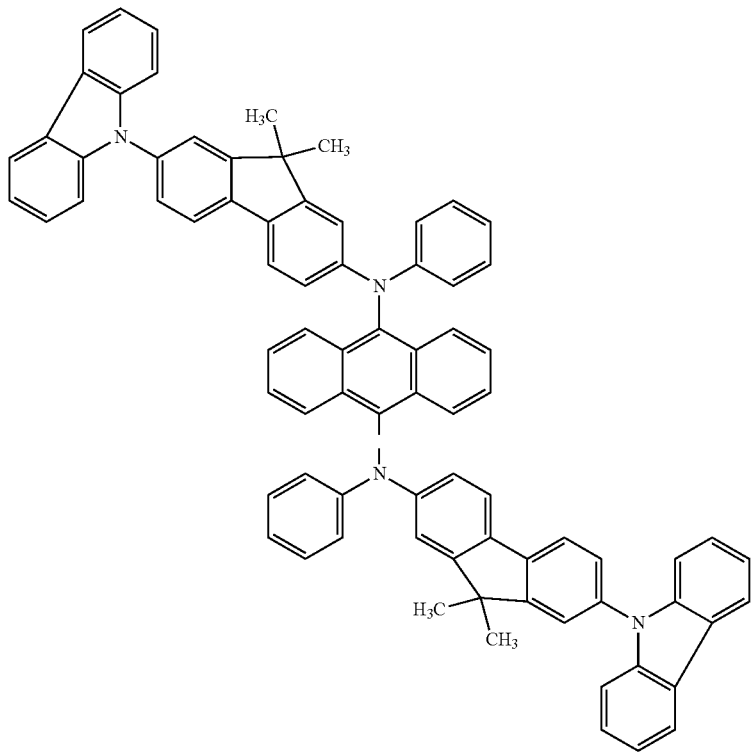
(342)

-continued
(343)
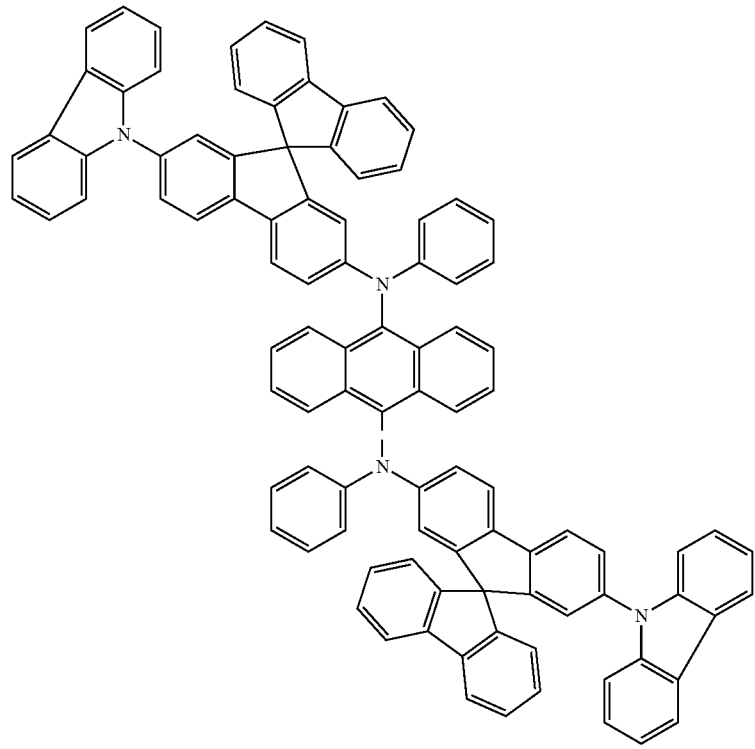
(344)
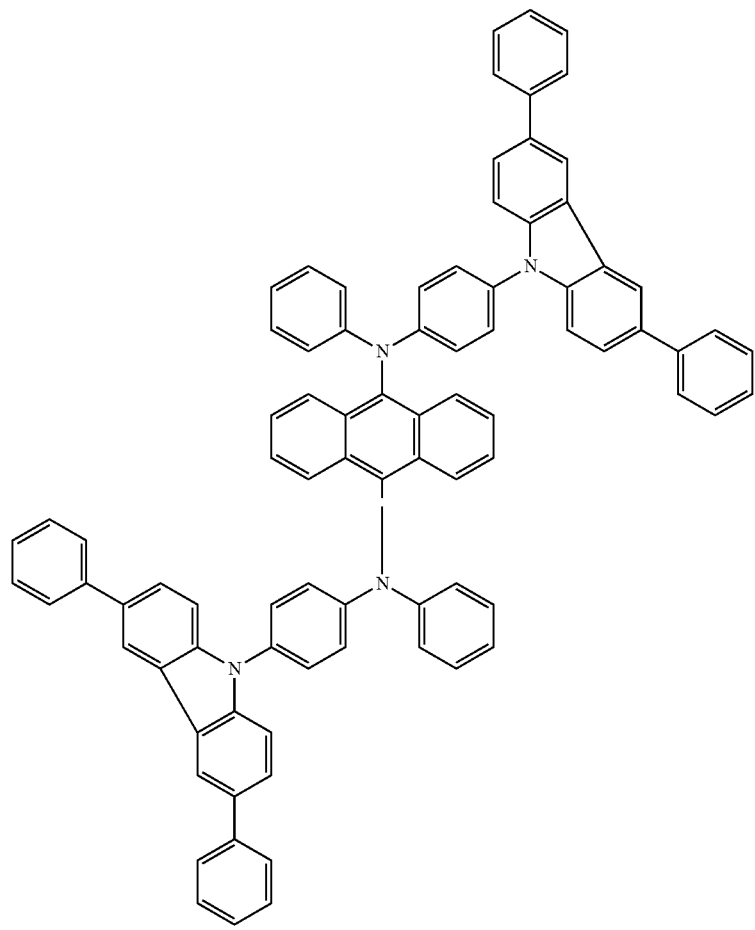

-continued
(345)
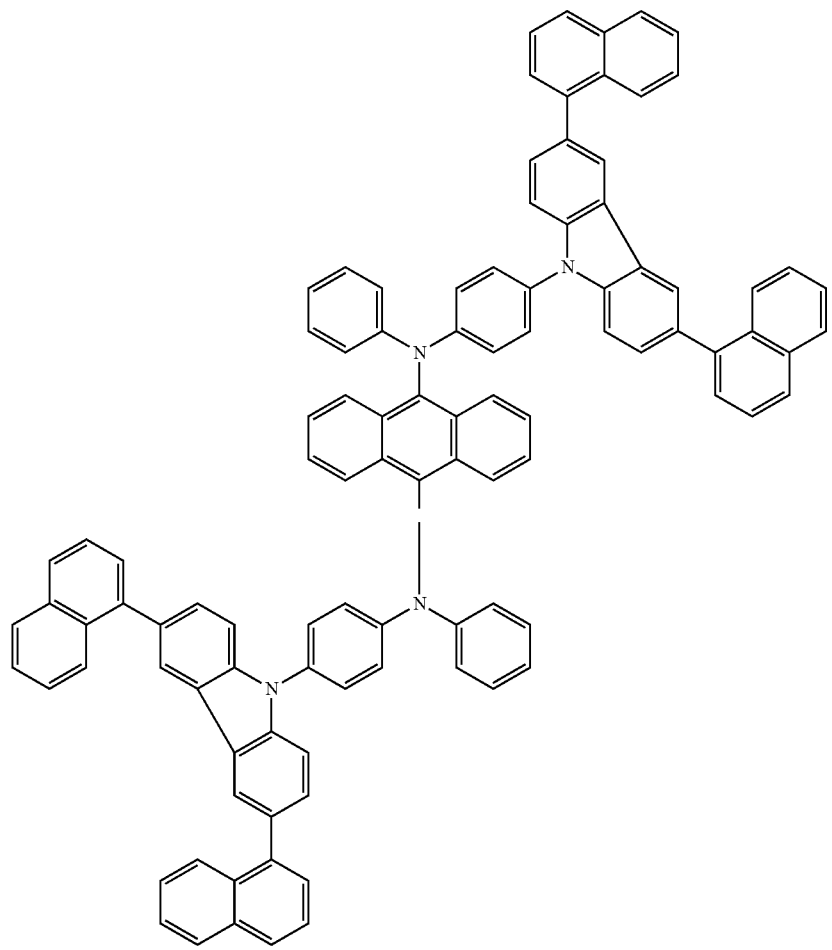
(346)
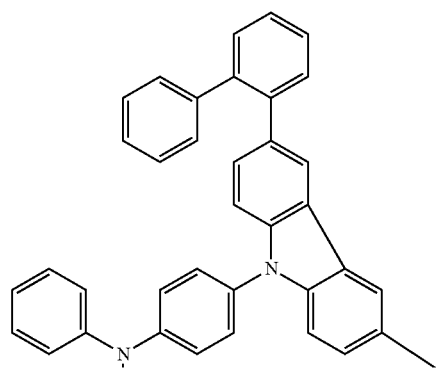

109
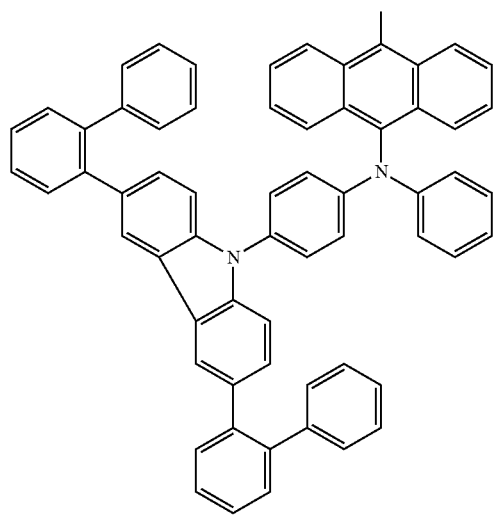
110
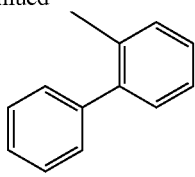
(347)
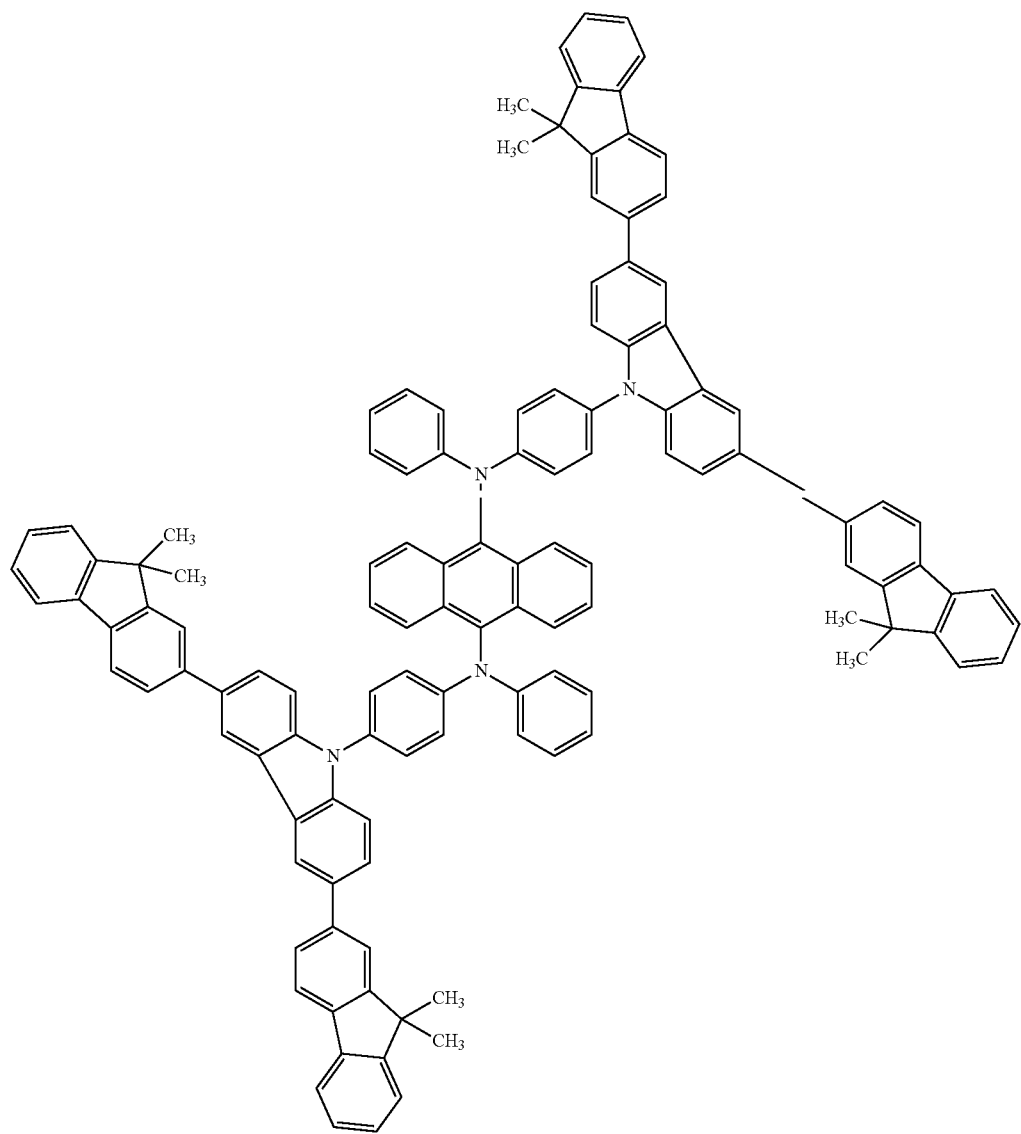

(348)

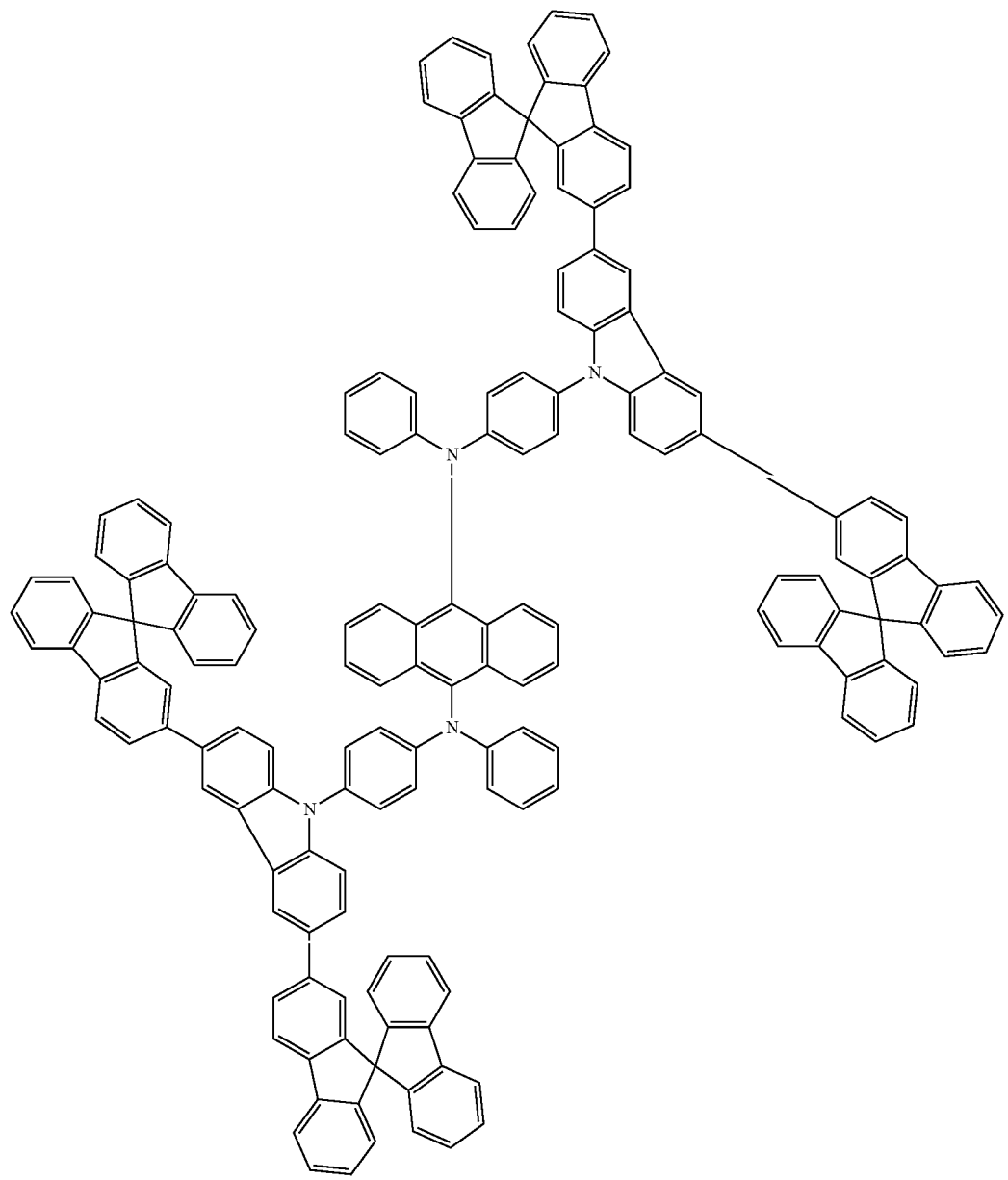

The anthracene derivatives represented by Structural Formulae (201) to (238) are specific examples of the case where A is represented by General Formula (1-2) in General Formula (1), and the anthracene derivatives represented by Structural Formulae (301) to (334) are specific examples of the case where A is represented by General Formula (1-3) in General Formula (1). The anthracene derivatives represented by Structural Formulae (239) to (256) are specific examples of the case where A is represented by General Formula (5-2) in General Formula (5), and the anthracene derivatives represented by Structural Formulae (335) to (348) are specific examples of the case where A is represented by General Formula (5-3) in General Formula (5).

As a synthesizing method of an anthracene derivative of the present invention, various reactions can be applied. For example, an anthracene derivative of the present invention can be synthesized by any of synthesizing methods shown in Synthetic Schemes (A-1) to (A-9) below.

First, a carbazole derivative can be synthesized using the method shown in Synthetic Scheme (A-1) or (A-2).

As shown in Synthetic Scheme (A-1), a carbazole derivative (Compound A) is reacted with halogen or a halide such as N-bromosuccinimide (NBS), N-iodosuccinimide (NIS), bromine ($Br_2$), potassium iodide (KI), or iodine ($I_2$) to synthesize a 3-halide carbazole derivative (Compound B), and then the 3-halide carbazole derivative (Compound B) is subjected to a coupling reaction with arylamine using metal such as copper, a metal compound such as copper(I) iodide, or a metal catalyst such as a palladium catalyst (Pd catalyst), so that a carbazol-3-amine derivative (Compound C) can be obtained. In Synthetic Scheme (A-1), a halogen element ($X^1$) is preferably iodine or bromine. $R^{31}$ represents any of a hydrogen atom, an alkyl group having 1 to 4 carbon atoms, and an aryl group having 6 to 25 carbon atoms. $R^{32}$ represents an alkyl group having 1 to 4 carbon atoms or an aryl group having 6 to 25 carbon atoms. Further, $Ar^{21}$ represents an aryl group having 6 to 25 carbon atoms.

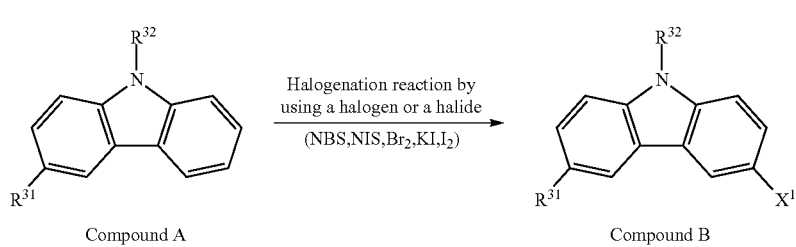

(A-1)

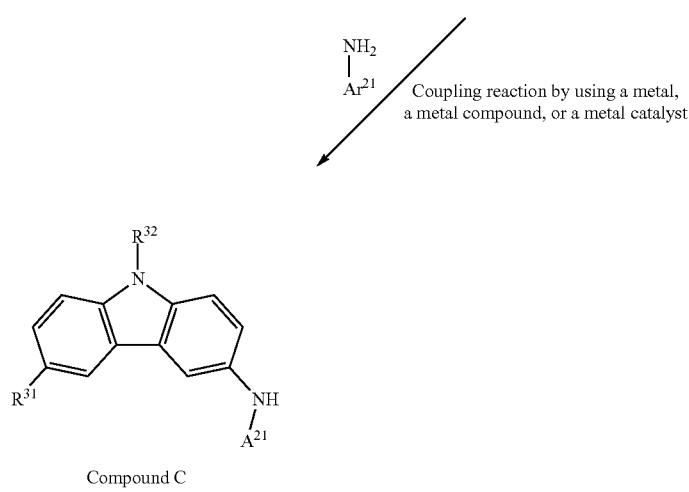

As shown in Synthetic Scheme (A-2), a carbazole derivative (Compound E) is reacted with a dihalide (Compound D) of an aromatic compound to synthesize a N-(aryl halide) carbazole derivative (Compound F), and then the N-(aryl halide)carbazole derivative (Compound F) is subjected to a coupling reaction with arylamine using metal such as copper, a metal compound such as copper(I) iodide, or a metal catalyst such as a palladium catalyst (Pd catalyst), so that a carbazole derivative (Compound G) can be obtained. In Synthetic Scheme (A-2), a halogen element ($X^2$ and $X^3$) of the dihalide of an aromatic compound is preferably iodine or bromine. $X^2$ and $X^3$ may be the same or different from each other. Each of $R^{41}$ and $R^{42}$ represents any of a hydrogen atom, an alkyl group having 1 to 4 carbon atoms, and an aryl group having 6 to 25 carbon atoms. β represents an arylene group having 6 to 25 carbon atoms. $Ar^{31}$ represents an aryl group having 6 to 25 carbon atoms.

(A-2)

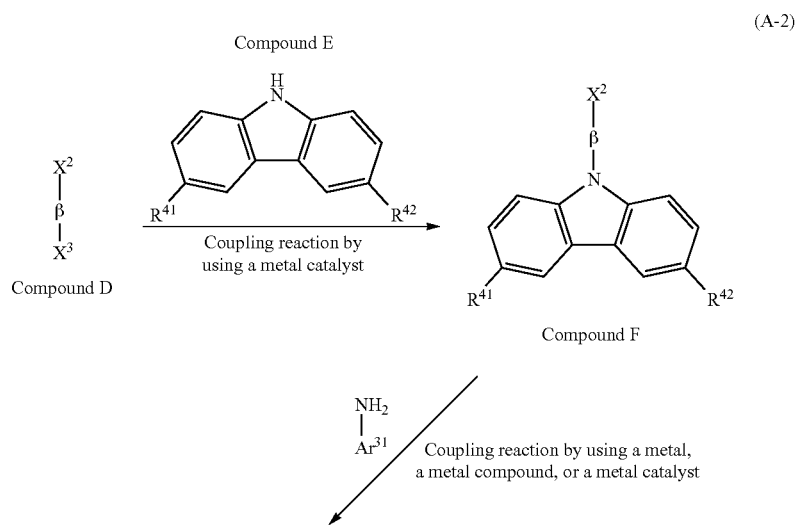

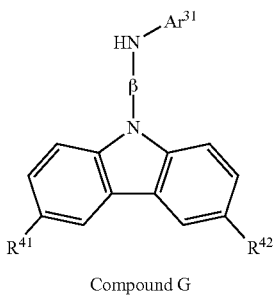

Compound G

An anthracene derivative can be synthesized by the methods shown in Synthetic Schemes (A-3) to (A-5).

As shown in Synthetic Scheme (A-3), a 9-anthracene halide derivative (Compound H) is subjected to a coupling reaction with arylboronic acid (Compound I) using a palladium catalyst, so that a 9-arylanthracene derivative (Compound J) can be obtained. A boronic acid of the arylboronic acid (Compound I) may be protected by an alkyl group or the like.

(A-3)

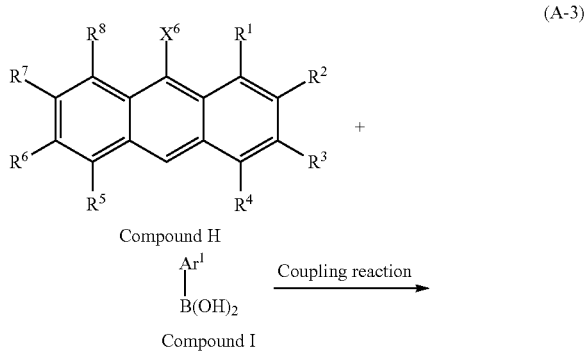

Next, as shown in Synthetic Scheme (A-4), the 9-arylanthracene derivative (Compound J) is halogenated, so that a 9-aryl-10-anthracene halide derivative (Compound L) can be obtained. When bromination is conducted in the halogenation reaction, the bromination can be conducted using bromine, N-bromosuccinimide (NBS), or the like. In the case where iodination is conducted, the iodination can be conducted using iodine, orthoperiodic acid, potassium iodide, N-iodosuccinimide (NIS), or the like.

(A-4)

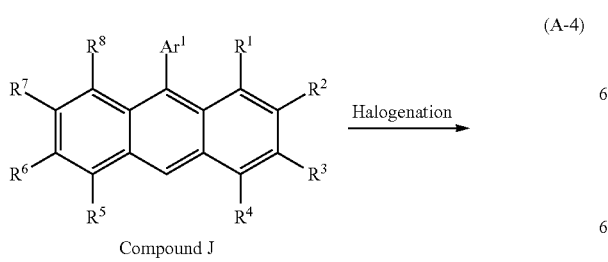

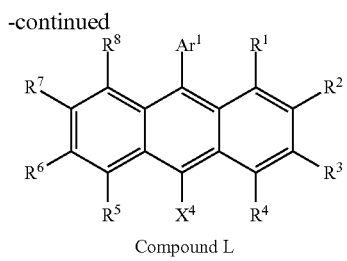

Compound L

Alternatively, the 9-aryl-10-anthracene halide derivative (Compound L) can also be synthesized by a method shown in Synthetic Scheme (A-5). Specifically, a 9,10-anthracene dihalide derivative (Compound K), in which carbon at position 9 and carbon at position 10 are halogenated, is subjected to a coupling reaction with the arylboronic acid (Compound I) using a palladium catalyst, so that the 9-aryl-10-anthracene halide derivative (Compound L) can be obtained. A boronic acid of the arylboronic acid (Compound I) may be protected by an alkyl group or the like.

(A-5)

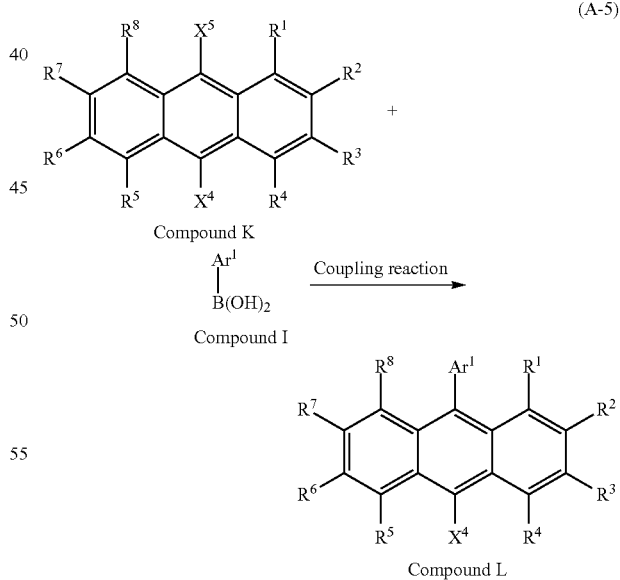

In Synthetic Scheme (A-3) to (A-5), $Ar^1$ represents an aryl group having 6 to 25 carbon atoms, each of $R^1$ to $R^8$ represents a hydrogen atom or an alkyl group having 1 to 4 carbon atoms, and each of $X^4$ to $X^6$ represents halogen.

Next, as shown in Synthetic Scheme (A-6), the 9-aryl-10-anthracene halide derivative (Compound L) obtained by Synthetic Schemes (A-3) to (A-5) is subjected to a coupling reaction with the carbazole derivative (Compound C) obtained by Synthetic Scheme (A-1) using metal such as copper, a metal compound such as copper(I) iodide, or a metal catalyst such as a palladium catalyst (Pd catalyst), so that an anthracene derivative represented by General Formula (1-2a) can be obtained. The anthracene derivative represented by General Formula (1-2a) corresponds to the case where A is represented by General Formula (1-2) in General Formula (1).

atoms; and $R^{32}$ represents either of an alkyl group having 1 to 4 carbon atoms or an aryl group having 6 to 25 carbon atoms.

As shown in Synthetic Scheme (A-7), the 9-aryl-10-anthracene halide derivative (Compound L) is subjected to a coupling reaction, with the carbazole derivative (Compound G) obtained by Synthetic Scheme (A-2) using metal such as copper, a metal compound such as copper(I) iodide, or a metal catalyst such as a palladium catalyst (Pd catalyst), so that an anthracene derivative represented by General Formula (1-3a) can be obtained. The anthracene derivative represented by General Formula (1-3a) corresponds to the case where A is represented by General Formula (1-3) in General Formula (1).

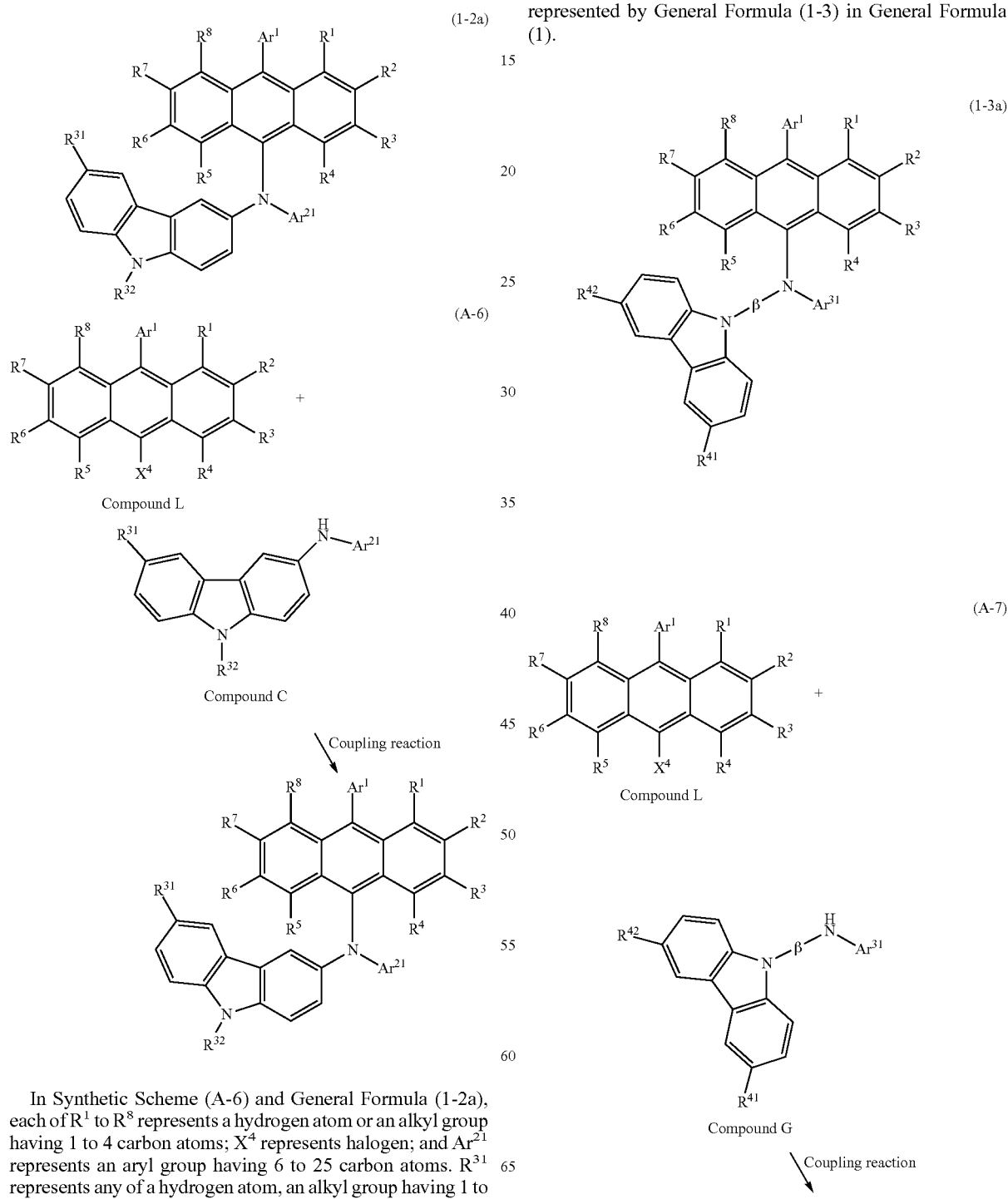

In Synthetic Scheme (A-6) and General Formula (1-2a), each of $R^1$ to $R^8$ represents a hydrogen atom or an alkyl group having 1 to 4 carbon atoms; $X^4$ represents halogen; and $Ar^{21}$ represents an aryl group having 6 to 25 carbon atoms. $R^{31}$ represents any of a hydrogen atom, an alkyl group having 1 to 4 carbon atoms, and an aryl group having 6 to 25 carbon -continued

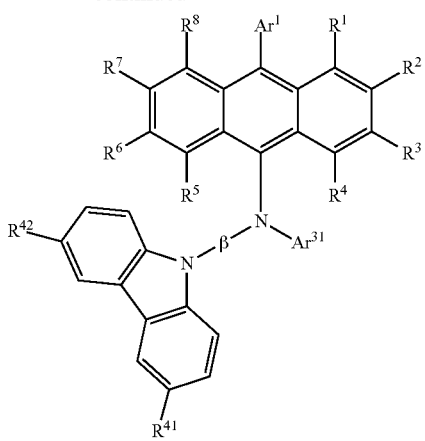

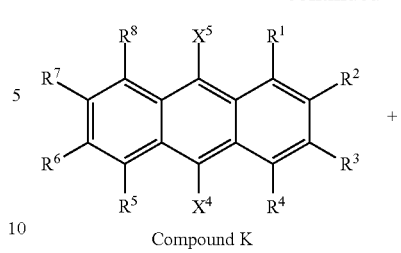

Compound K

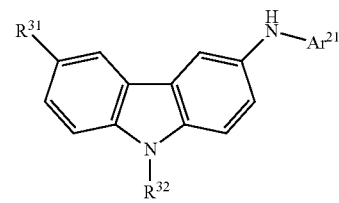

Compound C

↘ Coupling reaction

In Synthetic Scheme (A-7) and General Formula (1-3a), each of $R^1$ to $R^8$ represents a hydrogen atom or an alkyl group having 1 to 4 carbon atoms; $X^4$ represents halogen; and $Ar^{31}$ represents an aryl group having 6 to 25 carbon atoms. β represents an arylene group having 6 to 25 carbon atoms; and each of $R^{41}$ and $R^{42}$ represents any of a hydrogen atom, an alkyl group having 1 to 4 carbon atoms, and an aryl group having 6 to 25 carbon atoms.

As shown in Synthetic Scheme (A-8), the 9,10-anthracene dihalide derivative (Compound K) is subjected to a coupling reaction with the carbazole derivative (Compound C) obtained by Synthetic Scheme (A-1) using metal such as copper, a metal compound such as copper(I) iodide, or a metal catalyst such as a palladium catalyst (Pd catalyst), so that an anthracene derivative represented by General Formula (5-2a) can be obtained. The anthracene derivative represented by General Formula (5-2a) corresponds to the case where A is represented by General Formula (5-2) in General Formula (5).

(A-8)

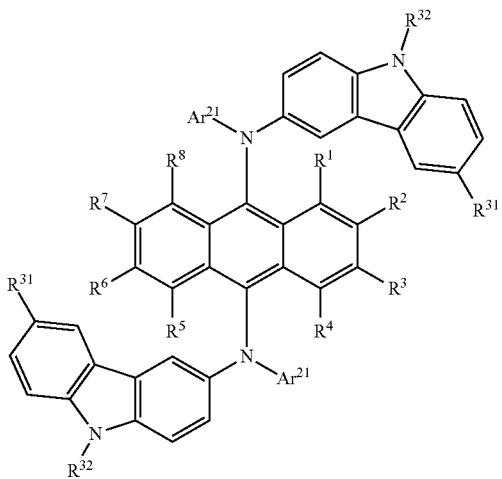

(5-2a)

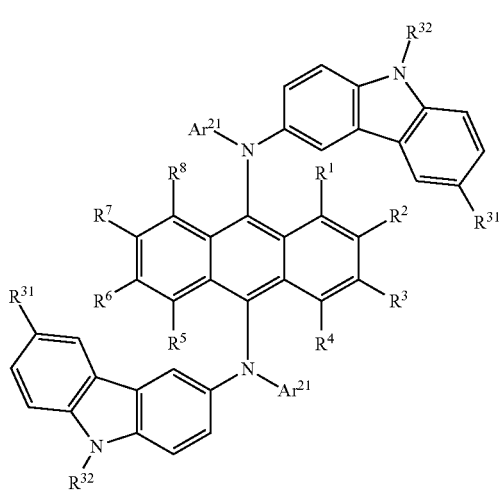

In Synthetic Scheme (A-8) and General Formula (5-2a), each of $R^1$ to $R^8$ represents a hydrogen atom or an alkyl group having 1 to 4 carbon atoms; each of $X^4$ and $X^5$ represents halogen; and $Ar^{21}$ represents an aryl group having 6 to 25 carbon atoms. $R^{31}$ represents any of a hydrogen atom, an alkyl group having 1 to 4 carbon atoms, and an aryl group having 6 to 25 carbon atoms; and $R^{32}$ represents either of an alkyl group having 1 to 4 carbon atoms or an aryl group having 6 to 25 carbon atoms.

As shown in Synthetic Scheme (A-9), the 9,10-anthracene dihalide derivative (Compound K) is subjected to a coupling reaction with the carbazole derivative (Compound G) obtained by Synthetic Scheme (A-2) using metal such as copper, a metal compound such as copper(I) iodide, or a metal catalyst such as a palladium catalyst (Pd catalyst), so that an anthracene derivative represented by General Formula (5-3a) can be obtained. The anthracene derivative represented by General Formula (5-3a) corresponds to the case where A is represented by General Formula (5-3) in General Formula (5).

(5-3a)

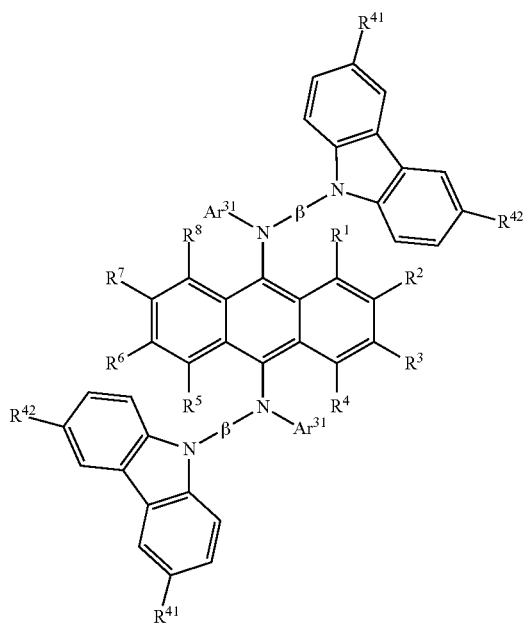

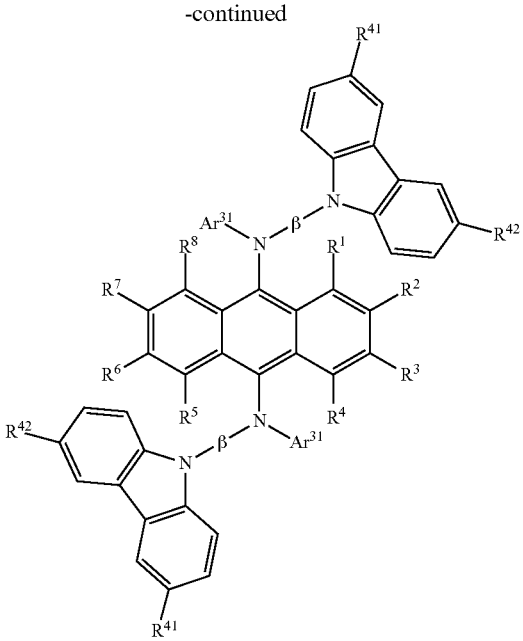

(A-9)

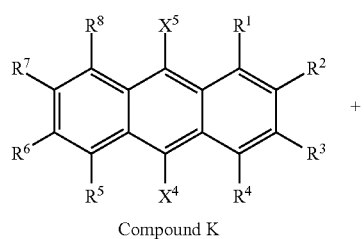

Compound K

+

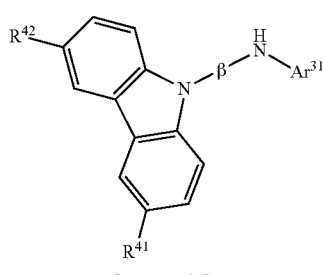

Compound G

↘ Coupling reaction

In Synthetic Scheme (A-9) and General Formula (5-3a), each of $R^1$ to $R^8$ represents a hydrogen atom or an alkyl group having 1 to 4 carbon atoms; each of $X^4$ and $X^5$ represents halogen; and $Ar^{31}$ represents an aryl group having 6 to 25 carbon atoms. β represents an arylene group having 6 to 25 carbon atoms; and each of $R^{41}$ and $R^{42}$ represents any of a hydrogen atom, an alkyl group having 1 to 4 carbon atoms, and an aryl group having 6 to 25 carbon atoms.

The synthesizing method of an anthracene derivative of the present invention is not limited to the above-described methods, and the anthracene derivative can be synthesized by various methods.

The anthracene derivative of the present invention emits visible light efficiently. In particular, light of green to red can be obtained efficiently. Therefore, the anthracene derivative of the present invention can favorablly be used in a light emitting element.

The anthracene derivative of the present invention is stable even when oxidation and reduction reactions are repeated. Therefore, when the anthracene derivative of the present invention is used for a light emitting element, the light emitting element can have a long lifetime.

Further, the anthracene derivative of the present invention emits visible light efficiently. Thus, when the anthracene derivative is used in a light emitting element, the light emitting element can have a high luminous efficiency.

Since the anthracene derivative of the present invention emits visible light efficiently, a light emitting element with reduced power consumption can be provided.

Furthermore, the anthracene derivative of the present invention has a carbazole skeleton. A carbazole derivative is superior in heat resistance to a diphenylamine derivative, which has a similar molecule structure to the carbazole derivative. Therefore, when the anthracene derivative of the present invention is used in a light emitting element, the light emitting element can have high heat resistance.

In the case where a film of the anthracene derivative of the present invention is formed by an evaporation method, the evaporation rate can be easily controlled. Therefore, the anthracene derivative of the present invention can favorably be used in a light emitting element.

Embodiment Mode 2

One mode of a light emitting element using an anthracene derivative of the present invention will be described below with reference to FIG. 1A.

A light emitting element of the present invention has a plurality of layers between a pair of electrodes. The plurality of layers is a combination of layers formed of a substance having a high carrier injecting property and a substance having a high carrier transporting property which are stacked so that a light emitting region is formed in a place away from the electrodes, that is, recombination of carriers is performed in an area away from the electrodes.

In this embodiment mode, a light emitting element includes a first electrode 102; a first layer 103, a second layer 104, a third layer 105, and a fourth layer 106 which are sequentially stacked over the first electrode 102; and a second electrode 107 provided thereover. It is to be noted that description will be made below in this embodiment mode with an assumption that the first electrode 102 functions as an anode and the second electrode 107 functions as a cathode.

A substrate 101 is used as a support of the light emitting element. For the substrate 101, glass, plastic, or the like can be used, for example. It is to be noted that another material may be used as long as it functions as a support in a manufacturing process of the light emitting element.

For the first electrode 102, a metal, an alloy, an electrically conductive compound, a mixture thereof, or the like having a high work function (specifically, 4.0 eV or more) is preferably used. Specifically, indium oxide-tin oxide (ITO: Indium Tin Oxide), indium oxide-tin oxide including silicon or silicon oxide, indium oxide-zinc oxide (IZO: Indium Zinc Oxide), indium oxide including tungsten oxide and zinc oxide (IWZO), or the like can be used, for example. Although these conductive metal oxide films are generally formed by sputtering, they may be formed by applying a sol-gel method or the like. For example, a film of indium oxide-zinc oxide (IZO) can be formed by a sputtering method using a target in which 1 to 20 wt % of zinc oxide is added to indium oxide. A film of indium oxide including tungsten oxide and zinc oxide (IWZO) can be formed by a sputtering method using a target in which 0.5 to 5 wt % of tungsten oxide and 0.1 to 1 wt % of zinc oxide are included in indium oxide. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), or the like is exemplified.

The first layer 103 is a layer including a substance having a high hole injecting property. Molybdenum oxide, vanadium oxide, ruthenium oxide, tungsten oxide, manganese oxide, or the like can be used. Alternatively, the first layer 103 can be formed using phthalocyanine (abbreviation: H$_2$Pc); a phthalocyanine-based compound such as copper phthalocyanine (CuPc); an aromatic amine compound such as 4,4'-bis[N-(4-diphenylaminophenyl)-N-phenylamino]biphenyl (abbreviation: DPAB) or 4,4'-bis(N-{4-[N-(3-methylphenyl)-N-phenylamino]phenyl}-N-phenylamino)biphenyl (abbreviation: DNTPD); a high molecular material such as poly(3,4-ethylene dioxythiophene)/poly(styrenesulfonic acid) (PEDOT/PSS); or the like.

Alternatively, a composite material formed by composition of an organic compound and an inorganic compound can be used for the first layer 103. In particular, a composite material including an organic compound and an inorganic compound having an electron accepting property with respect to the organic compound has excellent hole injecting property and hole transporting property because the electron transfer takes place between the organic compound and the inorganic compound, increasing the carrier density.

In a case of using a composite material formed by composition of an organic compound and an inorganic compound for the first layer 103, the first layer 103 can achieve an ohmic contact with the first electrode 102; therefore, the material of the first electrode 102 can be selected regardless of work function.

As the inorganic compound used for the composite material, an oxide of a transition metal is preferably used. Further, oxides of metals belonging to Groups 4 to 8 in the periodic table can be given. Specifically, it is preferable to use vanadium oxide, niobium oxide, tantalum oxide, chromium oxide, molybdenum oxide, tungsten oxide, manganese oxide, and rhenium oxide because of their high electron accepting properties. Among them, molybdenum oxide is particularly preferable because it is stable under air, has a low moisture absorption property, and is easily handled.

As the organic compound used for the composite material, various compounds such as an aromatic amine compound, a carbazole derivative, an aromatic hydrocarbon, and a high molecular compound (such as oligomer, dendrimer, or polymer) can be used. The organic compound used for the composite material is preferably an organic compound having a high hole transporting property. Specifically, a substance having a hole mobility of greater than or equal to $10^{-6}$ cm$^2$/Vs is preferably used. However, other materials than these materials may also be used as long as the hole transporting properties thereof are higher than the electron transporting properties thereof. The organic compounds which can be used for the composite material will be specifically described below.

For example, the following can be given as the aromatic amine compound: N,N'-di(p-tolyl)-N,N'-diphenyl-p-phenylenediamine (abbreviation: DTDPPA); 4,4'-bis[N-(4-diphenylaminophenyl)-N-phenylamino]biphenyl (abbreviation: DPAB); 4,4'-bis(N-{4-[N'-(3-methylphenyl)-N'-phenylamino]phenyl}-N-phenylamino)biphenyl (abbreviation: DNTPD); 1,3,5-tris[N-(4-diphenylaminophenyl)-N-phenylamino]benzene (abbreviation: DPA3B); and the like.

As the carbazole derivative which can be used for the composite material, the following can be given specifically: 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphtyl)-N-(9-phenylcarbazol-3-yl)amino]-9-phenylcarbazole (abbreviation: PCzPCN1); and the like.

Moreover, as the carbazole derivative which can be used for the composite material, the following can be given: 4,4'-di(N-carbazolyl)biphenyl (abbreviation: CBP); 1,3,5-tris[4-(N-carbazolyl)phenyl]benzene (abbreviation: TCPB); 9-[4-(N-carbazolyl)]phenyl-10-phenylanthracene (abbreviation: CzPA); 1,4-bis[4-(N-carbazolyl)phenyl]-2,3,5,6-tetraphenylbenzene; and the like.

As the aromatic hydrocarbon which can be used for the composite material, the following can be given for example: 2-tert-butyl-9,10-di(2-naphthyl)anthracene (abbreviation: t-BuDNA); 2-tert-butyl-9,10-di(1-naphthyl)anthracene; 9,10-bis(3,5-diphenylphenyl)anthracene (abbreviation: DPPA); 2-tert-butyl-9,10-bis(4-phenylphenyl)anthracene (abbreviation: t-BuDBA); 9,10-di(2-naphthyl)anthracene (abbreviation: DNA); 9,10-diphenylanthracene (abbreviation: DPAnth); 2-tert-butylanthracene (abbreviation: t-BuAnth); 9,10-bis(4-methyl-1-naphthyl)anthracene (abbreviation: DMNA); 2-tert-butyl-9,10-bis[2-(1-naphthyl)phenyl]anthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene; 2,5,8,11-tetra(tert-butyl)perylene; and the like. Besides these compounds, pentacene, coronene, or the like can also be used. Thus, an aromatic hydrocarbon which has a hole mobility of greater than or equal to $1 \times 10^{-6}$ cm$^2$/Vs and which has 14 to 42 carbon atoms is more preferable.

The aromatic hydrocarbon which can be used for the composite material may have a vinyl skeleton. As the aromatic hydrocarbon having a vinyl group, the following are given for example: 4,4'-bis(2,2-diphenylvinyl)biphenyl (abbreviation: DPVBi); 9,10-bis[4-(2,2-diphenylvinyl)phenyl]anthracene (abbreviation: DPVPA); and the like.

Moreover, a high molecular compound such as poly(N-vinylcarbazole) (abbreviation: PVK) or poly(4-vinyltriphenylamine) (abbreviation: PVTPA) can also be used.

As a substance forming the second layer 104, a substance having a high hole transporting property, specifically, an aromatic amine compound (that is, a compound having a benzene ring-nitrogen bond) is preferable. As a material that is widely used, 4,4'-bis[N-(3-methylphenyl)-N-phenylamino]biphenyl, a derivative thereof, that is 4,4'-bis[N-(1-naphthyl)-N-phenylamino]biphenyl (hereinafter referred to as NPB), and star burst aromatic amine compounds such as 4,4',4''-tris(N,N-diphenyl-amino)triphenylamine and 4,4',4''-tris[N-(3-methylphenyl)-N-phenylamino]triphenylamine can be given. These materials described here are mainly substances each having a hole mobility of greater than or equal to $10^{-6}$ cm$^2$/Vs. However, other materials than these compounds may also be used as long as the hole transporting properties thereof are higher than the electron transporting properties. The second layer 104 is not limited to a single layer, and a mixed layer of the aforementioned substances, or a stacked layer which includes two or more layers each including the aforementioned substance may be used.

The third layer 105 is a layer including a light emitting substance. In this embodiment mode, the third layer 105 includes the anthracene derivative of the present invention described in Embodiment Mode 1. The anthracene derivative of the present invention can favorably be applied to a light emitting element as a light emitting substance since the anthracene derivative of the present invention exhibits light emission of visible light.

As the fourth layer 106, a substance having a high electron transporting property can be used. For example, a layer including a metal complex or the like having a quinoline or benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq) can be used. Alternatively, a metal complex or the like having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$) can be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances described here are mainly substances each having an electron mobility of greater than or equal to $10^{-6}$ cm$^2$/Vs. The electron transporting layer may be formed using other materials than those described above as long as the materials have higher electron transporting properties than hole transporting properties. Furthermore, the electron transporting layer is not limited to a single layer, and two or more layers in which each layer is made of the aforementioned material may be stacked.

As a substance forming the second electrode 107, a metal, an alloy, an electrically conductive compound, a mixture thereof, or the like having a low work function (specifically, 3.8 eV or less) is preferably used. As a specific example of such a cathode material, an element belonging to Group 1 or Group 2 in the periodic table, that is, an alkali metal such as lithium (Li) or cesium (Cs), an alkaline earth metal such as magnesium (Mg), calcium (Ca), or strontium (Sr), or an alloy including these metals (MgAg, AlLi) can be employed. A rare earth metal such as europium (Eu) or ytterbium (Yb), an alloy including these rare earth metals, or the like is also suitable. However, by providing a layer having a function to promote electron injection between the second electrode 107 and the fourth layer 106 so as to stack on the second electrode 107, various conductive materials such as Al, Ag, ITO, or ITO including silicon or silicon oxide can be used for the second electrode 107 regardless of the magnitude of the work function.

For the layer having a function of promoting electron injection, an alkali metal, an alkaline earth metal, or a compound thereof such as lithium fluoride (LiF), cesium fluoride (CsF), or calcium fluoride (CaF$_2$) can be used. For example, a layer which contains substance having an electron transporting property and further includes an alkali metal, an alkaline earth metal, or a compound thereof such as a layer of Alq including magnesium (Mg) for example, can be used. It is preferable to use such a layer as the electron injecting layer since electron injection from the second electrode 107 proceeds efficiently.

Various methods can be used for forming the first layer 103, the second layer 104, the third layer 105, and the fourth layer 106. For example, an evaporation method, an ink-jet method, a spin coating method, or the like may be used. Furthermore, each electrode or each layer may be formed by a different film formation method.

By difference in potential between the first electrode 102 and the second electrode 107 in the light emitting element having the above-described structure of the present invention, current flows and holes and electrons are recombined in the third layer 105 including a substance with a high light emitting property, which results in light emission. That is, the light emitting element of the present invention has a structure in which a light emitting region is formed in the third layer 105.

Figure 1B:
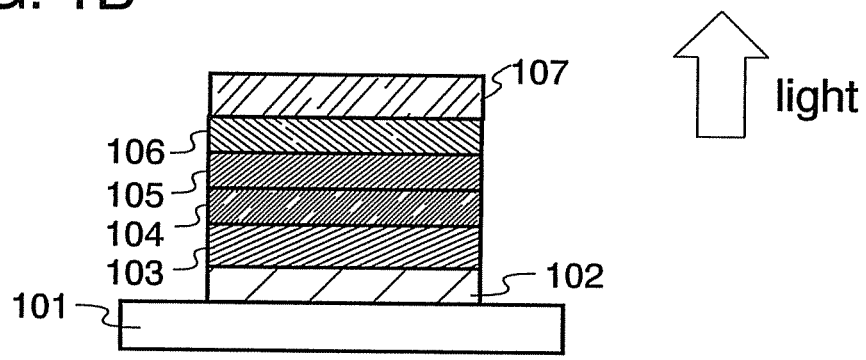
Figure 1C:
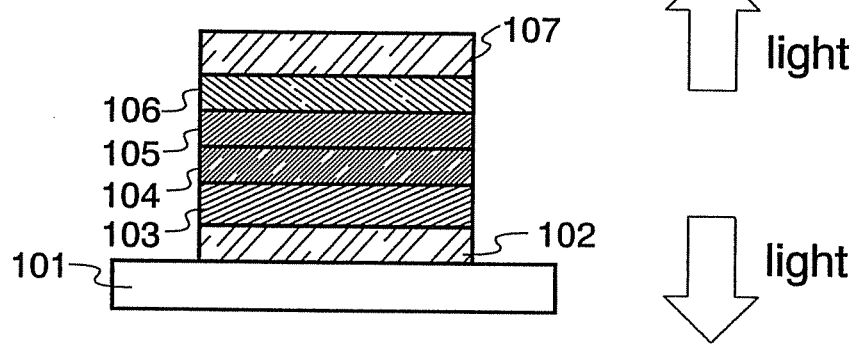

Light emission is extracted outside through one or both of the first electrode 102 and the second electrode 107. Therefore, one or both of the first electrode 102 and the second electrode 107 has/have a light transmitting property. In the case where only the first electrode 102 has a light transmitting property, light emission is extracted from a substrate side through the first electrode 102 as shown in FIG. 1A. In the case where only the second electrode 107 has a light transmitting property, light emission is extracted from the side opposite to the substrate through the second electrode 107 as shown in FIG. 1B. In the case where both of the first electrode 102 and the second electrode 107 have a light transmitting property, light emission is extracted from both of the substrate side and the side opposite to the substrate through the first electrode 102 and the second electrode 107, as shown in FIG. 1C.

A structure of layers provided between the first electrode 102 and the second electrode 107 is not limited to the above-described structure. A structure other than the above-described structure may be used as long as the light emitting region, in which holes and electrons are recombined, is located away from the first electrode 102 and the second electrode 107, which prevents quenching caused by adjacence of the light emitting region and the metal.

In other words, a stacked structure of the layers is not strictly limited to the above-mentioned structure, and a layer formed using a substance having a high electron transporting property, a substance having a high hole transporting property, a substance having a high electron injecting property, a substance having a high hole injecting property, a bipolar substance (substance having a high electron transporting property and a high hole transporting property), a hole blocking material, or the like may be freely combined with the anthracene derivative of the present invention.

Figure 2:
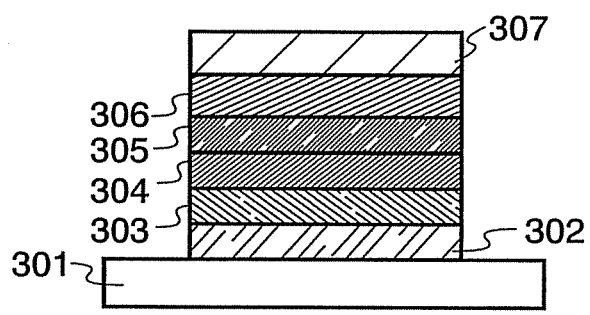
FIG. 2 shows a light emitting element according to the present invention.

A light emitting element shown in FIG. 2 has a structure in which a first electrode 302 serving as a cathode, a first layer 303 formed using a substance having a high electron transporting property, a second layer 304 including a light emitting substance, a third layer 305 formed using a substance having a high hole transporting property, a fourth layer 306 formed using a substance having a high hole injecting property, and a second electrode 307 serving as an anode are sequentially stacked over a substrate 301.

In this embodiment mode, a light emitting element is manufactured over a substrate made of glass, plastic, or the like. By manufacturing a plurality of such light emitting elements described above over one substrate, a passive matrix type light emitting device can be manufactured. Alternatively, for example, a thin film transistor (TFT) may be formed over a substrate made of glass, plastic, or the like, and a light emitting element may be manufactured so as to be connected to the TFT electrically. Accordingly, an active matrix light emitting device can be manufactured, in which driving of the light emitting element is controlled by the TFT. The structure of the ITT is not particularly limited, and the TFT may be a staggered TFT or an inversely staggered TFT. Crystallinity of a semiconductor used for the TFT is not particularly limited as well, and an amorphous semiconductor or a crystalline semiconductor may be used. In addition, a driving circuit formed over a TFT substrate may be formed using an N-type TFT and a P-type TFT, or may be formed using one of an N-type TFT and a P-type TFT.

Since the anthracene derivative of the present invention exhibits light emission of visible light, the anthracene derivative can be used for a light emitting layer without being added with any other light emitting substance, as shown in this embodiment mode.

Since the anthracene derivative of the present invention has a high luminous efficiency, a light emitting element with a high luminous efficiency can be obtained by using the anthracene derivative in a light emitting element. In addition, since the anthracene derivative of the present invention has an excellent hole transporting property, by using the anthracene derivative in a light emitting element, a light emitting element with a reduced driving voltage can be obtained.

Embodiment Mode 3

In Embodiment Mode 3, a light emitting element having a different structure from that described in Embodiment Mode 2 will be described.

The third layer 105 described in Embodiment Mode 2 is formed by dispersing an anthracene derivative of the present invention into another substance, whereby light emission can be obtained from the anthracene derivative of the present invention. Since the anthracene derivative of the present invention exhibits light emission of visible light, a light emitting element exhibiting light emission of visible light can be obtained.

Here, various materials can be used as a substance in which the anthracene derivative of the present invention is dispersed. In addition to the substance having a high hole transporting property and the substance having a high electron transporting property, which are described in Embodiment Mode 2, 4,4'-bis(N-carbazolyl)-biphenyl (abbreviation: CBP), 2,2',2"-(1,3,5-benzenetri-yl)-tris[1-phenyl-1H-benzimidazole] (abbreviation: TPBI), 9,10-di(2-naphthyl)anthracene (abbreviation: DNA), 2-tert-butyl-9,10-di(2-naphthyl)anthracene (abbreviation: t-BuDNA), 9-[4-(N-carbazolyl)]phenyl-10-phenylanthracene (abbreviation: CzPA), and the like are exemplified.

Since the anthracene derivative of the present invention has a high luminous efficiency, a light emitting element with a high luminous efficiency can be obtained by using the anthracene derivative in a light emitting element. In addition, since the anthracene derivative of the present invention has an excellent hole transporting property, by using the anthracene derivative of the present invention in a light emitting element, a light emitting element with a reduced driving voltage can be obtained.

Regarding the layers other than the third layer 105, the structure described in Embodiment Mode 2 can be appropriately used.

Embodiment Mode 4

In Embodiment Mode 4, a light emitting element with a structure different from the structures described in Embodiment Modes 2 and 3 will be described.

The third layer 105 described in Embodiment Mode 2 is formed by dispersing a light emitting substance in the anthracene derivative of the present invention, whereby light emission from the light emitting substance can be obtained.

In the case where the anthracene derivative of the present invention is used as a material in which another light emitting substance is dispersed, a light emission color derived from the light emitting substance can be obtained. Further, a mixed color resulted from the anthracene derivative of the present invention and the light emitting substance dispersed in the anthracene derivative can also be obtained.

Here, various materials can be used as a light emitting substance dispersed in the anthracene derivative of the present invention. Specifically, a fluorescent substance that emits fluorescence such as 4-(dicyanomethylene)-2-methyl-6-(p-dimethylaminostyryl)-4H-pyran (abbreviation: DCM1), 4-(dicyanomethylene)-2-methyl-6-(julolidine-4-yl-vinyl)-4H-pyran (abbreviation: DCM2), N,N-dimethylquinacridone (abbreviation: DMQd), or rubrene can be used. Further, a phosphorescent substance that emits phosphorescence such as (acetylacetonato)bis[2,3-bis(4-fluorophenyl)quinoxalinato]iridium(III) (abbreviation: Ir(Fdpq)$_2$(acac)), 2,3,7,8,12,13,17,18-octaethyl-21H,23H-porphyrinplatinum(II) (abbreviation: PtOEP), or the like can be used.

Regarding the layers other than the third layer 105, the structure described in Embodiment Mode 2 can be appropriately used.

Embodiment Mode 5

In Embodiment Mode 5, a light emitting element with a structure different from the structures described in Embodiment Modes 2 and 3 will be described.

An anthracene derivative of the present invention has an excellent hole transporting property. Therefore, a layer including the anthracene derivative of the present invention can be provided between the anode and the light emitting layer. Specifically, the anthracene derivative of the present invention can be used in the first layer 103 or the second layer 104 described in Embodiment Mode 1.

Also, in a case of applying the anthracene derivative of the present invention for the first layer 103, it is preferable to use as a composite material the anthracene derivative of the present invention and an inorganic compound having an electron accepting property with respect to the anthracene derivative of the present invention. By using such a composite material, carrier density increases, which contributes to improvement of the hole injecting property and the hole transporting property. Also, in a case of using the composite material for the first layer 103, the first layer 103 can achieve an ohmic contact with the first electrode 102; therefore, a material of the first electrode 102 can be selected regardless of work function.

As the inorganic compound used for the composite material, an oxide of a transition metal is preferably used. Moreover, oxides of metals belonging to Groups 4 to 8 in the periodic table can be used. Specifically, it is preferable to use vanadium oxide, niobium oxide, tantalum oxide, chromium oxide, molybdenum oxide, tungsten oxide, manganese oxide, and rhenium oxide, because of their high electron accepting properties. Among them, molybdenum oxide is preferable because it is stable under air, has a low moisture absorption property, and is easily handled.

Note that this embodiment mode can be appropriately combined with any of the other embodiment modes.

Embodiment Mode 6

In Embodiment Mode 6, a light emitting element in which a plurality of light emitting units according to the present invention is stacked (hereinafter, referred to as a stacked type element) will be described with reference to FIG. 3. This light emitting element is a light emitting element that has a plurality of light emitting units between a first electrode and a second electrode.

Figure 3:
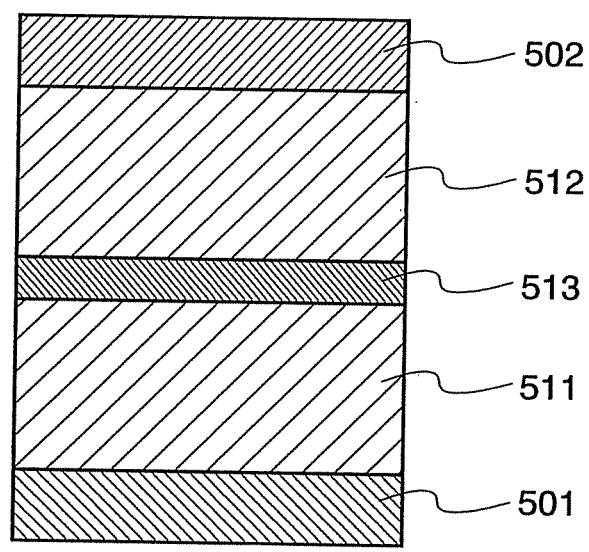
FIG. 3 shows a light emitting element according to the present invention.

In FIG. 3, a first light emitting unit 511 and a second light emitting unit 512 are stacked between a first electrode 501 and a second electrode 502. An electrode similar to that described in Embodiment Mode 2 can be applied to the first electrode 501 and the second electrode 502. The first light emitting unit 511 and the second light emitting unit 512 may have the same structure or different structures, and a structure similar to those described in Embodiment Modes 2 to 5 can be applied.

A charge generation layer 513 includes a composite material of an organic compound and metal oxide. The composite material of an organic compound and metal oxide is the composite material described in Embodiment Mode 2 or 5, and includes an organic compound and metal oxide such as $V_2O_5$, $MoO_3$, or $WO_3$. As the organic compound, various compounds such as an aromatic amine compound, a carbazole derivative, aromatic hydrocarbon, and a high molecular compound (oligomer, dendrimer, polymer, or the like) can be used. An organic compound having a hole mobility of greater than or equal to $10^{-6}$ cm$^2$/Vs is preferably applied as the hole transporting organic compound. However, other substances than these compounds may also be used as long as the hole transporting properties thereof are higher than the electron transporting properties thereof. The composite material of an organic compound and metal oxide is superior in carrier injecting property and carrier transporting property; therefore, low-voltage driving and low-current driving can be realized.

It is to be noted that the charge generation layer 513 may be formed with a combination of a composite material of an organic compound and metal oxide and another material. For example, the charge generation layer 513 may be formed with a combination of a layer including the composite material of an organic compound and metal oxide and a layer including one compound selected from electron donating substances and a compound having a high electron transporting property. Further, the charge generation layer 513 may be formed with a combination of a layer including the composite material of an organic compound and metal oxide and a transparent conductive film.

In any case, the charge generation layer 513, which is interposed between the first light emitting unit 511 and the second light emitting unit 512, is acceptable as long as electrons are injected to one of the light emitting units and holes are injected to the other of the light emitting units when a voltage is applied to the first electrode 501 and the second electrode 502.

In this embodiment mode, the light emitting element having two light emitting units is described; however, the present invention can be applied similarly to a light emitting element in which three or more light emitting units are stacked. By arranging a plurality of light emitting units between a pair of electrodes in such a manner that the plurality of light emitting units is partitioned with a charge generation layer as in the light emitting element of this embodiment mode, a long-life element which emits light at a high luminance and a low current density, can be realized. When the light emitting element is applied to a lighting device, since voltage drop owing to resistance of the electrode material can be small, uniform light emission from a large area is possible. Further, a light emitting device capable of low-voltage driving and low-power consumption can be realized.

This embodiment mode can be appropriately combined with any of the other embodiment modes.

Embodiment Mode 7

In Embodiment Mode 7, a light emitting device manufactured using an anthracene derivative of the present invention will be described.

Figure 4A:
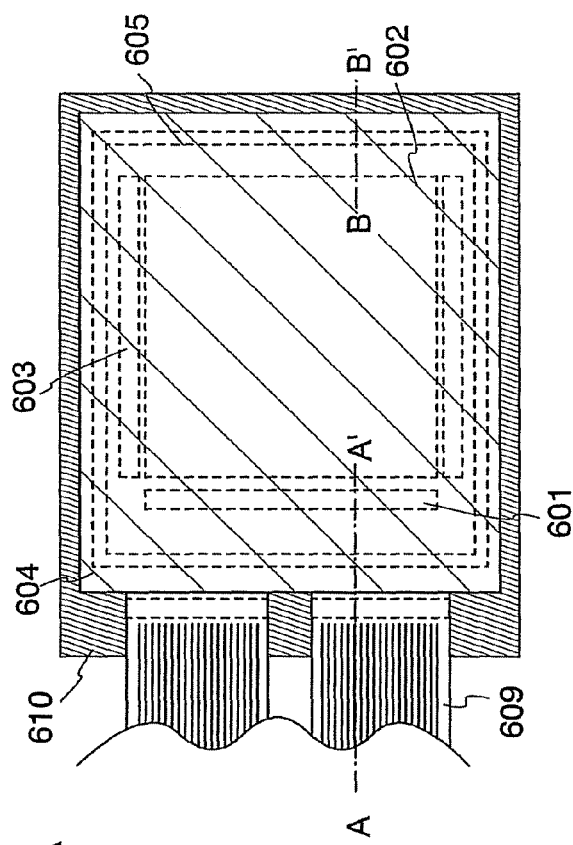
FIGS. 4A and 4B show a light emitting device according to the present invention.
Figure 4B:
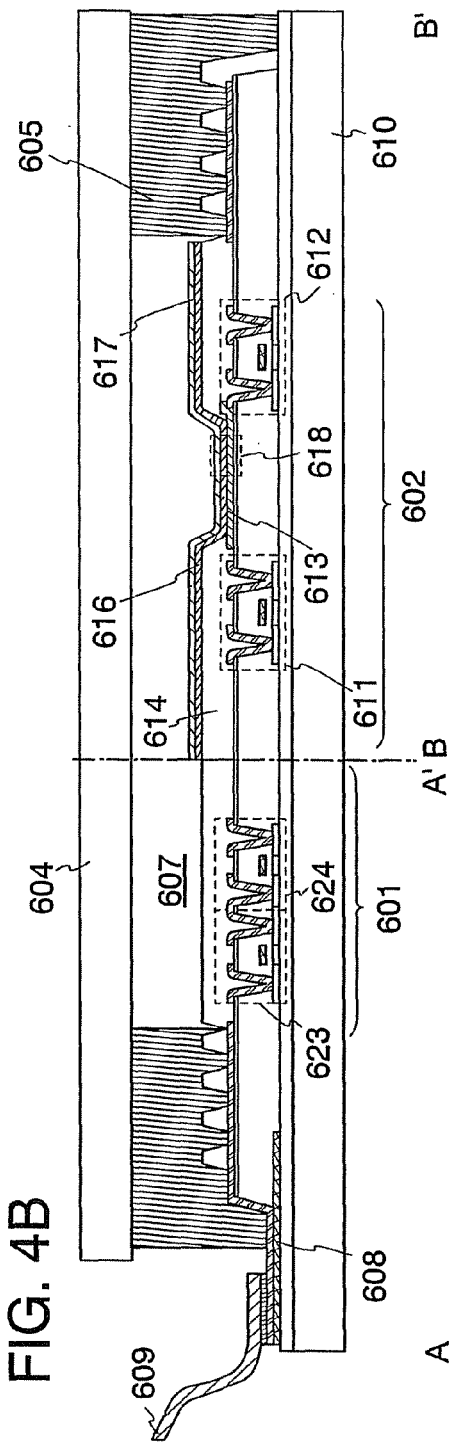

In this embodiment mode, a light emitting device manufactured using the anthracene derivative of the present invention will be described with reference to FIGS. 4A and 4B. FIG. 4A is a top view showing a light emitting device, and FIG. 4B is a cross-sectional view of FIG. 4A taken along lines A-A' and B-B'. A driver circuit portion (source side driver circuit) 601, a pixel portion 602, and a driver circuit portion (gate side driver circuit) 603, which are indicated by dotted lines, are included to control light emission of a light emitting element in this light emitting device. In addition, a sealing substrate and a sealing material are denoted by reference numerals 604 and 605, respectively, and a portion surrounded by the sealing material 605 corresponds to a space 607.

A leading wiring 608 is a wiring for transmitting a signal to be input to the source side driver circuit 601 and the gate side driver circuit 603, and this wiring 608 receives a video signal, a clock signal, a start signal, a reset signal, and the like from an FPC (flexible printed circuit) 609 that is an external input terminal. It is to be noted that only the FPC is shown here; however, the FPC may be provided with a printed wiring board (PWB). The light emitting device in this specification includes not only a light emitting device itself but also a light emitting device attached with an FPC or a PWB.

Next, a cross-sectional structure will be described with reference to FIG. 4B. The driver circuit portion and the pixel portion are formed over an element substrate 610. Here, the source side driver circuit 601, which is the driver circuit portion, and one pixel in the pixel portion 602 are shown.

A CMOS circuit which is a combination of an n-channel TFT 623 and a p-channel TFT 624 is formed as the source side driver circuit 601. The driver circuit may be formed using various circuits such as a CMOS circuit, a PMOS circuit, and an NMOS circuit. A driver-integration type device, in which a driver circuit is formed over a substrate over which a pixel portion is also formed, is described in this embodiment mode; however, a driver circuit is not necessarily formed over a substrate, over which a pixel portion is formed, and can be formed outside the substrate.

The pixel portion 602 has a plurality of pixels, each of which includes a switching TFT 611, a current controlling TFT 612, and a first electrode 613 which is electrically connected to a drain of the current controlling TFT 612. It is to be noted that an insulator 614 is formed so as to cover an end portion of the first electrode 613. Here, a positive photosensitive acrylic resin film is used for the insulator 614.

The insulator 614 is formed so as to have a curved surface having curvature at an upper end portion or a lower end portion thereof in order to obtain favorable coverage. For example, in a case of using positive photosensitive acrylic resin as a material for the insulator 614, the insulator 614 is preferably formed so as to have a curved surface with a curvature radius (0.2 μm to 3 μm) only at the upper end portion thereof. Either a negative type resin which becomes insoluble in an etchant by photo-irradiation or a positive type resin which becomes soluble in an etchant by photo-irradiation can be used for the insulator 614.

A layer 616 including a light emitting substance and a second electrode 617 are formed over the first electrode 613. Here, a material having a high work function is preferably used as a material for the first electrode 613 serving as an anode. For example, the first electrode 613 can be formed by using stacked layers of a titanium nitride film and a film including aluminum as its main component; a three-layer structure of a titanium nitride film, a film including aluminum as its main component, and a titanium nitride film; or the like as well as a single-layer film such as an ITO film, an indium tin oxide film including silicon, an indium oxide film including 2 to 20 wt % of zinc oxide, a titanium nitride film, a chromium film, a tungsten film, a Zn film, or a Pt film. When the first electrode 613 has a stacked structure, the first electrode 613 shows low resistance enough to serve as a wiring, giving an good ohmic contact, and can function as an anode.

In addition, the layer 616 including a light emitting substance is formed by various methods such as an evaporation method using an evaporation mask, an ink-jet method, and a spin coating method. The layer 616 including a light emitting substance has the anthracene derivative of the present invention described in Embodiment Mode 1. Further, the layer 616 including a light emitting substance may be formed using another material including a low molecular compound or a high molecular compound (including oligomer and dendrimer). As a material used for the EL layer, not only an organic compound but also an inorganic compound may be used.

As a material used for the second electrode 617, which is formed over the layer 616 including a light emitting substance and serves as a cathode, a material having a low work function (Al, Mg, Li, Ca, or an alloy or a compound thereof such as MgAg, MgIn, AlLi, LiF, or $CaF_2$) is preferably used. In a case where light generated in the layer 616 including a light emitting substance is transmitted through the second electrode 617, stacked layers of a metal thin film and a transparent conductive film (ITO, indium oxide including 2 to 20 wt % of zinc oxide, indium oxide-tin oxide including silicon or silicon oxide, zinc oxide (ZnO), or the like) are preferably used as the second electrode 617.

By attachment of the sealing substrate 604 to the element substrate 610 with the sealing material 605, a structure where a light emitting element 618 is provided in the space 607 surrounded by the element substrate 610, the sealing substrate 604, and the sealing material 605 is formed. It is to be noted that the space 607 is filled with a filler; there is a case where an inert gas (nitrogen, argon, or the like) is used or a case where the sealing material 605 is used.

It is to be noted that an epoxy-based resin is preferably used as the sealing material 605. It is desired that the material allows as little moisture and oxygen as possible to penetrate. As the sealing substrate 604, a plastic substrate formed using FRP (Fiberglass-Reinforced Plastics), PVF (polyvinyl fluoride), polyester, acrylic resin, or the like can be used as well as a glass substrate or a quartz substrate.

By the above-described process, a light emitting device having the anthracene derivative of the present invention can be obtained.

Since the anthracene derivative described in Embodiment Mode 1 is used for the light emitting device of the present invention, the light emitting device can have favorable characteristics. Specifically, a light emitting device capable of light emission with a high luminous efficiency can be obtained.

Further, since the anthracene derivative of the present invention has a high luminous efficiency, a light emitting device with low power consumption can be obtained.

Figure 5A:
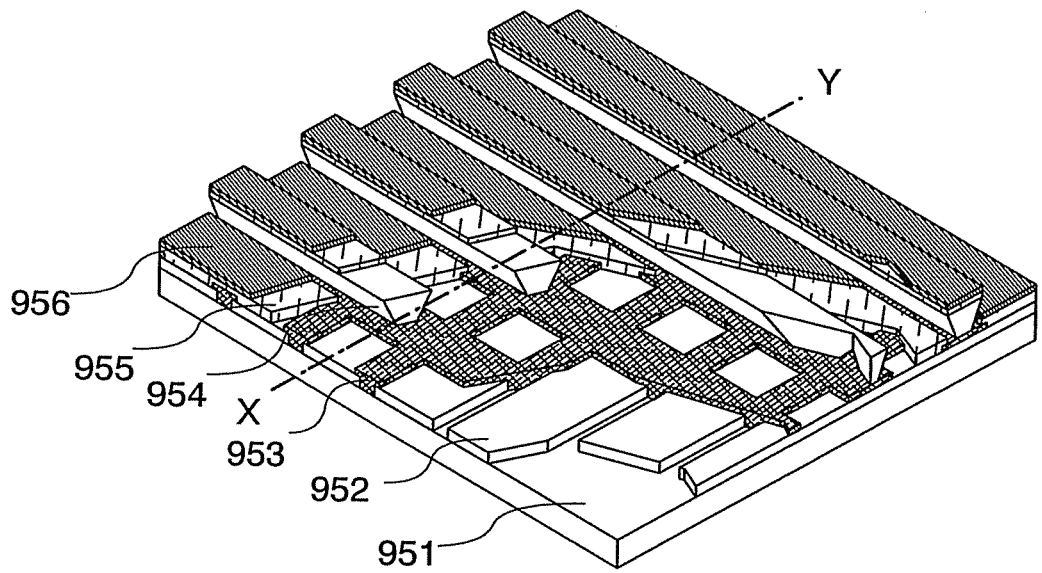
FIGS. 5A and 5B show a light emitting device according to the present invention.
Figure 5B:
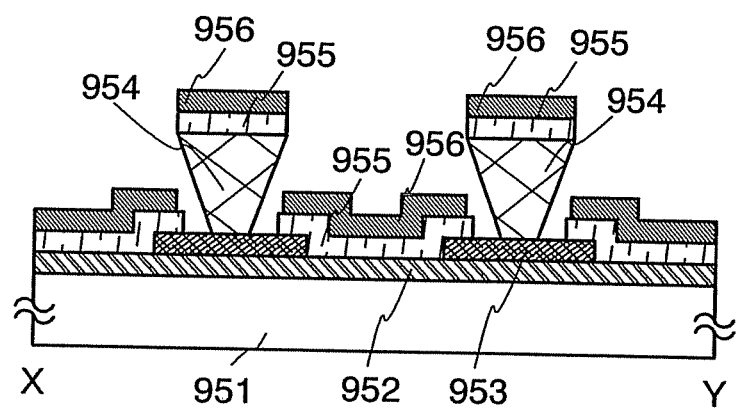

As described above, in this embodiment mode, an active matrix type light emitting device in which driving of a light emitting element is controlled by a transistor is described. Alternatively, a passive matrix type light emitting device may also be used. FIG. 5 shows a perspective view of a passive matrix type light emitting device which is manufactured by applying the present invention. In FIG. 5, a layer 955 including a light emitting substance is provided between an electrode 952 and an electrode 956 over a substrate 951. An end portion of the electrode 952 is covered with an insulating layer 953. Then, a partition layer 954 is provided over the insulating layer 953. A side wall of the partition layer 954 slopes so that a distance between one side wall and the other side wall becomes narrow toward a substrate surface. In other words, a cross section of the partition layer 954 in the direction of a short side is trapezoidal, and a base (a side extending in a similar direction as a plane direction of the insulating layer 953 and in contact with the insulating layer 953) is shorter than an upper side (a side extending in a similar direction as the plane direction of the insulating layer 953 and not in contact with the insulating layer 953). The partition layer 954 provided in this manner can prevent a defect of the light emitting element owing to static electricity or the like. A light emitting device with a long lifetime can be obtained in the case where the light emitting device is passive matrix type by using the light emitting element of the present invention. Further, a light emitting device with low power consumption can be obtained.

Embodiment Mode 8

In Embodiment Mode 8, an electronic device of the present invention including the light emitting device described in Embodiment Mode 7 will be described. The electronic device of the present invention includes the anthracene derivative described in Embodiment Mode 1, and has a display portion with a long lifetime. Also, the electronic device of the present invention possesses a display portion with reduced power consumption.

As an electronic device including a light emitting element manufactured using the anthracene derivative of the present invention, a camera such as a video camera or a digital camera, a goggle type display, a navigation system, an audio reproducing device (car audio component stereo, audio component stereo, or the like), a computer, a game machine, a portable information terminal (mobile computer, mobile phone, portable game machine, electronic book, or the like), and an image reproducing device provided with a recording medium (specifically, a device capable of reproducing a recording medium such as a Digital Versatile Disc (DVD) and provided with a display device that can display the image), and the like are given. Specific examples of these electronic devices are shown in FIGS. 6A to 6D.

Figure 6A:
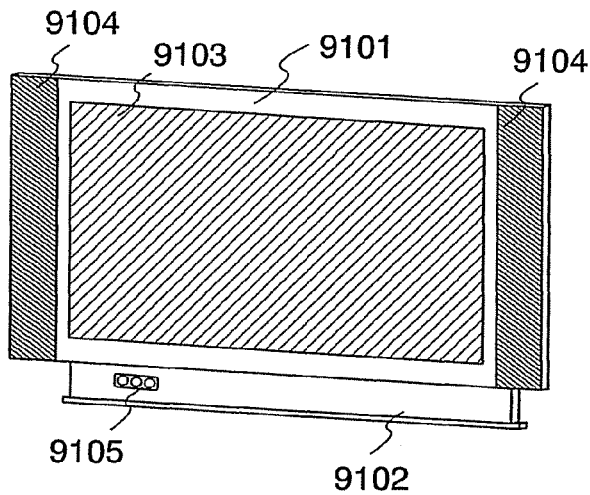
FIGS. 6A to 6D show electronic devices according to the present invention.

FIG. 6A shows a television device according to the present invention, which includes a housing 9101, a supporting base 9102, a display portion 9103, speaker portions 9104, a video input terminal 9105, and the like. In the television device, the display portion 9103 has light emitting elements similar to those described in Embodiment Modes 2 to 5, and the light emitting elements are arranged in matrix. The features of the light emitting element are exemplified by a high luminous efficiency and a low driving voltage. The light emitting element also has a feature of excellent heat resistance. The display portion 9103 which includes the light emitting element has similar features. Therefore, in the television device, image quality is scarcely deteriorated and light emission with a high luminance and low power consumption are achieved. Therefore, deterioration compensation function circuits and power supply circuits can be significantly reduced or downsized in the television device, which enables reduction in size and weight of the housing 9101 and the supporting base 9102. In the television device according to the present invention, low power consumption, high image quality, and reduction in size and weight are achieved; therefore, a product which is suitable for living environment can be provided. Further, since the anthracene derivative described in Embodiment Mode 1 is capable of green light emission, a full-color display is possible, and a television device having a display portion with a long life can be obtained.

Figure 6B:
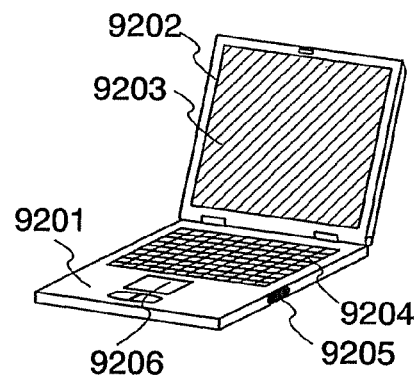

FIG. 6B shows a computer according to the present invention, which includes a main body 9201, a housing 9202, a display portion 9203, a keyboard 9204, an external connection port 9205, a pointing device 9206, and the like. In the computer, the display portion 9203 has light emitting elements similar to those described in Embodiment Modes 2 to 5, and the light emitting elements are arranged in matrix. The features of the light emitting element are a high luminous efficiency and a low driving voltage. In addition, the light emitting element also has a feature of excellent heat resistance. The display portion 9203 which includes the light emitting element has similar features. Therefore, in the computer, image quality is scarcely deteriorated and light emission with a high luminance and low power consumption are achieved. Due to these features, deterioration compensation function circuits and power supply circuits can be significantly reduced or downsized in the computer; therefore, reduction in size and weight of the main body 9201 and the housing 9202 can be achieved. In the computer according to the present invention, low power consumption, high image quality, and reduction in size and weight are achieved; therefore, a product which is suitable for the environment can be provided. Further, since the anthracene derivative described in Embodiment Mode 1 is capable of green light emission, a full-color display is possible, and a computer having a display portion with a long lifetime can be obtained.

Figure 6C:
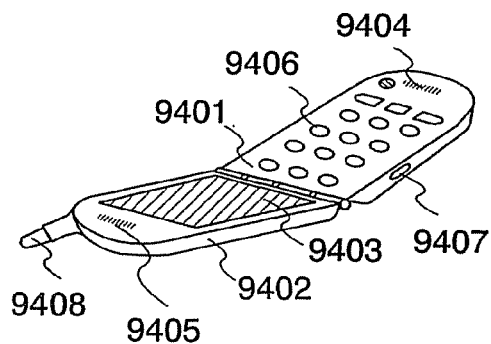

FIG. 6C shows a mobile phone according to the present invention, which includes a main body 9401, a housing 9402, a display portion 9403, an audio input portion 9404, an audio output portion 9405, an operation key 9406, an external connection port 9407, an antenna 9408, and the like. In the mobile phone, the display portion 9403 has light emitting elements similar to those described in Embodiment Modes 2 to 5, and the light emitting elements are arranged in matrix. The features of the light emitting element are exemplified by a high luminous efficiency and a low driving voltage. The light emitting element also has a feature of excellent heat resistance. The display portion 9403 which includes the light emitting element has similar features. Therefore, in the mobile phone, image quality is scarcely deteriorated and light emission with a high luminance and low power consumption are achieved. Owing to these features, deterioration compensation function circuits and power supply circuits can be significantly reduced or downsized in the mobile phone; therefore, reduction in size and weight of the main body 9401 and the housing 9402 can be achieved. In the mobile phone according to the present invention, low power consumption, high image quality, and reduction in size and weight are achieved; therefore, a product which is suitable for carrying can be provided. Further, since the anthracene derivative described in Embodiment Mode 1 is capable of green light emission, a full-color display is possible, and a mobile phone having a display portion with a long lifetime can be obtained.

Figure 6D:
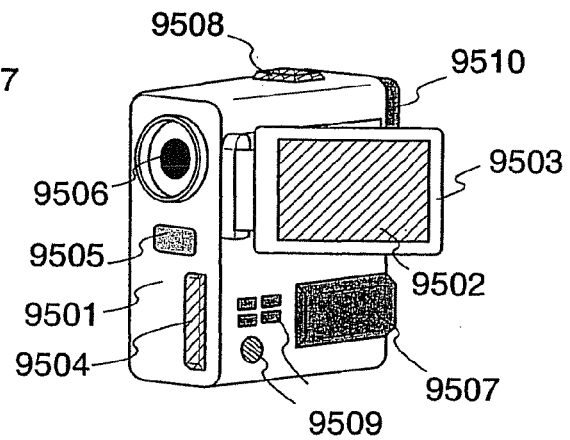

FIG. 6D shows a camera according to the present invention, which includes a main body 9501, a display portion 9502, a housing 9503, an external connection port 9504, a remote control receiving portion 9505, an image receiving portion 9506, a battery 9507, an audio input portion 9508, operation keys 9509, an eye piece portion 9510, and the like. In the camera, the display portion 9502 has light emitting elements similar to those described in Embodiment Modes 2 to 5, and the light emitting elements are arranged in matrix. The features of the light emitting element are a high luminous efficiency and a low driving voltage. The light emitting element also has a feature of excellent heat resistance. The display portion 9502 which includes the light emitting element has similar features. Therefore, in the camera, image quality is scarcely deteriorated and light emission with a high luminance and lower power consumption can be achieved. Owing to these features, deterioration compensation function circuits and power supply circuits can be significantly reduced or downsized in the camera; therefore, reduction in size and weight of the main body 9501 can be achieved. In the camera according to the present invention, low power consumption, high image quality, and reduction in size and weight are achieved; therefore, a product which is suitable for carrying can be provided. Further, the anthracene derivative described in Embodiment Mode 1 is capable of green light emission, full-color display is possible, and a camera having a display portion with a long lifetime can be obtained.

As described above, the applicable range of the light emitting device of the present invention is so wide that the light emitting device can be applied to electronic devices in various fields. By using the anthracene derivative of the present invention, an electronic device having a display portion with reduced power consumption can be provided. Further, an electronic device having a display portion with excellent heat resistance can be provided.

The light emitting device of the present invention can also be used as a lighting device. One mode using the light emitting element of the present invention as a lighting device will be described with reference to FIG. 7.

Figure 7:
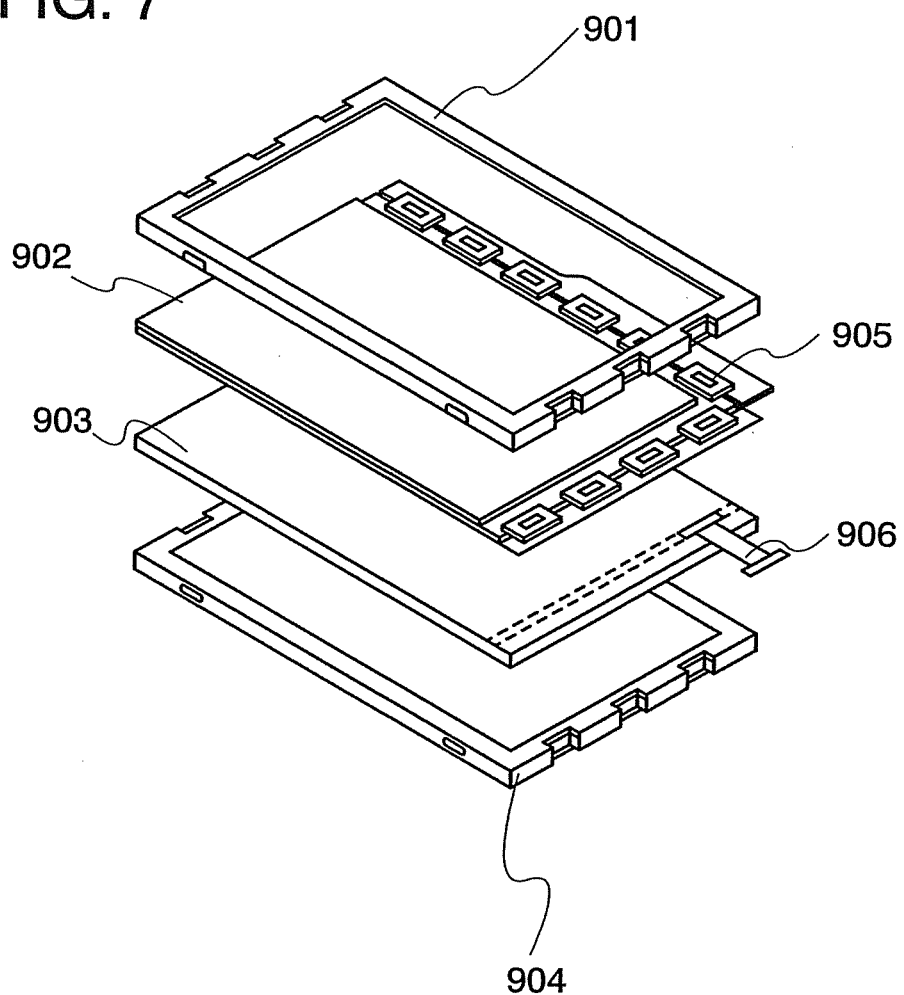
FIG. 7 shows an electronic device according to the present invention.

FIG. 7 shows an example of a liquid crystal display device using the light emitting device of the present invention as a backlight. The liquid crystal display device shown in FIG. 7 includes a housing 901, a liquid crystal layer 902, a backlight 903, and a housing 904, and the liquid crystal layer 902 is connected to a driver IC 905. The light emitting device of the present invention is used for the backlight 903, and current is supplied through a terminal 906.

By using the light emitting device of the present invention as the backlight of the liquid crystal display device, a backlight with reduced power consumption and a high luminous efficiency can be obtained. The light emitting device of the present invention is a lighting device with plane light emission, and can have a large area. Therefore, the backlight can have a large area, and a liquid crystal display device having a large area can be obtained. Furthermore, the light emitting device of the present invention has a thin shape and has low power consumption; therefore, a display device with a thin shape and low power consumption can also be achieved. Since the light emitting device of the present invention has excellent heat resistance, a liquid crystal display device using the light emitting device of the present invention also has excellent heat resistance. Further, since the light emitting device of the present invention is capable of light emission with a high luminance, a liquid crystal display device using the light emitting device of the present invention is also capable of light emission with a high luminance.

Figure 8:
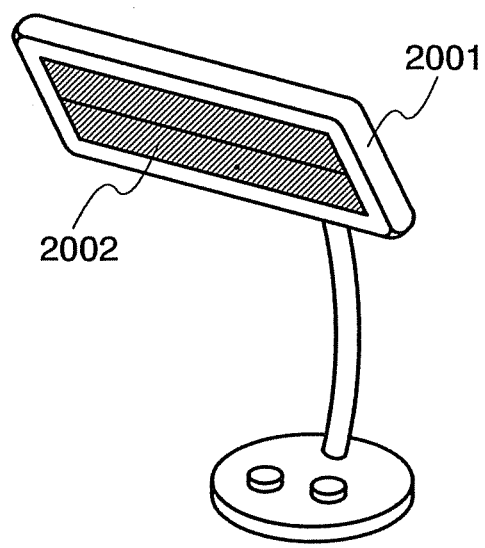
FIG. 8 shows a lighting device according to the present invention.

FIG. 8 shows an example where the light emitting device to which the present invention is applied is used as a table lamp, which is a lighting device. A table lamp shown in FIG. 8 has a housing 2001 and a light source 2002, and the light emitting device of the present invention is used as the light source 2002. The light emitting device of the present invention has a high luminous efficiency and low power consumption; therefore, a table lamp also has a high luminous efficiency and low power consumption.

Figure 9:
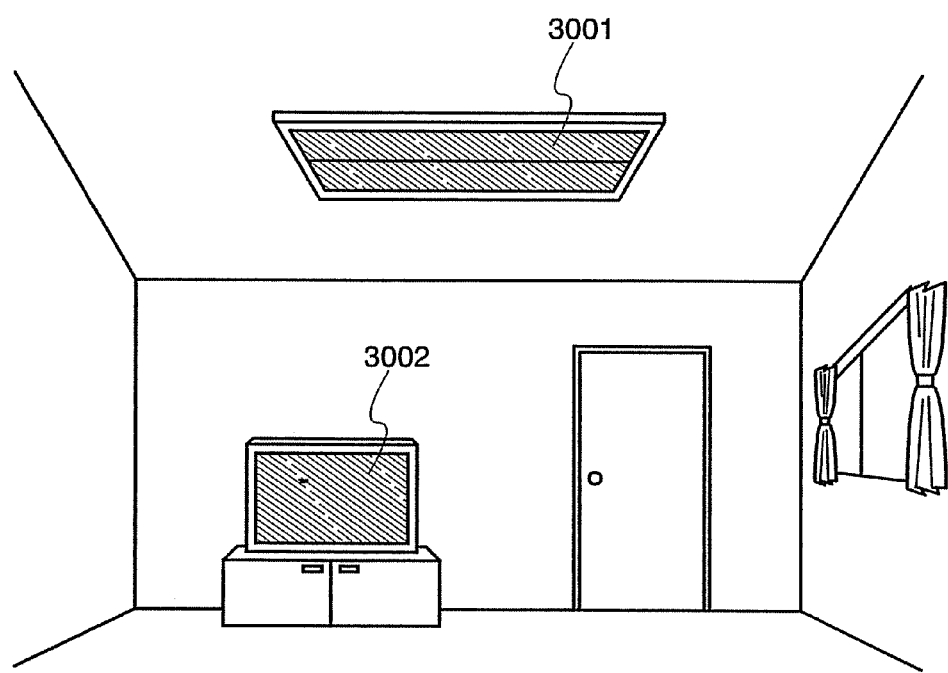
FIG. 9 shows a lighting device according to the present invention.

FIG. 9 shows an example where a light emitting device to which the present invention is applied is used as an indoor lighting device 3001. Since the light emitting device of the present invention can have a large area, the light emitting device of the present invention can be used as a lighting device having a large area. Further, the light emitting device of the present invention has a thin shape and consumes low power; therefore, the light emitting device of the present invention can be used as a lighting device having a thin shape and low power consumption. A television device 3002 according to the present invention as explained in FIG. 6A can be placed in a room where the light emitting device manufactured by the present invention is used as the indoor lighting device 3001, and public broadcasting and movies can be watched. In such a case, since both of the devices consume low power, a powerful image can be watched in a bright room without concern about electricity charges.

Example 1

Example 1 will specifically describe a synthetic method of 9-[N-phenyl-N-(9-phenylcarbazol-3-yl)amino]-10-phenylanthracene (abbreviation: PCAPhA), which is an anthracene derivative of the present invention represented by Structural Formula (201).

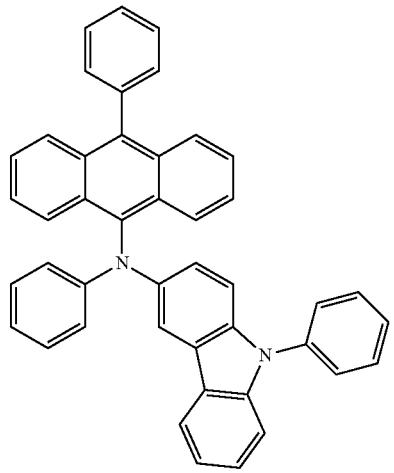

(201)

[Step 1] Synthesis of N,9-diphenyl-9H-carbazol-3-amine (abbreviation: PCA)

(i) Synthesis of 3-bromo-9-phenylcarbazole

A synthetic scheme of 3-bromo-9-phenylcarbazole is shown in (B-1).

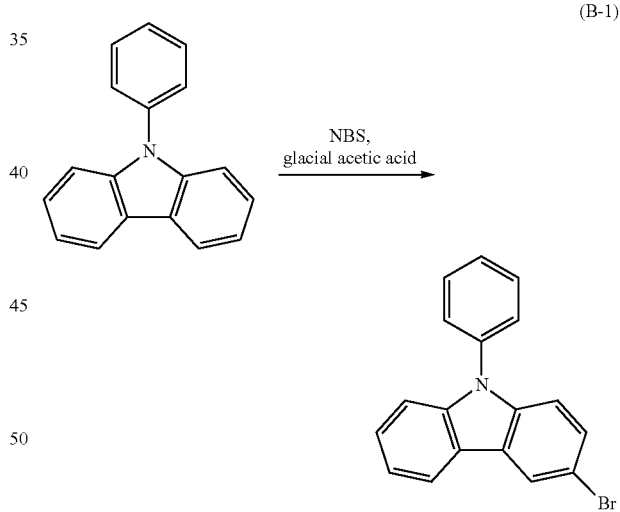

(B-1)

24.3 g (100 mmol) of 9-phenylcarbazole was put into a 2 L Meyer flask, and dissolved in 600 mL of glacial acetic acid. Then, 17.8 g (100 mmol) of N-bromosuccinimide was slowly added thereto, and the solution was stirred for about 12 hours at room temperature. This glacial acetic acid solution was dropped into 1 L of ice water while being stirred. A white solid precipitated was collected by suction filtration, and then washed with water three times. This solid was dissolved in 150 mL of diethyl ether, and the solution was washed with a saturated aqueous solution of sodium bicarbonate and then with water. The organic layer was dried with magnesium sulfate, the mixture was filtered, and the filtrate was concentrated. Thus, an oily substance was obtained. The oily substance was dissolved in about 50 mL of methanol. A precipitate of a white solid was produced by keeping this solution still. This solid was collected by suction filtration and dried. Then, 28.4 g (88% yield) of 3-bromo-9-phenylcarbazole was obtained as white powder.

(ii) Synthesis of N,9-diphenyl-9H-carbazol-3-amine (abbreviation: PCA)

A synthetic scheme of N,9-diphenyl-9H-carbazol-3-amine (abbreviation: PCA) is shown in (B-2).

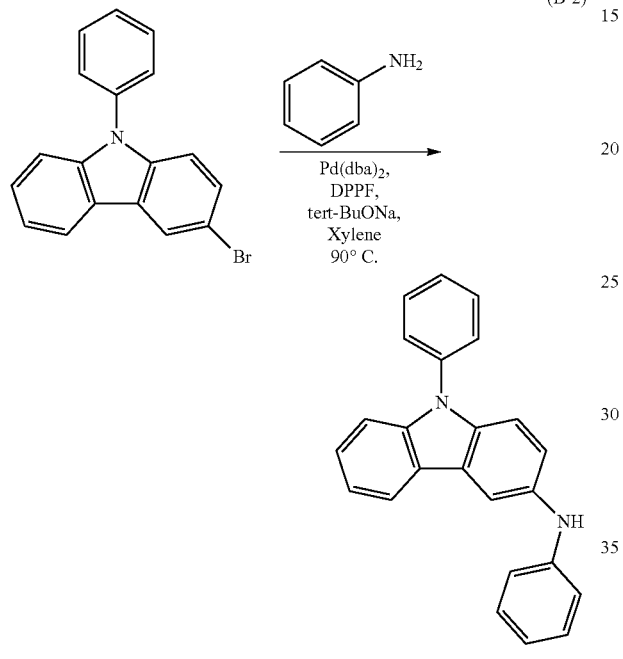

(B-2)

Into a 500 mL three-neck flask were added 19 g (60 mmol) of 3-bromo-9-phenylcarbazole, 340 mg (0.6 mmol) of bis(dibenzylideneacetone)palladium(0), 1.6 g (3.0 mmol) of 1,1-bis(diphenylphosphino)ferrocene, and 13 g (180 mmol) of sodium-tert-butoxide, and the atmosphere in the flask was substituted by nitrogen. Thereafter, 110 mL of dehydrated xylene and 7.0 g (75 mmol) of aniline were added to the mixture. This mixture was heated and stirred at 90° C. for 7.5 hours under nitrogen. After the reaction was completed, about 500 mL of hot toluene was added to the reacted mixture, and this mixture was filtered through Florisil, alumina, and celite. An oily substance was obtained by concentration of the filtrate, and hexane and ethyl acetate were added to the substance, which was followed by irradiation with ultrasound. A solid precipitated was collected by suction filtration and dried to give 15 g (75% yield) of N-phenyl-(9-phenyl-9H-carbazol-3-yl)amine (abbreviation: PCA) as cream colored powder. By a nuclear magnetic resonance measurement (NMR), it was confirmed that this compound was N,9-diphenyl-9H-carbazol-3-amine (abbreviation: PCA).

Figure 10A:
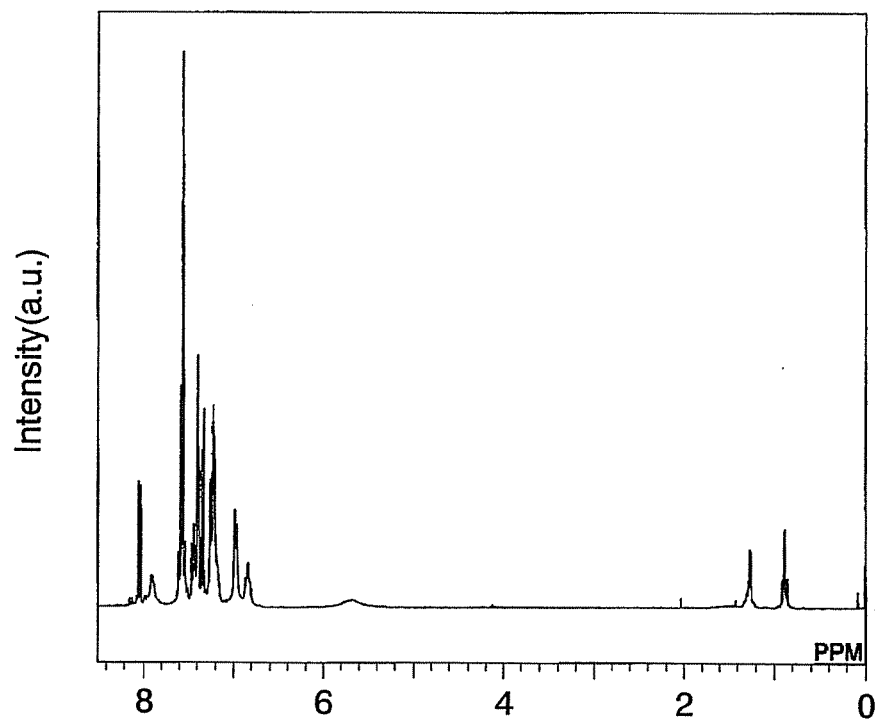
FIGS. 10A and 10B show $^1$H NMR charts of N-phenyl-(9-phenyl-9H-carbazol-3-yl)amine (abbreviation: PCA)
Figure 10B:
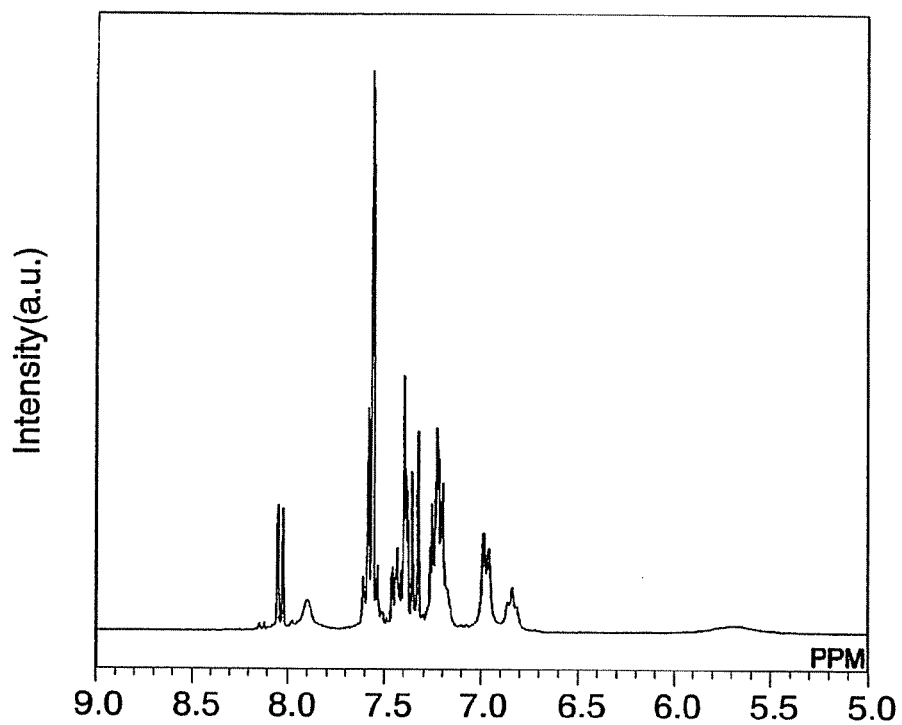

$^1$H NMR data of this compound is shown below. $^1$H NMR (300 MHz, CDCl$_3$); 6.84 (t, J=6.9 Hz, 1H), 6.97 (d, J=7.8 Hz, 2H), 7.20-7.61 (m, 13H), 7.90 (s, 1H), 8.04 (d, J=7.8 Hz, 1H). The $^1$H NMR chart is shown in FIGS. 10A and 10B. Note that the range of 5.0 ppm to 9.0 ppm in FIG. 10A is expanded and shown in FIG. 10B.

[Step 2] Synthesis of PCAPhA

A synthetic scheme of PCAPhA is shown in (B-3).

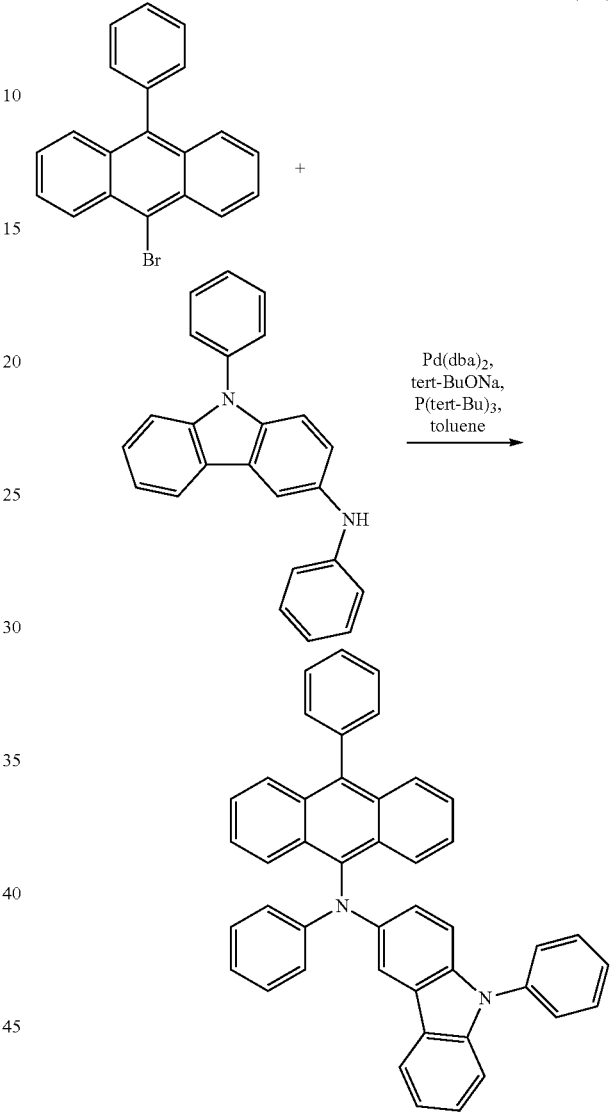

(B-3)

Into a 100 mL three-neck flask were added 501 mg (1.5 mmol) of 9-bromo-10-phenylanthracene, 504 mg (1.5 mmol) of N,9-diphenyl-9H-carbazol-3-amine (abbreviation: PCA), and 500 mg (5.2 mmol) of sodium-tert-butoxide, and the atmosphere in the flask was substituted by nitrogen. Thereafter, 10 mL of toluene and 0.1 mL of tri(tert-butyl)phosphine (10 wt % hexane solution) were added to the mixture. This mixture was stirred under reduced atmosphere to be degassed. After degassing, 43 mg (0.075 mmol) of bis(dibenzylideneacetone)palladium(0) was added. This mixture was stirred at 80° C. for 3 hours under nitrogen. After the reaction, the mixture was added with about 20 mL of toluene and then washed with water. An aqueous layer was extracted with toluene, and the extracted solution was combined with an organic layer and washed with saturated saline. The organic layer was dried with magnesium sulfate, this mixture was naturally filtered, and the filtrate was concentrated. A solid obtained was purified by silica gel column chromatography (developing solvent; hexane:toluene=7:3). Recrystallization of the obtained solid with a mixed solvent of chloroform and hexane gave 514 mg of 9-[N-phenyl-N-(9-phenylcarbazol-3-yl)amino]-10-phenylanthracene (abbreviation: PCAPhA) as yellow powder in 67% yield.

Figure 11:
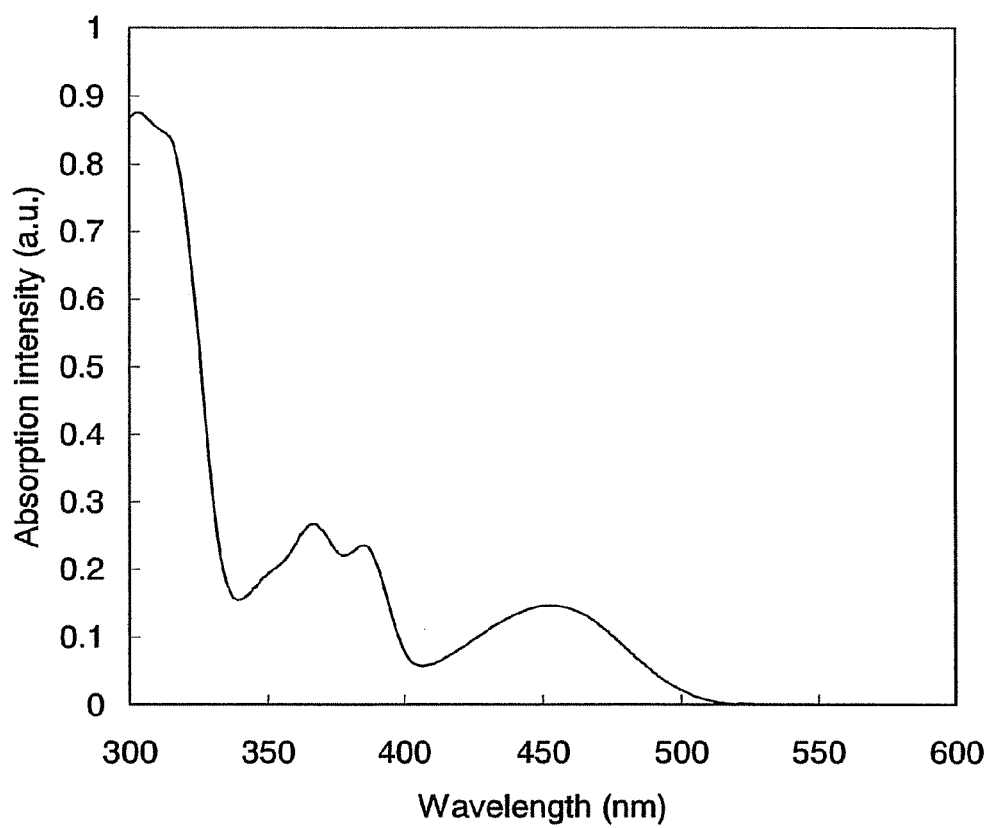
FIG. 11 shows an absorption spectrum of a toluene solution of 9-[N-phenyl-N-(9-phenylcarbazol-3-yl)amino]-10-phenylanthracene (abbreviation: PCAPhA)
Figure 12:
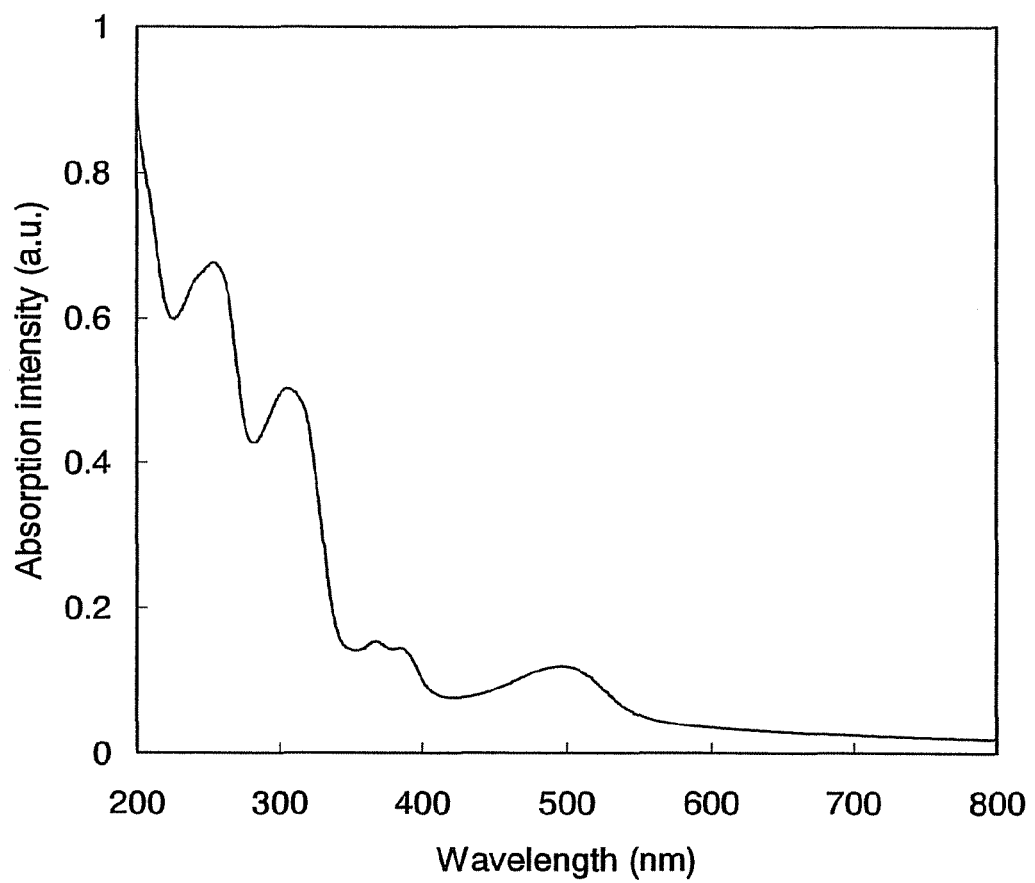
FIG. 12 shows an absorption spectrum of a thin film of 9-[N-phenyl-N-(9-phenylcarbazol-3-yl)amino]-10-phenylanthracene (abbreviation: PCAPhA)
Figure 13:
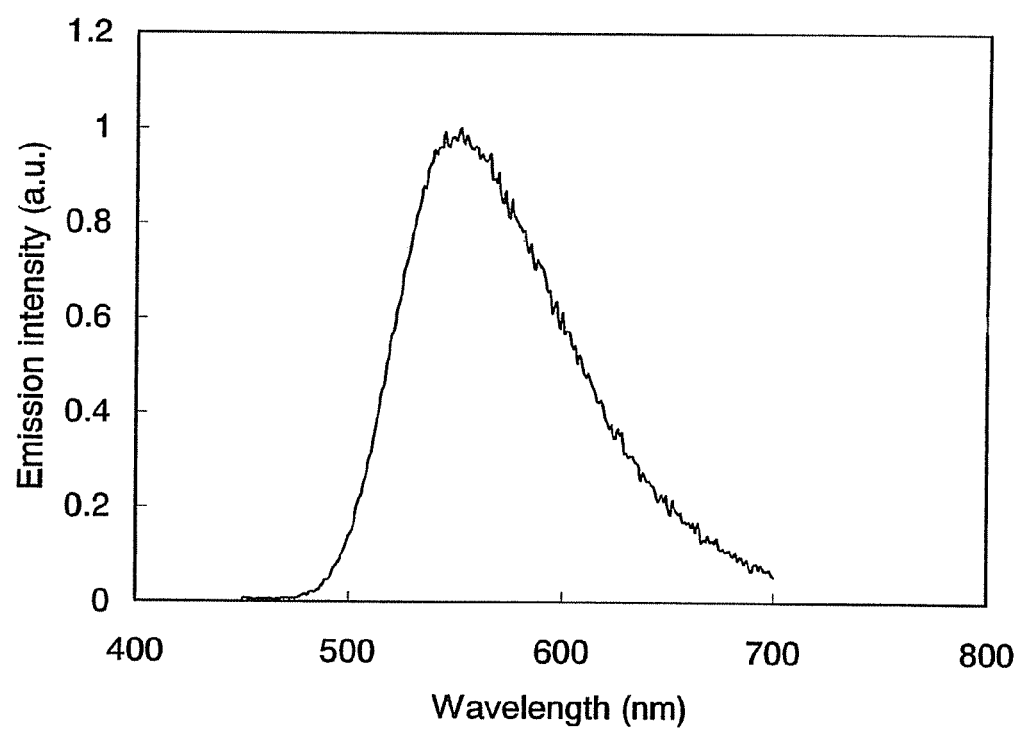
FIG. 13 shows an emission spectrum of a toluene solution of 9-[N-phenyl-N-(9-phenylcarbazol-3-yl)amino]-10-phenylanthracene (abbreviation: PCAPhA)
Figure 14:
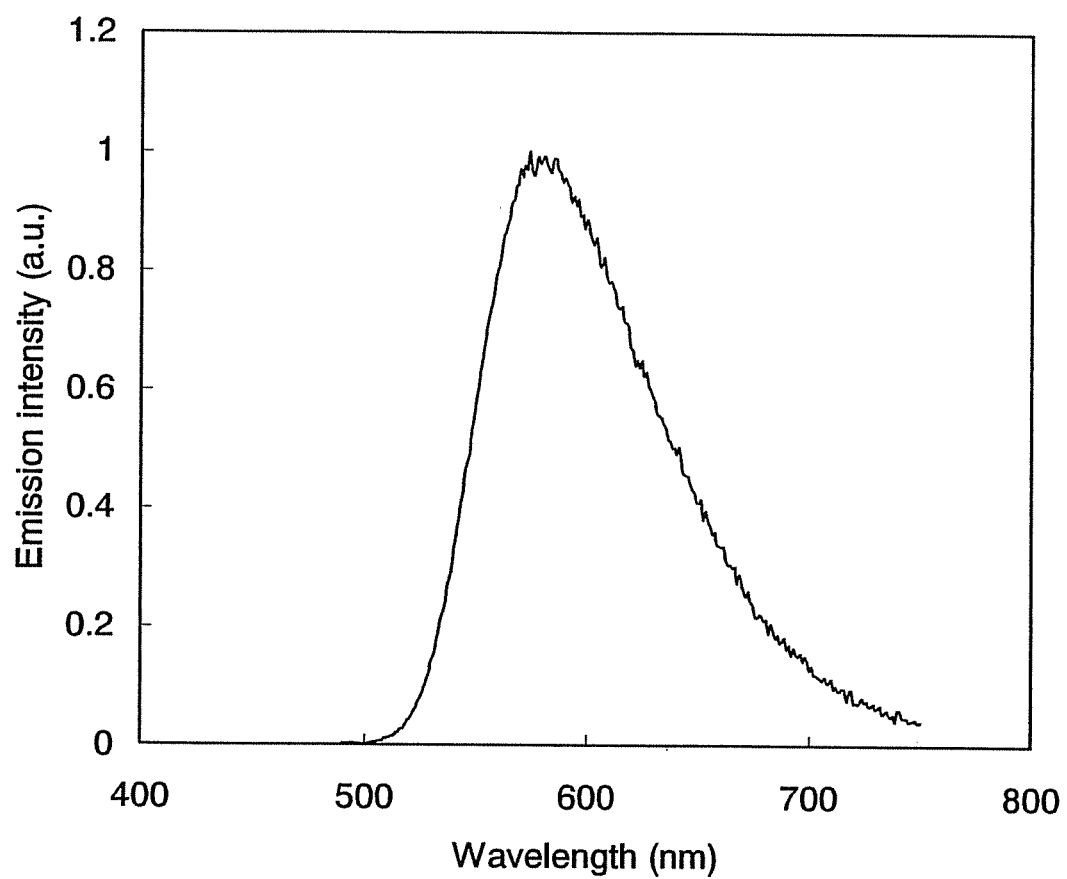
FIG. 14 shows an emission spectrum of a thin film of 9-[N-phenyl-N-(9-phenylcarbazol-3-yl)amino]-10-phenylanthracene (abbreviation: PCAPhA)

The absorption spectrum of a toluene solution of PCAPhA is shown in FIG. 11. In addition, an absorption spectrum of a thin film of PCAPhA is shown in FIG. 12. An ultraviolet-visible spectrophotometer (type V550, manufactured by Japan Spectroscopy Corporation) was used for measurement. The solution was put into a quartz cell and the thin film sample was manufactured by vapor deposition of PCAPhA on a quartz substrate. The absorption spectra thereof, from each of which the absorption spectrum of quartz was subtracted, are shown in FIGS. 11 and 12. In each of FIGS. 11 and 12, the horizontal axis shows wavelength (nm) and the vertical axis shows absorption intensity (an arbitrary unit). In the case of the toluene solution, absorption was observed at around 450 nm, and in the case of the thin film, absorption was observed at around 497 nm. Further, an emission spectrum of the toluene solution (excitation wavelength of 370 nm) of PCAPhA is shown in FIG. 13, and an emission spectrum of the thin film (excitation wavelength of 480 nm) of PCAPhA is shown in FIG. 14. In each of FIGS. 13 and 14, the horizontal axis shows wavelength (nm) and the vertical axis shows emission intensity (an arbitrary unit). In the case of the toluene solution, the maximum light emission wavelength was 552 nm (excitation wavelength of 370 nm), and in the case of the thin film, the maximum emission wavelength was 574 nm (excitation wavelength of 480 nm).

The HOMO level of PCAPhA in a thin film state which was measured by a photoelectron spectrometer (AC-2, manufactured by Riken Keiki Co., Ltd.) under air was −5.33 eV. By the absorption edge obtained from a Tauc plot of the absorption spectrum of the thin film of PCAPhA shown in FIG. 12, the optical energy gap was estimated to be 2.27 eV, which means that LUMO level of PCAPhA is −3.06 eV.

An oxidation-reduction characteristic of PCAPhA was measured by a cyclic voltammetry (CV) measurement. For the measurement, an electrochemical analyzer (ALS model 600A, manufactured by BAS Inc.) was used.

As for a solution used in the CV measurement, dehydrated dimethylformamide (DMF) (manufactured by Aldrich, 99.8%, catalog number: 22705-6) was used as a solvent. Tetra-n-butylammonium perchlorate (n-Bu$_4$NClO$_4$) (manufactured by Tokyo Chemical Industry Co., Ltd., catalog number: T0836), which is a supporting electrolyte, was dissolved in DMF at a concentration of 100 mmol/L to prepare the electrolysis solution. The sample solution was prepared by dissolving the measurement object in the electrolysis solution to be at a concentration of 1 mmol/L. A platinum electrode (a PTE platinum electrode, manufactured by BAS Inc.) was used as a working electrode. A platinum electrode (a VC-3 Pt counter electrode (5 cm), manufactured by BAS Inc.) was used as a counter electrode. An Ag/Ag$^+$ electrode (an RE5 non-aqueous solvent type reference electrode, manufactured by BAS Inc.) was used as a reference electrode. The measurement was conducted at room temperature.

The oxidation characteristic of PCAPhA was evaluated in the following manner. The potential of the working electrode with respect to the reference electrode was shifted from −0.17 V to 0.80 V, which was followed by shifting the potential from 0.80 V to −0.17 V. This cycle was set as one cycle, and 100 cycles were performed. In addition, the reduction characteristic of PCAPhA was evaluated in the following manner. The potential of the working electrode with respect to the reference electrode was shifted from −0.07 V to −2.50 V, which was followed by shifting the potential from −2.50 V to −0.07 V. This cycle was set as one cycle, and 100 cycles were performed. The scanning rate of the CV measurement was set to be 0.1 V/s.

Figure 15:
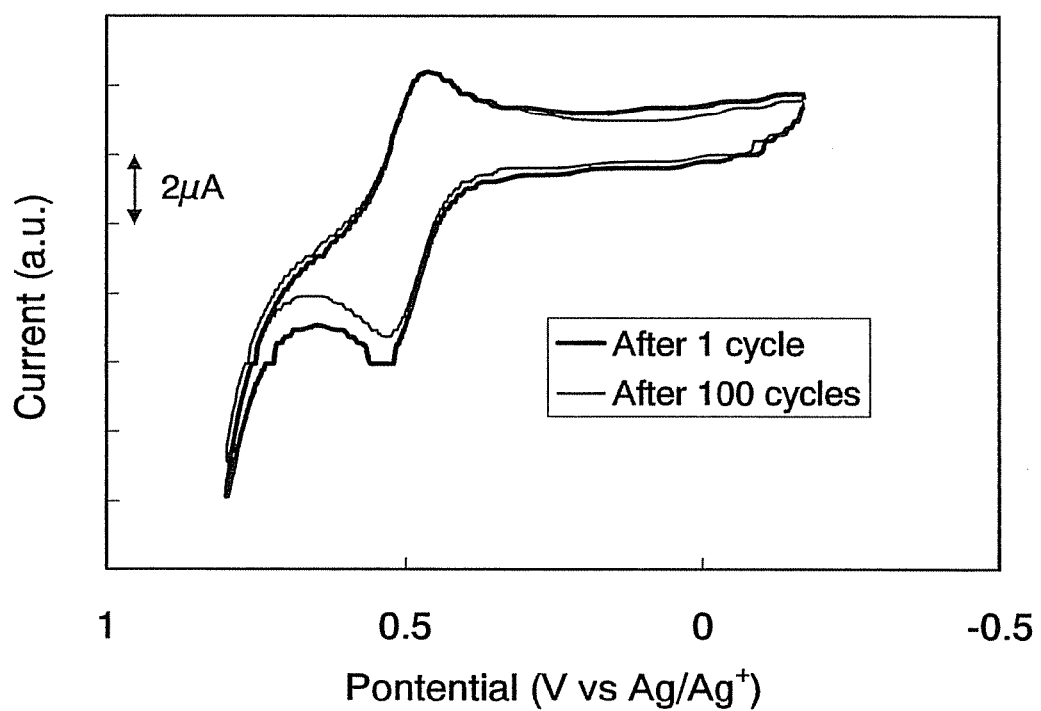
FIG. 15 shows a CV measurement result of an oxidation side of 9-[N-phenyl-N-(9-phenylcarbazol-3-yl)amino]-10-phenylanthracene (abbreviation: PCAPhA)
Figure 16:
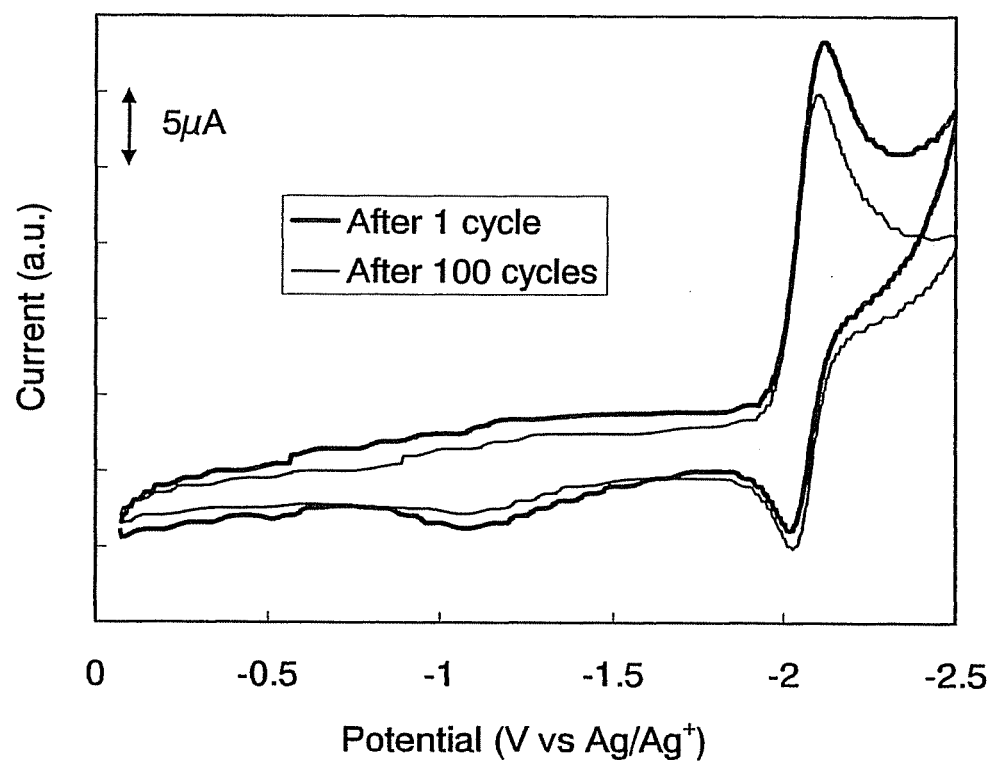
FIG. 16 shows a CV measurement of a reduction side of 9-[N-phenyl-N-(9-phenylcarbazol-3-yl)amino]-10-phenylanthracene (abbreviation: PCAPhA)

The CV measurement result of oxidation of PCAPhA and the CV measurement result of reduction of PCAPhA are shown in FIGS. 15 and 16, respectively. In each of FIGS. 15 and 16, the horizontal axis shows a potential (V) of the working electrode with respect to the reference electrode, and the vertical axis shows a current value (μA) that flowed between the working electrode and the counter electrode. From FIG. 15, a current exhibiting oxidation was observed around 0.53 V (vs. Ag/Ag$^+$ electrode). From FIG. 16, a current exhibiting reduction was observed around −2.11 V (vs. Ag/Ag$^+$ electrode).

In spite of the fact that as many as 100 cycles of shifting were performed, a peak position and a peak intensity of the CV curve scarcely changed in the oxidation and reduction, which reveals that the anthracene derivative of the present invention is extremely stable against repetition of oxidation and reduction.

Example 2

Example 2 will specifically describe a synthetic method of 9,10-bis[N-phenyl-N-(9-phenylcarbazol-3-yl)amino]anthracene (abbreviation: PCA2A), that is an anthracene derivative of the present invention represented by Structural Formula (238).

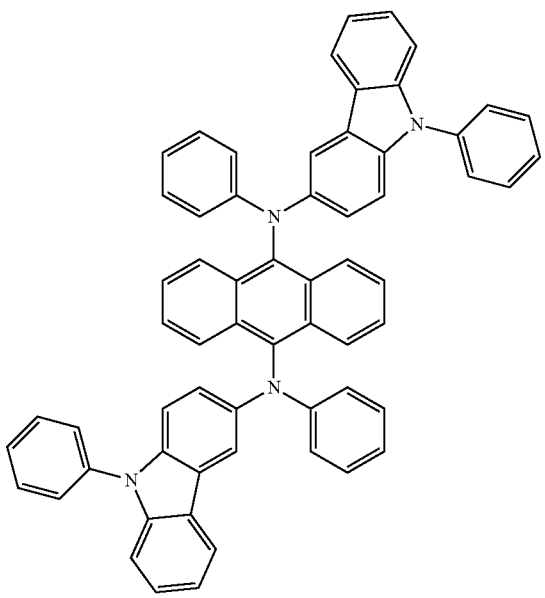

(238)

[Step 1] Synthesis of PCA2A

A synthetic scheme of PCA2A is shown in (B-4).

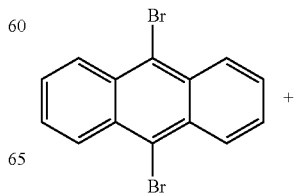

(B-4)

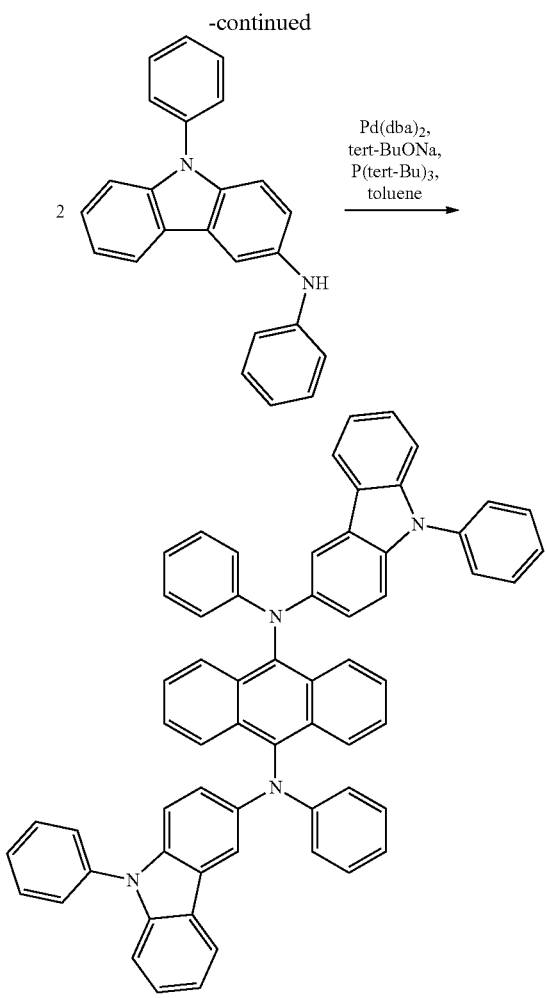

Into a 100 mL three-neck flask were added 835 mg (2.5 mmol) of 9,10-dibromoanthracene, 1.7 g (5.0 mmol) of N,9-diphenyl-9H-carbazol-3-amine (abbreviation: PCA), and 1.0 g (10 mmol) of sodium-tert-butoxide, and the atmosphere in the flask was substituted by nitrogen. Thereafter, 25 mL of toluene and 0.1 mL of tri(tert-butyl)phosphine (10 wt % hexane solution) were added to the mixture. This mixture was stirred under reduced atmosphere to be degassed. After degassing, 72 mg (0.13 mmol) of bis(dibenzylideneacetone)palladium(0) was added. This mixture was stirred at 80° C. for 5 hours under nitrogen. After the reaction, the mixture was added with about 20 mL of toluene and then washed with water. An aqueous layer was extracted with toluene, and the extracted solution was combined with an organic layer and washed with saturated saline. The organic layer was dried with magnesium sulfate, this mixture was naturally filtered, and the filtrate was concentrated. A solid obtained was purified by silica gel column chromatography (developing solvent; hexane:toluene=7:3). Recrystallization of the obtained solid with a mixed solvent of dichloromethane and hexane gave 1.4 g of 9,10-bis[N-phenyl-N-(9-phenylcarbazol-3-yl)amino]anthracene (abbreviation: PCA2A) as orange powder in 67% yield. By a nuclear magnetic resonance measurement, it was confirmed that this compound was 9,10-bis[N-phenyl-N-(9-phenylcarbazol-3-yl)amino]anthracene (abbreviation: PCA2A).

Figure 17A:
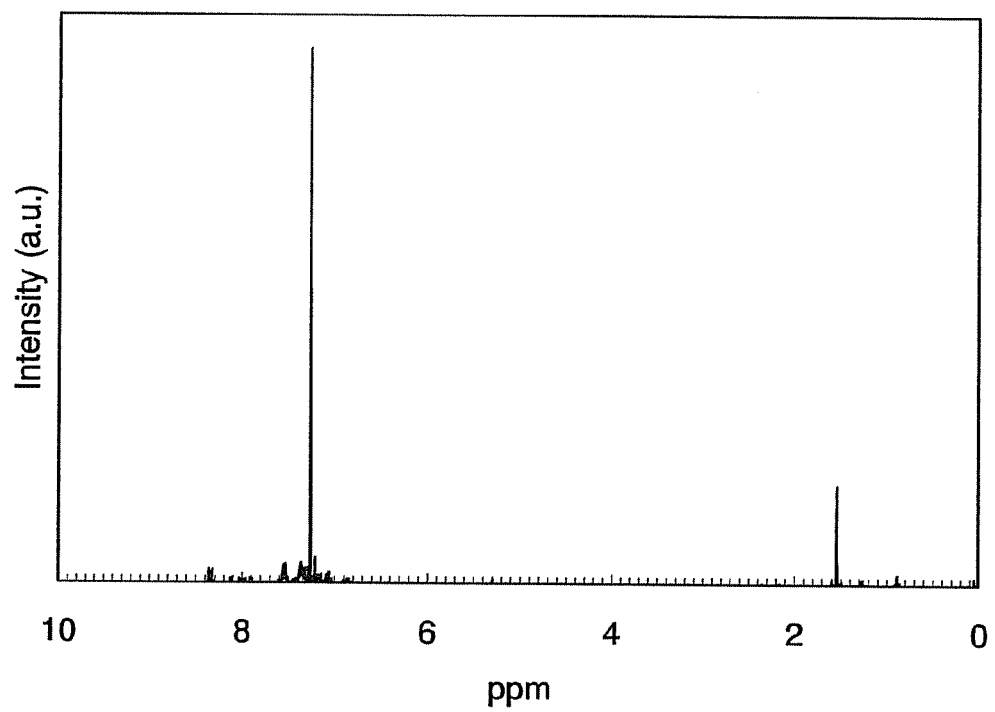
FIGS. 17A and 17B show $^1$H NMR charts of 9,10-bis[N-phenyl-N-(9-phenylcarbazol-3-yl)amino]anthracene (abbreviation: PCA2A)
Figure 17B:
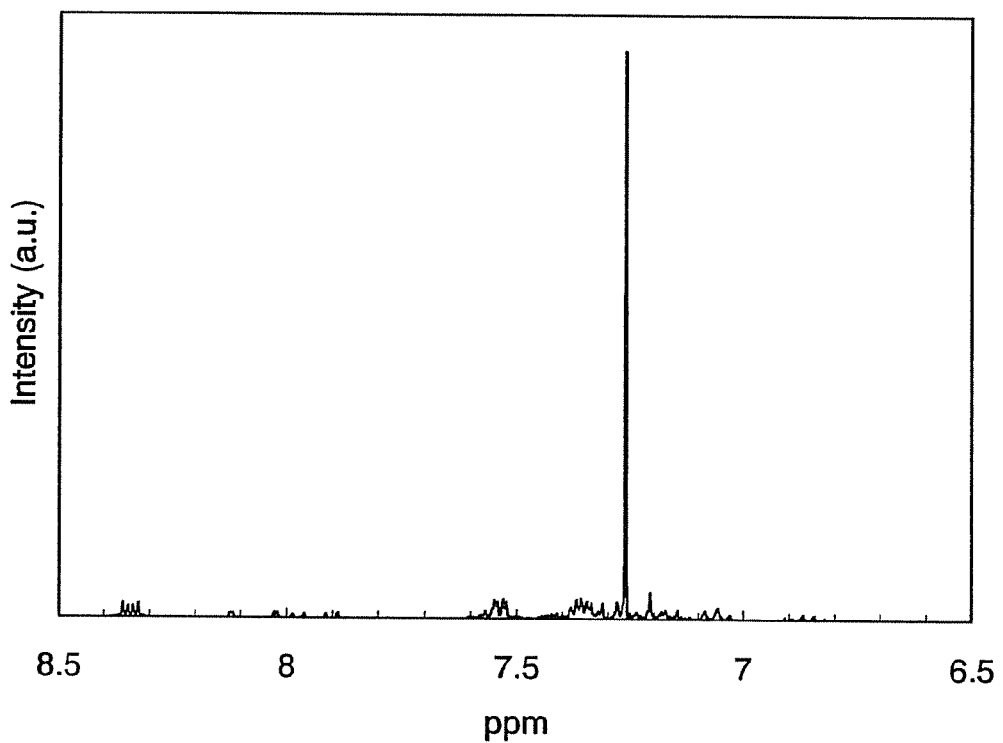

$^1$H NMR data of this compound is shown below. $^1$H NMR (300 MHz, CDCl$_3$) δ=6.82-6.90 (m, 2H), 7.03-7.21 (m, 10H), 7.28-7.60 (m, 22H), 7.90 (d, J=7.8 Hz, 1H), 7.97 (d, J=7.8 Hz, 1H), 8.02 (d, J=2.4 Hz, 1H), 8.12 (s, 1H), 8.32-8.36 (m, 4H). The $^1$H NMR chart is shown in FIGS. 17A and 17B. Note that the range of 6.5 ppm to 8.5 ppm in FIG. 17A is expanded and shown in FIG. 17B.

Thermogravimetry-differential thermal analysis (TG-DTA) of PCA2A was carried out. In measuring, a thermogravimetric/differential thermal analyzer (TG/DTA 320, manufactured by Seiko Instruments Inc.) was used, and the thermophysical properties were evaluated under a nitrogen atmosphere at a rate of temperature rise of 10° C./min. From the relationship between the weight and the temperature (thermogravimetry), the temperature at which the weight is less than or equal to 95% of the weight at the onset of measurement was 367° C. at normal pressure.

Figure 18:
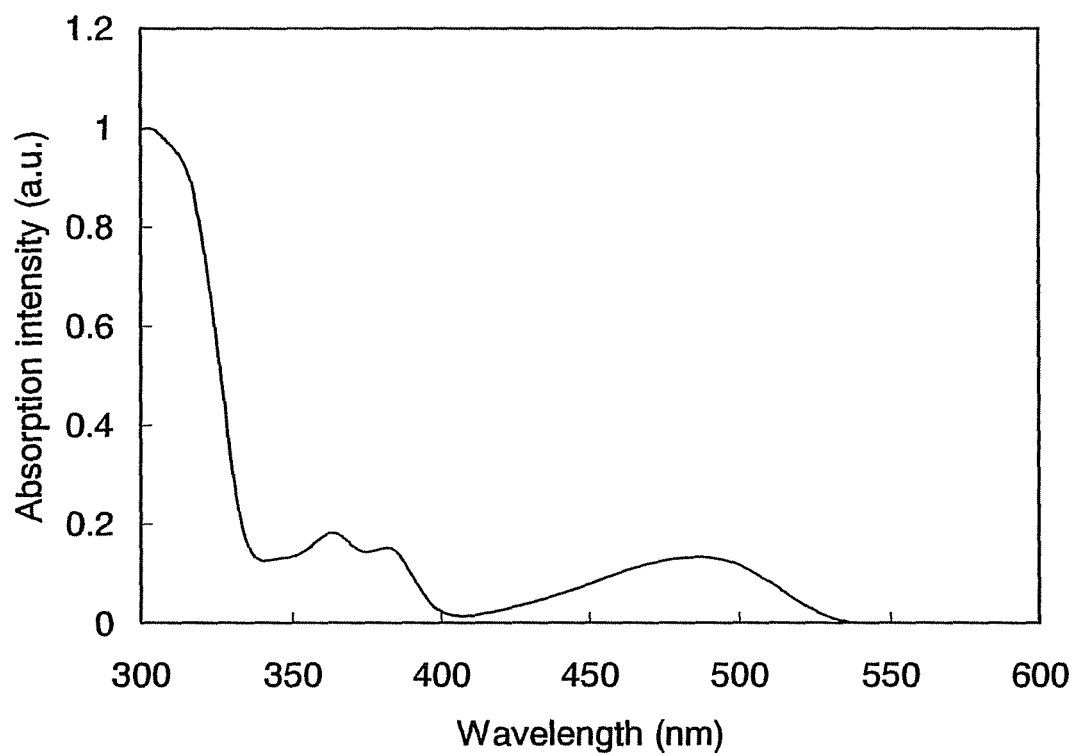
FIG. 18 shows an absorption spectrum of a toluene solution of 9,10-bis[N-phenyl-N-(9-phenylcarbazol-3-yl)amino]anthracene (abbreviation: PCA2A)
Figure 19:
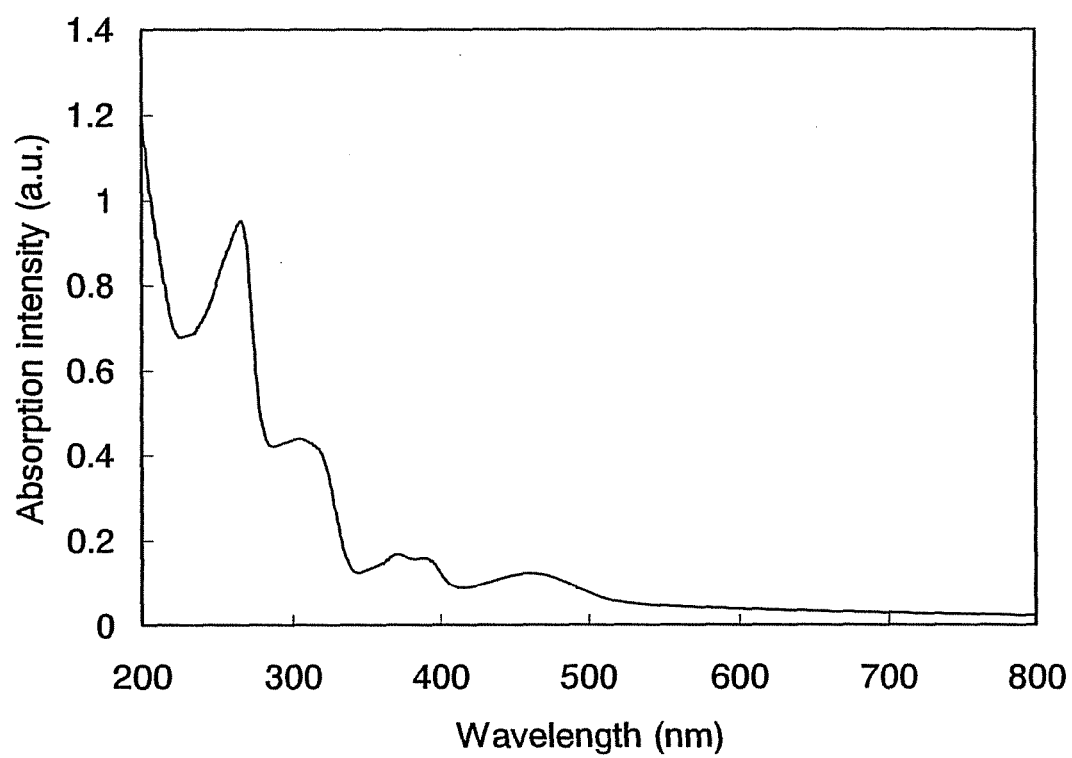
FIG. 19 shows an absorption spectrum of a thin film of 9,10-bis[N-phenyl-N-(9-phenylcarbazol-3-yl)amino]anthracene (abbreviation: PCA2A)
Figure 20:
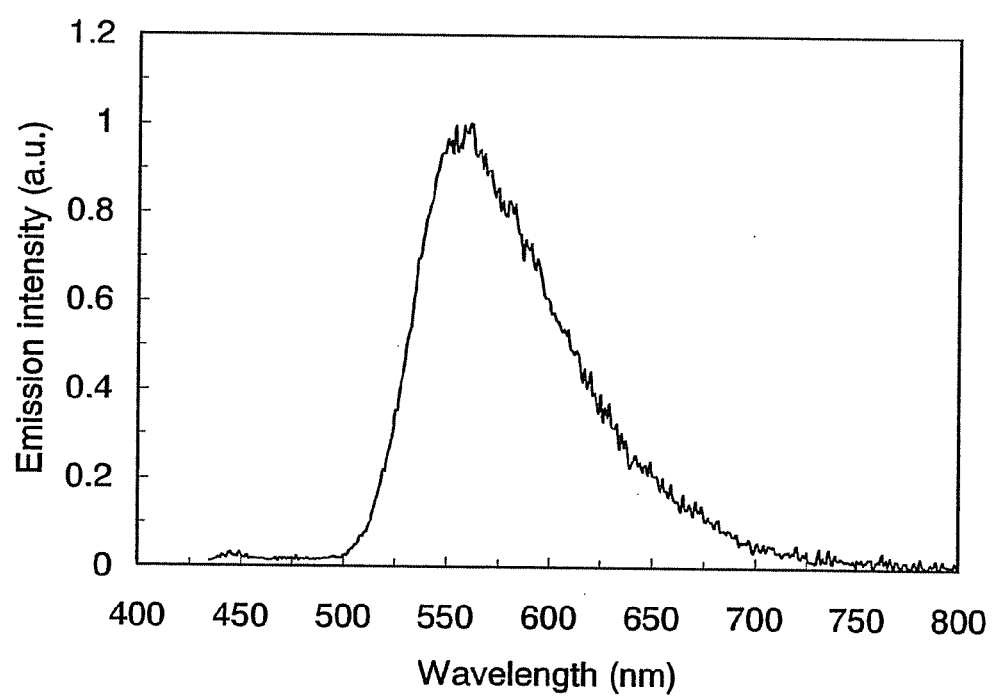
FIG. 20 shows an emission spectrum of a toluene solution of 9,10-bis[N-phenyl-N-(9-phenylcarbazol-3-yl)amino]anthracene (abbreviation: PCA2A)
Figure 21:
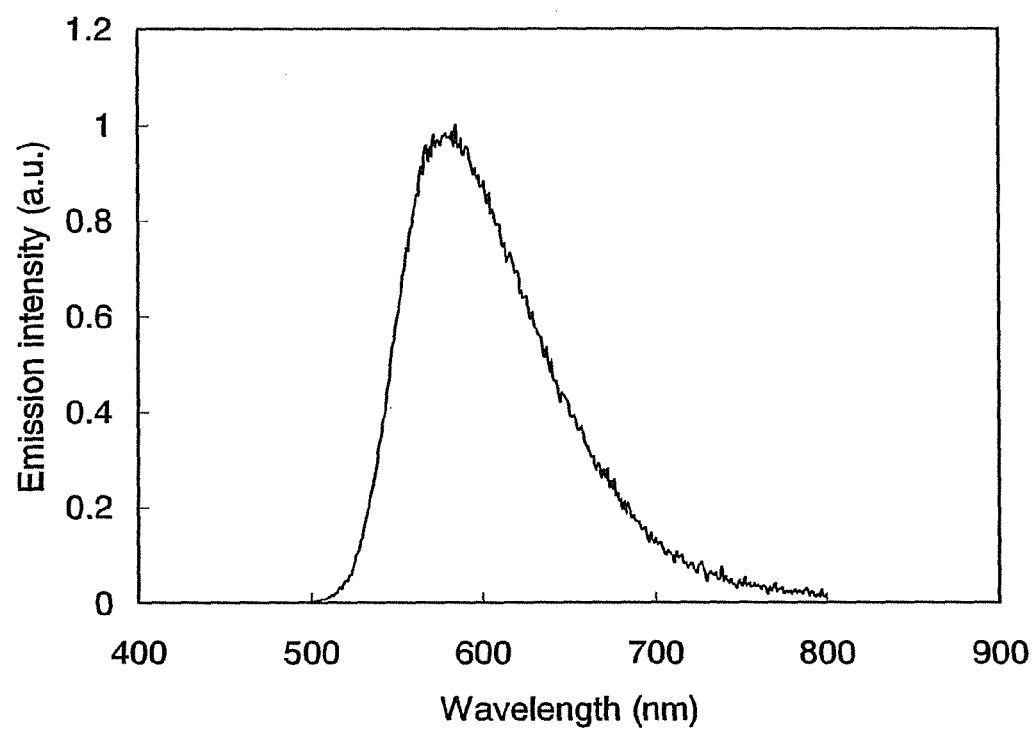
FIG. 21 shows an emission spectrum of a thin film of 9,10-bis[N-phenyl-N-(9-phenylcarbazol-3-yl)amino]anthracene (abbreviation: PCA2A)

The absorption spectrum of a toluene solution of PCA2A is shown in FIG. 18. In addition, an absorption spectrum of a thin film of PCA2A is shown in FIG. 19. An ultraviolet-visible spectrophotometer (type V550, manufactured by Japan Spectroscopy Corporation) was used for measurement. The solution was put into a quartz cell and the thin film sample was manufactured by vapor deposition of PCA2A on a quartz substrate. The absorption spectra thereof, from each of which the absorption spectrum of quartz was subtracted, are shown in FIGS. 18 and 19. In each of FIGS. 18 and 19, the horizontal axis shows wavelength (nm) and the vertical axis shows absorption intensity (an arbitrary unit). In the case of the toluene solution, absorption was observed at around 484 nm, and in the case of the thin film, absorption was observed at around 461 nm. Further, an emission spectrum of the toluene solution (excitation wavelength of 430 nm) of PCA2A is shown in FIG. 20, and an emission spectrum of the thin film (excitation wavelength of 497 nm) of PCA2A is shown in FIG. 21. In each of FIGS. 20 and 21, the horizontal axis shows wavelength (nm) and the vertical axis shows emission intensity (an arbitrary unit). In the case of the toluene solution, the maximum light emission wavelength was 558 nm (excitation wavelength of 430 nm), and in the case of the thin film, the maximum emission wavelength was 585 nm (excitation wavelength of 497 nm).

The HOMO level of PCA2A in a thin film state which was measured by a photoelectron spectrometer (AC-2, manufactured by Riken Keiki Co., Ltd.) under air was −5.28 eV. By the absorption edge obtained from a Tauc plot of the absorption spectrum of the thin film of PCA2A shown in FIG. 19, the optical energy gap was estimated to be 2.40 eV, which means that LUMO level of PCA2A is −2.88 eV.

An oxidation-reduction characteristic of PCA2A was measured by a cyclic voltammetry (CV) measurement. For the measurement, an electrochemical analyzer (ALS model 600A, manufactured by BAS Inc.) was used.

As for a solution used in the CV measurement, dehydrated dimethylformamide (DMF) (manufactured by Aldrich, 99.8%, catalog number: 22705-6) was used as a solvent. Tetra-n-butylammonium perchlorate (n-Bu$_4$NClO$_4$) (manufactured by Tokyo Chemical Industry Co., Ltd., catalog number: T0836), which is a supporting electrolyte, was dissolved in DMF at a concentration of 100 mmol/L to prepare the electrolysis solution. The sample solution was prepared by dissolving the measurement object in the electrolysis solution to be at a concentration of 1 mmol/L. A platinum electrode (a PIE platinum electrode, manufactured by BAS Inc.) was used as a working electrode. A platinum electrode (a VC-3 Pt counter electrode (5 cm), manufactured by BAS Inc.) was used as a counter electrode. An Ag/Ag$^+$ electrode (an RE5 non-aqueous solvent type reference electrode, manufactured by BAS Inc.) was used as a reference electrode. The measurement was conducted at room temperature.

The oxidation characteristic of PCA2A was evaluated in the following manner. The potential of the working electrode with respect to the reference electrode was shifted from −0.27 V to 0.60 V, which was followed by shifting the potential from 0.60 V to −0.27 V. This cycle was set as one cycle, and 100 cycles were performed. In addition, the reduction characteristic of PCA2A was evaluated in the following manner. The potential of the working electrode with respect to the reference electrode was shifted from −0.19 V to −2.40 V, which was followed by shifting the potential from −2.40 V to −0.19 V. This cycle was set as one cycle, and 100 cycles were performed. The scanning rate of the CV measurement was set to be 0.1 V/s.

Figure 22:
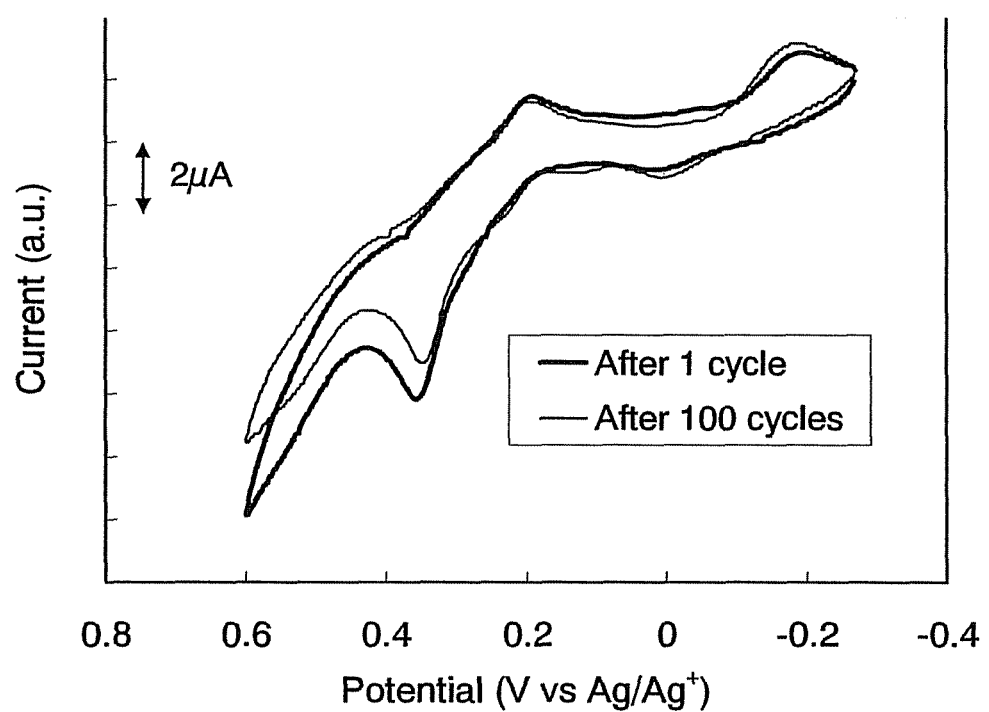
FIG. 22 shows a CV measurement result of oxidation of 9,10-bis[N-phenyl-N-(9-phenylcarbazol-3-yl)amino]anthracene (abbreviation: PCA2A)
Figure 23:
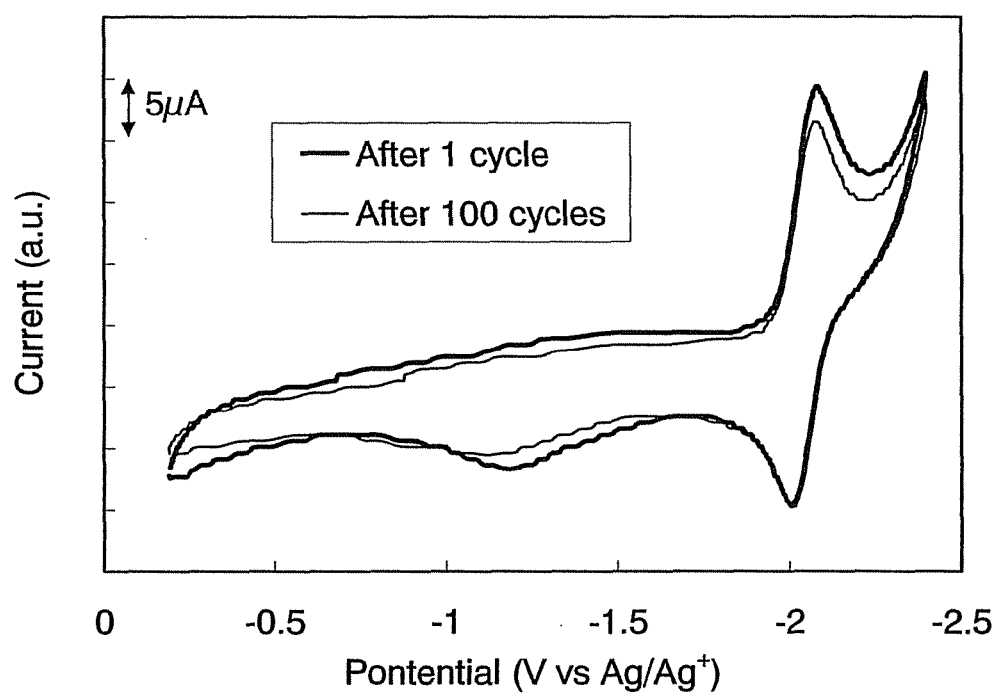
FIG. 23 shows a CV measurement of reduction of 9,10-bis[N-phenyl-N-(9-phenylcarbazol-3-yl)amino]anthracene (abbreviation: PCA2A)

The CV measurement result of oxidation of PCA2A and the CV measurement result of reduction of PCA2A are shown in FIGS. 22 and 23, respectively. In each of FIGS. 22 and 23, the horizontal axis shows a potential (V) of the working electrode with respect to the reference electrode, and the vertical axis shows a current value (μA) that flowed between the working electrode and the counter electrode. From FIG. 22, a current exhibiting oxidation was observed around 0.35 V (vs. Ag/Ag$^+$ electrode). From FIG. 23, a current exhibiting reduction was observed around −2.08 V (vs. Ag/Ag$^+$ electrode).

In spite of the fact that as many as 100 cycles of shifting were performed, a peak position and a peak intensity of the CV curve scarcely changed in the oxidation and reduction, which reveals that the anthracene derivative of the present invention is extremely stable against repetition of oxidation and reduction.

Example 3

Example 3 will specifically describe a synthetic method of 9-{N-[4-(carbazole-9-yl)phenyl]-N-phenylamino}-10-phenylanthracene (abbreviation: YGAPhA), which is an anthracene derivative of the present invention represented by Structural Formula (301).

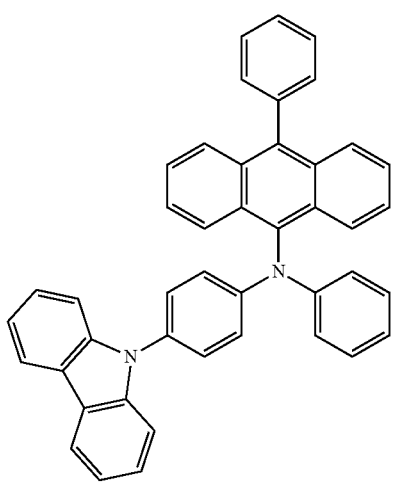

(301)

[Step 1] Synthesis of 4-(carbazole-9-yl)diphenylamine (abbreviation: YGA)

(i) Synthesis of N-(4-bromophenyl)carbazole

A synthetic scheme of N-(4-bromophenyl)carbazole is shown in (B-5).

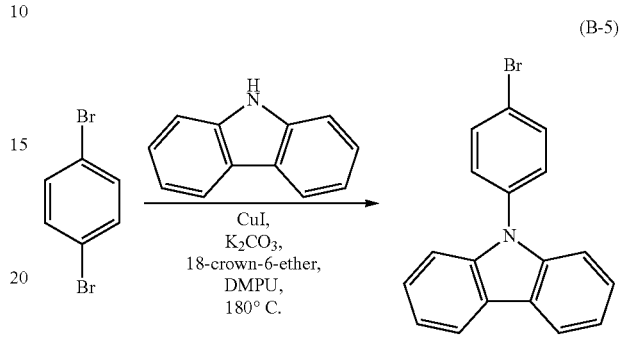

(B-5)

First, a synthetic method of N-(4-bromophenyl)carbazole is described. 56.3 g (0.24 mol) of 1,4-dibromobenzene, 31.3 g (0.18 mol) of carbazole, 4.6 g (0.024 mol) of copper(I) iodide, 66.3 g (0.48 mol) of potassium carbonate, and 2.1 g (0.008 mol) of 18-crown-6-ether were put into a 300 mL three-neck flask, and the atmosphere in the flask was substituted by nitrogen. Thereafter, 8 mL of 1,3-dimethyl-3,4,5,6-tetrahydro-2(1H)-pyrimidinone (abbreviation: DMPU) was added to the mixture, and then the mixture was stirred at 180° C. for 6 hours. After the reaction mixture was cooled to room temperature, the precipitate was removed by suction filtration. The filtrate was washed with a diluted hydrochloric acid, a saturated sodium bicarbonate aqueous solution, and then saturated saline, and dried with magnesium sulfate. After drying, the mixture was filtered naturally, and the filtrate was concentrated to yield an oily substance. The oily substance was purified by silica gel column chromatography (developing solvent; hexane:ethyl acetate=9:1). The resulting solid was recrystallized with a mixed solvent of chloroform and hexane, obtaining 20.7 g of N-(4-bromophenyl)carbazole, which is the object substance, as a light brown plate-like crystal in 35% yield. By the nuclear magnetic resonance measurement (NMR), it was confirmed that this compound was N-(4-bromophenyl)carbazole.

$^1$H NMR data of this compound is shown below. $^1$H NMR (300 MHz, CDCl$_3$): δ=8.14 (d, J=7.8 Hz, 2H), 7.73 (d, J=8.7 Hz, 2H), 7.46 (d, J=8.4 Hz, 2H), 7.42-7.26 (m, 6H).

(ii) Synthesis of 4-(carbazol-9-yl)diphenylamine (abbreviation: YGA)

A synthetic scheme of 4-(carbazol-9-yl)diphenylamine (abbreviation: YGA) is shown in (B-6).

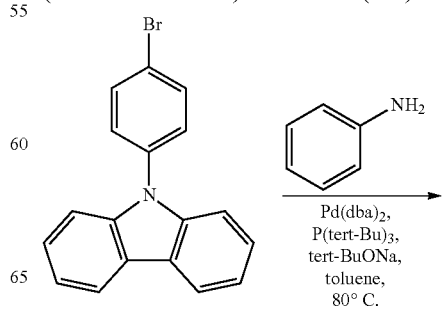

(B-6)

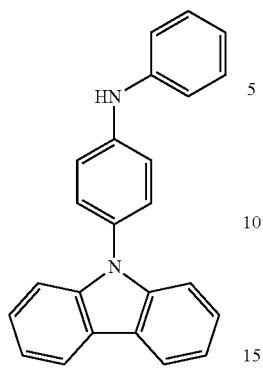

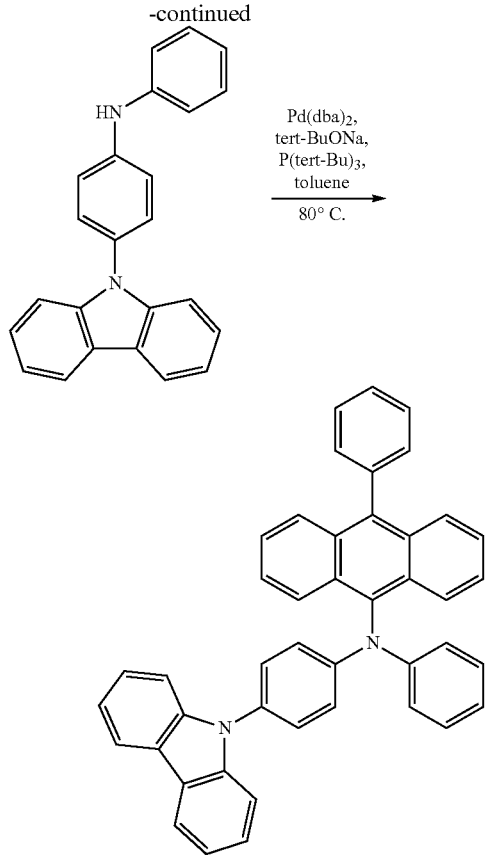

5.4 g (17.0 mmol) of N-(4-bromophenyl)carbazole obtained in the above-mentioned step (i), 1.8 mL (20.0 mmol) of aniline, 100 mg (0.17 mmol) of bis(dibenzylideneacetone)palladium(0), and 3.9 g (40 mmol) of sodium-tert-butoxide were put into a 200 mL three-neck flask, and the atmosphere in the flask was substituted by nitrogen. Thereafter, 0.1 mL of tri-(tert-butyl)phosphine (10 wt % hexane solution) and 50 mL of toluene were added to the flask, and the solution was stirred at 80° C. for 6 hours. The reaction mixture was filtered through Florisil, celite, and then alumina. The filtrate was washed with water, and then saturated brine, and dried with magnesium sulfate. The mixture was filtered naturally, and the filtrate was concentrated to obtain an oily substance. The oily substance was purified by silica gel column chromatography (developing solvent; hexane:ethyl acetate=9:1). Then, 4.1 g of 4-(carbazol-9-yl)diphenylamine (abbreviation: YGA), which is the object substance, was obtained in 73% yield. It was confirmed by a nuclear magnetic resonance measurement (NMR) that this compound was 4-(carbazol-9-yl)diphenylamine (abbreviation: YGA).

Figure 24A:
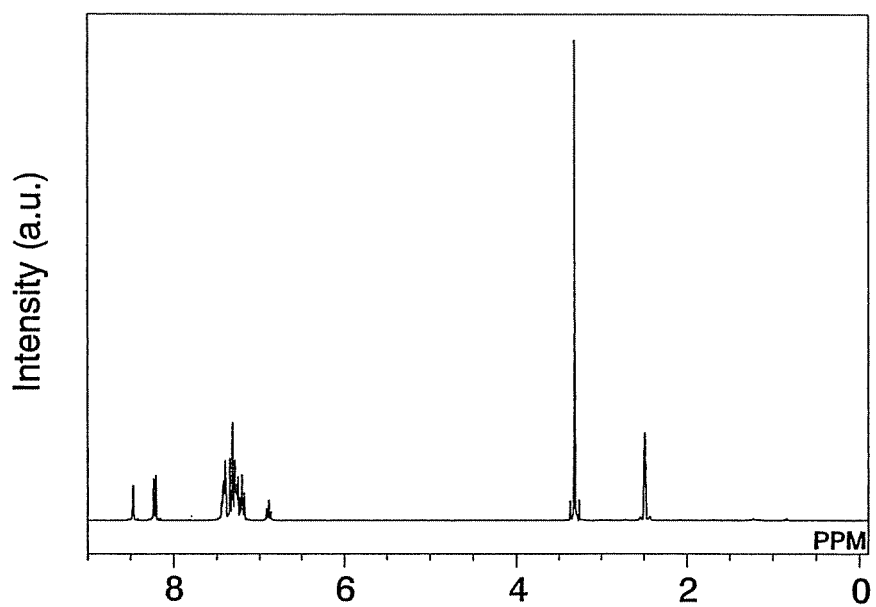
FIGS. 24A and 24B show $^1$H NMR charts of 4-(carbazol-9-yl)diphenylamine (abbreviation: YGA)
Figure 24B:
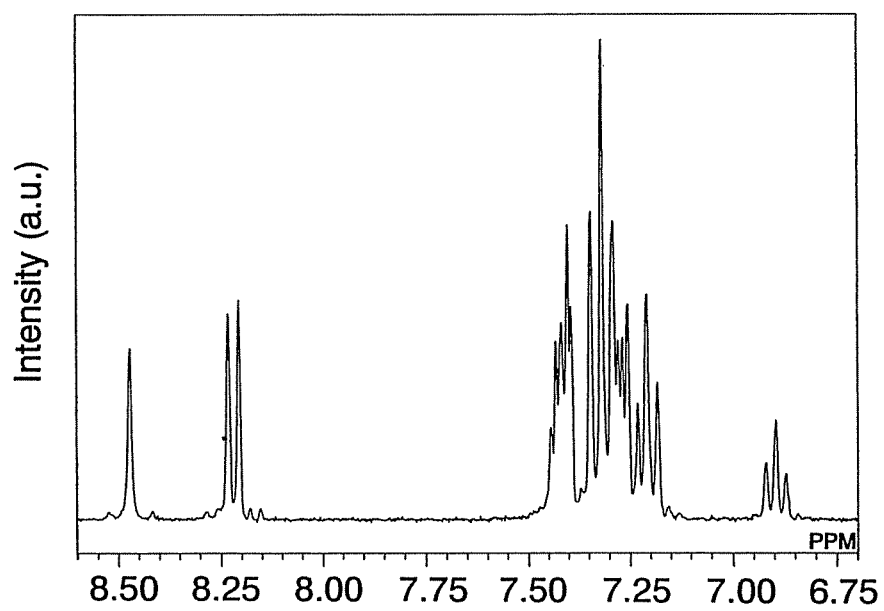

$^1$H NMR data of this compound is shown below. $^1$H NMR (300 MHz, DMSO-$d_6$): δ=8.47 (s, 1H), 8.22 (d, J=7.8 Hz, 2H), 7.44-7.16 (m, 14H), 6.92-6.87 (m, 1H). FIGS. 24A and 24B each show a $^1$H NMR chart. Note that the range of 6.70 ppm to 8.60 ppm in FIG. 24A is expanded and shown in FIG. 24B.

[Step 2] Synthesis of YGAPhA

A synthetic scheme of YGAPhA is shown in (B-7).

(B-7)

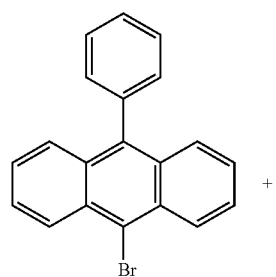

+

Into a 100 mL three-neck flask were added 2.0 g (6.0 mmol) of 9-bromo-10-phenylanthracene, 2.4 g (7.2 mmol) of 4-(carbazol-9-yl)diphenylamine (abbreviation: YGA), 0.17 g (0.30 mmol) of bis(dibenzylideneacetone)palladium(0), and 2.9 g (30 mmol) of sodium-tert-butoxide, and the atmosphere in the flask was substituted by nitrogen. Thereafter, 20 mL of toluene and 0.61 g (0.30 mmol) of tri(tert-butyl)phosphine (10 wt % hexane solution) were added to the mixture. This mixture was stirred at 80° C. for 13 hours. After the reaction, the mixture was washed with water. An aqueous layer was extracted with ethyl acetate, and the extracted solution was combined with an organic layer and dried with magnesium sulfate. After drying, the mixture was subjected to suction filtration, and the filtrate was concentrated. A residue obtained was dissolved in toluene and this solution was filtered through Florisil, celite, and alumina by suction filtration. The filtrate was concentrated to obtain a solid. Recrystallization of the solid with chloroform and hexane gave 3.2 g of 9-{N-[4-(carbazol-9-yl)phenyl]-N-phenylamino}-10-phenylanthracene (abbreviation: YGAPhA), that is the object substance, as yellow powder in 91% yield.

Figure 25A:
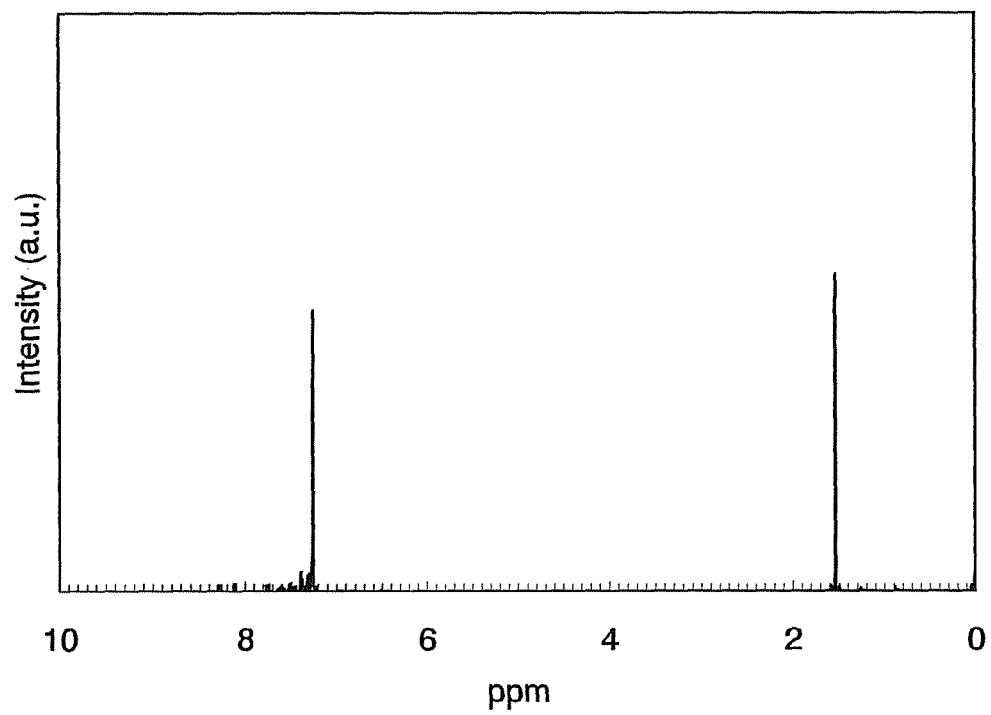
FIGS. 25A and 25B show $^1$H NMR charts of 9-{N-[4-(carbazol-9-yl)phenyl]-N-phenylamino}-10-phenylanthracene (abbreviation: YGAPhA)
Figure 25B:
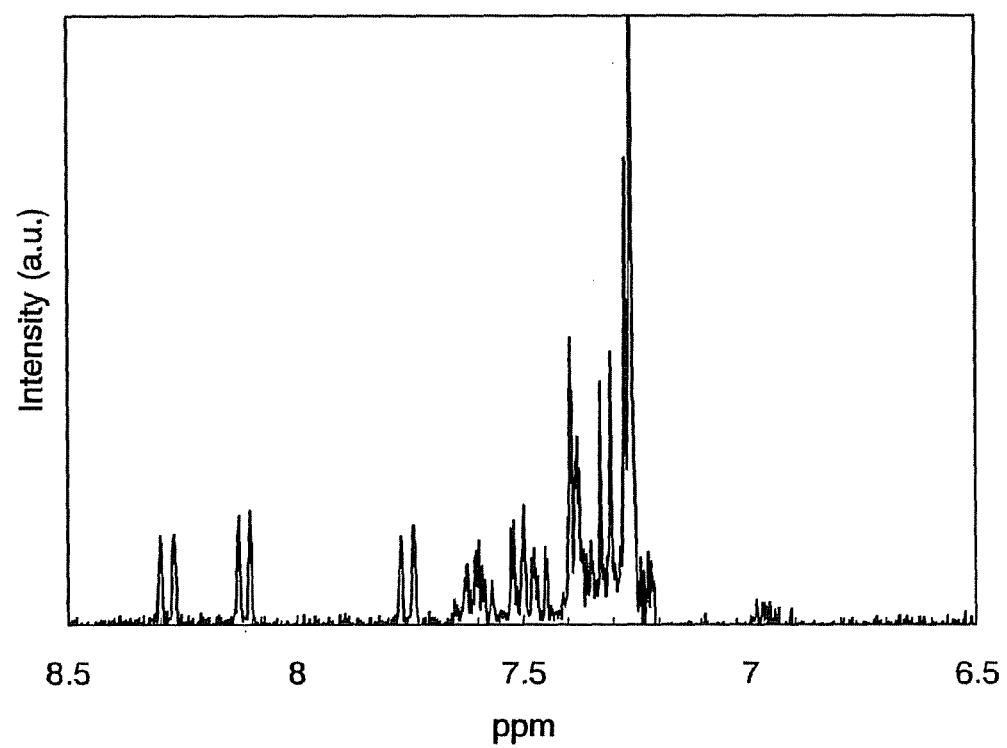

$^1$H NMR data of this compound is shown below. $^1$H NMR (300 MHz, CDCl$_3$); δ=7.21-7.39 (m, 17H), 7.45-7.53 (m, 4H), 7.57-7.63 (m, 3H), 7.74-7.77 (m, 2H), 8.10-8.13 (m, 2H), 8.27-8.30 (m, 2H). The $^1$H NMR chart is shown in FIGS. 25A and 25B. Note that the range of 6.5 ppm to 8.5 ppm in FIG. 25A is expanded and shown in FIG. 25B.

Thermogravimetry-differential thermal analysis (TG-DTA) of YGAPhA was carried out. In measuring, a thermogravimetric/differential thermal analyzer (TG/DTA 320, manufactured by Seiko Instruments Inc.) was used, and the thermophysical properties were evaluated under a nitrogen atmosphere at a rate of temperature rise of 10° C./min. From the relationship between the weight and the temperature (thermogravimetry), the temperature at which the weight is less than or equal to 95% of the weight at the onset of measurement was 404° C. at normal pressure, and this shows YGAPhA has favorable heat resistance.

Figure 26:
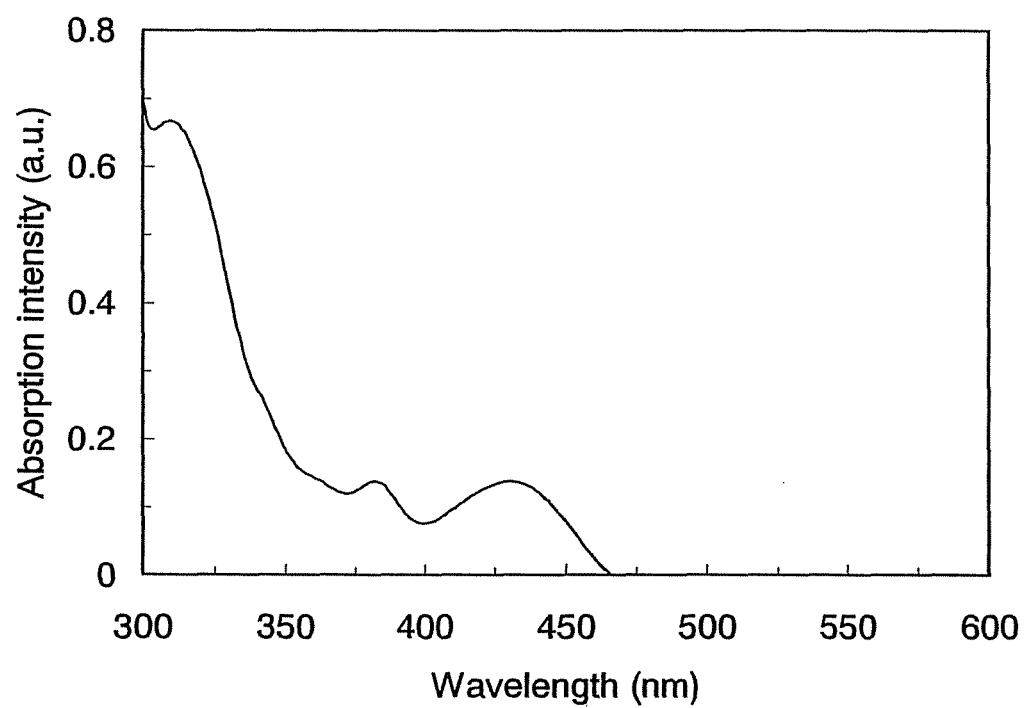
FIG. 26 shows an absorption spectrum of a toluene solution of 9-{N-[4-(carbazol-9-yl)phenyl]-N-phenylamino}-10-phenylanthracene (abbreviation: YGAPhA)
Figure 27:
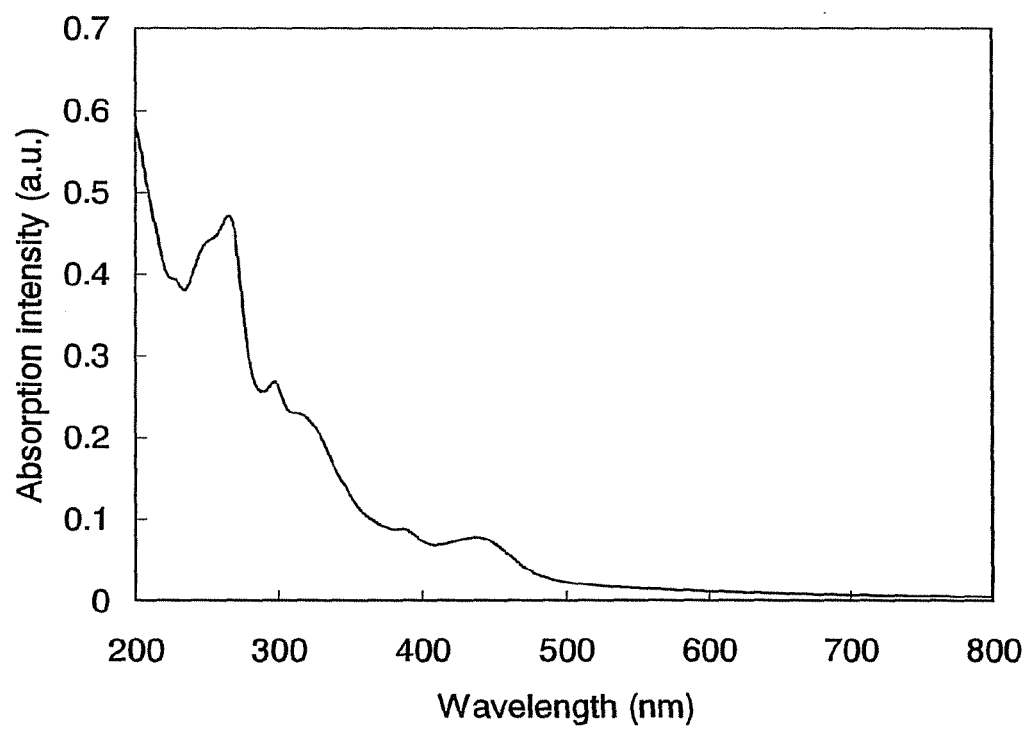
FIG. 27 shows an absorption spectrum of a thin film of 9-{N-[4-(carbazol-9-yl)phenyl]-N-phenylamino}-10-phenylanthracene (abbreviation: YGAPhA)
Figure 28:
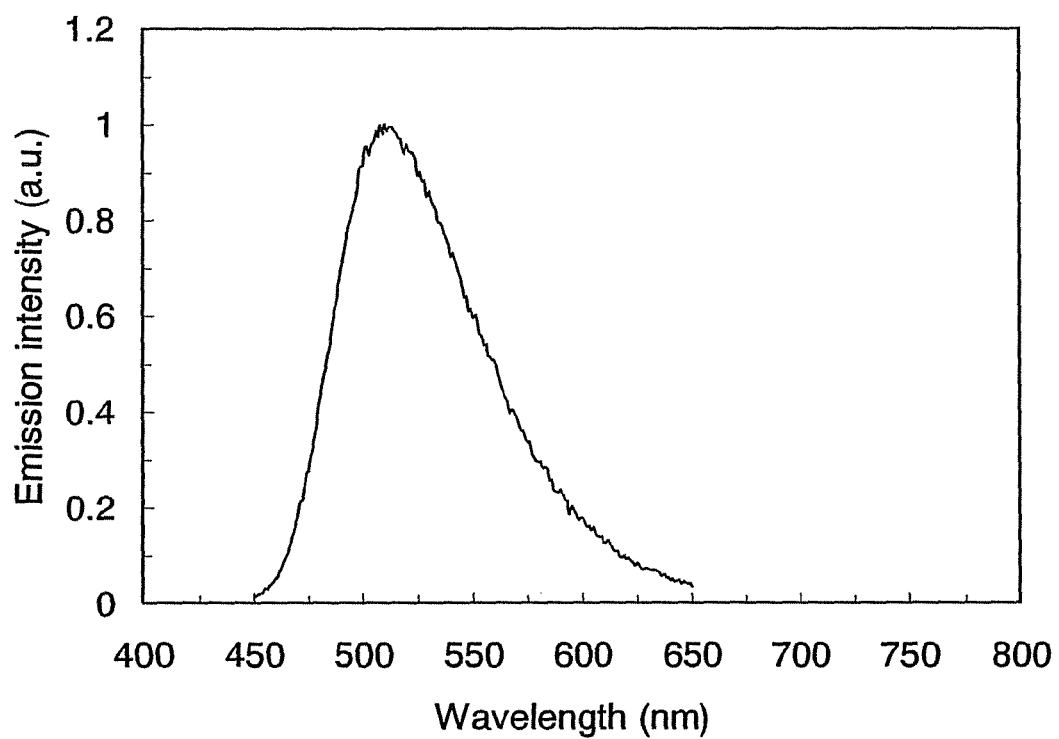
FIG. 28 shows an emission spectrum of a toluene solution of 9-{N-[4-(carbazol-9-yl)phenyl]-N-phenylamino}-10-phenylanthracene (abbreviation: YGAPhA)
Figure 29:
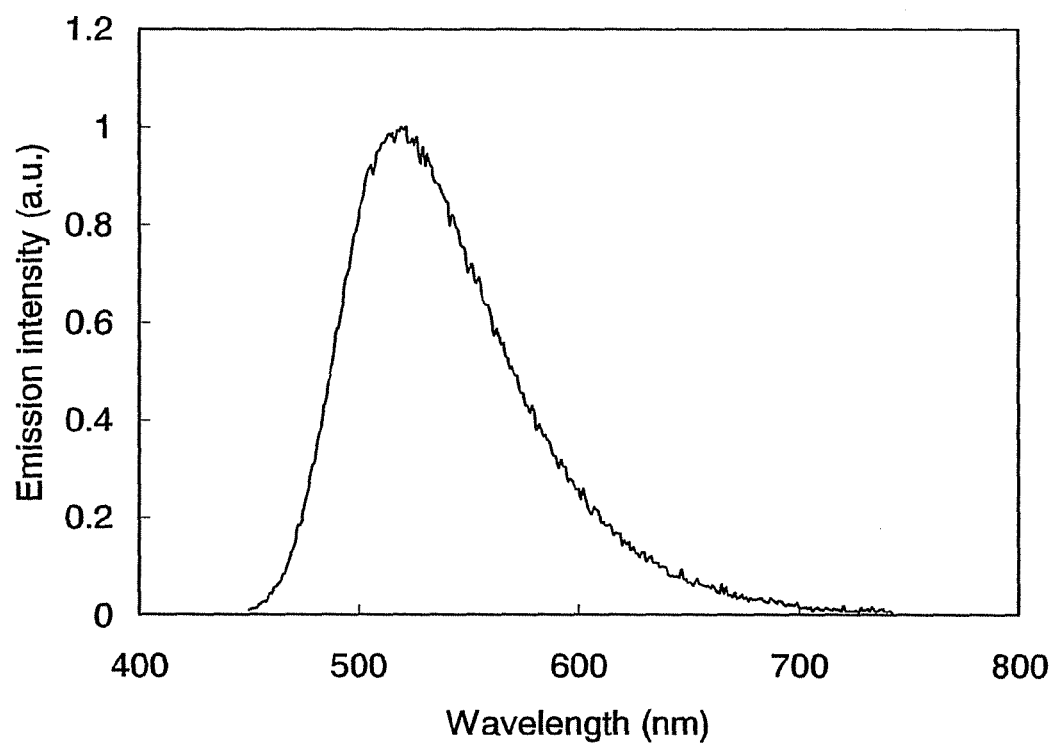
FIG. 29 shows an emission spectrum of a thin film of 9-{N-[4-(carbazol-9-yl)phenyl]-N-phenylamino}-10-phenylanthracene (abbreviation: YGAPhA)

The absorption spectrum of a toluene solution of YGAPhA is shown in FIG. 26. In addition, an absorption spectrum of a thin film of YGAPhA is shown in FIG. 27. An ultraviolet-visible spectrophotometer (type V550, manufactured by Japan Spectroscopy Corporation) was used for measurement. The solution was put into a quartz cell and the thin film sample was manufactured by vapor deposition of YGAPhA on a quartz substrate. The absorption spectra thereof, from each of which the absorption spectrum of quartz was subtracted, are shown in FIGS. 26 and 27. In each of FIGS. 26 and 27, the horizontal axis shows wavelength (nm) and the vertical axis shows absorption intensity (an arbitrary unit). In the case of the toluene solution, absorption was observed at around 430 nm, and in the case of the thin film, absorption was observed at around 436 nm. Further, an emission spectrum of the toluene solution (excitation wavelength of 430 nm) of YGAPhA is shown in FIG. 28, and an emission spectrum of the thin film (excitation wavelength of 497 nm) of YGAPhA is shown in FIG. 29. In each of FIGS. 28 and 29, the horizontal axis shows wavelength (nm) and the vertical axis shows emission intensity (an arbitrary unit). In the case of the toluene solution, the maximum light emission wavelength was 510 nm (excitation wavelength of 430 nm), and in the case of the thin film, the maximum emission wavelength was 520 nm (excitation wavelength of 497 nm).

The HOMO level of YGAPhA in a thin film state which was measured by a photoelectron spectrometer (AC-2, manufactured by Riken Keiki Co., Ltd.) under air was −5.49 eV. By the absorption edge obtained from a Tauc plot of the absorption spectrum of the thin film of YGAPhA shown in FIG. 27, the optical energy gap was estimated to be 2.60 eV, which means that LUMO level of YGAPhA is −2.89 eV.

Example 4

Example 4 will specifically describe a synthetic method of 9,10-bis[N-(4-carbazol-9-yl)phenyl-N-phenylamino]anthracene (abbreviation: YGA2A), which is an anthracene derivative of the present invention represented by Structural Formula (335).

(335)

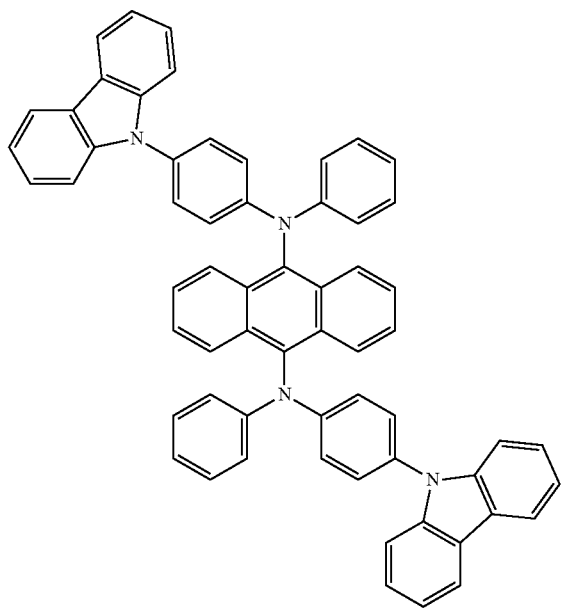

[Step 1] Synthesis of YGA2A

A synthetic scheme of YGA2A is shown in (B-8).

(B-8)

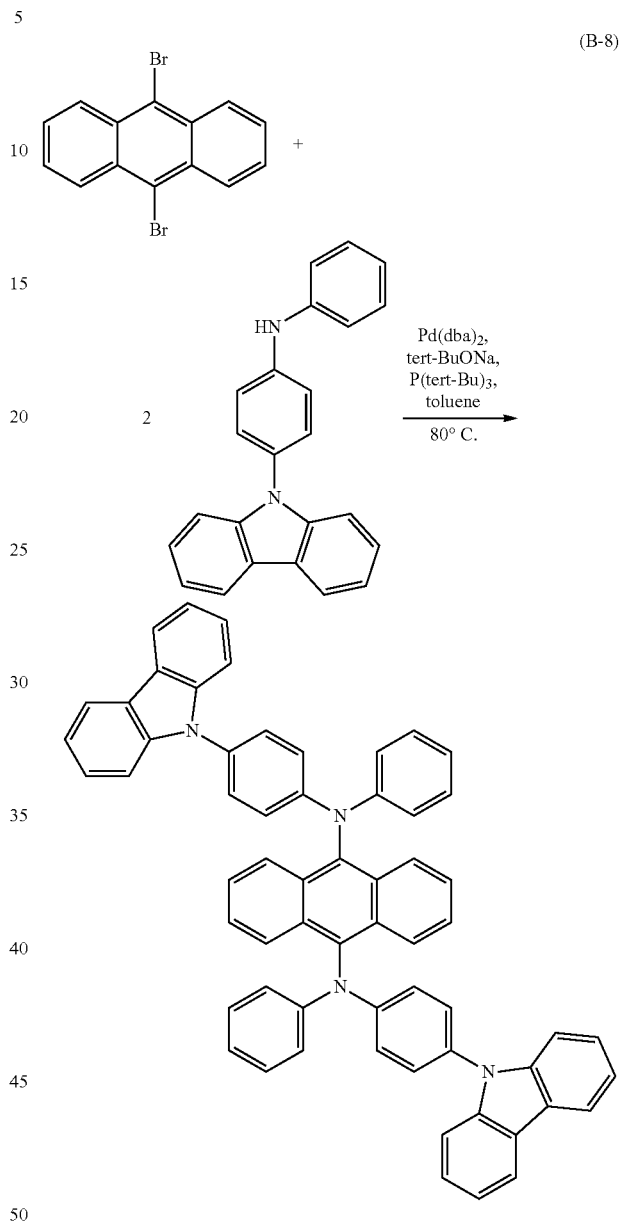

Into a 100 mL three-neck flask were added 2.0 g (6.0 mmol) of 9,10-dibromoanthracene, 4.4 g (13 mmol) of 4-(carbazole-9-yl)diphenylamine (abbreviation: YGA), 0.17 g (0.30 mmol) of bis(dibenzylideneacetone)palladium(0), and 2.9 g (30 mmol) of sodium-tert-butoxide, and the atmosphere in the flask was substituted by nitrogen. 20 mL of toluene and 0.60 g (0.30 mmol) of tri(tert-butyl)phosphine (10 wt % hexane solution) were added to the mixture. This mixture was stirred at 80° C. for 10 hours. After the reaction was completed, the solution was washed with water, and a precipitate in the solution was collected by suction filtration. The solid obtained was dissolved in chloroform and filtered through Florisil, celite, and alumina by suction filtration. The filtrate was concentrated, and a solid obtained was recrystallized with a mixed solvent of chloroform and hexane to give 3.9 g of 9,10-bis[N-(4-carbazol-9-yl)phenyl-N-phenylamino]anthracene (abbreviation: YGA2A), which is the object substance, as yellow colored powder in 79% yield.

Figure 30A:
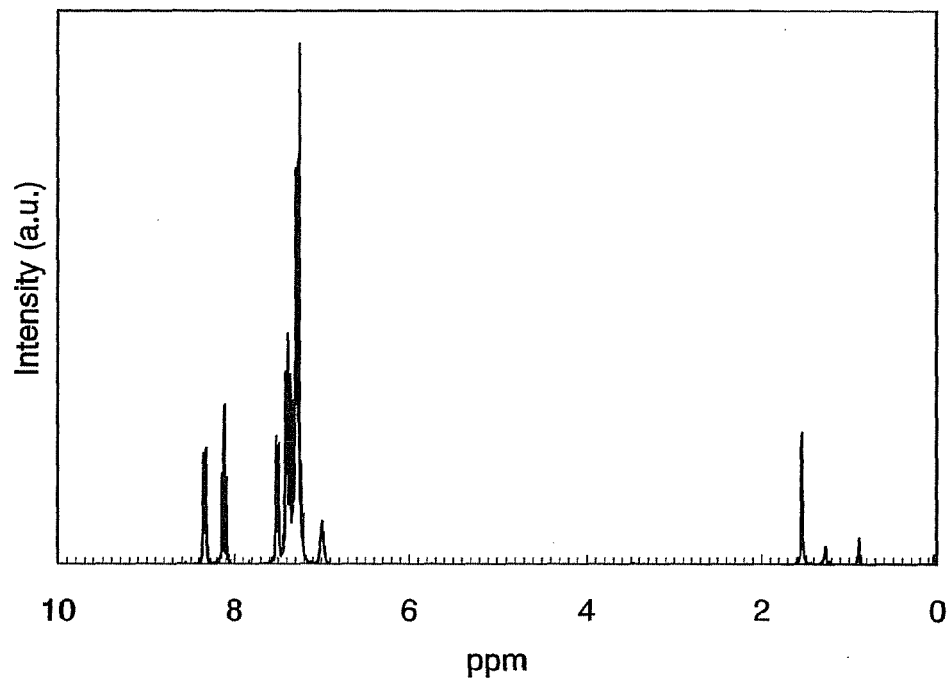
FIGS. 30A and 30B show $^1$H NMR charts of 9,10-bis[N-(4-carbazol-9-yl)phenyl-N-phenylamino]anthracene (abbreviation: YGA2A)
Figure 30B:
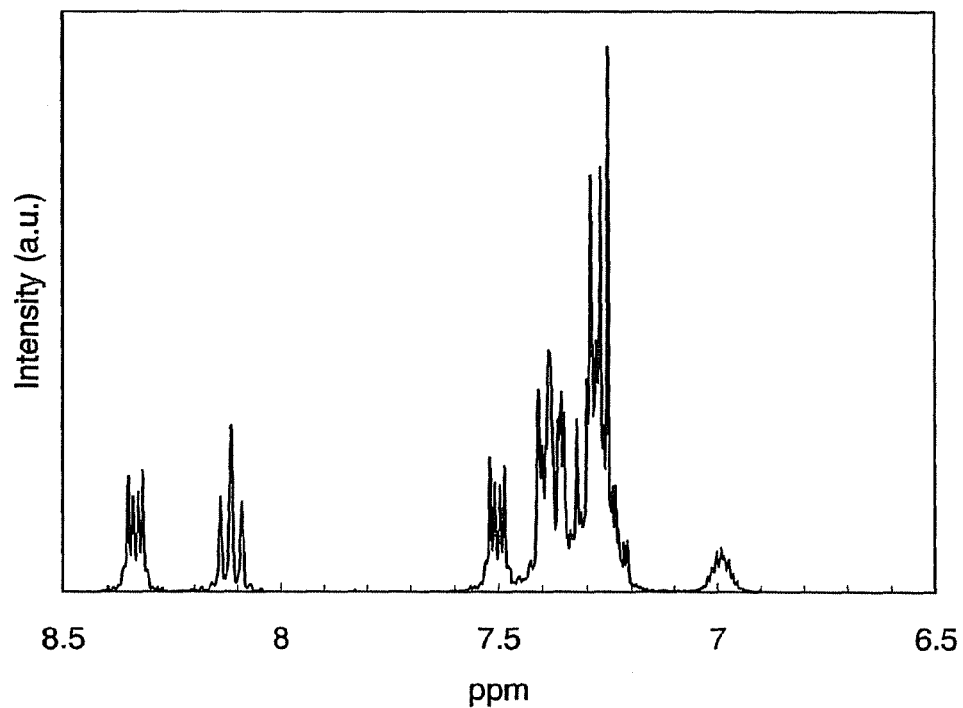

$^1$H NMR data of this compound is shown below. $^1$H NMR (300 MHz, CDCl$_3$); δ=6.99-7.00 (m, 2H), 7.21-7.41 (m, 28H), 7.49-7.52 (m, 4H), 8.09-8.14 (m, 4H), 8.32-8.35 (m, 4H). The $^1$H NMR chart is shown in FIGS. 30A and 30B. Note that the range of 6.5 ppm to 8.5 ppm in FIG. 30A is expanded and shown in FIG. 30B.

Thermogravimetry-differential thermal analysis (TG-DTA) of YGA2A was carried out. In measuring, a thermogravimetric/differential thermal analyzer (TG/DTA 320, manufactured by Seiko Instruments Inc.) was used, and the thermophysical properties were evaluated under a nitrogen atmosphere at a rate of temperature rise of 10° C./min. From the relationship between the weight and the temperature (thermogravimetry), the temperature at which the weight is less than or equal to 95% of the weight at the onset of measurement was 478.1° C. at normal pressure, and this shows YGA2A has favorable heat resistance.

Figure 31:
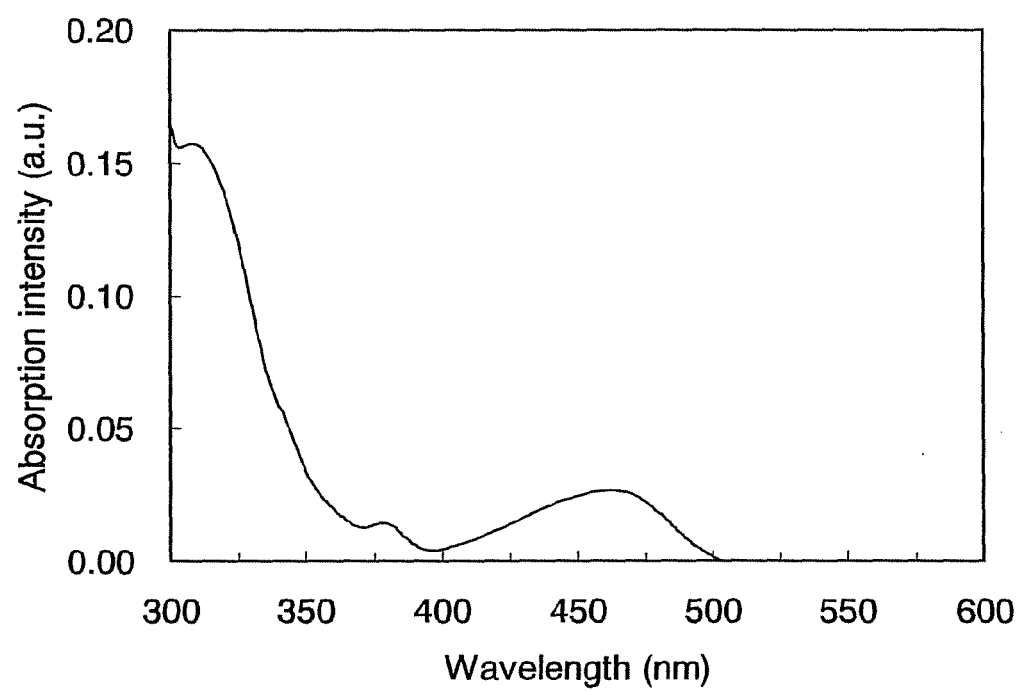
FIG. 31 shows an absorption spectrum of a toluene solution of 9,10-bis[N-(4-carbazol-9-yl)phenyl-N-phenylamino]anthracene (abbreviation: YGA2A)
Figure 32:
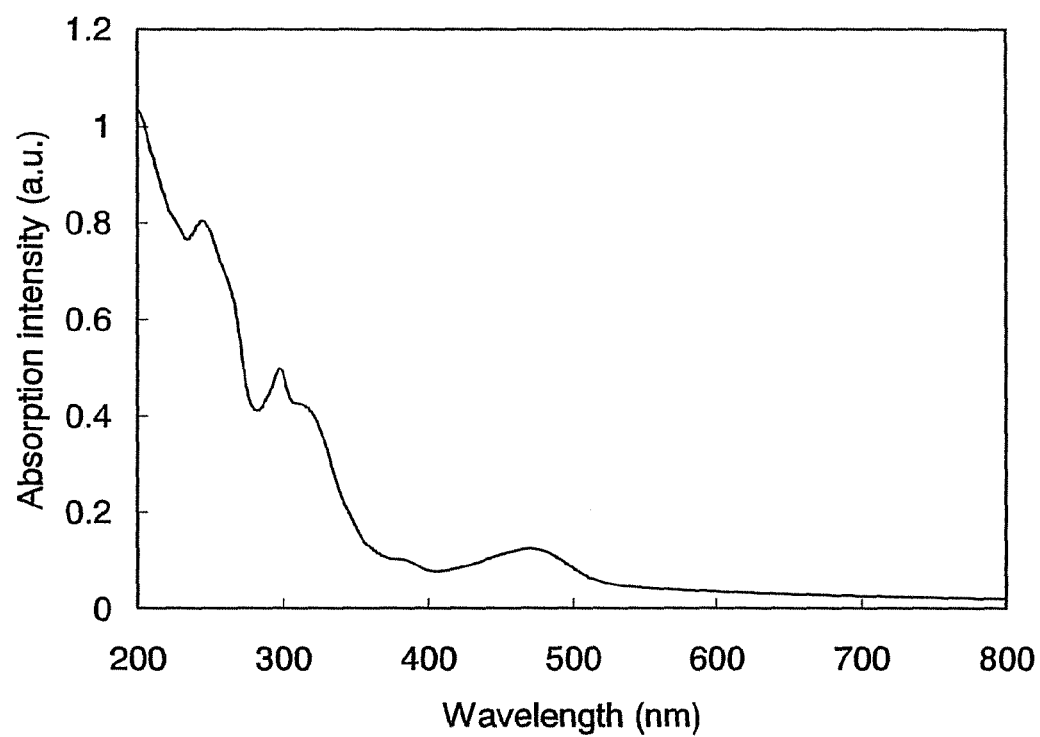
FIG. 32 shows an absorption spectrum of a thin film of 9,10-bis[N-(4-carbazol-9-yl)phenyl-N-phenylamino]anthracene (abbreviation: YGA2A)
Figure 33:
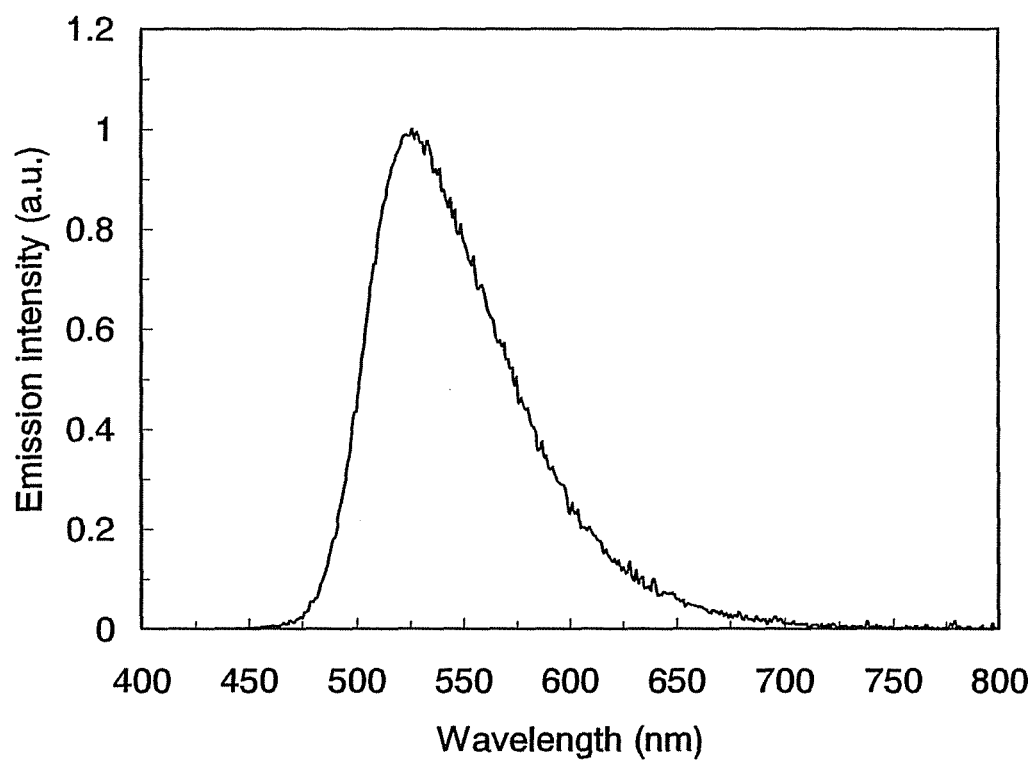
FIG. 33 shows an emission spectrum of a toluene solution of 9,10-bis[N-(4-carbazol-9-yl)phenyl-N-phenylamino]anthracene (abbreviation: YGA2A)
Figure 34:
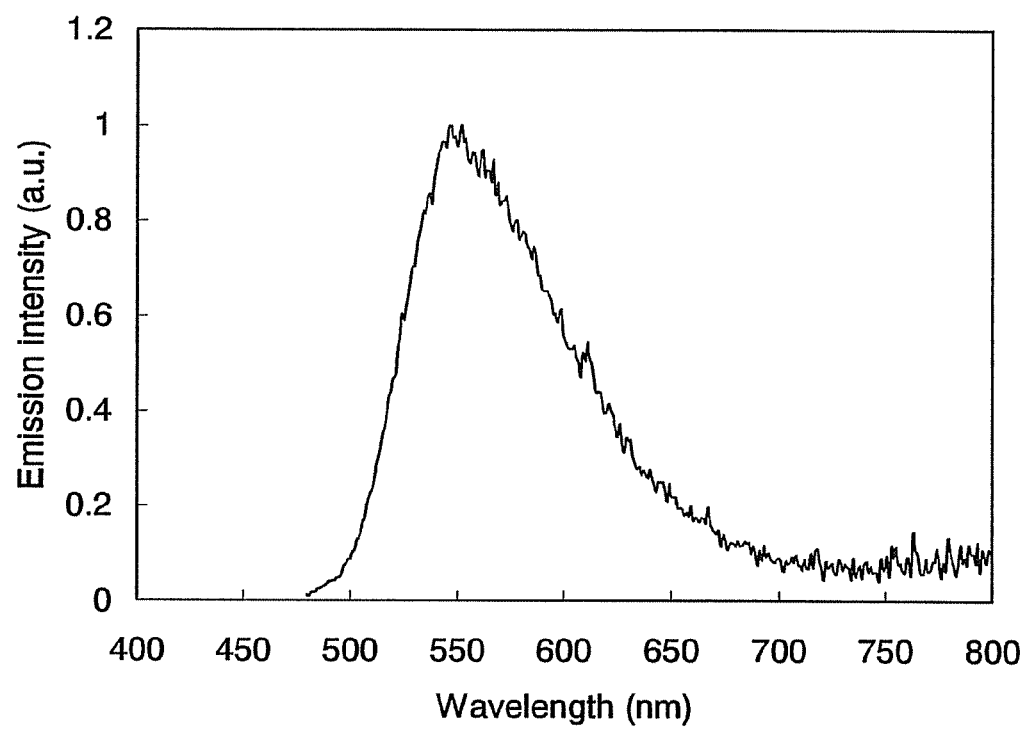
FIG. 34 shows an emission spectrum of a thin film of 9,10-bis[N-(4-carbazol-9-yl)phenyl-N-phenylamino]anthracene (abbreviation: YGA2A)

The absorption spectrum of a toluene solution of YGA2A is shown in FIG. 31. In addition, an absorption spectrum of a thin film of YGA2A is shown in FIG. 32. An ultraviolet-visible spectrophotometer (type V550, manufactured by Japan Spectroscopy Corporation) was used for measurement. The solution was put into a quartz cell and the thin film sample was manufactured by vapor deposition of YGA2A on a quartz substrate. The absorption spectra thereof, from each of which the absorption spectrum of quartz was subtracted, are shown in FIGS. 31 and 32. In each of FIGS. 31 and 32, the horizontal axis shows wavelength (nm) and the vertical axis shows absorption intensity (an arbitrary unit). In the case of the toluene solution, absorption was observed at around 463 nm, and in the case of the thin film, absorption was observed at around 470 nm. Further, an emission spectrum of the toluene solution (excitation wavelength of 461 nm) of YGA2A is shown in FIG. 33, and an emission spectrum of the thin film (excitation wavelength of 450 nm) of YGA2A is shown in FIG. 34. In each of FIGS. 33 and 34, the horizontal axis shows wavelength (nm) and the vertical axis shows emission intensity (an arbitrary unit). In the case of the toluene solution, the maximum light emission wavelength was 526 nm (excitation wavelength of 461 nm), and in the case of the thin film, the maximum emission wavelength was 552 nm (excitation wavelength of 450 nm).

The HOMO level of YGA2A in a thin film state which was measured by a photoelectron spectrometer (AC-2, manufactured by Riken Keiki Co., Ltd.) under air was −5.37 eV. By the absorption edge obtained from a Tauc plot of the absorption spectrum of the thin film of YGA2A shown in FIG. 32, the optical energy gap was estimated to be 2.40 eV, which means that LUMO level of YGA2A is −2.97 eV.

Example 5

Figure 35:
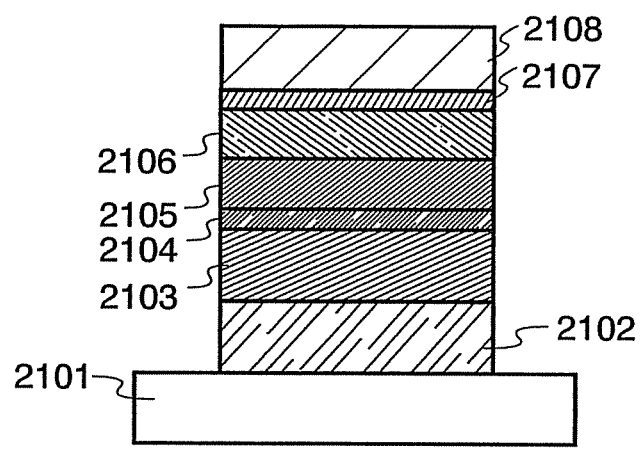
FIG. 35 shows a light emitting element of examples.

Example 5 will describe a light emitting element of the present invention with reference to FIG. 35. Structural formulae of materials used in Examples 5 to 8 are shown below.

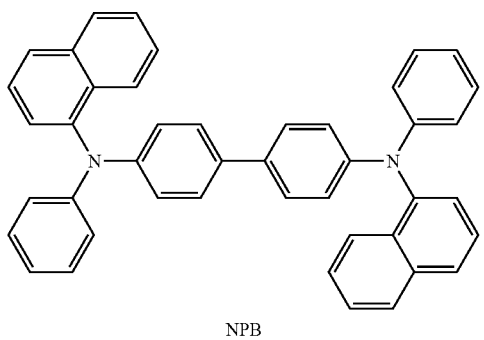

NPB

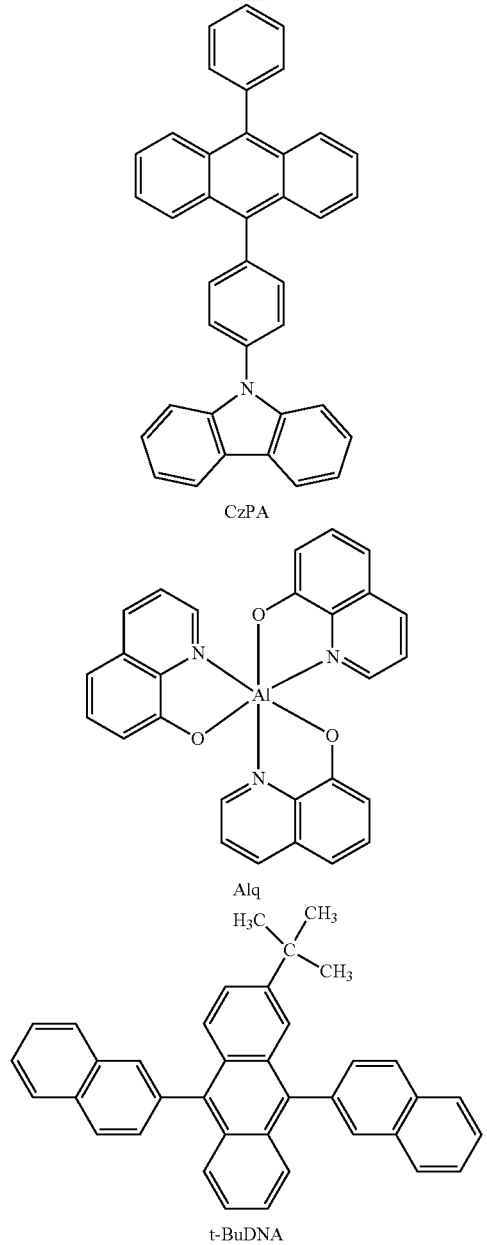

CzPA

Alq t-BuDNA

Hereinafter, a manufacturing method of a light emitting element of this example is described.

First, a film of indium tin oxide containing silicon oxide (ITSO) was formed by a sputtering method over a glass substrate 2101 to form a first electrode 2102. Note that the film thickness of the first electrode 2102 was 110 nm, and the area of the electrode was 2 mm×2 mm.

Next, the substrate over which the first electrode 2102 was formed was fixed to a substrate holder provided in a vacuum evaporation apparatus so that a surface of the substrate over which the first electrode 2102 was formed faced down. Then, after reducing the pressure of the vacuum evaporation apparatus to about 10$^{-4}$ Pa, a layer 2103 containing a composite material of an organic compound and an inorganic compound was formed on the first electrode 2102 by co-evaporating 4,4'-bis[N-(1-naphthyl)-N-phenylamino]biphenyl (abbreviation: NPB) and molybdenum(VI) oxide. The film thickness of the layer 2103 was to be 50 nm, and the weight ratio of NPB and molybdenum(VI) oxide was adjusted to be 4:1 (=NPB: molybdenum oxide). Note that the co-evaporation method is an evaporation method in which evaporation is carried out from a plurality of evaporation sources at the same time in one treatment chamber.

Then, a film of 4,4'-bis[N-(1-naphthyl)-N-phenylamino] biphenyl (abbreviation: NPB) was formed at a thickness of 10 nm on the layer 2103 containing the composite material by the evaporation method using resistance heating, thereby forming a hole transporting layer 2104.

Further, by co-evaporating 9,10-di(2-naphthyl)-2-tert-butylanthracene (abbreviation: t-BuDNA) and 9-[N-phenyl-N-(9-phenylcarbazol-3-yl)amino]-10-phenylanthracene (abbreviation: PCAPhA) represented by Structural Formula (201), a light emitting layer 2105 with a thickness of 40 nm was formed on the hole transporting layer 2104. The weight ratio of t-BuDNA and PCAPhA was adjusted to be 1:0.2 t-BuDNA:PCAPhA).

Thereafter, tris(8-quinolinolato)aluminum (abbreviation: Alq) was formed at a film thickness of 30 nm on the light emitting layer 2105 by means of the evaporation method using resistance heating, resulting in the formation of an electron transporting layer 2106.

Furthermore, a film of lithium fluoride (LiF) was formed at a thickness of 1 nm on the electron transporting layer 2106 to form an electron injecting layer 2107.

Lastly, by forming a film of aluminum with a film thickness of 200 nm on the electron injecting layer 2107 by means of the evaporation method using resistance heating, a second electrode 2108 was formed. Thus, a light emitting element 1 was manufactured.

Figure 36:
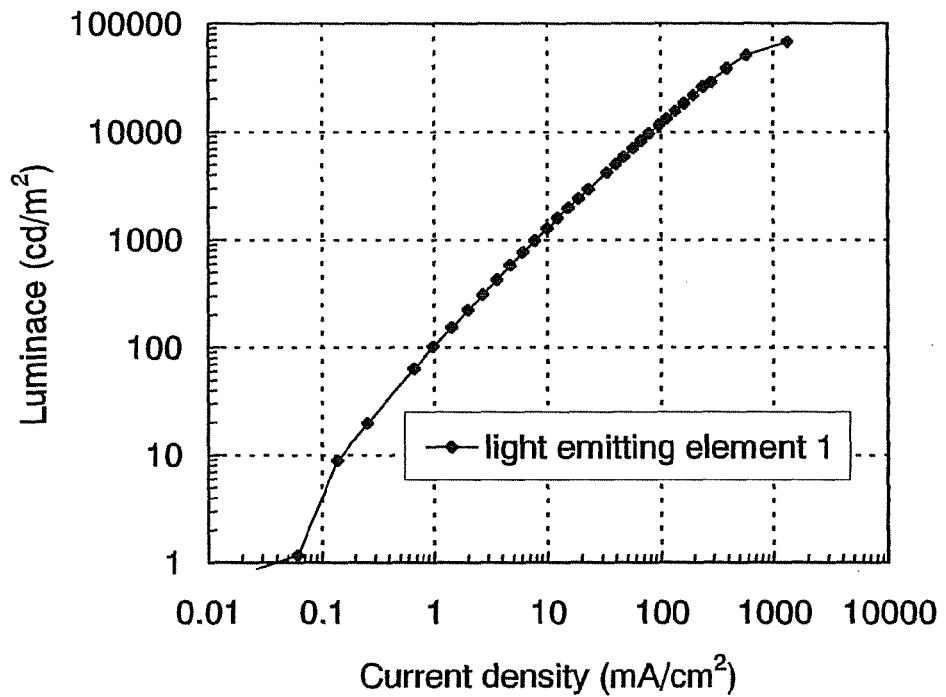
FIG. 36 shows luminance-current density characteristics of a light emitting element 1.
Figure 37:
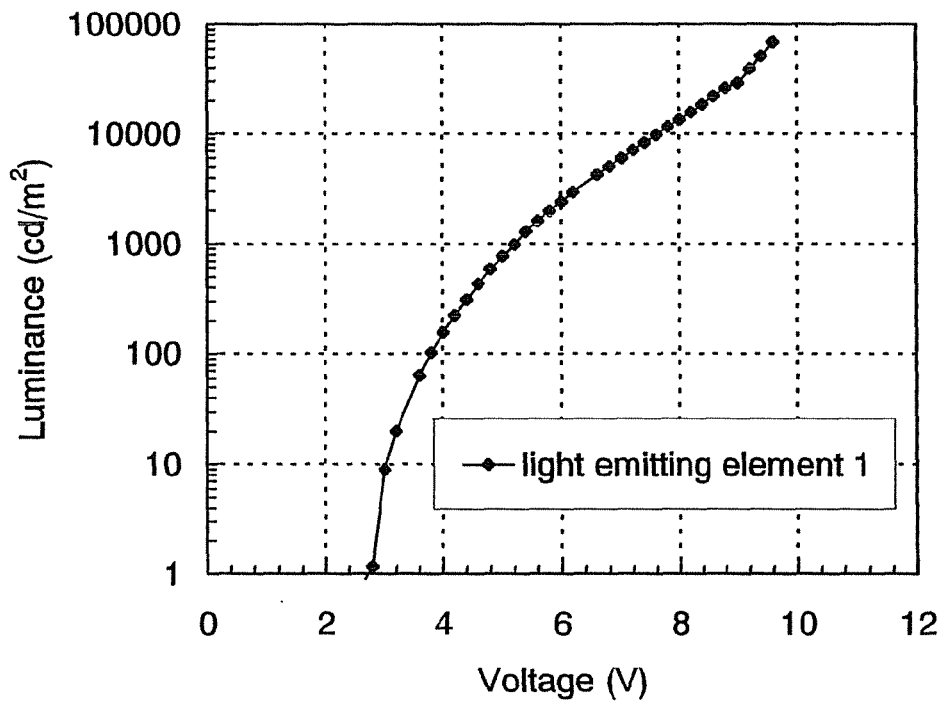
FIG. 37 shows luminance-voltage characteristics of the light emitting element 1.
Figure 38:
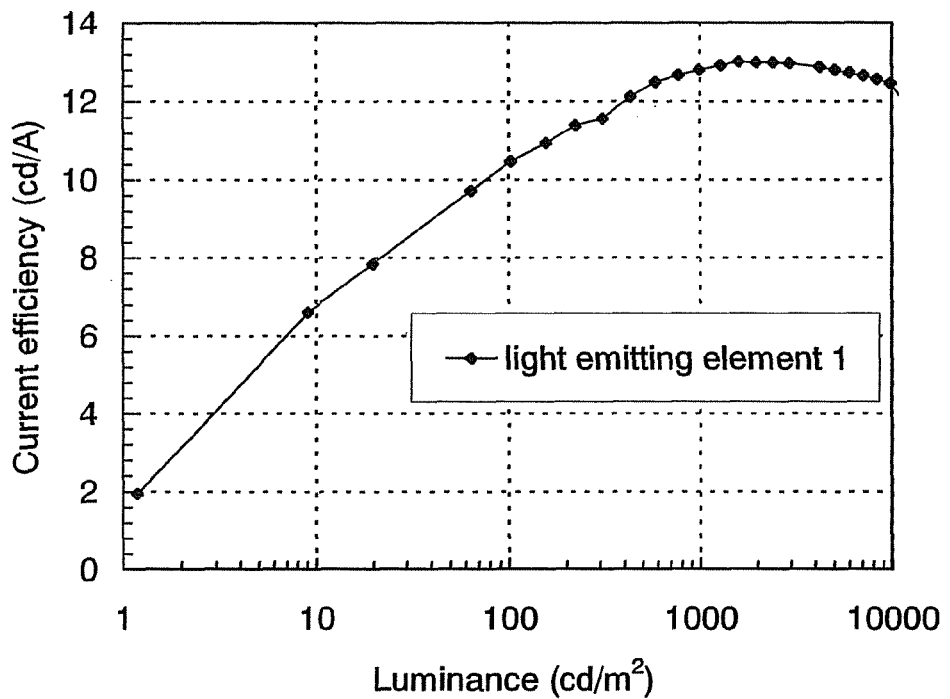
FIG. 38 shows current efficiency-luminance characteristics of the light emitting element 1.
Figure 39:
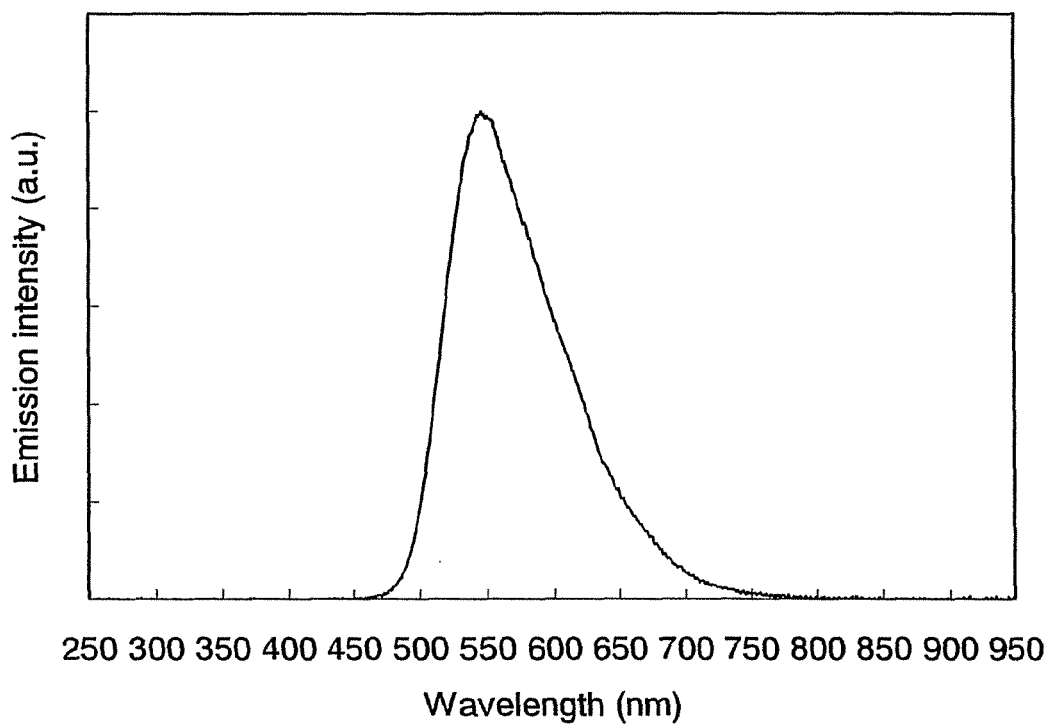
FIG. 39 shows an emission spectrum of the light emitting element 1.

A luminance-current density characteristic, a luminance-voltage characteristic, and a current efficiency-luminance characteristic of the light emitting element 1 are shown in FIGS. 36, 37, and 38, respectively. Also, the emission spectrum which was obtained at a current of 1 mA is illustrated in FIG. 39. The CIE chromaticity coordinates of the light emitting element 1 at a luminance of 990 cd/m² was (x=0.41, y=0.56), and light emission was yellow green. At a luminance of 990 cd/m², the current efficiency was 13 cd/A and the external quantum efficiency was 3.9%, meaning that high current efficiency and high external quantum efficiency were exhibited. In addition, at a luminance of 990 cd/m², the voltage was 5.2 V, the current density was 7.7 mA/cm², and the power efficiency was 7.7 (lm/W). As shown in FIG. 39, the maximum emission wavelength at a current of 1 mA was 546 nm.

Example 6

Example 6 will describe a light emitting element of the present invention with reference to FIG. 35. A manufacturing method of a light emitting element of this example is described below.

First, a film of indium tin oxide containing silicon oxide (ITSO) was formed by a sputtering method over a glass substrate 2101 to form a first electrode 2102. Note that the film thickness of the first electrode 2102 was 110 nm, and the area of the electrode was 2 mm×2 mm.

Next, the substrate over which the first electrode 2102 was formed was fixed to a substrate holder provided in a vacuum evaporation apparatus so that a surface of the substrate over which the first electrode 2102 was formed faced down. Then, after reducing the pressure of the vacuum evaporation apparatus to about $10^{-4}$ Pa, a layer 2103 containing a composite material of an organic compound and an inorganic compound was formed on the first electrode 2102 by co-evaporating 4,4'-bis[N-(1-naphthyl)-N-phenylamino]biphenyl (abbreviation: NPB) and molybdenum(VI) oxide. The film thickness of the layer 2103 was to be 50 nm, and the weight ratio of NPB and molybdenum(VI) oxide was adjusted to be 4:1 (=NPB: molybdenum oxide). Note that the co-evaporation method is an evaporation method in which evaporation is carried out from a plurality of evaporation sources at the same time in one treatment chamber.

Then, a film of 4,4'-bis[N-(1-naphthyl)-N-phenylamino] biphenyl (abbreviation: NPB) was formed at a thickness of 10 nm on the layer 2103 containing the composite material by the evaporation method using resistance heating, thereby forming a hole transporting layer 2104.

Further, by co-evaporating 9-[4-(N-carbazolyl)]phenyl-10-phenylanthracene (abbreviation: CzPA) and 9,10-bis[N-phenyl-N-(9-phenylcarbazol-3-yl)amino]anthracene (abbreviation: PCA2A) represented by Structural Formula (238), a light emitting layer 2105 with a thickness of 40 nm was formed on the hole transporting layer 2104. The weight ratio of CzPA and PCA2A in the light emitting element 2 was adjusted to be 1:0.05 (=CzPA:PCA2A), and the weight ratio in the light emitting element 3 was adjusted to be 1:0.2 (=CzPA:PCA2A).

Thereafter, tris(8-quinolinolato)aluminum (abbreviation: Alq) was formed at a film thickness of 30 nm on the light emitting layer 2105 by means of the evaporation method using resistance heating, resulting in the formation of an electron transporting layer 2106.

Furthermore, a film of lithium fluoride (LiF) was formed at a thickness of 1 nm on the electron transporting layer 2106 to form an electron injecting layer 2107.

Lastly, by forming a film of aluminum with a film thickness of 200 nm on the electron injecting layer 2107 by means of the evaporation method using resistance heating, a second electrode 2108 was formed. Thus, a light emitting element 2 and a light emitting element 3 were manufactured.

Figure 40:
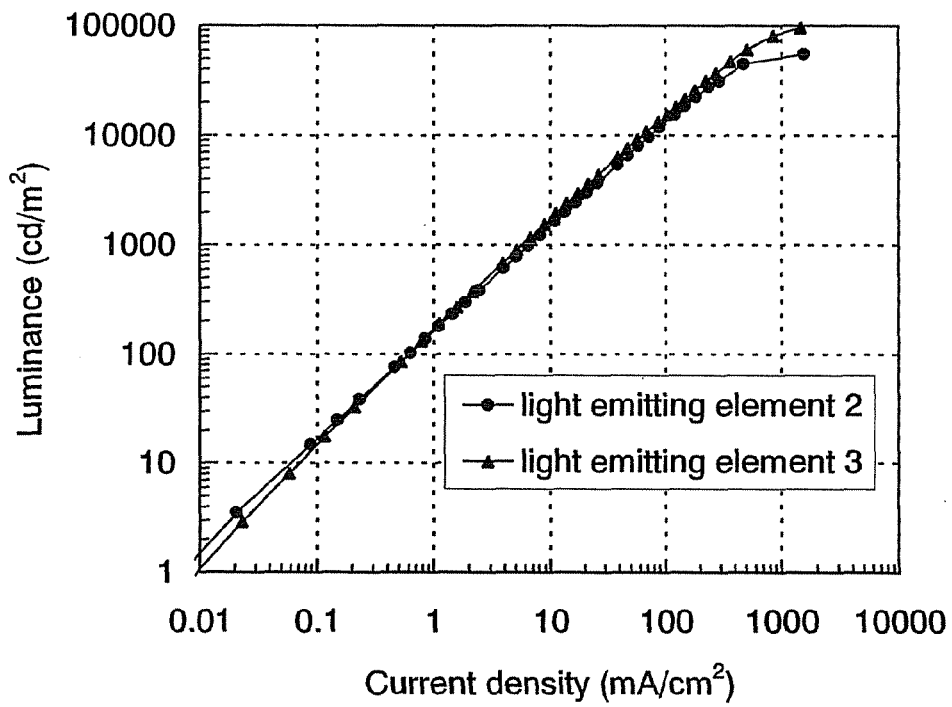
FIG. 40 shows luminance-current density characteristics of a light emitting element 2 and a light emitting element 3.
Figure 41:
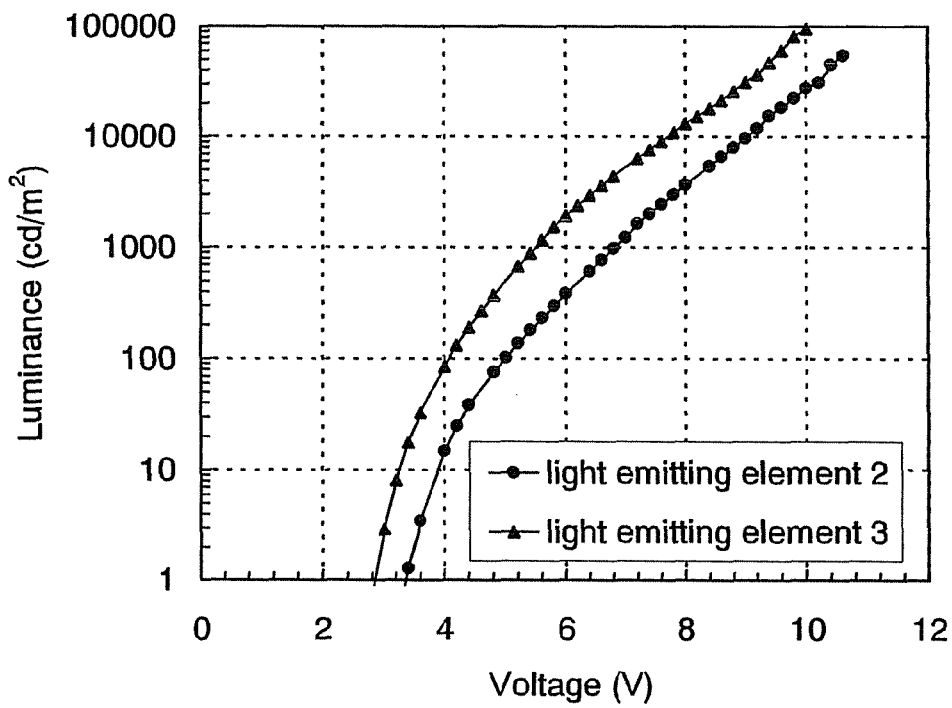
FIG. 41 shows luminance-voltage characteristics of the light emitting element 2 and the light emitting element 3.
Figure 42:
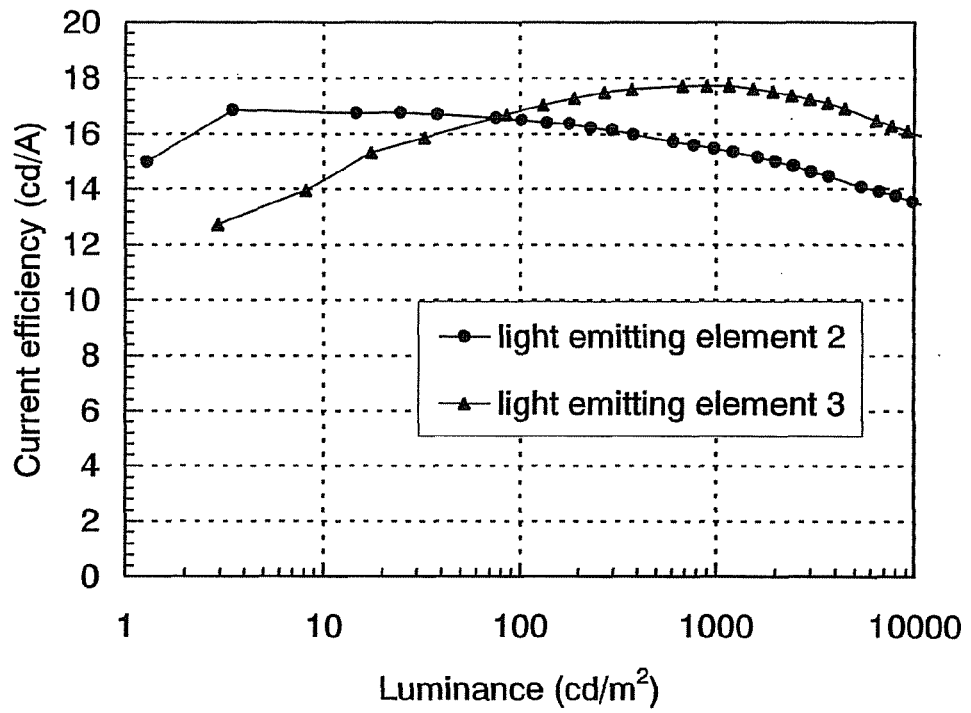
FIG. 42 shows current efficiency-luminance characteristics of the light emitting element 2 and the light emitting element 3.
Figure 43:
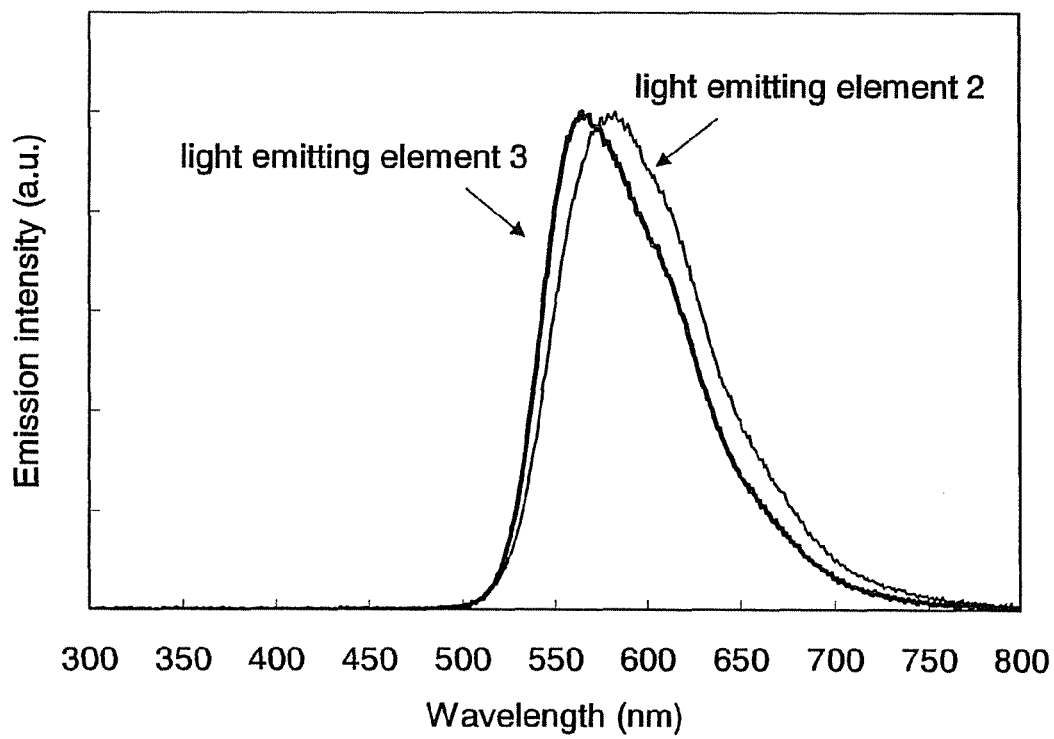
FIG. 43 shows emission spectra of the light emitting element 2 and the light emitting element 3.

Luminance-current density characteristics, luminance-voltage characteristics, and current efficiency-luminance characteristics of the light emitting element 2 and the light emitting element 3 are shown in FIGS. 40, 41, and 42, respectively. Also, the emission spectrum which was obtained at a current of 1 mA is illustrated in FIG. 43. The CIE chromaticity coordinates of the light emitting element 2 at a luminance of 980 cd/m² was (x=0.48, y=0.52), and light emission was yellow. At a luminance of 980 cd/m², the current efficiency was 16 cd/A and the external quantum efficiency was 5.6%, meaning that high current efficiency and high external quantum efficiency were exhibited. In addition, at a luminance of 980 cd/m², the voltage was 6.8 V, the current density was 6.3 mA/cm², and the power efficiency was 7.1 (1 m/W). As shown in FIG. 43, the maximum emission wavelength at a current of 1 mA was 583 nm. The CIE chromaticity coordinates of the light emitting element 3 at a luminance of 900 cd/m² was (x=0.50, y=0.50), and light emission was yellow. At a luminance of 900 cd/m², the current efficiency was 18 cd/A and the external quantum efficiency was 5.8%, meaning that high current efficiency and high external quantum efficiency were exhibited. In addition, at a luminance of 900 cd/m², the voltage was 5.4 V, the current density was 5.0 mA/cm², and the power efficiency was 10 (lm/W). As shown in FIG. 43, the maximum emission wavelength at a current of 1 mA was 565 nm.

Seen in FIGS. 40 to 43, the light emitting element 3 has a much higher current efficiency than the light emitting element 2. In addition, the light emitting element 3 has a lower driving voltage than the light emitting element 2, which means the light emitting element 3 has less power consumption.

Figure 44:
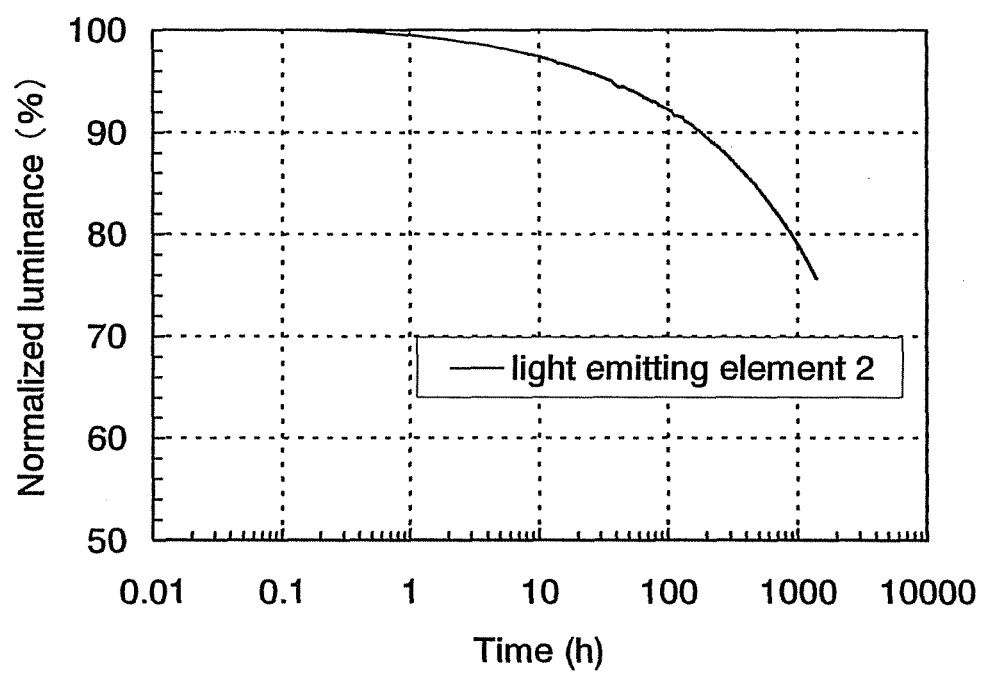
FIG. 44 shows time dependence of normalized luminance of the light emitting element 2.

A continuous lighting test was conducted on the light emitting element 2 by constant current driving at an initial luminance of 3000 cd/m². FIG. 44 shows the result, where time dependence of normalized luminance at the time when initial luminance is considered to be 100% is shown. From FIG. 44, it is seen that the light emitting element 2 maintains 76% of the initial luminance even after 1400 hours, and this shows the light emitting element 2 has a long lifetime. Accordingly, by using an anthracene derivative of the present invention, a long-life light emitting element can be obtained. In particular, when 9,10-bis[N-phenyl-N-(9-phenylcarbazol-3-yl)amino]anthracene (abbreviation: PCA2A) represented by Structural Formula (238) is used, a long-life light emitting element can be obtained. Compounds having a partial structure of N,9-diphenyl-9H-carbazol-3-amine (abbreviation: PCA) are extremely stable against repetition of oxidation and reduction. By provision of a substituent at position 9 and position 10 of anthracene, the value of HOMO level can become an appropriate value for a light emitting layer. Accordingly, PCA2A used in this example is preferable for light emitting elements.

Example 7

Example 7 will describe a light emitting element of the present invention with reference to FIG. 35. A manufacturing method of a light emitting element of this example is described below.

First, a film of indium tin oxide containing silicon oxide (ITSO) was formed by a sputtering method over a glass substrate 2101 to form a first electrode 2102. Note that the film thickness of the first electrode 2102 was 110 nm, and the area of the electrode was 2 mm×2 mm.

Next, the substrate over which the first electrode 2102 was formed was fixed to a substrate holder provided in a vacuum evaporation apparatus so that a surface of the substrate over which the first electrode 2102 was formed faced down. Then, after reducing the pressure of the vacuum evaporation apparatus to about $10^{-4}$ Pa, a layer 2103 containing a composite material of an organic compound and an inorganic compound was formed on the first electrode 2102 by co-evaporating 4,4'-bis[N-(1-naphthyl)-N-phenylamino]biphenyl (abbreviation: NPB) and molybdenum(VI) oxide. The film thickness of the layer 2103 was to be 50 nm, and the weight ratio of NPB and molybdenum(VI) oxide was adjusted to be 4:1 (=NPB:molybdenum oxide). Note that the co-evaporation method is an evaporation method in which evaporation is carried out from a plurality of evaporation sources at the same time in one treatment chamber.

Then, a film of 4,4'-bis[N-(1-naphthyl)-N-phenylamino]biphenyl (abbreviation: NPB) was formed at a thickness of 10 nm on the layer 2103 containing the composite material by the evaporation method using resistance heating, thereby forming a hole transporting layer 2104.

Further, by co-evaporating tris(8-quinolinolato)aluminum (abbreviation: Alq) and 9-{N-[4-(carbazol-9-yl)phenyl]-N-phenylamino}-10-phenylanthracene (abbreviation: YGAPhA), which is an anthracene derivative represented by Structural Formula (301), a light emitting layer 2105 with a thickness of 40 nm was formed on the hole transporting layer 2104. The weight ratio of Alq and YGAPhA was adjusted to be 1:0.5 (=Alq:YGAPhA).

Thereafter, tris(8-quinolinolato)aluminum (abbreviation: Alq) was formed at a film thickness of 30 nm on the light emitting layer 2105 by means of the evaporation method using resistance heating, resulting in the formation of an electron transporting layer 2106.

Furthermore, a film of lithium fluoride (LiF) was formed at a thickness of 1 nm on the electron transporting layer 2106 to form an electron injecting layer 2107.

Lastly, by forming a film of aluminum with a film thickness of 200 nm on the electron injecting layer 2107 by means of the evaporation method using resistance heating, a second electrode 2108 was formed. Thus, a light emitting element 4 was manufactured.

Comparative Example 1

Hereinafter, a method for fabricating a light emitting element of a comparative example is described. A structural formula of a material used in this comparative example is shown below.

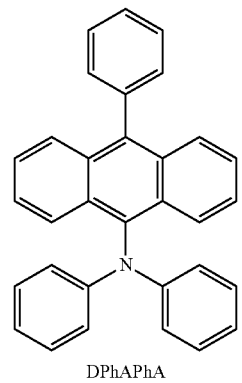 [SMILES: c1ccc(-c2c3ccccc3c(N(c3ccccc3)c3ccccc3)c3ccccc23)cc1 ; "DPhAPhA"]

DPhAPhA

First, a film of indium tin oxide containing silicon oxide (ITSO) was formed by a sputtering method over a glass substrate to form a first electrode. Note that the film thickness of the first electrode was 110 nm, and the area of the electrode was 2 mm×2 mm.

Next, the substrate over which the first electrode was formed was fixed to a substrate holder provided in a vacuum evaporation apparatus so that a surface of the substrate over which the first electrode was formed faced down. Then, after reducing the pressure of the vacuum evaporation apparatus to about $10^{-4}$ Pa, a layer containing a composite material of an organic compound and an inorganic compound was formed on the first electrode by co-evaporating 4,4'-bis[N-(1-naphthyl)-N-phenylamino]biphenyl (abbreviation: NPB) and molybdenum(VI) oxide. The film thickness of the layer was to be 50 nm, and the weight ratio of NPB and molybdenum (VI) oxide was adjusted to be 4:1 (=NPB:molybdenum oxide). Note that the co-evaporation method is an evaporation method in which evaporation is carried out from a plurality of evaporation sources at the same time in one treatment chamber.

Then, a film of 4,4'-bis[N-(1-naphthyl)-N-phenylamino]biphenyl (abbreviation: NPB) was formed at a thickness of 10 nm on the layer containing the composite material by the evaporation method using resistance heating, thereby forming a hole transporting layer.

Further, by co-evaporating tris(8-quinolinolato)aluminum (abbreviation: Alq) and 9-diphenylamino-10-phenylanthracene (abbreviation: DPhAPhA), a light emitting layer with a thickness of 40 nm was formed on the hole transporting layer. The weight ratio of Alq and DPhAPhA was adjusted to be 1:0.5 (=Alq:DPhAPhA).

Thereafter, tris(8-quinolinolato)aluminum (abbreviation: Alq) was formed at a film thickness of 30 nm on the light emitting layer by means of the evaporation method using resistance heating, resulting in the formation of an electron transporting layer.

Furthermore, a film of lithium fluoride (LiF) was formed at a thickness of 1 nm on the electron transporting layer to form an electron injecting layer.

Lastly, by forming a film of aluminum with a film thickness of 200 nm on the electron injecting layer by means of the evaporation method using resistance heating, a second electrode was formed. Thus, a comparative light emitting element 5 was manufactured.

Figure 45:
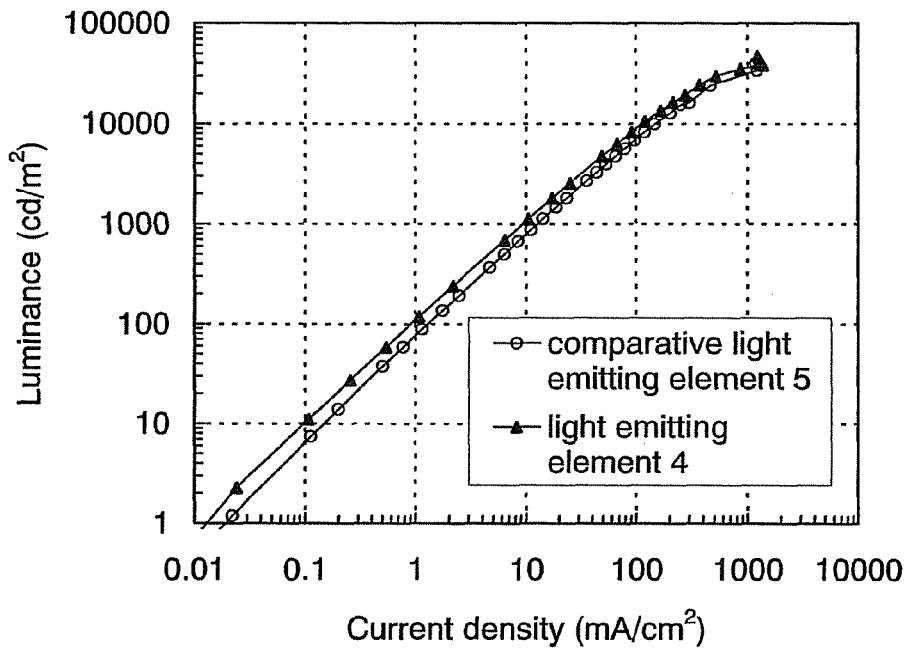
FIG. 45 shows luminance-current density characteristics of a light emitting element 4 and a comparative light emitting element 5.
Figure 46:
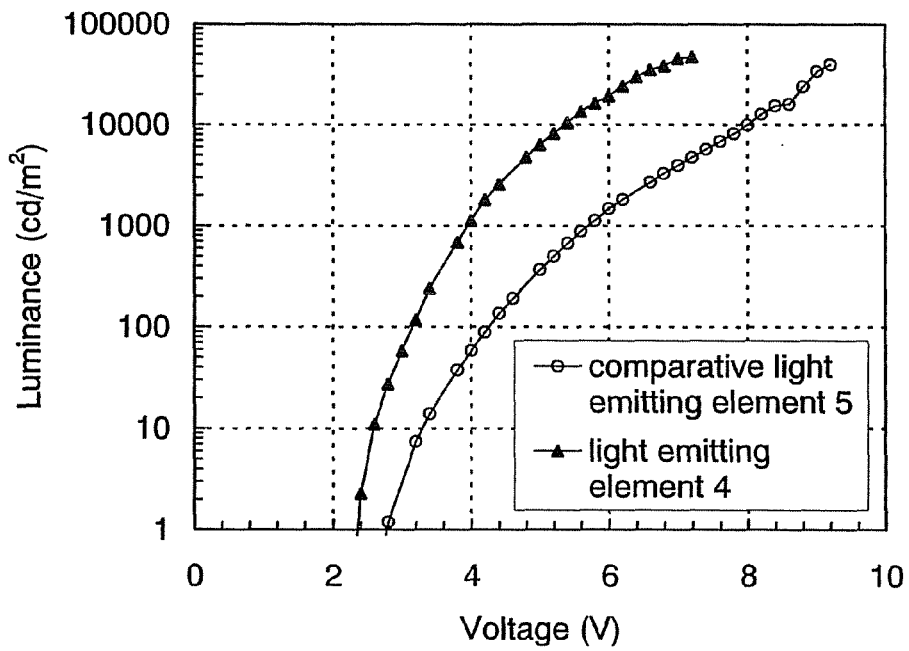
FIG. 46 shows luminance-voltage characteristics of the light emitting element 4 and the comparative light emitting element 5.
Figure 47:
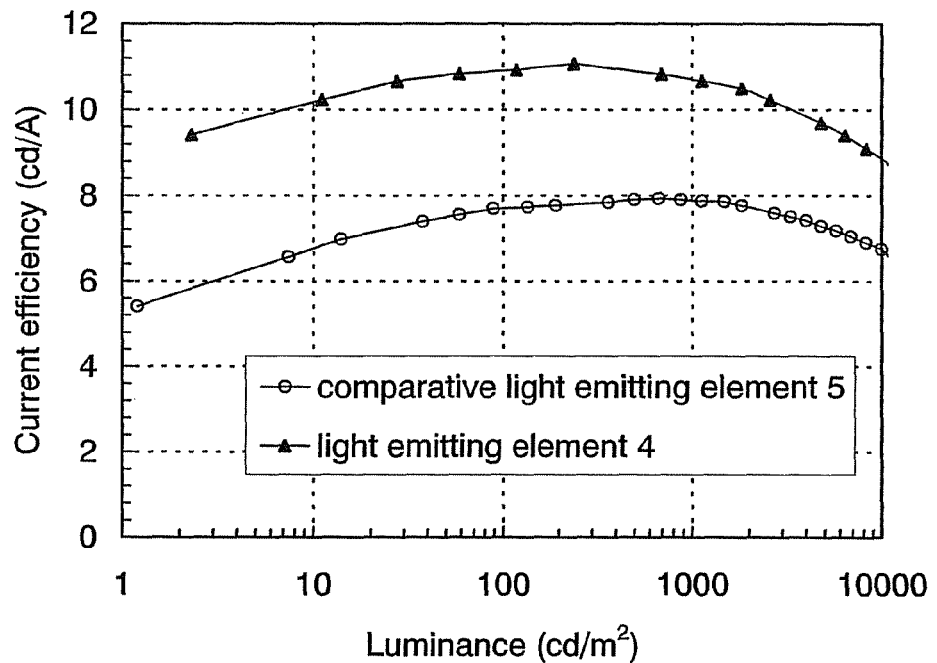
FIG. 47 shows current efficiency-luminance characteristics of the light emitting element 4 and the comparative light emitting element 5.
Figure 48:
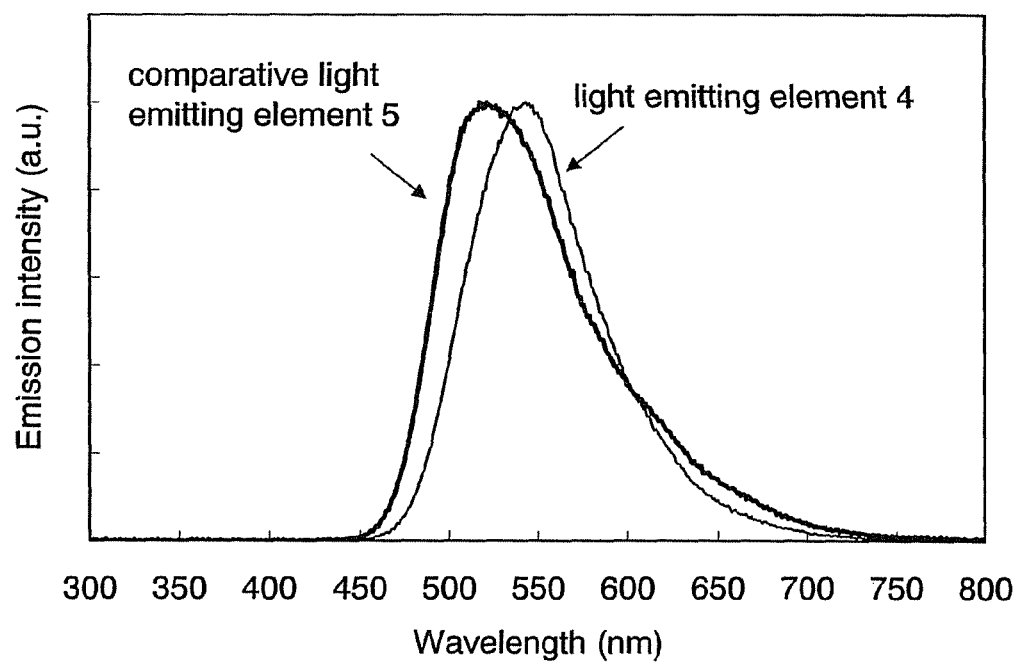
FIG. 48 shows emission spectra of the light emitting element 4 and the comparative light emitting element 5.

Luminance-current density characteristics, luminance-voltage characteristics, and current efficiency-luminance characteristics of the light emitting element 4 and the comparative light emitting element 5 are shown in FIGS. 45, 46, and 47, respectively. Also, the emission spectrum which was obtained at a current of 1 mA is illustrated in FIG. 48. The CIE chromaticity coordinates of the light emitting element 4 at a luminance of 1100 cd/m$^2$ was (x=0.35, y=0.60), and light emission was green. At a luminance of 1100 cd/m$^2$, the current efficiency was 11 cd/A and the external quantum efficiency was 3.0%, meaning that high current efficiency and high external quantum efficiency were exhibited. In addition, at a luminance of 1100 cd/m$^2$, the voltage was 4.0 V, the current density was 11 mA/cm$^2$, and the power efficiency was 7.1 (1 m/W). As shown in FIG. 48, the maximum emission wavelength at a current of 1 mA was 543 nm.

The CIE chromaticity coordinates of the comparative light emitting element 5 at a luminance of 870 cd/m$^2$ was (x=0.32, y=0.58), and light emission was green. At a luminance of 870 cd/m$^2$, the current efficiency was 7.9 cd/A and the external quantum efficiency was 2.5%. In addition, at a luminance of 870 cd/m$^2$, the voltage was 5.6 V, the current density was 11 mA/cm$^2$, and the power efficiency was 4.4 (lm/W). As shown in FIG. 48, the maximum emission wavelength at a current of 1 mA was 517 nm.

Seen in FIGS. 45 to 48, the light emitting element 4 has a higher current efficiency and a higher external quantum efficiency than the comparative light emitting element 5. In addition, the light emitting element 4 has a higher power efficiency than the comparative light emitting element 5, which means the light emitting element 4 has less power consumption. Accordingly, by applying an anthracene derivative of the present invention for a light emitting element, a high luminous efficiency can be achieved. In addition, a light emitting element with low power consumption can be obtained.

Example 8

Example 8 will describe a light emitting element of the present invention with reference to FIG. 35. A manufacturing method of a light emitting element of this example is described below.

First, a film of indium tin oxide containing silicon oxide (ITSO) was formed by a sputtering method over a glass substrate 2101 to form a first electrode 2102. Note that the film thickness of the first electrode 2102 was 110 nm, and the area of the electrode was 2 mm×2 mm.

Next, the substrate over which the first electrode 2102 was formed was fixed to a substrate holder provided in a vacuum evaporation apparatus so that a surface of the substrate over which the first electrode 2102 was formed faced down. Then, after reducing the pressure of the vacuum evaporation apparatus to about 10$^{-4}$ Pa, a layer 2103 containing a composite material of an organic compound and an inorganic compound was formed on the first electrode 2102 by co-evaporating 4,4'-bis[N-(1-naphthyl)-N-phenylamino]biphenyl (abbreviation: NPB) and molybdenum(VI) oxide. The film thickness of the layer 2103 was to be 50 nm, and the weight ratio of NPB and molybdenum(VI) oxide was adjusted to be 4:1 (=NPB: molybdenum oxide). Note that the co-evaporation method is an evaporation method in which evaporation is carried out from a plurality of evaporation sources at the same time in one treatment chamber.

Then, a film of 4,4'-bis[N-(1-naphthyl)-N-phenylamino]biphenyl (abbreviation: NPB) was formed at a thickness of 10 nm on the layer 2103 containing the composite material by the evaporation method using resistance heating, thereby forming a hole transporting layer 2104.

Further, by co-evaporating 9-[4-(N-carbazolyl)]phenyl-10-phenylanthracene (abbreviation: CzPA) and 9,10-bis[N-(4-carbazol-9-yl)phenyl-N-phenylamino]anthracene (abbreviation: YGA2A), which is an anthracene derivative represented by Structural Formula (335), a light emitting layer 2105 with a thickness of 40 nm was formed on the hole transporting layer 2104. The weight ratio of CzPA and YGA2A was adjusted to be 1:0.2 (=CzPA:YGA2A).

Thereafter, tris(8-quinolinolato)aluminum (abbreviation: Alq) was formed at a film thickness of 30 nm on the light emitting layer 2105 by means of the evaporation method using resistance heating, resulting in the formation of an electron transporting layer 2106.

Furthermore, a film of lithium fluoride (LiF) was formed at a thickness of 1 nm on the electron transporting layer 2106 to form an electron injecting layer 2107.

Lastly, by forming a film of aluminum with a film thickness of 200 nm on the electron injecting layer 2107 by means of the evaporation method using resistance heating, a second electrode 2108 was formed. Thus, a light emitting element 6 was manufactured.

Comparative Example 2

Hereinafter, a method for fabricating a light emitting element of a comparative example is described. A structural formula of a material used in this comparative example is shown below.

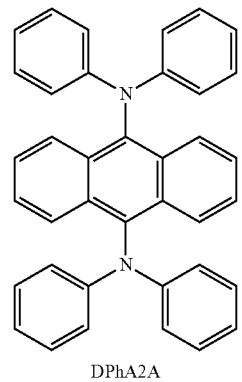

DPhA2A

First, a film of indium tin oxide containing silicon oxide (ITSO) was formed by a sputtering method over a glass substrate to form a first electrode. Note that the film thickness of the first electrode was 110 nm, and the area of the electrode was 2 mm×2 mm.

Next, the substrate over which the first electrode was formed was fixed to a substrate holder provided in a vacuum evaporation apparatus so that a surface of the substrate over which the first electrode was formed faced down. Then, after reducing the pressure of the vacuum evaporation apparatus to about 10$^{-4}$ Pa, a layer containing a composite material of an organic compound and an inorganic compound was formed on the first electrode by co-evaporating 4,4'-bis[N-(1-naphthyl)-N-phenylamino]biphenyl (abbreviation: NPB) and molybdenum(VI) oxide. The film thickness of the layer was to be 50 nm, and the weight ratio of NPB and molybdenum (VI) oxide was adjusted to be 4:1 (=NPB:molybdenum oxide). Note that the co-evaporation method is an evaporation method in which evaporation is carried out from a plurality of evaporation sources at the same time in one treatment chamber.

Then, a film of 4,4'-bis[N-(1-naphthyl)-N-phenylamino] biphenyl (abbreviation: NPB) was formed at a thickness of 10 nm on the layer containing the composite material by the evaporation method using resistance heating, thereby forming a hole transporting layer.

Further, by co-evaporating 9-[4-(N-carbazolyl)]phenyl-10-phenylanthracene (abbreviation: CzPA) and 9,10-bis (diphenylamino)anthracene (abbreviation: DPhA2A), a light emitting layer with a thickness of 40 nm was formed on the hole transporting layer. The weight ratio of CzPA and DPhA2A was adjusted to be 1:0.25 (=CzPA:DPhA2A).

Thereafter, tris(8-quinolinolato)aluminum (abbreviation: Alq) was formed at a film thickness of 30 nm on the light emitting layer by means of the evaporation method using resistance heating, resulting in the formation of an electron transporting layer.

Furthermore, a film of lithium fluoride (LiF) was formed at a thickness of 1 nm on the electron transporting layer to form an electron injecting layer.

Lastly, by forming a film of aluminum with a film thickness of 200 nm on the electron injecting layer by means of the evaporation method using resistance heating, a second electrode was formed. Thus, a comparative light emitting element 7 was manufactured.

Figure 49:
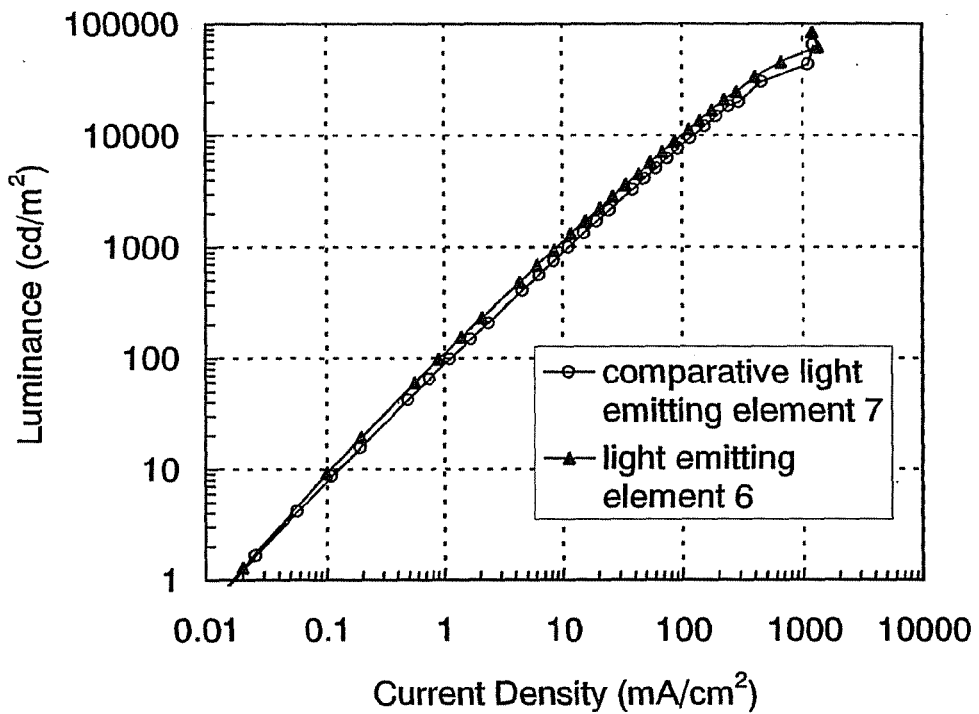
FIG. 49 shows luminance-current density characteristics of the light emitting element 6 and the comparative light emitting element 7.
Figure 50:
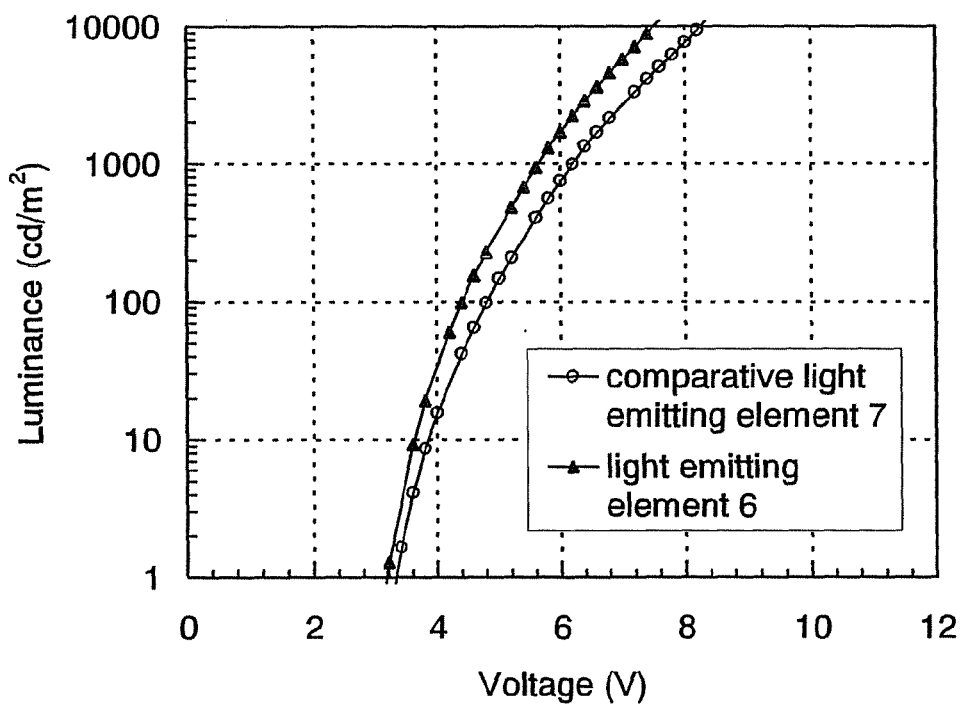
FIG. 50 shows luminance-voltage characteristics of the light emitting element 6 and the comparative light emitting element 7.
Figure 51:
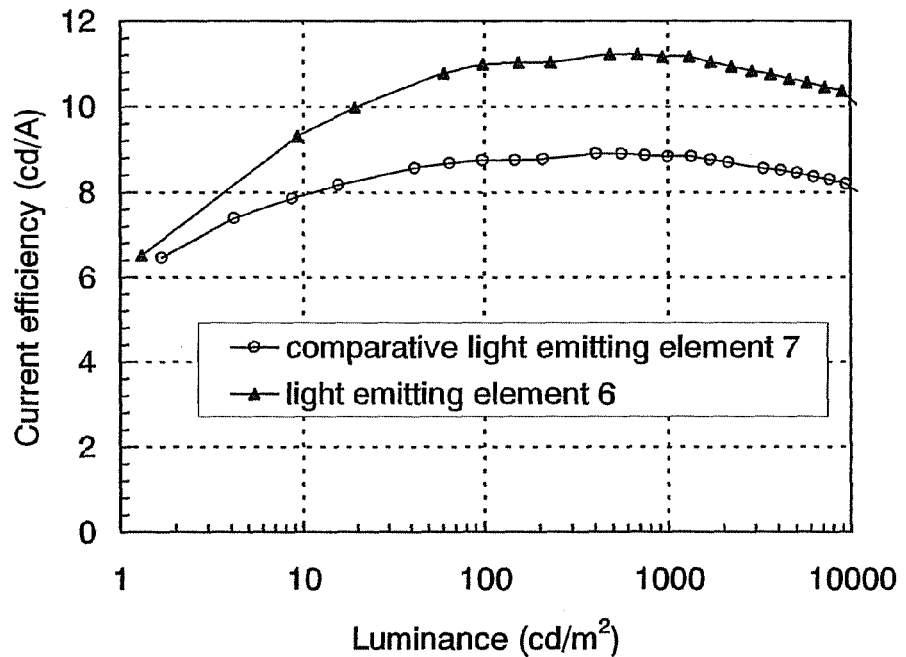
FIG. 51 shows current efficiency-luminance characteristics of the light emitting element 6 and the comparative light emitting element 7.
Figure 52:
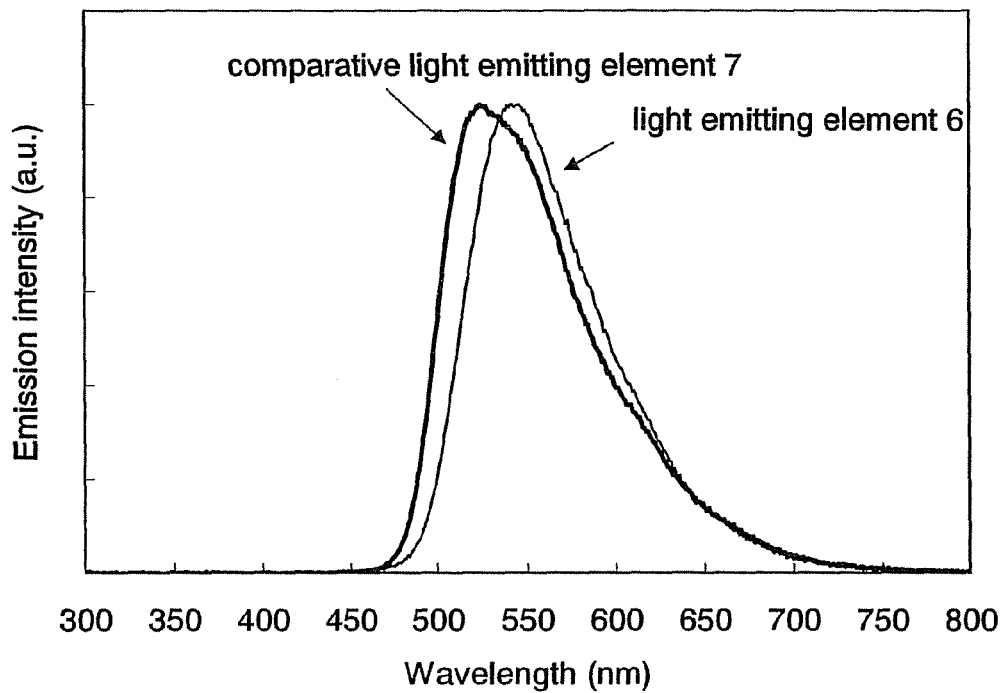
FIG. 52 shows emission spectra of the light emitting element 6 and the comparative light emitting element 7.

Luminance-current density characteristics, luminance-voltage characteristics, and current efficiency-luminance characteristics of the light emitting element 6 and the comparative light emitting element 7 are shown in FIGS. 49, 50, and 51, respectively. Also, the emission spectrum which was obtained at a current of 1 mA is illustrated in FIG. 52. The CIE chromaticity coordinates of the light emitting element 6 at a luminance of 940 cd/m$^2$ was (x=0.39, y=0.58), and light emission was yellow green. At a luminance of 940 cd/m$^2$, the current efficiency was 11 cd/A and the external quantum efficiency was 3.2%, meaning that high current efficiency and high external quantum efficiency were exhibited. In addition, at a luminance of 940 cd/m$^2$, the voltage was 5.6 V, the current density was 8.4 mA/cm$^2$, and the power efficiency was 6.3 (lm/W). As shown in FIG. 52, the maximum emission wavelength at a current of 1 mA was 542 nm.

The CIE chromaticity coordinates of the comparative light emitting element 7 at a luminance of 750 cd/m$^2$ was (x=0.36, y=0.60), and light emission was yellow green. At a luminance of 750 cd/m$^2$, the current efficiency was 8.9 cd/A and the external quantum efficiency was 2.7%. In addition, at a luminance of 750 cd/m$^2$, the voltage was 6.0 V, the current density was 8.4 mA/cm$^2$, and the power efficiency was 4.6 (1 m/W). As shown in FIG. 52, the maximum emission wavelength at a current of 1 mA was 524 nm.

Seen in FIGS. 49 to 52, the light emitting element 6 has a higher current efficiency and a higher external quantum efficiency than the comparative light emitting element 7. In addition, the light emitting element 6 has a higher power efficiency than the comparative light emitting element 7, which means the light emitting element 6 has less power consumption. Accordingly, by applying an anthracene derivative of the present invention for a light emitting element, a high luminous efficiency can be achieved. In addition, a light emitting element with low power consumption can be obtained.

Example 9

Figure 53:
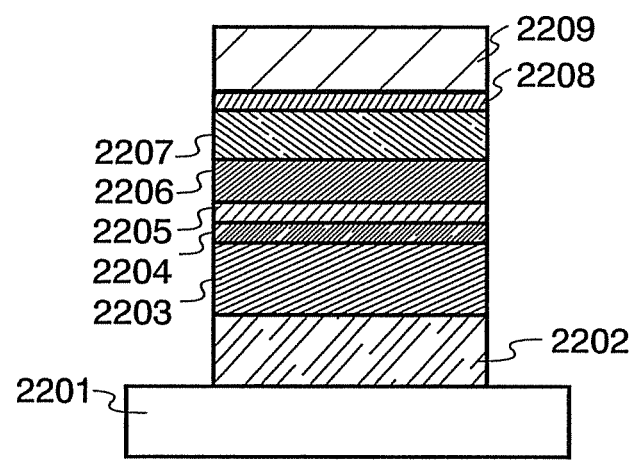
FIG. 53 shows a light emitting element of an example.

Example 9 will describe a light emitting element of the present invention with reference to FIG. 53. In this example, a light emitting element exhibiting whitish light emission is manufactured by using an anthracene derivative of the present invention. Structural formulae of materials used in this example are shown below. Note that the structural formulae of the materials described in Examples 3 to 8 are omitted.

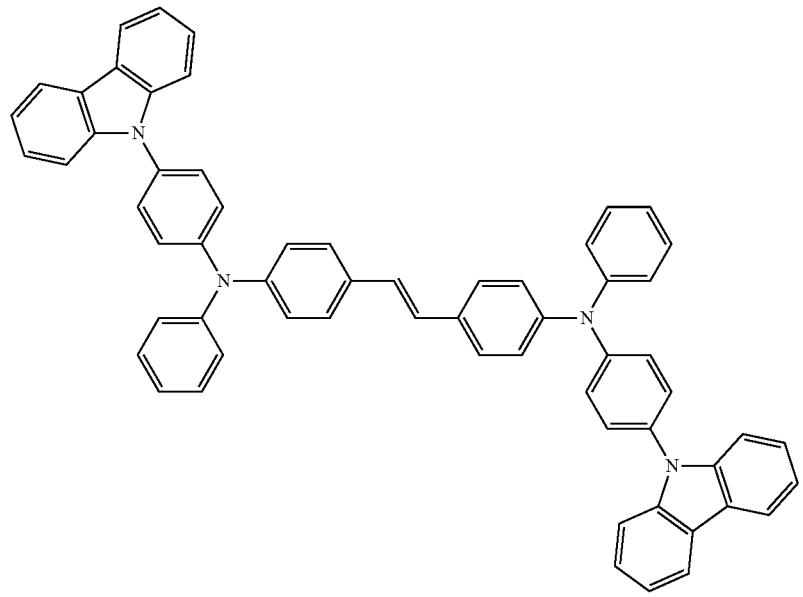

YGA2S

-continued

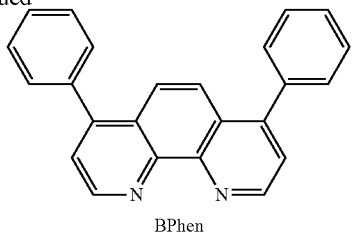
BPhen

Hereinafter, a manufacturing method of a light emitting element of this example is described.

First, a film of indium tin oxide containing silicon oxide (ITSO) was formed by a sputtering method over a glass substrate 2201 to form a first electrode 2202. Note that the film thickness of the first electrode 2202 was 110 nm, and the area of the electrode was 2 mm×2 mm.

Next, the substrate over which the first electrode 2202 was formed was fixed to a substrate holder provided in a vacuum evaporation apparatus so that a surface of the substrate over which the first electrode 2202 was formed faced down. Then, after reducing the pressure of the vacuum evaporation apparatus to about $10^{-4}$ Pa, a layer 2203 containing a composite material of an organic compound and an inorganic compound was formed on the first electrode 2202 by co-evaporating 4,4'-bis[N-(1-naphthyl)-N-phenylamino]biphenyl (abbreviation: NPB) and molybdenum(VI) oxide. The film thickness of the layer 2203 was to be 50 nm, and the weight ratio of NPB and molybdenum(VI) oxide was adjusted to be 4:1 (=NPB: molybdenum oxide).

Then, a film of 4,4'-bis[N-(1-naphthyl)-N-phenylamino]biphenyl (abbreviation: NPB) was formed at a thickness of 10 nm on the layer 2203 containing the composite material by the evaporation method using resistance heating, thereby forming a hole transporting layer 2204.

Further, by co-evaporating 4,4'-bis[N-(1-naphthyl)-N-phenylamino]biphenyl (abbreviation: NPB) and 9,10-bis[N-phenyl-N-(9-phenylcarbazol-3-yl)amino]anthracene (abbreviation: PCA2A), which is an anthracene derivative represented by Structural Formula (238), a first light emitting layer 2205 with a thickness of 10 nm was formed on the hole transporting layer 2204. The weight ratio of NPB and PCA2A in the light emitting element 8 was adjusted to be 1:0.01 (=NPB:PCA2A) and the weight ratio in the light emitting element 9 was adjusted to be 1:0.005 (=NPB:PCA2A).

Further, by co-evaporating 9-[4-(N-carbazolyl)]phenyl-10-phenylanthracene (abbreviation: CzPA) and N,N'-bis[4-(9H-carbazol-9-yl)phenyl]-N,N'-diphenylstilbene-4,4'-diamine (abbreviation: YGA2S), a second light emitting layer 2206 with a thickness of 20 nm was formed on the first light emitting layer 2205. The weight ratio of CzPA and YGA2S was adjusted to be 1:0.04 (=CzPA:YGA2S).

Thereafter, bathophenanthroline (abbreviation: Bphen) was formed at a film thickness of 30 nm on the second light emitting layer 2206 by means of the evaporation method using resistance heating, resulting in the formation of an electron transporting layer 2207.

Furthermore, a film of lithium fluoride (LiF) was formed at a thickness of 1 nm on the electron transporting layer 2207 to form an electron injecting layer 2208.

Lastly, by forming a film of aluminum with a film thickness of 200 nm on the electron injecting layer 2208 by means of the evaporation method using resistance heating, a second electrode 2209 was formed. Thus, a light emitting element 8 and a light emitting element 9 were manufactured.

Figure 54:
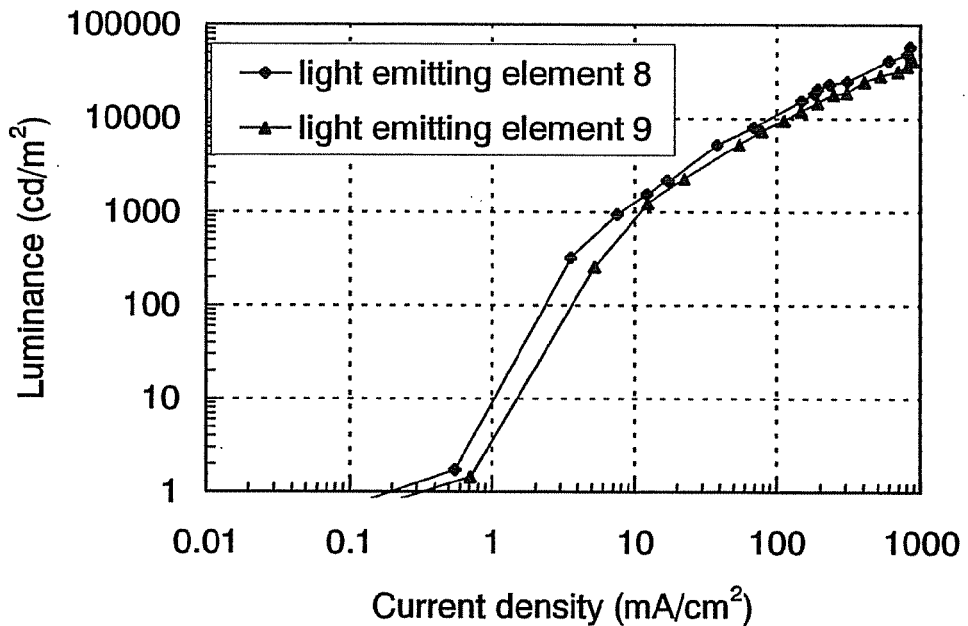
FIG. 54 shows luminance-current density characteristics of a light emitting element 8 and a light emitting element 9.
Figure 55:
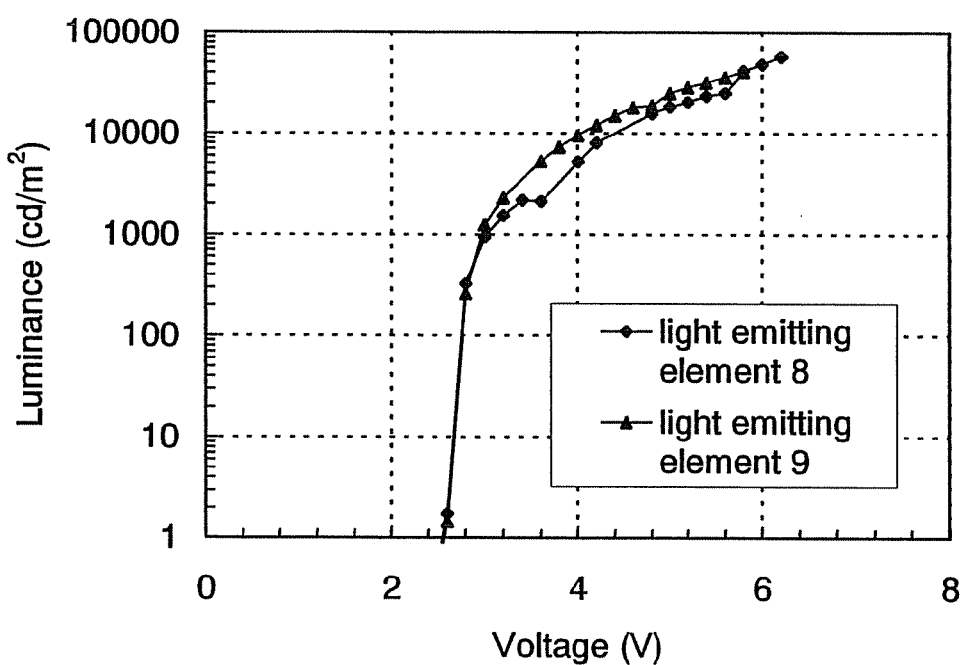
FIG. 55 shows luminance-voltage characteristics of the light emitting element 8 and the light emitting element 9.
Figure 56:
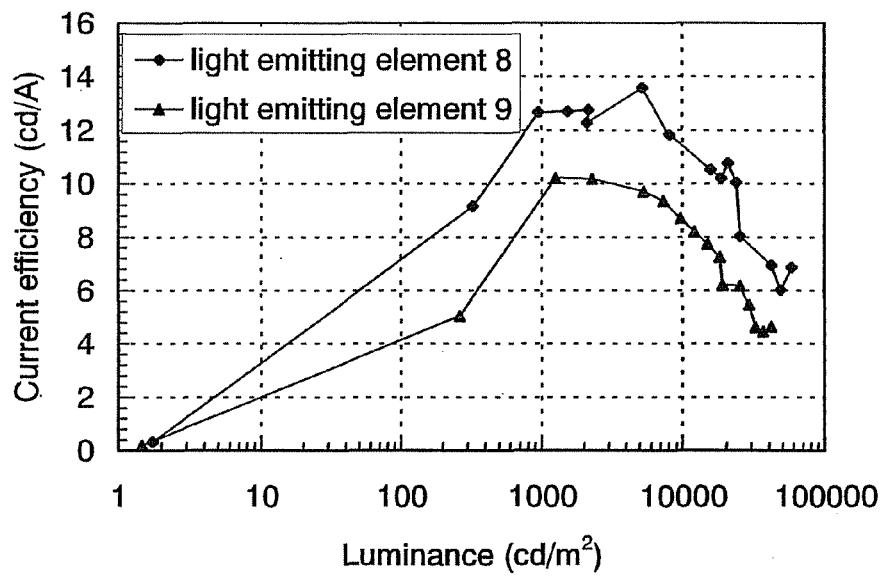
FIG. 56 shows current efficiency-luminance characteristics of the light emitting element 8 and the light emitting element 9.
Figure 57:
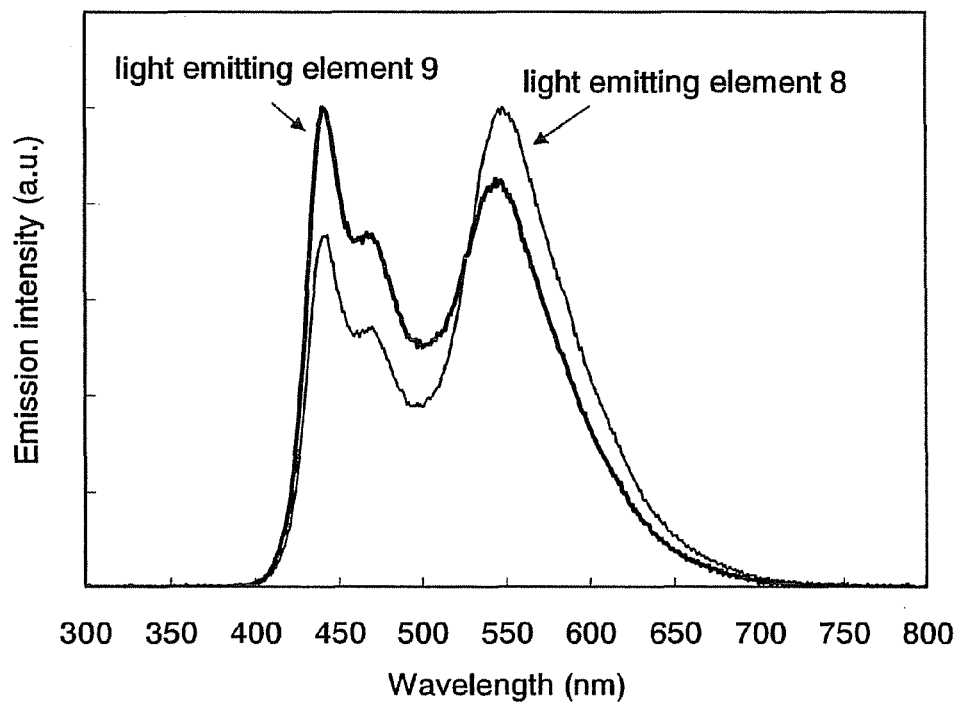
FIG. 57 shows emission spectra of the light emitting element 8 and the light emitting element 9.

Luminance-current density characteristics, luminance-voltage characteristics, and current efficiency-luminance characteristics of the light emitting element 8 and the light emitting element 9 are shown in FIGS. 54, 55, and 56, respectively. Also, the emission spectrum which was obtained at a current of 1 mA is illustrated in FIG. 57. The CM chromaticity coordinates of the light emitting element 8 at a luminance of 950 cd/m$^2$ was (x=0.29, y=0.37), and light emission was white. At a luminance of 950 cd/m$^2$, the current efficiency was 13 cd/A, meaning that high current efficiency was exhibited. In addition, at a luminance of 950 cd/m$^2$, the voltage was 3.0 V, the current density was 7.5 mA/cm$^2$, and the power efficiency was 13 (lm/W), meaning that high power efficiency was exhibited. As shown in FIG. 57, the light emitting element 8 exhibits a broad emission spectrum and emits white light with high color rendering properties.

The CIE chromaticity coordinates of the light emitting element 9 at a luminance of 1250 cd/m$^2$ was (x=0.25, y=0.31), and light emission was bluish white. At a luminance of 1250 cd/m$^2$, the current efficiency was 10 cd/A and the external quantum efficiency was 2.7%, meaning that high current efficiency was exhibited. In addition, at a luminance of 1250 cd/m$^2$, the voltage was 3.0 V, the current density was 12.2 mA/cm$^2$, and the power efficiency was 11 (lm/W), meaning that high power efficiency was exhibited. As shown in FIG. 57, the light emitting element 9 exhibits a broad emission spectrum and emits white light with high color rendering properties.

Seen in FIGS. 54 to 57, the light emitting element 8 and the light emitting element 9 have high current efficiency. It is noticed that they also have high power efficiency, meaning they have low power consumption. Accordingly, by applying an anthracene derivative of the present invention to a light emitting element, a high luminous efficiency can be achieved. In addition, a light emitting element with low power consumption can be obtained. As is seen from FIG. 57, when an anthracene derivative of the present invention is applied to a white light emitting element, the white-light emitting element can have a broad emission spectrum and high color rendering properties. Further, a white light emitting element with a high luminous efficiency and low power consumption can be obtained.

This application is based on Japanese Patent Application serial no. 2006-266002 filed in Japan Patent Office on Sep. 28, 2006, the entire contents of which are hereby incorporated by reference.

EXPLANATION OF REFERENCE

101: substrate, 102: first electrode, 103: first layer, 104: second layer, 105: third layer, 106: fourth layer, 107: second electrode, 301: substrate, 302: first electrode, 303: first layer, 304: second layer, 305: third layer, 306: fourth layer, 307: second electrode, 501: first electrode, 502: second electrode, 511: first light emitting unit, 512: second light emitting unit, 513: charge generation layer, 601: source side driver circuit, 602: pixel portion, 603: gate side driver circuit, 604: sealing substrate, 605: sealing material, 607; space, 608: wiring, 609: FPC (flexible printed circuit), 610: element substrate, 611: switching TFT, 612: current controlling TFT, 613: first electrode, 614: insulator, 616: layer containing a light emitting substance, 617: second electrode, 618: light emitting element, 623: n-channel TFT, 624: p-channel TFT, 901: housing, 902: liquid crystal layer, 903: backlight, 904: housing, 905: driver IC, 906: terminal, 951: substrate, 952: electrode, 953: insulating layer, 954: partition layer, 955: layer containing a light emitting substance, 956: electrode, 2001: housing, 2002: light source, 2101: glass substrate, 2102: first electrode, 2103: layer containing a composite material, 2104: hole transporting layer, 2105: light emitting layer, 2106: electron transporting layer, 2107: electron injecting layer, 2108: second electrode, 2201: glass substrate, 2202: first electrode, 2203: layer containing a composite material, 2204: hole transporting layer, 2205: first light emitting layer, 2206: second light emitting layer, 2207: electron transporting layer, 2208: electron injecting layer, 2209: second electrode, 3001: lighting device, 3002: television device, 9101: housing, 9102: supporting base, 9103: display portion, 9104: speaker portion, 9105: video input terminal, 9201: main body, 9202: housing, 9203: display portion, 9204: keyboard, 9205: external connection port, 9206: pointing device, 9401: main body, 9402: housing, 9403: display portion, 9404: audio input portion, 9405: audio output portion, 9406: operation key, 9407: external connection port, 9408: antenna, 9501: main body, 9502: display portion, 9503: housing, 9504: external connection port, 9505: remote control receiving portion, 9506: image receiving portion, 9507: battery, 9508: audio input portion, 9509: operation keys, and 9510: eye piece portion.

The invention claimed is:

1. An anthracene derivative represented by a general formula (6):

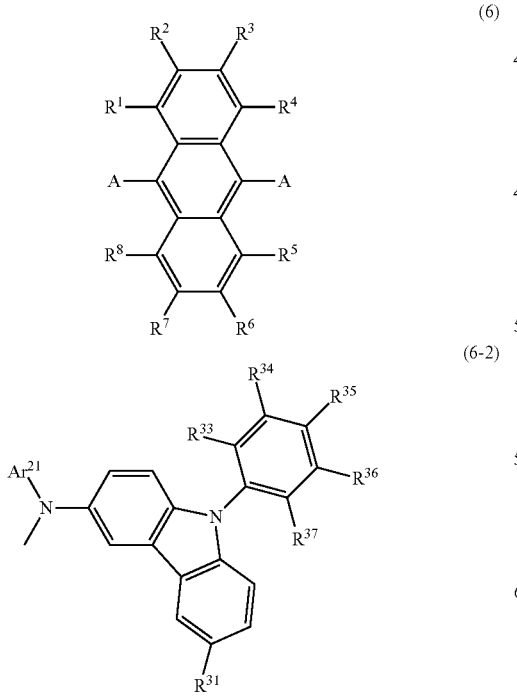

(6)

wherein each of $R^1$ to $R^8$ represents a hydrogen atom or an alkyl group having 1 to 4 carbon atoms, wherein A represents a substituent, the substituent is represented by a general formula (6-2), wherein $Ar^{21}$ represents an aryl group having 6 to 25 carbon atoms, wherein $R^{31}$ represents any of a hydrogen atom, an alkyl group having 1 to 4 carbon atoms, and an aryl group having 6 to 25 carbon atoms, and wherein each of $R^{33}$ to $R^{37}$ represents a hydrogen atom, an alkyl group having 1 to 4 carbon atoms, or an aryl group having 6 to 15 carbon atoms.

2. The anthracene derivative according to claim 1, wherein $Ar^{21}$ represents any of a phenyl group, a 1-naphthyl group, and a 2-naphthyl group.

3. A light emitting device comprising:

a first electrode;

a second electrode; and a layer provided between the first electrode and the second electrode;

wherein the layer comprises an anthracene derivative represented by a general formula (6),

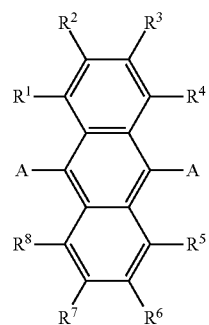

(6)

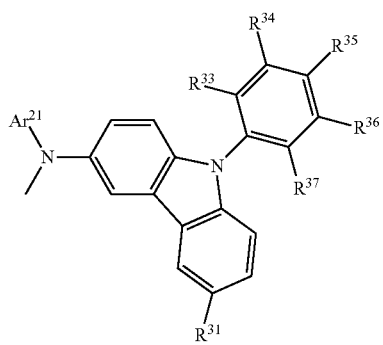

(6-2)

wherein each of $R^1$ to $R^8$ represents a hydrogen atom or an alkyl group having 1 to 4 carbon atoms, wherein A represents a substituent, the substituent is represented by a general formula (6-2), wherein $Ar^{21}$ represents an aryl group having 6 to 25 carbon atoms, wherein $R^{31}$ represents any of a hydrogen atom, an alkyl group having 1 to 4 carbon atoms, and an aryl group having 6 to 25 carbon atoms, and wherein each of $R^{33}$ to $R^{37}$ represents a hydrogen atom, an alkyl group having 1 to 4 carbon atoms, or an aryl group having 6 to 15 carbon atoms.

4. The light emitting device according to claim 3, wherein $Ar^{21}$ represents any of a phenyl group, a 1-naphthyl group, and a 2-naphthyl group.

5. The light emitting device according to claim 3,
wherein the layer is a light emitting layer.

6. The light emitting device according to claim 3,
wherein the layer further includes an inorganic compound.

7. A lighting device comprising the light emitting device according to claim 3.

8. A light emitting device comprising:
a first electrode;
a second electrode;
a plurality of light emitting units provided between the first electrode and the second electrode,
wherein at least one of the plurality of light emitting units comprises a layer,
wherein the layer comprises an anthracene derivative represented by a general formula (6),

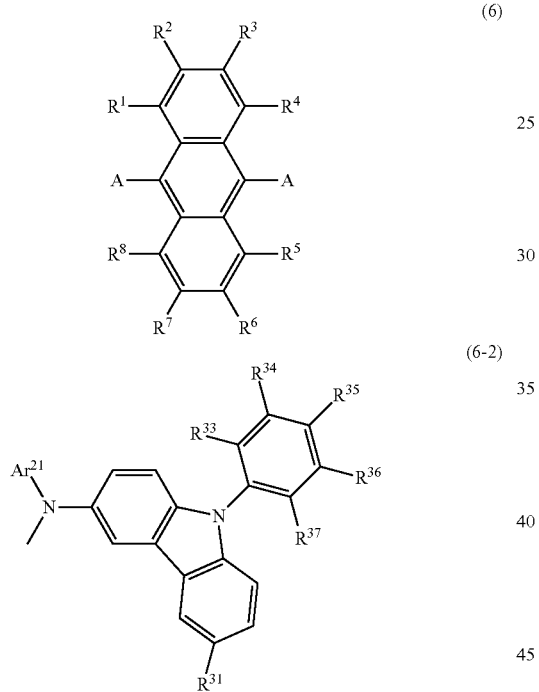

wherein each of $R^1$ to $R^8$ represents a hydrogen atom or an alkyl group having 1 to 4 carbon atoms,
wherein A represents a substituent, the substituent is represented by a general formula (6-2),
wherein $Ar^{21}$ represents an aryl group having 6 to 25 carbon atoms,
wherein $R^{31}$ represents any of a hydrogen atom, an alkyl group having 1 to 4 carbon atoms, and an aryl group having 6 to 25 carbon atoms, and
wherein each of $R^{33}$ to $R^{37}$ represents a hydrogen atom, an alkyl group having 1 to 4 carbon atoms, or an aryl group having 6 to 15 carbon atoms.

9. The light emitting device according to claim 8,
wherein $Ar^{21}$ represents any of a phenyl group, a 1-naphthyl group, and a 2-naphthyl group.

10. A lighting device comprising the light emitting device according to claim 8.

11. An anthracene derivative represented by a following formula (238):

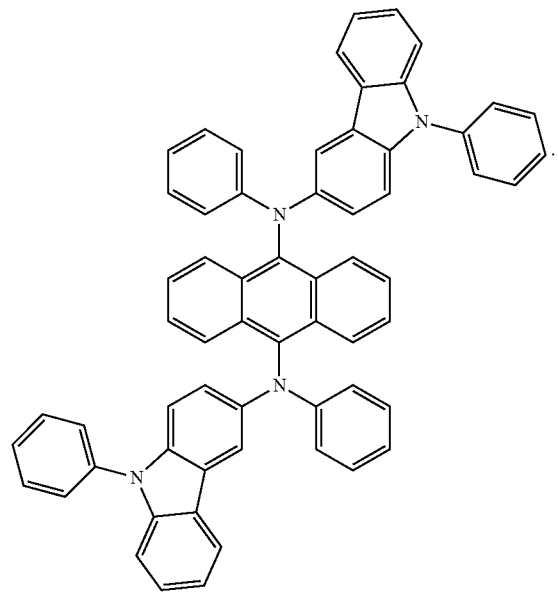

12. A light emitting device comprising:
a first electrode;
a second electrode; and
a layer provided between the first electrode and the second electrode;
wherein the layer comprises an anthracene derivative represented by following formula (238),

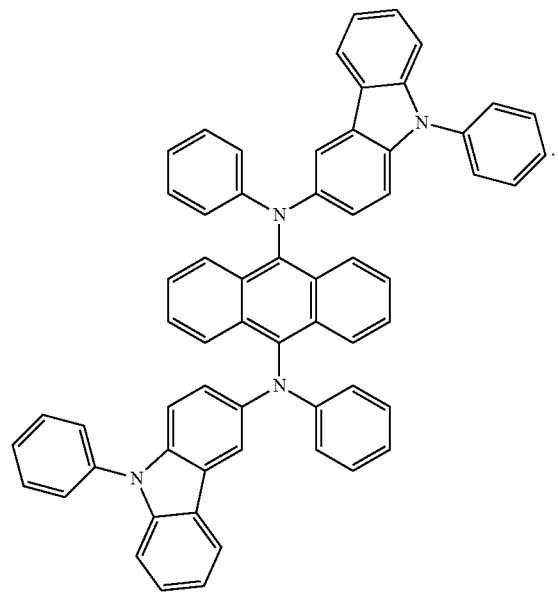

13. A light emitting device comprising:
a first electrode;
a second electrode;
a plurality of light emitting units provided between the first electrode and the second electrode,
wherein at least one of the plurality of light emitting units comprises a layer, and
wherein the layer comprises an anthracene derivative represented by following formula (238),

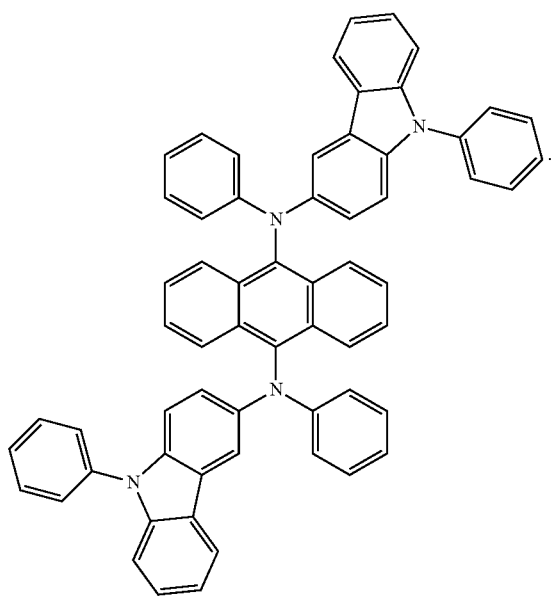

(238)

14. A lighting device comprising the light emitting device according to claim 12.

15. A lighting device comprising the light emitting device according to claim 13.

16. An organic compound represented by general formula (1),

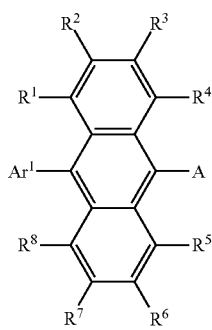

(1)

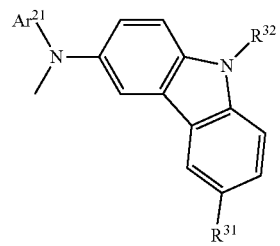

(1-2)

wherein $Ar^1$ represent an aryl group having 6 to 25 carbon atoms,
wherein each of $R^1$ to $R^8$ represents a hydrogen atom or an alkyl group having 1 to 4 carbon atoms,
wherein A represents a substituent which is represented by a general formula (1-2),
wherein $Ar^{21}$ represents an aryl group having 6 to 25 carbon atoms,
wherein $R^{31}$ represents any of a hydrogen atom an alkyl group having 1 to 4 carbon aroms, and an aryl group having 6 to 25 carbon atoms, and
wherein $R^{32}$ represents any of an alkyl group having 1 to 4 carbon atoms and an aryl group having 6 to 25 carbon atoms.

17. The organic compound according to claim 16, wherein the organic compound is represented by structural formula (201),

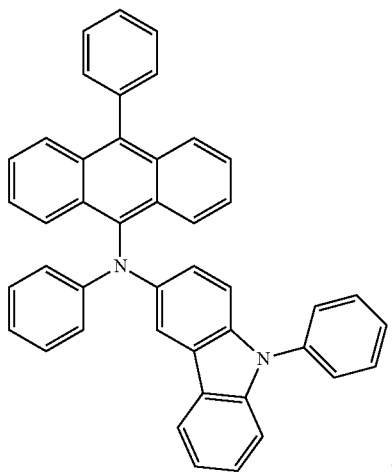

(201)

18. A light emitting device comprising:
a first electrode;
a second electrode; and
a layer between the first electrode and the second electrode;
wherein the layer comprises the organic compound according to claim 16.

19. A light emitting device comprising:
a first electrode;
a second electrode;
a plurality of light emitting units between the first electrode and the second electrode,
wherein at least one of the plurality of light emitting units comprises a layer, and
wherein the comprises the layer organic compound according to claim 16.

20. A lighting device comprising the light emitting device according to claim 18.

21. A lighting device comprising the light emitting device according to claim 19.

* * * * *

UNITED STATES PATENT AND TRADEMARK OFFICE
CERTIFICATE OF CORRECTION

PATENT NO.        : 8,546,792 B2
APPLICATION NO.   : 13/014887
DATED             : October 1, 2013
INVENTOR(S)       : Masakazu Egawa et al.

Page 1 of 1

It is certified that error appears in the above-identified patent and that said Letters Patent is hereby corrected as shown below:

In the Specification:

Column 118, line 6; Change "reaction, with" to --reaction with--.
Column 127, line 39; Change "of the ITT is not" to --of the TFT is not--.
Column 142, line 63; Change "PIE platinum" to --PTE platinum--.
Column 151, line 19; Change "t-BuDNA:PCAPhA)." to --(= t-BuDNA:PCAPhA).--.
Column 160, line 20; Change "The CM" to --The CIE--.

In the Claims:

Column 166, line 22, Claim 16; Change "atom an" to --atom, an--.
Column 166, line 23, Claim 16; Change "aroms, and" to --atoms, and--.
Column 166, line 66, Claim 19; Change "the layer organic" to --the organic--.

Signed and Sealed this
Thirty-first Day of December, 2013

Margaret A. Focarino
*Commissioner for Patents of the United States Patent and Trademark Office*